(12) United States Patent
Kamen et al.

(10) Patent No.: US 9,151,646 B2
(45) Date of Patent: Oct. 6, 2015

(54) SYSTEM, METHOD, AND APPARATUS FOR MONITORING, REGULATING, OR CONTROLLING FLUID FLOW

(71) Applicant: DEKA Products Limited Partnership, Manchester, NH (US)

(72) Inventors: Dean Kamen, Bedford, NH (US); Bob D. Peret, Bedford, NH (US); Derek G. Kane, Manchester, NH (US); John M. Kerwin, Manchester, NH (US); Colin H. Murphy, Cambridge, MA (US); Brian H. Yoo, Cambridge, MA (US); Brian D. Tracey, Litchfield, NH (US); Matthew J. Johnson, Dunbarton, NH (US); Thomas S. Schnellinger, North Andover, MA (US); Christopher C. Langenfeld, Nashua, NH (US); Michael J. Slate, Merrimack, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 412 days.

(21) Appl. No.: 13/723,244

(22) Filed: Dec. 21, 2012

(65) Prior Publication Data

US 2013/0188040 A1    Jul. 25, 2013

Related U.S. Application Data

(63) Continuation-in-part of application No. 13/333,574, filed on Dec. 21, 2011, and a continuation-in-part of application No. PCT/US2011/066588, filed on Dec. 21, 2011.

(Continued)

(51) Int. Cl.
*G01F 1/00* (2006.01)
*A61M 5/168* (2006.01)

(Continued)

(52) U.S. Cl.
CPC ............ *G01F 1/00* (2013.01); *A61B 17/00234* (2013.01); *A61M 5/16886* (2013.01); *A61M 25/00* (2013.01); *G06F 19/3418* (2013.01); *G06F 19/3468* (2013.01)

(58) Field of Classification Search
None
See application file for complete search history.

(56) References Cited

U.S. PATENT DOCUMENTS

| 2,888,877 A | 6/1959 | Shellman et al. |
| 3,173,372 A | 3/1965 | Baldwin |

(Continued)

FOREIGN PATENT DOCUMENTS

| AU | 2247783 A | 6/1985 |
| CA | 1213749 A1 | 11/1986 |

(Continued)

OTHER PUBLICATIONS

AAMI and FDA, Infusing Patients Safely: Priority Issues from the AAMI/FDA Infusion Device Summit, Symposium, Oct. 5-6, 2010, pp. 1-42, AAMI, Arlington, VA, USA.

(Continued)

*Primary Examiner* — Neal Sereboff
(74) *Attorney, Agent, or Firm* — James D. Wyninegar, Jr.

(57) ABSTRACT

An apparatus, system and method for regulating fluid flow are disclosed. The apparatus includes a curved, elongated support member elastically deformable and having first and second ends. The apparatus also include an opposing support member configured to position a tube against the curved, elongated support member between the first and second ends. Deformation of the curved, elongated support member by movement of the first and second ends toward each other reduces an internal volume of the tube.

28 Claims, 115 Drawing Sheets

Related U.S. Application Data

(60) Provisional application No. 61/578,649, filed on Dec. 21, 2011, provisional application No. 61/578,658, filed on Dec. 21, 2011, provisional application No. 61/578,674, filed on Dec. 21, 2011, provisional application No. 61/651,322, filed on May 24, 2012, provisional application No. 61/679,117, filed on Aug. 3, 2012.

(51) Int. Cl.
*A61B 17/00* (2006.01)
*A61M 25/00* (2006.01)
*G06F 19/00* (2011.01)

(56) References Cited

U.S. PATENT DOCUMENTS

| | | | |
|---|---|---|---|
| 3,384,336 A | 5/1968 | Pulman | |
| 3,609,379 A | 9/1971 | Hildebrandt | |
| 3,685,787 A | 8/1972 | Adelberg | |
| 3,733,149 A | 5/1973 | Jacobson | |
| 3,790,042 A | 2/1974 | McCormick et al. | |
| 3,831,600 A | 8/1974 | Yum et al. | |
| 4,038,982 A | 8/1977 | Burke et al. | |
| 4,105,028 A | 8/1978 | Sadlier et al. | |
| 4,155,362 A | 5/1979 | Jess | |
| 4,303,376 A | 12/1981 | Siekmann | |
| 4,321,461 A * | 3/1982 | Walter et al. | 377/21 |
| 4,328,800 A | 5/1982 | Marx et al. | |
| 4,328,801 A | 5/1982 | Marx et al. | |
| 4,397,642 A | 8/1983 | Lamadrid | |
| 4,421,506 A | 12/1983 | Danby et al. | |
| 4,449,534 A | 5/1984 | Leibinsohn Saul | |
| 4,469,480 A | 9/1984 | Figler et al. | |
| 4,504,263 A | 3/1985 | Steuer et al. | |
| 4,525,163 A | 6/1985 | Slavik et al. | |
| 4,583,975 A | 4/1986 | Pekkarinen et al. | |
| RE32,294 E | 11/1986 | Knute | |
| 4,634,426 A | 1/1987 | Kamen | |
| 4,648,869 A | 3/1987 | Bobo, Jr. | |
| 4,662,829 A | 5/1987 | Nehring | |
| 4,668,216 A | 5/1987 | Martin et al. | |
| 4,673,820 A | 6/1987 | Kamen | |
| 4,680,977 A | 7/1987 | Conero et al. | |
| 4,703,314 A | 10/1987 | Spani | |
| 4,718,896 A | 1/1988 | Arndt et al. | |
| 4,720,636 A | 1/1988 | Benner, Jr. | |
| 4,820,281 A | 4/1989 | Lawler, Jr. | |
| 4,834,744 A | 5/1989 | Ritson | |
| 4,837,708 A | 6/1989 | Wright | |
| 4,846,792 A | 7/1989 | Bobo, Jr. et al. | |
| 4,909,786 A | 3/1990 | Gijselhart et al. | |
| 4,920,336 A | 4/1990 | Meijer | |
| 4,936,828 A | 6/1990 | Chiang | |
| 4,959,050 A | 9/1990 | Bobo, Jr. | |
| 4,979,940 A | 12/1990 | Bobo, Jr. et al. | |
| 4,981,467 A | 1/1991 | Bobo, Jr. et al. | |
| 5,002,539 A | 3/1991 | Coble et al. | |
| 5,045,069 A | 9/1991 | Imparato | |
| 5,057,090 A | 10/1991 | Bessman | |
| 5,154,704 A | 10/1992 | Archibald | |
| 5,181,910 A | 1/1993 | Scanlon | |
| 5,186,057 A | 2/1993 | Everhart | |
| RE34,413 E | 10/1993 | McCullough | |
| 5,267,980 A | 12/1993 | Dirr, Jr. et al. | |
| 5,314,316 A | 5/1994 | Shibamoto et al. | |
| 5,328,341 A | 7/1994 | Forni | |
| 5,331,309 A | 7/1994 | Sakai | |
| 5,415,641 A | 5/1995 | Yerlikaya et al. | |
| 5,482,446 A | 1/1996 | Williamson et al. | |
| 5,562,615 A | 10/1996 | Nassif | |
| 5,588,963 A | 12/1996 | Roelofs | |
| 5,718,562 A | 2/1998 | Lawless et al. | |
| 5,753,820 A | 5/1998 | Reed et al. | |
| 5,782,805 A | 7/1998 | Meinzer et al. | |
| 5,800,140 A | 9/1998 | Forni | |
| 5,899,665 A | 5/1999 | Makino et al. | |
| 6,049,381 A | 4/2000 | Reintjes et al. | |
| 6,050,713 A | 4/2000 | O'Donnell et al. | |
| 6,083,206 A | 7/2000 | Molko | |
| 6,110,153 A | 8/2000 | Davis et al. | |
| 6,149,631 A | 11/2000 | Haydel, Jr. | |
| 6,159,186 A | 12/2000 | Wickham et al. | |
| 6,213,354 B1 | 4/2001 | Kay | |
| 6,228,047 B1 | 5/2001 | Dadson | |
| D446,860 S | 8/2001 | Mezière et al. | |
| 6,328,712 B1 | 12/2001 | Cartledge | |
| 6,362,887 B1 | 3/2002 | Meisberger | |
| 6,500,151 B1 | 12/2002 | Cobb et al. | |
| 6,503,221 B1 | 1/2003 | Briggs et al. | |
| 6,523,414 B1 | 2/2003 | Malmstrom et al. | |
| 6,562,012 B1 * | 5/2003 | Brown et al. | 604/253 |
| 6,599,282 B2 | 7/2003 | Burko | |
| 6,641,556 B1 | 11/2003 | Shigezawa | |
| 6,657,545 B1 | 12/2003 | Lin et al. | |
| 6,736,801 B1 | 5/2004 | Gallagher | |
| 6,984,052 B1 | 1/2006 | Del Castillo | |
| 7,001,365 B2 | 2/2006 | Makkink | |
| 7,190,275 B2 | 3/2007 | Goldberg et al. | |
| 7,338,475 B2 | 3/2008 | Brown | |
| 7,498,563 B2 | 3/2009 | Mandro et al. | |
| 7,499,581 B2 | 3/2009 | Tribble et al. | |
| 7,540,859 B2 | 6/2009 | Claude et al. | |
| 7,695,448 B2 | 4/2010 | Cassidy et al. | |
| 7,767,991 B2 | 8/2010 | Sacchetti | |
| 7,892,204 B2 | 2/2011 | Kraus | |
| 7,905,859 B2 | 3/2011 | Bynum et al. | |
| 7,918,834 B2 | 4/2011 | Mernoe et al. | |
| 7,933,780 B2 | 4/2011 | De La Huerga | |
| 8,025,634 B1 | 9/2011 | Moubayed et al. | |
| 8,038,657 B2 | 10/2011 | Davis et al. | |
| 8,147,448 B2 | 4/2012 | Sundar et al. | |
| 8,147,464 B2 | 4/2012 | Spohn et al. | |
| 8,256,984 B2 | 9/2012 | Fathallah et al. | |
| 8,529,511 B2 | 9/2013 | Boulanger et al. | |
| 8,531,517 B2 | 9/2013 | Tao | |
| 8,552,361 B2 | 10/2013 | Mandro et al. | |
| 8,622,979 B2 | 1/2014 | Hungerford et al. | |
| 8,834,429 B2 | 9/2014 | Grant et al. | |
| 2001/0026292 A1 * | 10/2001 | Ishizaki | 347/12 |
| 2002/0194933 A1 | 12/2002 | Roelofs | |
| 2003/0045840 A1 * | 3/2003 | Burko | 604/253 |
| 2003/0055406 A1 | 3/2003 | Lebel et al. | |
| 2003/0217962 A1 | 11/2003 | Childers et al. | |
| 2004/0171994 A1 | 9/2004 | Goldberg et al. | |
| 2005/0171491 A1 | 8/2005 | Minh Miner et al. | |
| 2006/0140466 A1 | 6/2006 | Seshimo et al. | |
| 2006/0291211 A1 | 12/2006 | Rodriguez et al. | |
| 2008/0004574 A1 | 1/2008 | Dyar et al. | |
| 2008/0051732 A1 | 2/2008 | Chen | |
| 2008/0147008 A1 | 6/2008 | Lewis et al. | |
| 2008/0147016 A1 | 6/2008 | Faries et al. | |
| 2008/0154214 A1 | 6/2008 | Spohn et al. | |
| 2008/0235765 A1 | 9/2008 | Shimizu | |
| 2009/0112115 A1 | 4/2009 | Huang et al. | |
| 2009/0224638 A1 | 9/2009 | Weber | |
| 2009/0254025 A1 | 10/2009 | Simmons | |
| 2009/0276167 A1 | 11/2009 | Glaser et al. | |
| 2009/0281460 A1 | 11/2009 | Lowery et al. | |
| 2010/0097451 A1 | 4/2010 | Bruce et al. | |
| 2010/0114027 A1 | 5/2010 | Jacobson et al. | |
| 2010/0168671 A1 | 7/2010 | Faries, Jr. et al. | |
| 2010/0211003 A1 | 8/2010 | Sundar et al. | |
| 2010/0292635 A1 | 11/2010 | Sundar | |
| 2010/0309005 A1 | 12/2010 | Warner et al. | |
| 2011/0004186 A1 | 1/2011 | Butterfield | |
| 2011/0125103 A1 | 5/2011 | Rondeau | |
| 2011/0166511 A1 | 7/2011 | Sharvit et al. | |
| 2011/0196306 A1 | 8/2011 | De La Huerga | |
| 2011/0208123 A1 | 8/2011 | Gray et al. | |
| 2011/0231204 A1 | 9/2011 | De La Huerga | |
| 2011/0251557 A1 | 10/2011 | Powers | |
| 2011/0313789 A1 | 12/2011 | Kamen et al. | |
| 2012/0013735 A1 | 1/2012 | Tao | |

(56) References Cited

U.S. PATENT DOCUMENTS

| | | |
|---|---|---|
| 2012/0059318 A1 | 3/2012 | Dewey |
| 2012/0059350 A1 | 3/2012 | Siefert |
| 2012/0095415 A1 | 4/2012 | Sharvit et al. |
| 2012/0095433 A1* | 4/2012 | Hungerford et al. .......... 604/500 |
| 2012/0185267 A1 | 7/2012 | Kamen et al. |
| 2012/0197185 A1 | 8/2012 | Tao |
| 2012/0238997 A1 | 9/2012 | Dewey |
| 2012/0265166 A1 | 10/2012 | Yodfat |
| 2012/0310153 A1 | 12/2012 | Moberg et al. |
| 2013/0035659 A1 | 2/2013 | Hungerford et al. |
| 2013/0083191 A1 | 4/2013 | Lowery et al. |
| 2013/0085443 A1* | 4/2013 | Lowery et al. ................. 604/65 |
| 2013/0177455 A1 | 7/2013 | Kamen et al. |
| 2013/0182381 A1 | 7/2013 | Gray et al. |
| 2013/0184676 A1 | 7/2013 | Kamen et al. |
| 2013/0188040 A1 | 7/2013 | Kamen et al. |
| 2013/0191513 A1 | 7/2013 | Kamen et al. |
| 2013/0197693 A1 | 8/2013 | Kamen et al. |
| 2013/0201482 A1 | 8/2013 | Munro |
| 2013/0204188 A1 | 8/2013 | Kamen et al. |
| 2013/0253442 A1 | 9/2013 | Travis et al. |
| 2013/0272773 A1 | 10/2013 | Kamen et al. |
| 2013/0281965 A1 | 10/2013 | Kamen et al. |
| 2013/0297330 A1 | 11/2013 | Kamen et al. |
| 2013/0310990 A1 | 11/2013 | Peret et al. |
| 2013/0317753 A1 | 11/2013 | Kamen et al. |
| 2013/0317837 A1 | 11/2013 | Ballantyne et al. |
| 2013/0336814 A1 | 12/2013 | Kamen et al. |
| 2013/0339049 A1 | 12/2013 | Blumberg, Jr. et al. |
| 2013/0346108 A1 | 12/2013 | Kamen et al. |
| 2014/0081233 A1 | 3/2014 | Hungerford et al. |
| 2014/0135695 A1 | 5/2014 | Grant et al. |
| 2014/0148757 A1 | 5/2014 | Ambrosina et al. |
| 2014/0165703 A1 | 6/2014 | Wilt et al. |
| 2014/0180711 A1 | 6/2014 | Kamen et al. |
| 2014/0194818 A1 | 7/2014 | Yodfat et al. |
| 2014/0227021 A1 | 8/2014 | Kamen et al. |
| 2014/0309612 A1 | 10/2014 | Smisson, III et al. |
| 2014/0318639 A1 | 10/2014 | Peret et al. |
| 2015/0002667 A1 | 1/2015 | Peret et al. |
| 2015/0002668 A1 | 1/2015 | Peret et al. |
| 2015/0002677 A1 | 1/2015 | Peret et al. |

FOREIGN PATENT DOCUMENTS

| | | |
|---|---|---|
| DE | 2023027 A1 | 11/1970 |
| DE | 3617723 A1 | 12/1987 |
| DE | 3822057 C2 | 1/1989 |
| DE | 69229832 T2 | 2/2000 |
| EP | 0112699 A2 | 7/1984 |
| EP | 1722310 A1 | 11/2006 |
| EP | 2319551 A2 | 5/2011 |
| FR | 2042606 A1 | 2/1971 |
| FR | 2458804 | 1/1981 |
| FR | 2617593 | 1/1989 |
| GB | 1301033 A | 12/1972 |
| GB | 2020735 A | 11/1979 |
| GB | 2207239 A | 1/1989 |
| GB | 2328982 A | 3/1999 |
| JP | 58163843 | 9/1983 |
| JP | 3110458 B2 | 11/2000 |
| JP | 2011 062371 A | 3/2011 |
| NL | 7006908 | 11/1970 |
| NL | 8801680 | 2/1989 |
| NL | 9101825 A | 5/1993 |
| SE | 376843 B | 6/1975 |
| WO | WO 81/02770 A1 | 10/1981 |
| WO | WO 93/09407 A1 | 5/1993 |
| WO | WO 00/72181 A3 | 11/2000 |
| WO | WO 02/40084 A2 | 5/2002 |
| WO | WO 02/100262 A1 | 12/2002 |
| WO | WO 2004/035116 A1 | 4/2004 |
| WO | WO 2005/094919 A1 | 10/2005 |
| WO | WO 2006/086723 A2 | 8/2006 |
| WO | WO 2008/022880 A1 | 2/2008 |
| WO | WO 2008/079023 A1 | 7/2008 |
| WO | WO 2009/039203 A2 | 3/2009 |
| WO | WO 2009/039214 A2 | 3/2009 |
| WO | WO 2009/055639 A2 | 4/2009 |
| WO | WO 2010/129720 A2 | 11/2010 |
| WO | WO 2011/021098 A1 | 2/2011 |
| WO | WO 2011/136667 A1 | 11/2011 |
| WO | WO 2013/095459 A9 | 6/2013 |
| WO | WO 2013/096713 A2 | 6/2013 |
| WO | WO 2013/096718 A2 | 6/2013 |
| WO | WO 2013/096722 A2 | 6/2013 |
| WO | WO 2013/096909 A2 | 6/2013 |
| WO | WO 2013/070337 A1 | 8/2013 |
| WO | WO 2014/160307 A1 | 10/2014 |

OTHER PUBLICATIONS

Conway, *"Analytical Analysis of Tip Travel in a Bourdon Tube"*, Master's Thesis, Naval Postgraduate School Monterey, CA, Dec. 1995, pp. i-89.

Darzynkiewicz, *"Cytometry"*, Methods in Cell Biology, 2011, Third Edition Part A, vol. 63, pp. 44-48, Academic Press, San Diego, 2001. And please see whole document generally.

"Feature Detection", *OpenCV Wiki*, 2011, 7 pgs, http://opencv.willowgarage.com/documentation/cpp/imgproc_feature_detection.html.

Galambos et al., *"Progressive Probabilistic Hough Transform for Line Detection"*, IEEE, 7 pgs, 1999.

*International Search Report & Written Opinion* dated May 14, 2012, received in International patent application No. PCT/US2011/066588 (197W0), 9 pgs.

*International Search Report & Written Opinion* dated Jun. 18, 2013, received in International patent application No. PCT/US2012/071142 (J79W0), 14 pgs.

*International Search Report & Written Opinion* dated Oct. 1, 2013, received in International patent application No. PCT/US2012/071490 (J76W0), 19 pgs.

*International Search Report & Written Opinion* dated Dec. 4, 2013, received in International patent application No. PCT/US2013/032445 (K14WO), 20 pgs.

*International Search Report & Written Opinion* dated Nov. 7, 2013, received in International patent application No. PCT/US2013/042350 (K66W0), 18 pgs.

*Invitation to Pay Additional Fees and, Where Applicable, Protest Fee* dated Sep. 9, 2013, received in International patent application No. PCT/US2013/032445 (K14WO), 10 pgs.

*Invitation to Pay Additional Fees and, Where Applicable, Protest Fee* dated Sep. 26, 2013, received in International patent application No. PCT/US2013/042350 (K66W0), 7 pgs.

Hofmann, *"Modeling Medical Devices for Plug-and-Play Interoperability"*, Master of Engineering Thesis, Massachusetts Institute of Technology, Jun. 2007, © Robert Matthew Hofmann, MMVII, pp. 1-187.

King et al., *"Prototyping Closed Loop Physiologic Control with the Medical Device Coordination Framework"*, University of Pennsylvania, Kansas State University, May 2010, Published in 2010 ICSE Workshop on Software Engineering in Health Care, ACM, New York, NY.

Jetley et al., *"Safety Requirements Based Analysis of Infusion Pump Software"*, Proceedings of the Workshop on Software and Systems for Medical Devices and Services, held in conjunction with IEEE Real Time Systems Symposium, Tucson, AZ, Dec. 2007, Office of Science and Engineering Laboratories, Center for Devices and Radiological Health, US Food and Drug Administration, Silver Spring, MD 20993-0002, pp. 21-24.

FDA US Food and Drug Administration, *"SEDASYS® Computer-Assisted Personalized Sedation System—P080009"*, Jul. 16, 2013, pp. 1-2, www.fda.gov/MedicalDevices/ProductsandMedicalProcedures/DeviceApprovalsandClearances/Recently-ApprovedDevices/ucm353950.htm.

Luerkens, Theory and Application of Morphological Analysis, Fine Particles and Surfaces, 1991, CRC Press, Inc., pp. 5-7.

(56) References Cited

OTHER PUBLICATIONS

Matas et al., "*Progressive Probabilistic Hough Transform*", University of Surrey, Czech Technical University, 1998, pp. 1-10.

"*Miscellaneous Image Transformations*", OpenCV Wiki, 2011, 9 pgs., http://opencv.willowgarage.com/documentation/cpp/miscellaneous_image_transformations.

National Patient Safety Agency, *Design for Patient Safety: A Guide to the Design of Electronic Infusion Devices*, Edition 1, 2010, National Patient Safety Agency and the Royal College of Art Helen Hamlyn Centre, pp. 1-92.

"*Object Detection*", OpenCV Wiki, 2011, 2 pgs., http://opencv.willowgarage.com/documentation/cpp/object_detection.html.

"*The OpenCV Reference Manual Release 2.4.6.0*", Jul. 1, 2013, pp. 1-813.

Leor at al., "*A System for the Measurement of Drop vol. Of Intravenous Solutions*", Proceedings Computers in Cardiology 1989, Jerusalem, IEEE, pp. 405-406.

Butterfield, Monitoring and Detection of IV Line Occlusions, Alaris SE Pump, 2010, 4 pgs., CareFusion Corporation.

"*Vista Basic: Instructions for Use: Software IFVB*", Manual, 2004, 3 pgs., B. Braun Medical Inc.

Hugli et al., "*Drop volume measurement by vision*." Proceedings of SPIE Electronic Imaging Conference, San Diego, Jan. 2000. SPIE vol. 3866-11, pp. 60-66.

\* cited by examiner

1. IF THE INPUT PIXEL IS TO THE LEFT OR RIGHT OF THE BASELINE (GREEN LINE) IN THE IMAGE, THEN ITS OUTPUT VALUE IS SET TO ZERO.

2. IF THE INPUT PIXEL'S BACKGROUND COUNT ARRAY INDICATES THAT FEWER THAN A PRE-DETERMINED NUMBER OF IMAGES (E.G., 100) HAVE BEEN USED TO MAKE THIS PIXEL'S BACKGROUND VALUE, THEN
   a. IF THE INPUT PIXEL'S INTENSITY IS LESS THAN THE THRESHOLD INTENSITY (E.G., 140 IN AN RANGE OF 0 - 255), THEN SET THE PIXEL'S OUTPUT VALUE TO NOT - ZERO (255).
   b. IF THE INPUT PIXEL'S INTENSITY IS GREATER THAN OR EQUAL TO THE THRESHOLD INTENSITY, THEN SET THE PIXEL'S OUTPUT VALUE TO ZERO.

3. IF THE INPUT PIXEL'S BACKGROUND COUNT ARRAY IS GREATER THAN THE PRE-DETERMINED NUMBER OF IMAGES, THEN:
   a. IF THE SQUARE OF THE DIFFERENCE BETWEEN THE INPUT PIXEL INTENSITY AND THE BACKGROUND PIXEL INTENSITY IS GREATER THAN THE PIXEL'S ESTIMATE OF BACKGROUND VARIANCE TIMES A CONSTANT $\gamma^2$, THEN SET THE PIXEL'S OUTPUT VALUE TO NOT-ZERO (255). *(THIS EFFECTIVELY SAYS IF THE CURRENT PIXEL VALUE IS MORE THAN $\gamma$, THEN THE PIXEL IS DISTINCT)*
   b. IF THE SQUARE OF THE DIFFERENCE BETWEEN THE INPUT PIXEL INTENSITY AND THE BACKGROUND PIXEL INTENSITY IS LESS THAN OR EQUAL TO THE PIXEL'S ESTIMATE OF BACKGROUND VARIANCE TIMES A CONSTANT $\gamma^2$, THEN SET THE PIXEL'S OUTPUT VALUE TO ZERO.

FIG. 32

1. PUSH THE LOCATION OF THE FIRST PIXEL ONTO A STACK
2. WHILE THE STACK IS NOT EMPTY:
    a. POP THE NEXT LOCATION $(i,j)$ OFF OF THE STACK
    b. MAKE THE OUTPUT PIXEL VALUE AT $(i,j)$ WHITE
    c. EXAMINE THE EIGHT PIXELS ADJACENT TO $(i,j)$ :

i. IF THE ADJACENT INPUT PIXEL $(i,\varphi)$ IS WHITE, BUT THE OUTPUT PIXEL $(i,\varphi)$ IS BLACK ADD THE LOCATION $(i,\varphi)$ TO THE STACK d. RETURN TO 2

FIG. 37

| LENS FOCAL LENGTH | LENS SEPARATION FROM THE CAMERA | FOCUS SEPARATION FROM THE CAMERA | FIELD OF VIEW | DEPTH OF FIELD ($D_{BLUR}/D_{PIXEL}$)=1 | DEPTH OF FIELD ($D_{BLUR}/D_{PIXEL}$)=2 |
|---|---|---|---|---|---|
| 20mm | 0mm | 18.6mm | ±9.7mm | ±2mm | ±4mm |
| 20mm | 60mm | 78.2mm | ±12.3mm | ±3mm | ±6mm |
| 40mm | 0mm | 34.8mm | ±18.2mm | ±5mm | ≥10mm |
| 40mm | 60mm | 93.5mm | ±22.6mm | ±10mm | ≥10mm |
| 60mm | 0mm | 48.9mm | ±25.6mm | ≥10mm | ≥10mm |
| 60mm | 60mm | 106.4mm | ±31.4mm | ≥10mm | ≥10mm |

FIG. 42

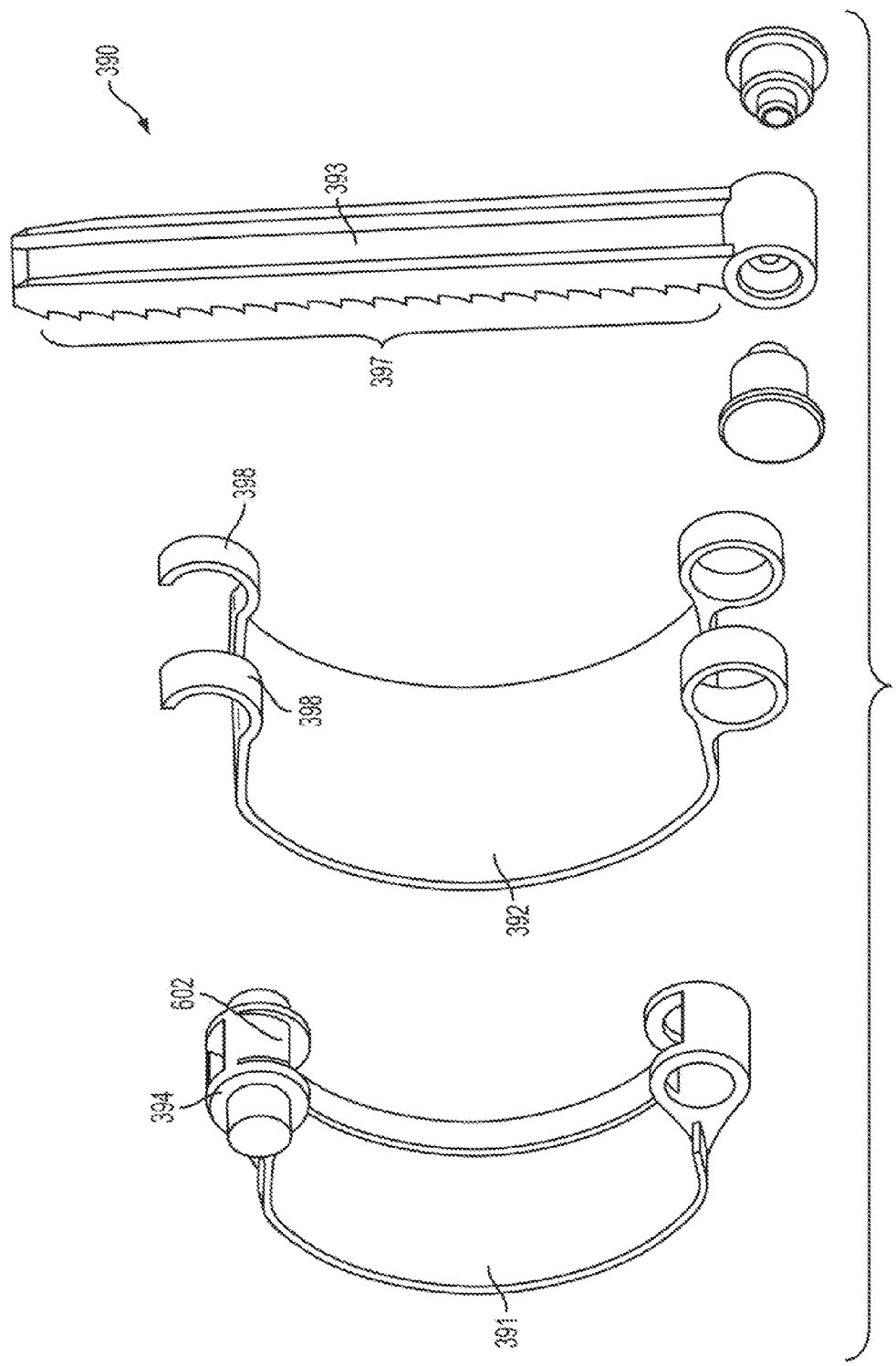

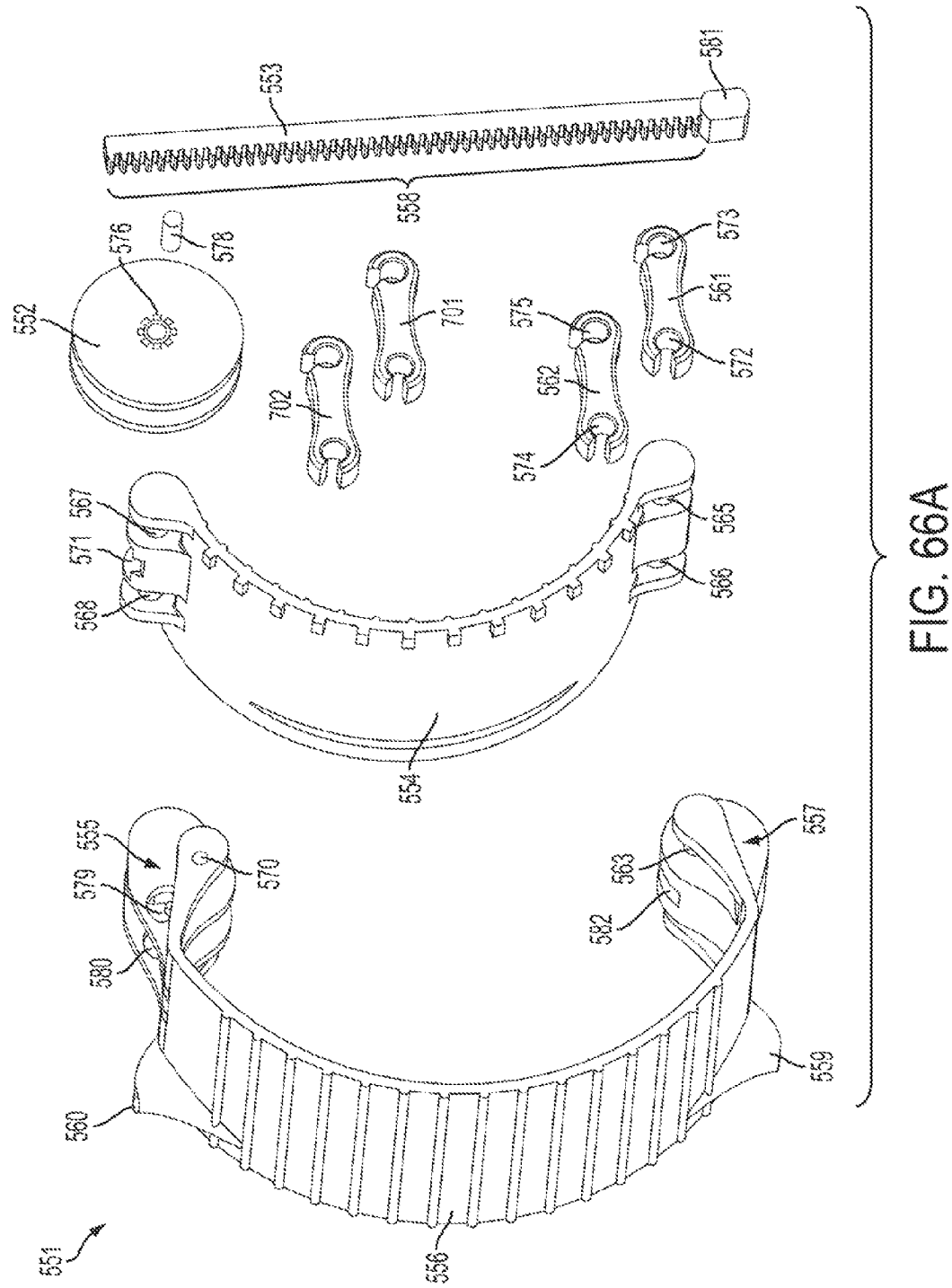

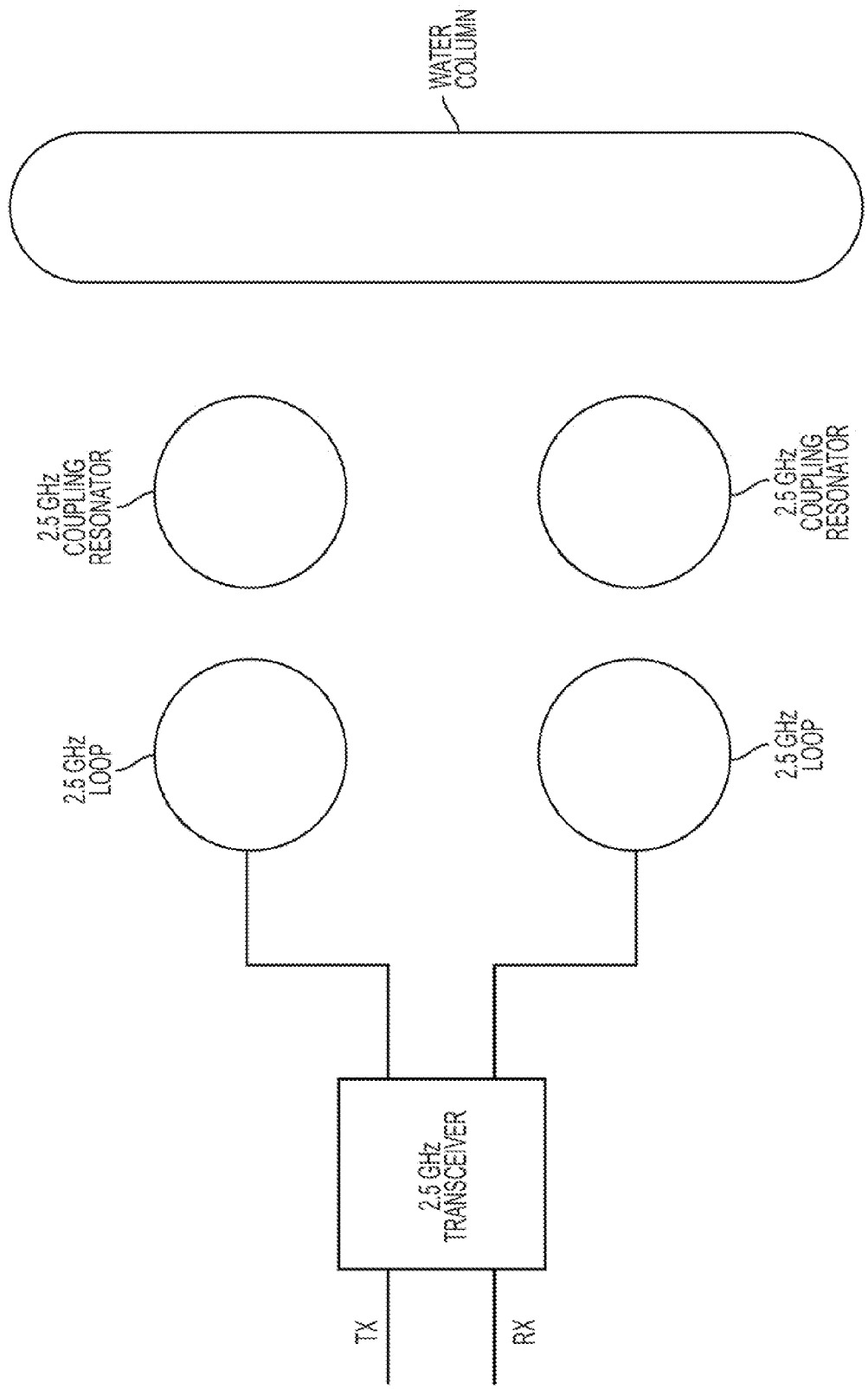

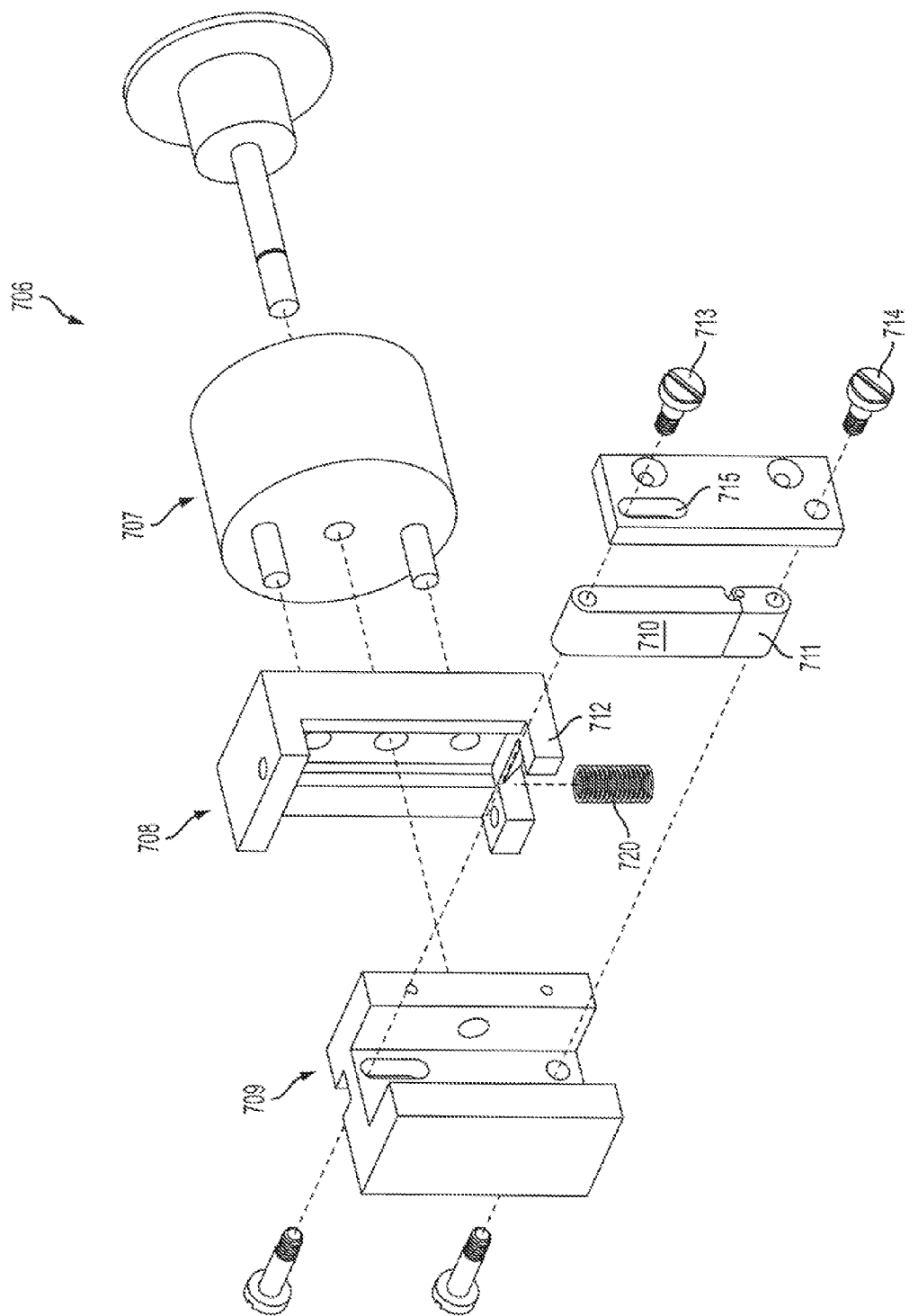

SYSTEM, METHOD, AND APPARATUS FOR MONITORING, REGULATING, OR CONTROLLING FLUID FLOW

CROSS REFERENCE TO RELATED APPLICATIONS

The present application is a Non-Provisional which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

This application claims priority to, benefit of, and is also a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

This application may also be related to one or more of the following patent applications filed on Dec. 21, 2012, all of which are hereby incorporated herein by reference in their entireties:

Nonprovisional application for System, Method, and Apparatus for Clamping, Ser. No. 13/723,238;

Nonprovisional application for System, Method, and Apparatus for Dispensing Oral Medications, Ser. No. 13/723,235;

PCT application for System, Method, and Apparatus for Dispensing Oral Medications, Ser. No. PCT/US12/71131;

Nonprovisional application for System, Method, and Apparatus for Estimating Liquid Delivery, Ser. No. 13/724,568;

Nonprovisional application for System, Method, and Apparatus for Infusing Fluid, Ser. No. 13/725,790;

PCT application for System, Method, and Apparatus for Infusing Fluid, Ser. No. PCT/US12/71490;

Nonprovisional application for System, Method, and Apparatus for Electronic Patient Care, Ser. No. 13/723,239;

Nonprovisional application for System, Method, and Apparatus for Electronic Patient Care, Ser. No. 13/723,242;

PCT application for System, Method, and Apparatus for Monitoring, Regulating, or Controlling Fluid Flow, Ser. No. PCT/US12/71142;

Nonprovisional application for System, Method, and Apparatus for Estimating Liquid Delivery, Ser. No. 13/723,251;

PCT application for System, Method, and Apparatus for Estimating Liquid Delivery, Ser. No. PCT/US12/71112; and Nonprovisional application for System, Method, and Apparatus for Electronic Patient Care, Ser. No. 13/723,253.

BACKGROUND

1. Relevant Field

The present disclosure relates to monitoring, regulating, or controlling fluid flow. More particularly, the present disclosure relates to a system, method, and apparatus for monitoring, regulating, or controlling fluid flow, for example, for use in medical applications such as intravenous infusion therapy, dialysis, transfusion therapy, peritoneal infusion therapy, bolus delivery, enteral nutrition therapy, parenteral nutrition therapy, hemoperfusion therapy, fluid resuscitation therapy, or insulin delivery, among others.

2. Description of Related Art

In many medical settings, one common mode of medical treatment involves delivering fluids into a patient, such as a human, animal, or pet. The need may arise to rapidly infuse fluid into the patient, accurately infuse the fluid into the patient, and/or slowly infuse the fluid into the patient. Saline and lactated ringers are examples of commonly used fluids. Such fluids may be used to maintain or elevate blood pressure and promote adequate perfusion. In the shock-trauma setting or in septic shock, fluid resuscitation is often a first-line therapy to maintain or improve blood pressure.

Delivery of fluid into the patient may be facilitated by use of a gravity-fed line (or tube) inserted into the patient. Typically, a fluid reservoir (e.g., an IV bag) is hung on a pole and is connected to the fluid tube. The fluid tube is sometimes coupled to a drip chamber for trapping air and estimating fluid flow. Below the fluid tube may be a manually actuated valve used to adjust the flow of fluid. For example, by counting the number of drops formed in the drip chamber within a certain amount of time, a caregiver can calculate the rate of fluid that flows through the drip chamber and adjust the valve (if needed) to achieve a desired flow rate.

Certain treatments require that the fluid delivery system strictly adhere to the flow rate set by the caregiver. Typically, such applications use an infusion pump, but such pumps may not be used in all situations or environments.

SUMMARY

Briefly, and in general terms, the present disclosure relates to a system, method, and apparatus for monitoring, regulating, or controlling fluid flow, for example, for use in medical applications such as intravenous infusion therapy, dialysis, transfusion therapy, peritoneal infusion therapy, bolus delivery, enteral nutrition therapy, parenteral nutrition therapy, hemoperfusion therapy, fluid resuscitation therapy, or insulin delivery, among others. More particularly, the present disclosure relates to a fluid flow meter for monitoring the flow of fluids associated with a patient, a valve for regulating the flow of fluid associated with the patient, and/or a fluid flow meter coupled to a valve (e.g., arranged in a closed-loop, open-loop, or feedback configuration) to monitor, regulate and/or control the use of fluid associated with the patient.

In some embodiments of the present disclosure, a flow meter includes one or more optical sensors to monitor the flow of fluid within a tube, for example, using an image sensor to monitor drops within a drip chamber attached to the tube. The flow meter may be a stand-alone device, may be used in conjunction with either a pump or a valve, or both, and/or may be used to provide feedback to any electronic device. The flow meter may be remotely controlled, e.g., by a monitoring client, a remote communicator, a smart phone, a computer, etc.

The flow meter may measure the average flow rate, an instantaneous flow rate, a drop volume, a drop growth rate, or other parameter related to fluid flow.

The flow meter may use the flow rate or parameter related to fluid flow to: (1) display the flow rate or parameter on a screen, (2) provide feedback, such as the flow rate or parameter related to fluid flow (wirelessly or via wires), to an infusion pump such as a peristaltic pump, (3) provide feedback to a monitoring client or remote monitoring client such as a smart phone, (4) issue alarms when the flow rate or parameter related to fluid flow is outside a predetermined range, (5) issue an alarm with the flow rate or parameter related to fluid flow is above a predetermined threshold, (6) issue an alarm when a free flow is detected, (7) communicate alarms to a pump, a monitoring client, or a remote monitoring client, (8) instruct a valve to stop fluid flow when a free flow is detected, an alarm is issued, and/or the flow rate or parameter related to fluid flow is above a threshold or is outside of a predetermined range, and/or (9) broadcast the flow rate or parameter related to fluid flow.

In some embodiments described herein, a valve regulates the flow of fluid associated with a patient. The valves disclosed herein may be manually actuated or may be actuated with an actuator (or both). The valve may be used with or without a pump, with or without a flow meter, and/or may be a stand-alone device. The valve may be remotely controlled, e.g., by a monitoring client, a remote communicator, a smart phone, a computer, etc. The valve may compress a tube along a portion that is substantially greater than the diameter of the tube, e.g., 2 times greater, 5 times greater, 10 times greater, etc.

The valve may be made of two or more pieces that compress the tube or may be made of a single piece that compresses the tube as the piece is moved or deformed. The two or more pieces and/or the single piece may be made using injection molding, ultrasonic welding, using multiple pieces that are glued or molded together, or the like. Each of the two or more pieces may be made by one or more subparts that are attachable to each other either permanently or temporarily. The single piece may be made by one or more subparts that are coupled together either permanently or temporarily, e.g., using ultrasonic welding, gluing, latching, or other technique. The pieces may be plastic, metal, an alloy, a polymer, or other material.

In some embodiments of the present disclosure, a flow meter is coupled to a valve to regulate fluid flow, e.g., fluid flow into a patient. The flow meter coupled to the valve may be used in lieu of a pump, such as a peristaltic infusion pump. The flow meter and valve combination may be remotely controlled, e.g., by a monitoring client, a remote communicator, a smart phone, a computer, etc. or may be remotely monitored. A monitoring client may control the flow meter or valve, may be a relay between the flow meter and valve, may monitor the operation of the flow meter or valve, may communicate information related to the flow meter or valve to a server, and/or may not be used in the system.

The flow meter may monitor the flow of fluid and make adjustments, directly or indirectly, to a valve or a pump (e.g., an infusion pump). The flow meter may alarm when it detects free flow conditions, determines if the flow rate is greater than a predetermined threshold or is outside a predetermined range, and/or detects any abnormal behavior. The flow meter, in response to an alarm or condition, may cause the flow meter to stop fluid flow, instruct a valve to stop fluid flow, instruct a safety valve to stop fluid flow, notify a monitoring client or remote communicator, broadcast the detected condition, or perform a predefine routine or algorithm.

In certain embodiments of the present disclosure, an apparatus for regulating fluid flow includes a curved, elongated support member and an opposing support member. The curved, elongated support member is elastically deformable and has first and second ends. The opposing support member is configured to position a tube against the curved, elongated support member between the first and second ends such that deformation of the curved, elongated support member by movement of the first and second ends toward each other reduces an internal volume of the tube. The opposing support member may be another curved, elongated support member.

The apparatus may include an actuator coupled to the curved, elongated support member to deform the curved, elongated support member by movement of the first and second ends toward each other by actuation of the actuator. In some such embodiments, the actuator may be a lead screw, and a knob may be coupled to the lead screw to actuate the lead screw.

The actuator, the curved, elongated support member, and the opposing support member may be configured to regulate the fluid flow by actuation of the actuator in accordance with a Gompertz curve. The actuator may be further configured, in some embodiments, to actuate the first and second ends toward each other along a predetermined portion of the Gompertz curve. For example, the actuator may only actuate the actuator along a portion of the actuatable range of the curved, elongated support member and the opposing support member.

The actuator, the curved, elongated support member, and the opposing support member may be configured to regulate the fluid flow by actuation of the actuator in accordance with a sigmoid curve. The actuator may be further configured to actuate the first and second ends toward each other along a predetermined portion of the sigmoid curve.

The curved, elongated support member may be semi-rigid and/or may consist essentially of a stretchable material. The curved, elongated support member may be an arcuate, elongated support member, and/or may be C-shaped.

The apparatus may further comprise an elongated connecting member operatively coupled to the first and second ends of the curved, elongated support member.

In certain embodiments of the present disclosure, the apparatus may comprise an actuator coupled to the elongated connecting member and the curved, elongated support member to apply an outward expanding force to thereby deform the first and second ends of the curved, elongated support members toward each other.

In certain embodiments of the present disclosure, the curved, elongated support member is disposed about parallel to the another curved, elongated support member along a substantial portion thereof. For example, the curved, elongated support member defines a length, and the another curved, elongated support member defines a length and the length of the another curved, elongated support member is disposed approximately parallel with the length of the curved, elongated support member.

In certain embodiments of the present disclosure, the apparatus includes an actuator operatively coupled to the curved, elongated support member at the first and second ends, and to the another curved, elongated support member at first and second ends. The actuation of the actuator causes the first and second ends of the curved, elongated support member to approach each other and also causes the first and second ends of the another curved, elongated support member to approach each other to thereby cause a reduction in distance between the curved, elongated support member and the another curved, elongated support member to thereby compress the tube.

In certain embodiments of the present disclosure, the curved, elongated support member defines a length, and the opposing support member is disposed orthogonally from the length along a portion thereof.

In certain embodiments of the present disclosure, the curved, elongated support member includes a plurality of ridges disposed thereon to engage the tube.

In certain embodiments of the present disclosure, the opposing support member includes a plurality of ridges disposed thereon configured to engage the tube.

In certain embodiments of the present disclosure, the curved, elongated support member includes a flange extending from a length thereof configured to hold the tube. The opposing support member may include another flange extending from a length thereof configured to hold the tube such that the flange and the another flange are about parallel to each other and are about parallel to a central axis defined by the tube when the tube is disposed therebetween.

In certain embodiments of the present disclosure, an apparatus for regulating fluid flow includes a first elongated support member, a second elongated support member, and an actuator. The first elongated support member defines a length, and the second elongated support member also defines its own length such that the length of the second elongated support member is disposed in spaced relation with the length of the first elongated support member to cooperate with the first elongated support member to compress a tube. The actuator is in mechanical engagement with at least one of the first and second elongated support members to actuate the first and second elongated support members toward each other to thereby compress a tube disposed therebetween to regulate flow of fluid within the tube such that actuation of the actuator actuates the first and second elongated support members to regulate fluid flow within the tube in accordance with an approximate sigmoid curve.

The length of the second elongated support member may be disposed about parallel to the length of the first elongated support member. The first and second elongated support members may be configured to cooperate with each other to compress the tube along a length of the tube at least substantially greater than the diameter of the tube. The actuator may be configured to actuate the first and second elongated support members to compress the tube to regulate fluid flow within the tube along a predetermined portion of the sigmoid curve.

In certain embodiments of the present disclosure, an apparatus for regulating fluid flow includes first and second elongated support members. The first elongated support member defines a length and the second elongated support member defines a length. The length of the second elongated support member is disposed in spaced relation with the length of the first elongated support member to cooperate with the first elongated support member to compress a tube. The actuator is in mechanical engagement with at least one of the first and second elongated support members to actuate the first and second elongated support members toward each other to thereby compress a tube disposed therebetween to regulate flow of fluid within the tube such that actuation of the actuator actuates the first and second elongated support members to regulate fluid flow within the tube in accordance with an approximate Gompertz curve.

The length of the second elongated support member may be disposed about parallel to the length of the first elongated support member. The first and second elongated support members may be configured to cooperate with each other to compress the tube along a length at least substantially greater than the diameter of the tube.

The actuator may be configured to actuate the first and second elongated support members to compress the tube to regulate fluid flow within the tube in accordance with a predetermined portion of the Gompertz curve.

In certain embodiments of the present disclosure, an apparatus for regulating fluid flow includes first and second elongated support members. The first elongated support member defines a length, and the second elongated support member defines a length such that the length of the second elongated support member is disposed in spaced relation with the length of the first elongated support member to cooperate with the first elongated support member to compress a tube. The actuator is in mechanical engagement with at least one of the first and second elongated support members to actuate the first and second elongated support members toward each other to thereby compress a tube disposed therebetween to regulate flow of fluid within the tube such that actuation of the actuator actuates the first and second elongated support members to regulate fluid flow within the tube in accordance with an approximate generalized logistic function.

The length of the second elongated support member may be disposed about parallel to the length of the first elongated support member. The first and second elongated support members may be configured to cooperate with each other to compress the tube along a length of the tube at least substantially greater than the diameter of the tube. The actuator may be further configured to actuate the first and second elongated support members to compress the tube to regulate fluid flow within the tube in accordance with a predetermined portion of the generalized logistic function.

In certain embodiments of the present disclosure, an apparatus for regulating fluid flow includes first and second support members, and an actuator. The first support member forms at least one of an arc, a plurality of arcs, a curve, a plurality of curves, an arcuate shape, a plurality of arcuate shapes, an S-shape, a C-shape, a convex shape, a plurality of convex shapes, and a concave shape. The second support member is disposed in spaced relation with the first support member to cooperate with the first support member to compress a tube along a length of the tube at least substantially greater than the diameter of the tube. The actuator is in mechanical engagement with at least one of the first and second support members to actuate the first and second support members toward each other to thereby compress a tube disposed therebetween to regulate flow of fluid within the tube such that actuation of the actuator actuates the first and second support members to regulate fluid flow within the tube in accordance with an approximate nonlinear function.

The approximate nonlinear function may be an approximate generalized logistic function, an approximate sigmoid curve, and/or an approximate Gompertz curve. The actuator may be configured to actuate to thereby regulate the fluid flow within the tube in accordance with a predetermined portion of the approximate nonlinear function.

In certain embodiments of the present disclosure, the first support member forms an arc, has a shape consisting essentially of an arc, forms a plurality of arcs, has a shape consisting essentially of a plurality of arcs, forms a curve, has a shape consisting essentially of a curve, forms a plurality of curves, has a shape consisting essentially of a plurality of curves, forms an arcuate shape, has a shape consisting essentially of an arcuate shape, forms a plurality of arcuate shapes, has a shape consisting essentially of a plurality of arcuate shapes, forms an S-shape, has a shape consisting essentially of an S-shape, forms a C-shape, has a shape consisting essentially of a C-shape, forms a convex shape, has a shape consisting essentially of a convex shape, forms a plurality of convex shapes, has a shape consisting essentially of a plurality of convex shapes, forms a concave shape, has a shape consisting essentially of a concave shape, forms a plurality of concave shapes, and/or has a shape consisting essentially of a plurality of concave shapes.

A length of the second support member may be disposed about parallel to a length of the first support member. The first and second support members may be configured to cooperate with each other to compress the tube along a length of the tube at least substantially greater than the diameter of the tube.

In certain embodiments of the present disclosure, an apparatus for regulating fluid flow includes a curved, elongated support member and an opposing support member. The curved, elongated support member is elastically deformable and has first and second ends. The opposing support member is configured to define a conduit with the curved, elongated support member such that the conduit is defined between the curved, elongated support member and the opposing member; Deformation of the curved, elongated support member by movement of the first and second ends toward each other reduces an internal volume of the conduit. In some embodiments, the conduit may be configured to receive a tube. In yet additional embodiments, the conduit is fluidly sealed, and the apparatus further comprises first and second ports in fluid communication with the conduit such that each port is adapted for being coupled to a tube.

In certain embodiments of the present disclosure, a system for regulating fluid flow includes a flexible tube and an inverse-Bourdon-tube valve. The flexible fluid tube has a fluid path and is configured for passing fluid therethrough. The inverse-Bourdon-tube valve is coupled to the flexible fluid tube to regulate the fluid flowing through the fluid path of the flexible fluid tube. An actuator may be coupled to the inverse-Bourdon-tube valve to actuate the inverse-Bourdon-tube valve to regulate the fluid flowing through the fluid path of the flexible fluid tube. An inverse-Bourdon-tube valve works in an opposite way of a Bourdon tube in that a deformation of the fluid path causes changes in fluid flow rather than fluid flow causing deformation of the fluid path.

In certain embodiments of the present disclosure, a system for regulating fluid flow includes a fluid tube, a valve, and an actuator. The fluid tube defines a fluid path configured for passing fluid therethrough. The valve is operatively coupled to the fluid tube and includes first and second flexible members. The second flexible member is operatively coupled to the first flexible member. The fluid tube is disposed between the first and second flexible members, and the first and second flexible members are configured to flex to thereby regulate flow of fluid passing through the fluid tube. The actuator is coupled to at least a first end of the first flexible member and a second end of the first flexible member. The actuator may be a lead screw and there may be an electrically powered motor coupled to the lead screw to turn the lead screw.

In certain embodiments of the present disclosure, the system may include a knob coupled to the lead screw such that the knob is configured to rotate the lead screw. The knob may be engaged by a motor-driven actuator.

In certain embodiments of the present disclosure, the actuator is coupled to a first end of the first flexible member and a second end of the first flexible member, and the actuator is configured to at least one of flex the first and second ends toward each other and flex the first and second ends away from each other. The actuator may flex the first and second ends away from each other and/or the actuator flexes the first and second flexible members such that the first and second ends approach each other. The first and second flexible members may be generally rectangular. The first member and/or the second member may be tensioned to at least substantially stop fluid flow when the actuator ceases application of a force.

The system may include a flow meter coupled to a drip chamber that is coupled to the fluid tube such that the flow meter estimates fluid flow through the drip chamber and therefore also estimate fluid flow through the fluid tube. The flow meter may be an image-sensor-based, flow meter.

The flow meter may be operatively coupled to a motor to actuate the valve, and the system may include a control component to control the motor to actuate the valve to achieve a desired flow rate as estimated by the flow meter.

In certain embodiments of the present disclosure, an apparatus for regulating fluid flow includes first and second C-shaped members. The first C-shaped member defines inner and outer surfaces, and the second C-shaped member defines inner and outer surfaces. At least one of the outer surface of the first C-shaped member and the inner surface of the second C-shaped member is configured to receive a tube. The inner surface of the second C-shaped member is disposed in spaced relation to the outer surface of the first C-shaped member. A substantial area of the inner surface of the second C-shaped member may, in some specific embodiments, abut the outer surface of the first C-shaped member.

In certain embodiments of the present disclosure, the second C-shaped member is flexible and the first C-shaped member is semi-rigid, is rigid, and/or is an elastomer.

A flexible member may be formed from a material selected from the group consisting of a plastic, a polymer, a monomer, a polypropylene, a thermoplastic polymer, a ceramic, a polyvinyl chloride, and a polyethylene.

In certain embodiments of the present disclosure, an apparatus for regulating fluid flow includes first and second flexible sheets. The second flexible sheet is operatively coupled to the first flexible sheet. The first and second flexible sheets are configured to receive a fluid tube therebetween, and the first and second flexible sheets are also configured to flex to thereby regulate flow of fluid passing through the fluid tube.

The apparatus may include an actuator coupled to a first end of the first flexible sheet and a second end of the first flexible sheet. The actuator may be configured to at least one of flex the first and second ends toward each other and flex the first and second ends away from each other.

The apparatus may include a lead screw coupled to a first end of the first flexible sheet and a second end of the first flexible sheet, and a knob coupled to the lead screw such that rotation of the knob rotates the lead screw. The knob may be configured for engagement with a motor-driven actuator whereby the motor-driven actuator actuates the knob.

In certain embodiments of the present disclosure, an apparatus for regulating fluid flow includes first and second curve-shaped members. The first curve-shaped member defines inner and outer surfaces, and the second curve-shaped member also defines inner and outer surfaces. The inner surface of the second curve-shaped member is disposed in spaced relation to the outer surface of the first curve-shaped member.

At least one of the first and second curve-shaped members may be configured to position a fluid tube therebetween. The first curve-shaped member may be at least one of semi-rigid and rigid. The second curve-shaped member may be flexible. The second curve-shaped member may comprise an elastomer. The first and second curve-shaped members may be flexible.

The apparatus may comprise a connecting member operatively coupled to at least one of a first end of the first curve-shaped member and a first end of the second curve-shaped member such that the connecting member is also operatively coupled to at least one of a second end of the first curve-shaped member and a second end of the second curve-shaped member. The connecting member may be flexible, may be rigid, and/or may be semi-rigid.

The apparatus may include an actuator positioned between the connecting member and the second curve-shaped member to apply a force therebetween when actuated. The actuator may be a lead screw.

In certain embodiments of the present disclosure, an apparatus for regulating fluid flow includes first and second curve-shaped members. The first curve-shaped member defines inner and outer surfaces. The first curve-shaped member has first and second receiving members at opposite ends of the first curve-shaped member. The second curve-shaped member defines inner and outer surfaces. The second curve-shaped member has first and second fasteners at opposite ends of the second curve-shaped member. At least one of the first and second fasteners may be a hook. The first receiving member of the first curve-shaped member is configured to engage the first fastener of the second curve-shaped member, and the second receiving member of the first curve-shaped member is configured to engage the second fastener of the second curve-shaped member.

At least one of the receiving members may be a cylindrically-shaped member, such as a barrel nut, configured for coupling to a hook.

At least one of the receiving members may be operatively coupled to an actuator. One or more of the receiving members may be operatively coupled to an electric motor.

In certain embodiments of the present disclosure, the apparatus further includes an electric motor coupled to the first receiving member such that: (1) the electric motor turns a rotor coupled to a shaft having threads on an outer surface thereof; (2) the second receiving member defines a threaded hole configured to receive the shaft; and (3) the threaded hole and shaft cooperate together to at least one of increase or decrease the distance between the first and second receiving members when the electric motor rotates the rotor to thereby rotate the shaft.

In certain embodiments of the present disclosure, an apparatus for regulating fluid flow includes first and second curved, elongated support members. The first curved, elongated support member is elastically deformable and has first and second ends. The second curved, elongated support member is elastically deformable and has first and second ends. The second curved, elongated support member is configured to position a tube against the first curved, elongated support such that deformation of the first and second curved, elongated support members by movement of the first and second ends of the first curved, elongated support member toward each other reduces an internal volume of the tube.

The first connector is coupled to the first end of the first curved, elongated support member and is also coupled to the first end of the second curved, elongated support member. The second connector is coupled to the second end of the first curved, elongated support member and is also coupled to the second end of the second curved, elongated support member. The second connector defines a hole. The connecting member has an end coupled to the first connector and another end configured for insertion into the hole of the second connector. The connecting member defines a threaded rod at least along a portion thereof. The knob has a ratchet configured to ratchet onto the connector member when moved from the another end of the connecting member toward the end of the connecting member. The knob is further configured to engage the threaded rod of the connecting member. The knob may include a plurality of fingers configured to engage the threaded rod of the connecting member. The knob defines an outer periphery and includes a hole defined at the center of the outer periphery of the knob. The hole is configured to receive the threaded rod. The plurality of fingers each arc to engage the threaded rod at a respective end of each of the plurality of fingers.

The first curved, elongated support member defines a first hole adjacent to the first end of the first curved, elongated support member. The hole is configured to hold a fluid tube.

The first curved, elongated support member may define a first notch adjacent to the first end of the first curved, elongated support member such that the notch is configured to receive a fluid tube. The notch may include a neck configured to receive the fluid tube and a circular region configured to retain the fluid tube.

In certain embodiments of the present disclosure, an apparatus for regulating fluid flow includes a base, a plurality of fingers, and a ring. The base defines a hole configured to receive a fluid tube. The plurality of fingers each has an end coupled to the base. The ring is configured to slide from the base and along the plurality of fingers. Movement of the ring away from the base and toward the fingers compresses the fingers against the tube. The ring is configured to frictionally lock against the plurality of fingers. Each finger includes an elongated end coupled to the base and a curved end coupled to an opposite end relative to the base.

In certain embodiments of the present disclosure, an apparatus for regulating fluid flow includes a conically-shaped member, a complementing member, and an actuator. The conically-shaped member has a surface for wrapping a tube therearound. The complementing member is configured to engage the conically-shaped member for compressing the tube. The actuator is configured to compress the conically-shaped member against the complementing member to thereby compress the tube.

In certain embodiments of the present disclosure, an intravenous administration set includes: a flexible tube for directing fluid flow therewithin; a first port at a first end of the flexible tube; a second port at a second end of the flexible tube; a curved, elongated support member elastically deformable and having first and second ends; and an opposing support member configured to position the flexible tube against the curved, elongated support member between the first and second ends such that deformation of the curved, elongated support member by movement of the first and second ends toward each other reduces an internal volume of the tube.

The intravenous administration set may further include a drip chamber coupled to the flexible tube, another port configured to receive a syringe for injection of fluid into the fluid flow within the flexible tube, and/or a slide occluder coupled to the flexible tube configured to engage the flexible tube to occlude fluid flow therewithin.

The first end of the curved, elongated support member may define a first hole to receive the flexible tube, and the second end of the curved, elongated support member may define a second hole to receive the flexible tube.

In certain embodiments of the present disclosure, a flow meter includes a coupler, a support member, first and second image sensors, and at least one processor. The coupler is adapted to couple to a drip chamber. The support member is operatively coupled to the coupler. The first image sensor has a first field of view and is operatively coupled to the support member. The first image sensor is positioned to view the drip chamber within the first field of view. The second image sensor has a second field of view and is operatively coupled to the support member. The second image sensor is positioned to view the drip chamber within the second field of view.

The at least one processor is operatively coupled to the first and second image sensors. The at least one processor receives a first image data from the first image sensor and a second image data from the second image sensor, and the at least one processor estimates at least one parameter of the liquid within the drip chamber using the first and second image data.

The at least one parameter may be one of a type of formation of the liquid, the volume of the liquid, and the shape of the liquid. The at least one processor may determine an existence of a free flow condition using at least one of the first and second sets of image data.

The flow meter may further include a background pattern positioned within the field of view of the first image sensor such that the drip chamber is between the first image sensor and the background pattern.

The at least one processor of the flow meter may estimate the at least one parameter using the first set of image data by analyzing a distortion of the background pattern caused by the liquid within the first field of view as viewed by the first image sensor. The background pattern may be an array of lines having at least one angle relative to an opening of the drip chamber when viewed from the first image sensor within the first field of view using the first set of image data.

The at least processor may determine a free flow condition exists when the liquid causes the array of lines to change angles by distortion caused by the liquid when in the free flow condition as viewed within the first field of view from the first image sensor.

The at least one processor may compare at least one of the first and second image data to a background image to estimate the at least one parameter.

The at least one processor may compare at least one of the first and second image data to the background image by calculating at least one of a difference between the at least one of the first and second image data to the background image, an absolute difference between the at least one of the first and second image data to the background image, and/or a squared absolute difference between the at least one of the first and second image data to the background image.

The flow meter may include a non-transitory, processor-readable memory in operative communication with the at least one processor such that the memory stores an operative set of processor executable instructions configured for execution by the at least one processor. The operative set of processor executable instructions, when executed by the at least one processor, controls the operation of the at least one processor.

In certain embodiments of the present disclosure, a flow meter includes a coupler, a support member, a background pattern, and at least one processor. The coupler is adapted to couple to a drip chamber. The support member is operatively coupled to the coupler. The image sensor has a field of view and is operatively coupled to the support member. The image sensor is positioned to view the drip chamber within the field of view. The background pattern is positioned within the field of view of the image sensor. The background pattern is positioned such that the drip chamber is between the background pattern and the image sensor. The at least one processor is operatively coupled to the image sensor to receive image data therefrom. The at least one processor is configured to estimate at least one parameter of liquid within the drip chamber using distortion of the background pattern caused by the liquid as indicated by the image data. The distortion is viewable within the field of view of the image sensor by the image sensor. The at least one parameter is at least one of a type of formation of the liquid, a volume of the liquid, and a shape of the liquid. The background pattern may be an array of lines having at least one angle relative to an opening of the drip chamber when viewed from the image sensor using the image data.

The at least one processor may determine an existence of a free flow condition using the distortion of the background pattern caused by the liquid as indicated by the image data. The at least processor may determine that a free flow condition exists when the liquid causes the array of lines to change angles by distortion caused by the liquid when in the free flow condition as viewed within the field of view of the image sensor.

The flow meter may further include a non-transitory, processor-readable memory in operative communication with the at least one processor. The non-transitory, processor-readable memory may store an operative set of processor executable instructions configured for execution by the at least one processor such that the operative set of processor executable instructions, when executed by the at least one processor, controls the operation of the at least one processor.

In certain embodiments of the present disclosure, a flow meter includes a coupler, a support member, an image sensor, and at least one processor. The coupler is adapted to couple to a drip chamber. The support member is operatively coupled to the coupler. The image sensor has a field of view and is operatively coupled to the support member such that the image sensor is positioned to view the drip chamber within the field of view. The at least one processor is operatively coupled to the image sensor to receive image data therefrom such that the at least one processor compares an image of the image data to a reference image to estimate at least one parameter of liquid within the drip chamber. The reference image may be a dynamic reference image. The at least one processor may update the reference image by multiplying each pixel of the reference image by a first constant and adding a corresponding pixel of the image multiplied by a second constant.

The flow meter may include a non-transitory, processor-readable memory in operative communication with the at least one processor. The non-transitory, processor-readable memory may include an operative set of processor executable instructions configured for execution by the at least one processor such that the operative set of processor executable instructions, when executed by the at least one processor, controls the operation of the at least one processor.

In certain embodiments of the present disclosure, a method for exposing an image sensor implemented by an operative set of processor executable instructions configured for execution by at least one processor includes: selecting a region of interest; determining if a pixel is within the region of interest; activating a light of a backlight if the pixel is within the region of interest; and exposing the pixel. The activating act may activate a subset of lights including the light of the backlight. The light of the backlight may form a uniform backlight. The image sensor may include the region of interest and the pixel.

The operative set of processor executable instructions may be stored on a non-transitory, processor-readable memory in operative communication with the at least one processor such that the at least one processor can perform the method.

The at least one processor may be coupled to an image sensor such that the at least one processor performs the method using the image sensor. The region of interest may be a region of the image sensor that images a drip chamber. The region of interest may correspond to the drip chamber.

The method may further include: receiving a vertical sync signal from the image sensor; and receiving a horizontal sync signal from the image sensor. The at least one processor may receive the vertical and horizontal sync signals from the image sensor. The at least one processor may activate the light of the backlight in accordance with at least one of the vertical and horizontal sync signals. The light may be a light-emitting diode.

In certain embodiments of the present disclosure, a flow meter includes a coupler, a support member, an image sensor, a backlight, and at least one processor. The coupler is adapted to couple to a drip chamber. The support member operatively couples to the coupler. The image sensor has a field of view and is operatively coupled to the support member such that the image sensor is positioned to view the drip chamber within the field of view. The backlight has at least one light. The backlight is coupled to the support member such that the backlight is adapted to illuminate the image sensor to expose the image sensor. The field of view of the image sensor at least partially images at least a portion of the drip chamber. The least one processor is operatively coupled to the image sensor to receive image data therefrom.

The at least one processor is configured to: select a region of interest of the image sensor; determine if a pixel of the image sensor is within the region of interest; activate the light of the backlight if the pixel of the image sensor is within the region of interest; and expose the pixel of the image sensor.

The flow meter may further include a non-transitory, processor-readable memory readable by the at least one processor. The non-transitory, processor-readable memory includes an operative set of processor executable instructions stored thereon configured to cause the at least one processor, when executed, to: select the region of interest of the image sensor; determine if the pixel of the image sensor is within the region of interest; activate the light of the backlight if the pixel of the image sensor is within the region of interest; and expose the pixel of the image sensor. The at least one processor may be further configured to: receive a vertical sync signal from the image sensor, and receive a horizontal sync signal from the image sensor. The at least one processor may activate the light of the backlight in accordance with at least one of the vertical and horizontal sync signals.

The at least one processor may select the region of interest and determine if the pixel of the image sensor is within the region of interest in accordance with the image data. The region of interest is a region of the image sensor that images the drip chamber. The region of interest may correspond to the drip chamber.

The at least one processor may activate a subset of lights including the light of the backlight. The light of the backlight may form a uniform backlight.

In certain embodiments of the present disclosure, a method includes: capturing an image including an image of a drip chamber using an image sensor having a field of view including the drip chamber; subtracting the image from a background image to thereby generate a difference image; converting each pixel of the difference image to a true value if an absolute value of a respective pixel is beyond a predetermined threshold or to a false value if the absolute value of the respective pixel is less than the predetermined threshold; summing each row of the converted difference image to generate a plurality of summation values, wherein each summation value of the plurality of summation values corresponds to a respective row of the converted difference image; and examining the plurality of summation values. The method may be implemented by an operative set of processor executable instructions stored on a non-transitory, processor-readable memory in operative communication with at least one processor such that the at least one processor performs the method.

The act of examining the plurality of summation values may include determining if a free flow condition exists within the drip chamber.

The act of determining if the free flow condition exists may include determining if the plurality of summation values includes a plurality of contiguous summation values above another predetermined threshold.

The act of examining the plurality of summation values may include determining if a drop has been formed within the drip chamber.

The act of determining if the drop has been formed within the drip chamber may include determining if the plurality of summation values includes a plurality of contiguous summation values within a predetermined range greater than a minimum value and less than a maximum value.

The method may optionally include smoothing the plurality of summation values prior to the examining act. The smoothing act may be in accordance with at least one of a spline function, a cubic spline function, a B-spline function, a Bezier spline function, a polynomial interpolation, a moving average, a data smoothing function, and a cubic-spline-type function.

The at least one processor may optionally be coupled to the image sensor, and the at least one processor may perform the method using the image sensor.

The method may optionally include the act of converting each pixel of the difference image to an absolute value of each pixel after the subtracting act and prior to the converting act.

The method may optionally include the act of converting each pixel of the difference image to a squared value of each pixel after the subtracting act and prior to the converting act.

In certain embodiments of the present disclosure, a flow meter includes a coupler, a support member, a light, and at least one processor. The coupler is adapted to couple to a drip chamber. The support member is operatively coupled to the coupler. The image sensor has a field of view and is operatively coupled to the support member such that the image sensor is positioned to view the drip chamber within the field of view. The light is coupled to the support member and is adapted to illuminate the image sensor to expose the image sensor such that the field of view of the image sensor at least partially images at least a portion of the drip chamber.

The at least one processor is operatively coupled to the image sensor to receive image data therefrom, and the at least one processor is configured to: capture an image including an image of a drip chamber using the image sensor having a field of view including the drip chamber; subtract the image from a background image to thereby generate a difference image; convert each pixel of the difference image to a true value if an absolute value of a respective pixel is beyond a predetermined threshold or to a false value if the absolute value of the respective pixel is less than the predetermined threshold; sum each row of the converted difference image to generate a plurality of summation values, wherein each summation value of the plurality of summation values corresponds to a respective row of the converted difference image; and examine the plurality of summation values.

The flow meter may include a non-transitory, processor-readable memory readable by the at least one processor such that the non-transitory, processor-readable memory includes an operative set of processor executable instructions stored thereon configured to cause the at least one processor, when executed, to: capture the image including the image of a drip chamber using the image sensor having a field of view including the drip chamber; subtract the image from the background image to thereby generate the difference image; convert each pixel of the difference image to the true value if the absolute value of the respective pixel is beyond the predetermined threshold or to the false value if the absolute value of the respective pixel is less than the predetermined threshold; sum each row of the converted difference image to generate the plurality of summation values, wherein each summation value of the plurality of summation values corresponds to the respective row of the converted difference image; and examine the plurality of summation values.

The at least one processor may be further configured to determine if a free flow condition exists within the drip chamber when the processor examines the plurality of summation values.

The at least one processor may be further configured to determine if the plurality of summation values includes a plurality of contiguous summation values above another predetermined threshold when the at least one processor determines if the free flow condition exists.

The at least one processor may be further configured to determine if a drop has been formed within the drip chamber when the at least one processor examines the plurality of summation values.

The at least one processor may be further configured to determine that a drop has been formed if the plurality of summation values includes a plurality of contiguous summation values within a predetermined range greater than a minimum value and less than a maximum value and a location of the contiguous summation values corresponds to a predetermined range of locations in which a drop can form.

The at least one processor may be further configured to smooth the plurality of summation values prior to when the at least one processor examines the plurality of summation values.

The at least one processor may smooth in accordance with at least one of a spline function, a cubic spline function, a B-spline function, a Bezier spline function, a polynomial interpolation, a moving average, a data smoothing function, and/or a cubic-spline-type function.

The flow meter may further include a non-transitory, processor-readable memory having an operative set of processor executable instructions stored thereon. The non-transitory, processor-readable memory is in operative communication with at least one processor such that the operative set of processor executable instructions controls the operation of the at least one processor.

The at least one processor may be further configured to convert each pixel of the difference image to an absolute value of each pixel after the subtraction act and prior to the conversion.

The at least one processor may be further configured to convert each pixel of the difference image to a squared value of each pixel after the subtraction act and prior to the conversion.

In certain embodiments of the present disclosure, a method includes: capturing an image of a drip chamber using an image sensor; identifying a plurality of pixels of interest within the image; determining a subset of pixels within the plurality of pixels of interest, wherein each pixel of the plurality of pixels is determined to be within the subset of pixels when there is a path to a baseline corresponding to the drip chamber; performing a rotation operation on the subset of pixels; and estimating a volume of a drop within the drip chamber by counting a number of pixels within the rotated subset of pixels.

The baseline may be a predetermined set of pixels within the image sensor. The plurality of pixels of interests may be identified by comparing the image to a background image.

The method may optionally include one or more of: initializing the background image; updating the background image using the image captured by the image sensor; updating an array of variances using the image captured by the image sensor; and/or updating an array of integers in according with the image captured by the image sensor.

The background image may be updated in accordance with:

$$P_{background,i,j} = P_{background,i,j}(1-\alpha_{background}) + \alpha_{background}P_{input,i,j}.$$

The array of variances may be updated in accordance with:

$$\sigma_{temp}^2 = (P_{background,i,j} - P_{input,i,j})^2$$

$$\sigma_{background,i,j}^2 = \sigma_{background,i,j}^2(1-\beta_{background}) + \beta_{background}\sigma_{temp}^2.$$

Each integer of the array of integers may correspond to a number of updates of a pixel of the background image. In some specific embodiments, the comparison of the image to the background image only compares pixels within the image to pixels within the background image if a respective integer of the array of integers indicates a respective pixel within the background image has been updated at least a predetermined number of times.

The method may optionally include one or more of: identifying a drop in the image and a predetermined band near an edge of the drop; and initializing the background image by setting each pixel of the background image to the image unless it is within the identified drop or the predetermined band near the edge of the drop.

The method may further include setting a pixel of the background image to a predetermined value if a corresponding pixel of the image is within the identified drop or the predetermined band near the edge of the drop. The corresponding pixel of the image has a location corresponding to the pixel of the background image.

The method may further include determining a baseline corresponding to an opening of the drip chamber.

The act of determining a subset of pixels within the plurality of pixels of interest that corresponds to a drop may include determining each of the plurality of pixels of interest is within the subset of pixels if the respective pixel of the plurality of pixels has a contiguous path back to the baseline of the drop forming at an opening of the drip chamber.

The method may optionally include one or more of: capturing a first image using the image sensor; identifying the drop within the first image and a predetermined band near an edge of the drop; initializing the background image by setting each pixel to the first image unless it is within the identified drop or the predetermined band near the edge of the drop; setting pixels within the region of the drop or within the predetermined band to a predetermined value; initializing an array of integers; and initializing an array of variances.

The method may also include one or more of updating the background image, the array of integers, and/or the array of variances using the image.

In certain embodiments of the present disclosure, a flow meter includes a coupler, a support member, an image sensor, and at least one processor. The coupler is adapted to couple to a drip chamber. The support member is operatively coupled to the coupler. The image sensor has a field of view and is operatively coupled to the support member. The image sensor is positioned to view the drip chamber within the field of view.

The at least one processor is operatively coupled to the image sensor to receive image data therefrom, and the at least one processor is configured to: capture an image of a drip chamber using the image sensor; identify a plurality of pixels of interest within the image; determine a subset of pixels within the plurality of pixels of interest, wherein each pixel of the plurality of pixels is determined to be within the subset of pixels when there is a path to a baseline corresponding to the drip chamber; perform a rotation operation on the subset of pixels; and estimate a volume of a drop within the drip chamber by counting a number of pixels within the rotated subset of pixels.

The flow meter may also include a non-transitory, processor-readable memory having an operative set of processor executable instructions stored thereon. The non-transitory, processor-readable memory is in operative communication with the at least one processor such that the operative set of processor executable instructions controls the operation of the at least one processor.

The flow meter may also include a non-transitory, processor-readable memory readable by the at least one processor such that the non-transitory, processor-readable memory includes an operative set of processor executable instructions stored thereon configured to cause the at least one processor, when executed, to: capture an image of a drip chamber using the image sensor; identify a plurality of pixels of interest within the image; determine a subset of pixels within the plurality of pixels of interest, wherein each pixel of the plurality of pixels is determined to be within the subset of pixels when there is a path to a baseline corresponding to the drip chamber; perform a rotation operation on the subset of pixels; and estimate a volume of a drop within the drip chamber by counting a number of pixels within the rotated subset of pixels.

The baseline may be a predetermined set of pixels within the image sensor. The plurality of pixels of interests may be identified by comparing the image to a background image. The at least one processor may be further configured to initialize the background image and/or to update the background image using the image captured by the image sensor.

The background image may be updated in accordance with:

$$P_{background,i,j} = P_{background,i,j}(1-\alpha_{background}) + \alpha_{background}P_{input,i,j}.$$

The at least one processor may be further configured to update an array of variances using the image captured by the image sensor.

The array of variances may be updated in accordance with:

$$\sigma_{temp}^2 = (P_{background,i,j} - P_{input,i,j})^2$$

$$\sigma_{background,i,j}^2 = \sigma_{background,i,j}^2(1-\beta_{background}) + \beta_{background}\sigma_{temp}^2.$$

The at least one processor may be further configured to update an array of integers in according with the image captured by the image sensor. Each integer of the array of integers corresponds to a number of updates of a pixel of the background image.

Optionally, in some embodiments, the comparison of the image to the background image only compares pixels within the image to pixels within the background image if a respective integer of the array of integers indicates a respective pixel within the background image has been updated at least a predetermined number of times.

The at least one processor may be further configured to: identify a drop in the image and a predetermined band near an edge of the drop; and initialize the background image by setting each pixel of the background image to the image unless it is within the identified drop or the predetermined band near the edge of the drop.

The at least one processor may be further configured to set a pixel of the background image to a predetermined value if a corresponding pixel of the image is within the identified drop or the predetermined band near the edge of the drop.

In certain embodiments of the present disclosure, the corresponding pixel of the image has a location corresponding to a location of the pixel of the background image.

The at least one processor may be further configured to determine a baseline corresponding to an opening of the drip chamber.

The at least one processor may be further configured to determine whether each of the plurality of pixels of interest is within the subset of pixels if the respective pixel of the plurality of pixels has a contiguous path back to the baseline of the drop forming at an opening of the drip chamber to determine if the subset of pixels are within the plurality of pixels of interest that corresponds to a drop.

The at least one processor may be further configured to: capture a first image using the image sensor; identify the drop within the first image and a predetermined band near an edge of the drop; initialize the background image by setting each pixel to the first image unless it is within the identified drop or the predetermined band near the edge of the drop; set pixels within the region of the drop or within the predetermined band to a predetermined value; initialize an array of integers; and initialize an array of variances.

The at least one processor may be further configured to update the background image, the array of integers, and/or the array of variances using the image.

In certain embodiments of the present disclosure, a flow meter includes an image sensor means and a flow rate estimator means. The image sensor means is for capturing a plurality of images of a drip chamber. The flow rate estimator means is for estimating the flow of fluid through the drip chamber using the plurality of images.

The flow rate estimator means may include a processor means for estimating the flow of fluid through the drip chamber using the plurality of images.

The flow meter may further include a memory means in operative communication with the processor means to provide an operative set of processor executable instruction to cause the processor means to estimate the flow of fluid through the drip chamber using the plurality of images.

In certain embodiments of the present disclosure, a flow meter includes: a memory means having an operative set of processor executable instructions configured for being executed; and a processor means for executing the operative set of processor executable instructions for implementing a flow rate estimator means for estimating the flow of fluid through the drip chamber using the plurality of images.

In certain embodiments of the present disclosure, a method includes: a step for capturing a plurality of images of a drip chamber; and a step for estimating the flow of fluid through the drip chamber using the plurality of images. The method may be implemented by an operative set of processor executable instructions stored on a non-transitory memory and executed by at least one processor.

In certain embodiments of the present disclosure, an apparatus includes: a coupler adapted to couple to a drip chamber; a support member operatively coupled to the coupler; an image sensor having a field of view and is operatively coupled to the support member, wherein the image sensor is positioned to view the drip chamber within the field of view; a valve configured to couple to a fluid tube in fluid communication with the drip chamber, wherein the valve is configured to regulate flow through the fluid tube to thereby regulate the fluid flow through the drip chamber; and at least one processor operatively coupled to the image sensor to receive image data therefrom, wherein the at least one processor is configured to: capture a plurality of images of the drip chamber using the image sensor; estimate a volume growth rate of a drop within the drip chamber using the plurality of images; receive a set point corresponding to a fluid flow rate through the fluid tube; adjust a control system in accordance with the estimated volume growth rate of the drop to achieve the set point; and output a control signal from the control system to an actuator of the valve to control actuation of the valve in accordance with the adjusted control system.

The apparatus may include a non-transitory, processor-readable memory having an operative set of processor executable instructions stored thereon. The non-transitory, processor-readable memory may be in operative communication with at least one processor such that the operative set of processor executable instructions controls the operation of the at least one processor.

The apparatus may include a non-transitory, processor-readable memory readable by the at least one processor. The non-transitory, processor-readable memory may include an operative set of processor executable instructions stored thereon configured to cause the at least one processor, when executed, to: capture the plurality of images of the drip chamber using the image sensor; estimate the volume growth rate of the drop within the drip chamber using the plurality of images; receive the set point corresponding to a fluid flow rate through the fluid tube; adjust the control system in accordance with the estimated volume growth rate of the drop to achieve the set point; and output the control signal from the control system to an actuator of the valve to control actuation of the valve in accordance with the adjusted control system.

The control system may be at least one of a proportional-integral-derivative control system, a proportional-integral control system, a proportional-derivative control system, a proportional control system, an integral control system, a neural net control system, a fuzzy logic control system, and/or a bang-bang control system.

The control system may correlate the estimated volume growth rate of the drop with the fluid flow through the fluid tube.

The valve may include: a curved, elongated support member elastically deformable and having first and second ends; and an opposing support member configured to position the fluid tube against the curved, elongated support member between the first and second ends, wherein deformation of the curved, elongated support member by movement of the first and second ends toward each other reduces an internal volume of the fluid tube. The actuator may be configured to move the first and second ends toward each other.

The valve may include: a first elongated support member defining a length; and a second elongated support member defining a length, wherein the length of the second elongated support member is disposed in spaced relation with the length of the first elongated support member to cooperate with the first elongated support member to compress the fluid tube. The actuator may be in mechanical engagement with at least one of the first and second elongated support members to actuate the first and second elongated support members toward each other to thereby compress the fluid tube disposed therebetween to regulate flow of fluid within the fluid tube; Actuation of the actuator actuates the first and second elongated support members to regulate fluid flow within the tube in accordance with an approximate sigmoid curve.

The valve may include: a first elongated support member defining a length; and a second elongated support member defining a length, wherein the length of the second elongated support member is disposed in spaced relation with the length of the first elongated support member to cooperate with the first elongated support member to compress the fluid tube. The actuator is in mechanical engagement with at least one of the first and second elongated support members to actuate the first and second elongated support members toward each other to thereby compress the fluid tube disposed therebetween to regulate flow of fluid within the tube; Actuation of the actuator actuates the first and second elongated support members to regulate fluid flow within the fluid tube in accordance with an approximate Gompertz curve.

The valve may include: a first elongated support member defining a length; and a second elongated support member defining a length, wherein the length of the second elongated support member is disposed in spaced relation with the length of the first elongated support member to cooperate with the first elongated support member to compress the fluid tube. The actuator is in mechanical engagement with at least one of the first and second elongated support members to actuate the first and second elongated support members toward each other to thereby compress the fluid tube disposed therebetween to regulate flow of fluid within the fluid tube; Actuation of the actuator actuates the first and second elongated support members to regulate fluid flow within the tube in accordance with an approximate generalized logistic function.

The valve may include: a first support member that forms at least one of an arc, a plurality of arcs, a curve, a plurality of curves, an arcuate shape, a plurality of arcuate shapes, an S-shape, a C-shape, a convex shape, a plurality of convex shapes, and a concave shape; and a second support member disposed in spaced relation with the first support member to cooperate with the first support member to compress the fluid tube along a length of the fluid tube at least substantially greater than the diameter of the fluid tube. The actuator in is mechanical engagement with at least one of the first and second support members to actuate the first and second support members toward each other to thereby compress the fluid tube disposed therebetween to regulate flow of fluid within the fluid tube; Actuation of the actuator actuates the first and second support members to regulate fluid flow within the fluid tube in accordance with an approximate nonlinear function.

The valve may include: a curved, elongated support member elastically deformable and having first and second ends; and an opposing support member configured to define a conduit with the curved, elongated support member. The conduit is defined between the curved, elongated support member and the opposing member. The fluid tube is disposed within the conduit and deformation of the curved, elongated support member by movement of the first and second ends toward each other reduces an internal volume of the fluid tube within the conduit.

The valve may be an inverse-Bourdon-tube valve coupled to the fluid tube to regulate the fluid flowing through the fluid path of the fluid tube.

The valve may include: a first flexible member; and a second flexible member operatively coupled to the first flexible member. The fluid tube may be disposed between the first and second flexible members. The first and second flexible members are configured to flex to thereby regulate flow of fluid passing through the fluid tube, and the actuator is coupled to at least a first end of the first flexible member and a second end of the first flexible member.

The valve may include a first C-shaped member defining inner and outer surfaces; and a second C-shaped member defining inner and outer surfaces. At least one of the outer surface of the first C-shaped member and the inner surface of the second C-shaped member is configured to receive the fluid tube. The inner surface of the second C-shaped member is disposed in spaced relation to the outer surface of the first C-shaped member. The actuator is coupled to the first and second C-shaped members to bend the first and second C-shaped members to compress the fluid tube.

The valve may include: a first flexible sheet; and a second flexible sheet operatively coupled to the first flexible sheet. The first and second flexible sheets are configured to receive the fluid tube therebetween. The first and second flexible sheets are configured to flex to thereby regulate flow of fluid passing through the fluid tube. The actuator is coupled to the first and second flexible sheets to regulate flow of fluid passing through the fluid tube.

The valve may include: a first curve-shaped member defining inner and outer surfaces; and a second curve-shaped member defining inner and outer surfaces. The inner surface of the second curve-shaped member is disposed in spaced relation to the outer surface of the first curve-shaped member with the fluid tube disposed between the first and second curved-shaped members, and the actuator is coupled to the first and second curve-shaped members to bend the first and second curve-shaped members to thereby regulate the flow of fluid within the fluid tube.

The valve may include: a first curve-shaped member defining inner and outer surfaces, the first curve-shaped member having first and second receiving members at opposite ends of the first curve-shaped member; and a second curve-shaped member defining inner and outer surfaces, the second curve-shaped member having first and second fasteners at opposite ends of the second curve-shaped member. The first receiving member of the first curve-shaped member is configured to engage the first fastener of the second curve-shaped member. The second receiving member of the first curve-shaped member is configured to engage the second fastener of the second curve-shaped member. The actuator is coupled to the first and second curve-shaped members to bend the first and second curve-shaped members to regulate the flow of fluid within the fluid tube disposed therebetween.

The valve may include: a first curved, elongated support member elastically deformable and having first and second ends; and a second curved, elongated support member elastically deformable and having first and second ends, wherein the second curved, elongated support member is configured to position the fluid tube against the first curved, elongated support member, wherein deformation of the first and second curved, elongated support members by movement of the first and second ends of the first curved, elongated support member toward each other reduces an internal volume of the fluid tube; a first connector coupled to the first end of the first curved, elongated support member and coupled to the first end of the second curved, elongated support member; a second connector coupled to the second end of the first curved, elongated support member and coupled to the second end of the second curved, elongated support member, wherein the second connector defines a hole; a connecting member having an end coupled to the first connector and another end configured for insertion into the hole of the second connector, wherein the connecting member defines a threaded rod at least along a portion thereof; and a knob having a ratchet configured to ratchet onto the connecting member when moved from the another end of the connecting member toward the end of the connecting member, wherein the knob is further configured to engage the threaded rod of the connecting member; The actuator may be coupled to the knob to rotate the knob.

The valve may include: a base defining a hole configured to receive the fluid tube; a plurality of fingers each having an end coupled to the base; and a ring configured to slide from the base and along the plurality of fingers. Movement of the ring from the base compresses the fingers against the fluid tube. The ring is configured to frictionally lock against the plurality of fingers. The actuator is coupled to the ring to slide the ring.

The valve may include: a conically-shaped member having a surface for wrapping the fluid tube therearound; and a complementing member configured to engage the conically-shaped member for compressing the tube. The actuator is configured to compress the conically-shaped member against the complementing member to thereby compress the fluid tube.

The control system may be implemented in hardware, software, a combination of hardware and software, and/or by at least one operational amplifier.

The apparatus may include a non-transitory, processor-readable memory, wherein: the control system is implemented by an operative set of processor executable instructions configured for execution by the at least one processor, the operative set of processor executable instructions is stored on the non-transitory, processor-readable memory, and the non-transitory, processor-readable memory is in operative communication with the at least one processor to operatively communicate the operative set of processor executable instructions to the at least one processor for execution by the at least one processor.

The set point may be compared to the volume growth rate of the drop to adjust the control system. The set point may be compared to the volume growth rate of the drop to determine an error signal. The error signal may be the difference between the set point and the volume growth rate of the drop. The error signal may be passed through a signal processing apparatus to generate the output signal. The signal processing apparatus may implement a proportional-integral-derivative controller with at least one non-zero gain parameter.

In another embodiment of the present disclosure, an apparatus for regulating fluid flow includes a curved, elongated support member and an opposing support member. The curved, elongated support member is elastically deformable and has first and second ends. The first end is configured to pivotally couple to first and second dog bone linkers, and the second end is configured to pivotally couple to third and fourth dog bone linkers. The opposing support member is configured to position a tube against the curved, elongated support member between the first and second ends such that deformation of the curved, elongated support member by movement of the first and second ends toward each other reduces an internal cross-section along a length of the tube. The first end of the opposing support member is configured to pivotally couple to the first and second dog bone linkers, and a second end of the opposing support member is configured to pivotally couple to the third and fourth dog bone linkers.

The first end of the curved, elongated support member may include an engagement finger configured to engage a rack. The second end of the curved elongated may be configured to pivotally couple to the rack. The apparatus may include a knob coupled to the first end of the curved, elongated support member to move the rack.

In yet another embodiment of the present disclosure, a flow meter includes a coupler, a support member, an image sensor, a laser, and at least one processor. The coupler is adapted to couple to a drip chamber. The support member is operatively coupled to the coupler. The image sensor has a field of view and is operatively coupled to the support member, and the first image sensor is configured to view the drip chamber within the field of view. The laser is configured to shine the optical light onto the binary optics assembly.

The at least one processor is operatively coupled to the image sensor such that: (1) the at least one processor receives data from the image sensor having at least a portion of the back pattern represented therein; and (2) the at least one processor estimates at least one parameter of liquid within the drip chamber using the image data.

In yet another embodiment of the present disclosure, a flow meter includes a coupler, a support member, first and second electrodes, and at least one processor. The coupler is adapted to couple to a drip chamber. The support member is operatively coupled to the coupler. The first electrode is configured to couple to a fluid line in fluid communication with the drip chamber. The second electrode is configured to couple to the fluid line in fluid communication with the drip chamber.

The at least one processor is operatively coupled to the first and second electrodes to measure a capacitance therebetween, and the at least one processor is configured to monitor the capacitance. The at least one processor may be configured to determine if a streaming condition exists within the drip chamber using the monitored capacitance.

In yet another embodiment of the present disclosure, a safety valve includes a housing, first and second occluding arms, first and second axles, and a spring. The housing is configured to hold a tube. The first and second occluding arms are pivotally coupled together. The first axle is pivotally coupled to a distal end of the first occluding arm. The second axle is pivotally coupled to a distal end of the second occluding arm. The spring is disposed adjacent to the first and second occluding arms on an opposite side to the tube configured to spring load the first and second occluding arm. The safety valve is configured to discharge the spring and occlude the tube when the first and second occluding arms pivot away from the spring along their common pivot by a predetermined amount. A solenoid may be used to engage the first and second occluding arms to discharge the spring.

In yet another embodiment of the present disclosure, an apparatus includes a coupler, a support member, and at least one processor. The coupler is adapted to couple to a drip chamber. The support member is operatively coupled to the coupler. The image sensor has a field of view and is operatively coupled to the support member. The image sensor is configured to view the drip chamber within the field of view. The at least one processor is operatively coupled to the image sensor to receive image data therefrom, and the at least one processor is configured to: (1) capture an image of the drip chamber; (2) position a template within the captured image to a first position; (3) average the pixels within the template to determine a first average; (4) move the template to a second position; (5) average the pixels within the template to determine a second average; (6) determine that the template is located at an edge of a drop if a difference between the second average and the first average is greater than a predetermined threshold value; (7) and correlate the second position with a volume of the drop.

In yet another embodiment of the present disclosure, a method implemented by at least one processor executing an operative set of processor executable instructions configured for being executed by the at least one processor for estimating a flow rate is disclosed. The method includes: (1) capturing an image of the drip chamber; (2) positioning a template within the captured image to a first position; (3) averaging the pixels within the template to determine a first average; (4) moving the template to a second position; (5) averaging the pixels within the template to determine a second average; (6) determining that the template is located at an edge of a drop if a difference between the second average and the first average is greater than a predetermined threshold value; and (7) correlating the second position with a volume of the drop.

In yet another embodiment of the present disclosure, a flow meter includes a coupler, a support member, a modulatable backlight assembly, an image sensor, and at least one processor. The coupler is adapted to couple to a drip chamber. The support member is operatively coupled to the coupler. The modulatable backlight assembly is configured to provide a first backlight and a second backlight. The image sensor has a field of view and is operatively coupled to the support member. The image sensor is configured to view the drip chamber within the field of view and the modulatable backlight assembly. The at least one processor is operatively coupled to the image sensor and the modulatable backlight assembly such that the at least one processor receives data from the image sensor having at least a portion of the modulatable backlight assembly represented therein, and the at least one processor is configured to modulate the backlight assembly to the first backlight when estimating a drop size and to modulate the backlight assembly to the second backlight. The first backlight may be a diffuser backlight having no pattern and the second backlight may be a diffuser backlight having a striped pattern.

In yet another embodiment of the present disclosure, a tube restorer includes first and second gears. The second gear is disposed abutted against the first gear. The first and second gears define a space along radial portions of the first and second gears to allow a tube to flex therebetween. The first and second gears are further configured to restore the tube when rotated such that the space is not positioned between the first and second gears.

In yet another embodiment of the present disclosure, a valve includes first and second metallic strips, and first and second guiding members. The first guiding member is coupled to distal ends of the first and second metallic strips. The second guiding member is coupled to proximal ends of the first and second metallic strips. The first and second metallic strips are configured to compress a tube when the distal ends of the first and second metallic strips are actuated towards the proximal ends of the first and second metallic strips. The valve may further include a string (e.g., a metal string or a string made of any other material) threaded through the first and second metallic strips to spiral around the tube.

In yet another embodiment of the present disclosure, a valve includes first and second clamshells configured to provide a cavity between the first and second clamshells. The first and second clamshells are configure to receive a tube therebetween and within the cavity. The valve also includes a bladder disposed within the cavity and a pump configured to inflate or deflate the bladder to regulate flow of fluid within the tube.

In yet another embodiment of the present disclosure, an apparatus includes a coupler, a support member, an image sensor, and at least one processor. The coupler is adapted to couple to a drip chamber. The support member is operatively coupled to the coupler. The image sensor has a field of view and is operatively coupled to the support member. The image sensor is configured to view the drip chamber within the field of view.

The at least one processor is operatively coupled to the image sensor to receive image data therefrom and is configured to: (1) capture a first image; (2) create a first thresholded image from the first image by comparing each pixel of the first image to a threshold value; (3) determine a set of pixels within the first thresholded image connected to a predetermined set of pixels within the first thresholded image; (4) filter all remaining pixels of the first thresholded image that are not within the set of pixels, the filter operates on a pixel-by-pixel basis within the time domain to generate a first filtered image; (5) remove pixels determined to not be part of a drop from the first thresholded image using the first filtered image to generate a second image; (6) determine a second set of pixels within the second image connected to a predetermined set of pixels within the second image to generate a third image, the third image identifies the second set of pixels within the second image; (7) determine a first length of the drop by counting the number of rows containing pixels corresponding to the second set of pixels within the third image, the first length corresponding to a first estimated drop size; (8) update a background image using the first image; (9) create a second thresholded image by comparing the first image with the background image; (10) sum the rows of the second thresholded image to create a plurality of row sums, each row sum corresponds to a row of the second thresholded image; (11) start at a row position of the second thresholded image having a first sum of the plurality of sums that corresponds to the first length; (12) increment the row position until the row position corresponds to a corresponding row sum that is zero; (13) determine a second length is equal to the present row position, the second length corresponding to a second estimated drop size; and (14) average the first and second lengths to determine an average length, the average length corresponding to a third estimated drop size.

In yet another embodiment of the present disclosure, a method implemented by at least one processor executing an operative set of processor executable instructions configured for being executed by the at least one processor for estimating a flow rate includes: (1) capturing a first image; (2) creating a first thresholded image from the first image by comparing each pixel of the first image to a threshold value; (3) determining a set of pixels within the first thresholded image connected to a predetermined set of pixels within the first thresholded image; (4) filtering all remaining pixels of the first thresholded image that are not within the set of pixels, the filter operates on a pixel-by-pixel basis within the time domain to generate a first filtered image; (5) removing pixels determined to not be part of a drop from the first thresholded image using the first filtered image to generate a second image; (6) determining a second set of pixels within the second image connected to a predetermined set of pixels within the second image to generate a third image, the third image identifies the second set of pixels within the second image; (7) determining a first length of the drop by counting the number of rows containing pixels corresponding to the second set of pixels within the third image, the first length corresponding to a first estimated drop size; (8) updating a background image using the first image; (9) creating a second thresholded image by comparing the first image with the background image; (10) summing the rows of the second thresholded image to create a plurality of row sums, each row sum corresponds to a row of the second thresholded image; (11) starting at a row position of the second thresholded image having a first sum of the plurality of sums that corresponds to the first length; (12) incrementing the row position until the row position corresponds to a corresponding row sum that is zero; (13) determining a second length is equal to the present row position, the second length corresponding to a second estimated drop size; and (14) averaging the first and second lengths to determine a average length, the average length corresponding to a third estimated drop size.

In yet another embodiment of the present disclosure, a flow meter includes a coupler, a support member, first and second loop antennas, and at least one processor. The coupler is adapted to couple to a drip chamber. The support member is operatively coupled to the coupler. The first loop antenna is disposed adjacent to a fluid line in fluid communication with the drip chamber. The second loop antenna is disposed adjacent to the fluid line. The at least one processor is operatively coupled to the first and second loop antennas to measure a magnetic coupling therebetween. The at least one processor is configured to monitor the magnetic coupling therebetween to determine if a streaming condition exists within the drip chamber.

In yet another embodiment of the present disclosure, a method implemented by an operative set of processor executable instructions includes: (1) determining a plurality of points of interest in an image; (2) randomly selecting N-points of interest of the plurality of points of interest; and/or (3) identifying a single, unique, geometric feature characterized by N-parameters corresponding to N-points of interest.

In yet another embodiment of the present disclosure, a system includes a non-transitory memory and one or more processors. The non-transitory memory has stored thereon a plurality of instructions. The one or more processors are in operative communication with the non-transitory memory to execute the plurality of instructions. The plurality of instructions is configured to cause the processor to: (1) determine a plurality of points of interest in an image; (2) randomly select N-points of interest of the plurality of points of interest; and/or (3) identify a single, unique, geometric feature characterized by N-parameters corresponding to N-points of interest.

BRIEF DESCRIPTION OF THE DRAWINGS

These and other aspects will become more apparent from the following detailed description of the various embodiments of the present disclosure with reference to the drawings wherein:

FIG. 32 shows pseudo code for identifying a plurality of pixels of interest in accordance with the method of FIGS. 27-28 in accordance with an embodiment of the present disclosure;

FIG. 37 shows pseudo code for determining a subset of pixels within the plurality of pixels of interest that corresponds to a drop in accordance with an embodiment of the present disclosure;

FIG. 42 shows a table illustrating the corresponding fields of view about the optical axis for the corners of two configurations of an imaging system disclosed herein in accordance with an embodiment of the present disclosure;

FIGS. 57D-57E show two exploded views of the valve of FIGS. 57A-57C in accordance with an embodiment of the present disclosure;

FIGS. 66A-66G show several views of a valve having a knob to move a connecting member which is locked into position after movement of the knob in accordance with an embodiment of the present disclosure;

FIG. 68B shows the circuit for use with FIG. 68A in accordance with an embodiment of the present disclosure;

FIGS. 69A-69F show several views of a safety valve that may be used with a flow meter in accordance with an embodiment of the present disclosure;

DETAILED DESCRIPTION

Figure 1:
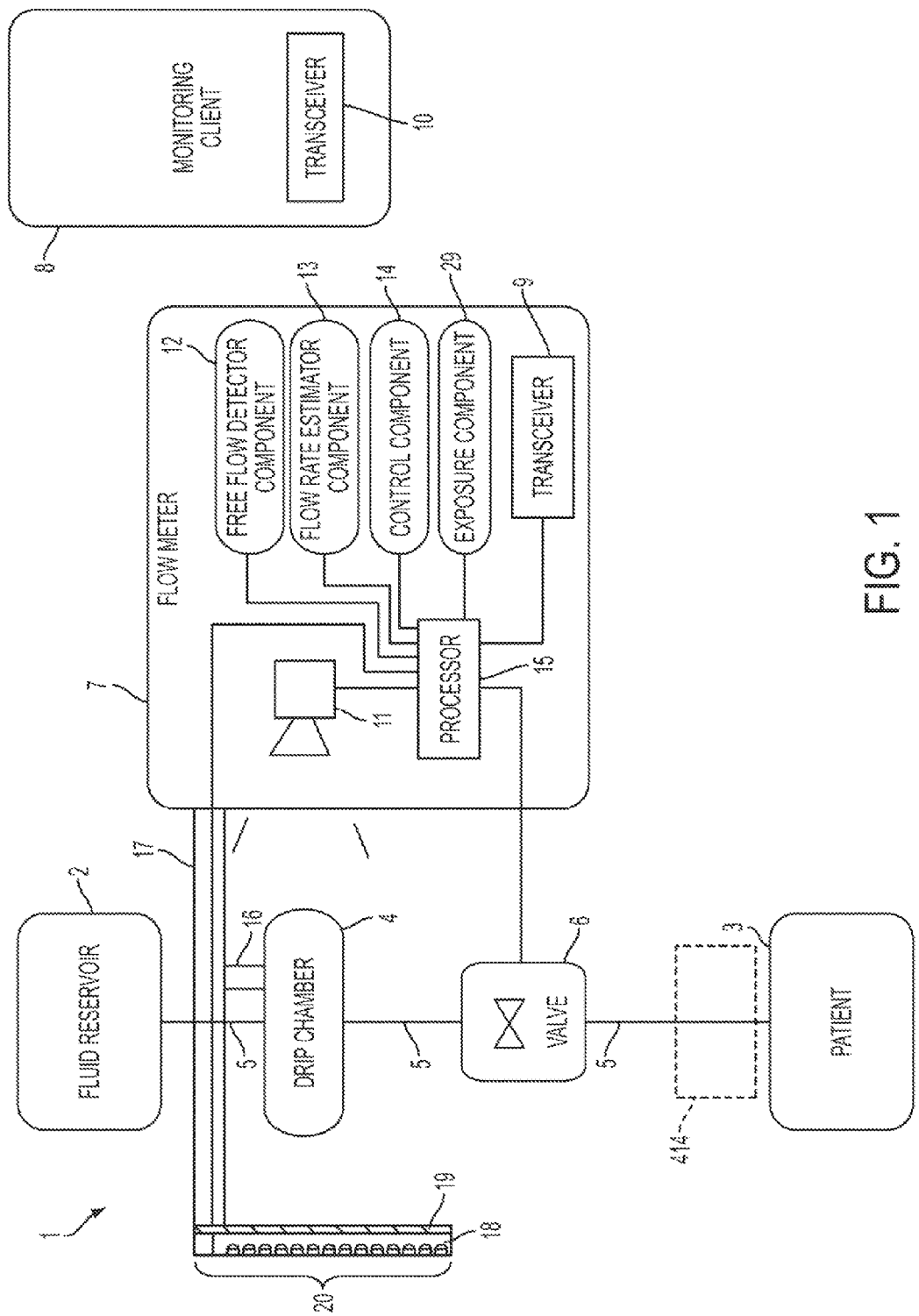
FIG. 1 shows a block diagram of a system for regulating fluid flow in accordance with an embodiment of the present disclosure.

FIG. 1 shows a block diagram of a system 1 for regulating fluid flow in accordance with an embodiment of the present disclosure. For example, system 1 may regulate, monitor, and/or control the flow of fluid into a patient 3. The system 1 includes a fluid reservoir 2 for infusing fluid contained therein into the patient 3. The fluid reservoir 2 is gravity fed into a drip chamber 4 via a fluid tube 5. The fluid reservoir 2, the drip chamber 4, and the patient 3 may be considered as part of the system 1 or may be considered as separate or optional work pieces for the system 1 (e.g., any fluid reservoir 2 and drip chamber 4 may be used to treat any patient 3).

A flow meter 7 monitors the drip chamber 4 to estimate a flow rate of liquid flowing through the drip chamber 4. The fluid from the drip chamber 4 is gravity fed into a valve 6. The valve 6 regulates (i.e., varies) the flow of fluid from the fluid reservoir 2 to the patient 3 by regulating fluid flow from the drip chamber 4 to the patient 3. The valve 6 may be any valve as described herein, including a valve having two curved-shaped members, a valve having two flexible sheets, a valve that pinches (or uniformly compresses) on the tube over a significant length of the tube, or the like. The valve 6 may be an inverse-Bourdon-tube valve that works in an opposite way of a Bourdon tube in that a deformation of the fluid path causes changes in fluid flow rather than fluid flow causing deformation of the fluid path.

In alternative embodiments, the system 1 optionally includes an infusion pump 414 (e.g., a peristaltic pump, a finger pump, a linear peristaltic pump, a rotary peristaltic pump, a cassette-based pump, a membrane pump, other pump, etc.) coupled to the fluid tube 5. The outlined box designated as 414 represents the optional nature of the infusion pump 414, e.g., the infusion pump may not be used in some embodiments. The infusion pump 414 may use the flow meter 7 as feedback to control the flow of fluid through the fluid tube 5. The infusion pump 414 may be in wireless communication with the flow meter 7 to receive the flow rate therefrom. The infusion pump 414 may use a feedback control algorithm (e.g., the control component 14 of FIG. 1) to adjust the flow of fluid, such as a proportional-integral-derivative ("PID"), bang-bang, neural network, and/or fuzzy logic control system. In this specific exemplary embodiment (i.e., an embodiment having the infusion pump 414), the valve 6 is optional. However, in other embodiments, the valve 6 may or may not be used, and/or is optional. The infusion pump 414 may adjust the rotation of a cam and/or a motor in accordance with measurements from the flow meter 7, such as flow rate, volume infused, total volume infused, etc. Additionally or alternatively, the infusion pump 414 may stop fluid flow (e.g., by stopping the pumping action) when the flow meter 7 communicates to the infusion pump 414 that a free flow condition exists. In yet additional embodiments, the monitoring client 8 controls the operation of the infusion pump 414 (e.g., via a wireless connection) and receives feedback from the flow meter 7.

In some embodiments, the fluid reservoir 2 is pressurized to facilitate the flow of fluid from the fluid reservoir 2 into the patient 3, e.g., in the case where the fluid reservoir 2 (e.g., an IV bag) is below the patient 3; The pressurization provides sufficient mechanical energy to cause the fluid to flow into the patient 3. A variety of pressure sources, such as physical pressure, mechanical pressure, and pneumatic pressure may be applied to the inside or outside of the fluid reservoir 2. In one such embodiment, the pressurization may be provided by a rubber band wrapped around an IV bag.

The flow meter 7 and the valve 6 may form a closed-loop system to regulate fluid flow to the patient 3. For example, the flow meter 7 may receive a target flow rate from a monitoring client 8 by communication using transceivers 9, 10. That is, the transceivers 9, 10 may be used for communication between the flow meter 7 and the monitoring client 8. The transceivers 9, 10 may communicate between each other using a modulated signal to encode various types of information such as digital data or an analog signal. Some modulation techniques used may include using carrier frequency with FM modulation, using AM modulation, using digital modulation, using analog modulation, or the like.

The flow meter 7 estimates the flow rate through the drip chamber 4 and adjusts the valve 6 to achieve the target flow rate received from the monitoring client 8. The valve 6 may be controlled by the flow meter 7 directly from communication lines coupled to an actuator of the valve 6 or via a wireless link from the flow meter 7 to onboard circuitry of the valve 6. The onboard electronics of the valve 6 may be used to control actuation of the valve 6 via an actuator coupled thereto. This closed-loop embodiment of the flow meter 7 and the valve 6 may utilize any control algorithm including a PID control algorithm, a neural network control algorithm, a fuzzy-logic control algorithm, the like, or some combination thereof.

The flow meter 7 is coupled to a support member 17 that is coupled to the drip chamber 4 via a coupler 16. The support member 17 also supports a backlight 18. The backlight 18 includes an array of LEDs 20 that provides illumination to the flow meter 7. In some specific embodiments, the backlight 18 includes a background pattern 19. In other embodiments, the backlight 18 does not include the background pattern 19. In some embodiments, the background pattern 19 is present in only the lower portion of the backlight 18 and there is no background pattern 19 on the top (e.g., away from the ground) of the backlight 18.

The flow meter 7 includes an image sensor 11, a free flow detector component 12, a flow rate estimator component 13, a control component 14, an exposure component 29, a processor 15, and a transceiver 9. The flow meter 7 may be battery operated, may be powered by an AC outlet, may include supercapacitors, and may include on-board, power-supply circuitry (not explicitly shown).

The image sensor 11 may be a CCD sensor, a CMOS sensor, or other image sensor. The image sensor 11 captures images of the drip chamber 4 and communicates image data corresponding to the captured images to the processor 15.

The processor 15 is also coupled to the free flow detector component 12, the flow rate estimator component 13, the control component 14, and the exposure component 29. The free flow detector component 12, the flow rate estimator component 13, the control component 14, and the exposure component 29 may be implemented as processor-executable instructions that are executable by the processor 15 and may be stored in memory, such as a non-transitory, processor-readable memory, ROM, RAM, EEPROM, a harddisk, a harddrive, a flashdrive, and the like.

The processor 15 can execute the instructions of the free flow detector component 12 to determine if a free flow condition exists within the drip chamber 4 by analyzing the image data from the image sensor 11. Various embodiments of the free flow detector component 12 for detecting a free flow condition are described below. In response to a detected free flow condition, the processor 15 can make a function call to the control component 14 to send a signal to the valve 6 to completely stop fluid flow to the patient 3. That is, if the free flow detector component 12 determines that a free flow condition exists, the flow meter 7 may instruct the valve 6 to stop fluid flow, may instruct the monitoring client 8 to stop fluid flow (which may communicate with the valve 6 or the pump 414), and/or may instruct the pump 414 to stop pumping or occlude fluid flow using an internal safety occluder.

The flow rate estimator component 13 estimates the flow rate of fluid flowing through the drip chamber 4 using the image data from the image sensor 11. The processor 15 communicates the estimated flow rate to the control component 14 (e.g., via a function call). Various embodiments of estimating the flow rate are described below. If the flow rate estimator component 13 determines that the flow rate is greater than a predetermined threshold or is outside a predetermined range, the flow meter 7 may instruct the valve 6 to stop fluid flow (which may communicate with the valve 6 or the pump 414), may instruct the monitoring client 8 to stop fluid flow (which may communicate with the valve 6 or the pump 414), and/or may instruct the pump 414 to stop pumping or occlude fluid flow using an internal safety occluder.

The processor 15 controls the array of LEDs 20 to provide sufficient light for the image sensor 11. For example, the exposure component 29 may be used by the processor 15 or in conjunction therewith to control the array of LEDs 20 such that the image sensor 11 captures image data sufficient for use by the free flow detector component 12 and the flow rate estimator component 13. The processor 15 may implement an exposure algorithm stored by the exposure component 29 (see FIG. 2) to control the lighting conditions and/or the exposure of the image sensor 11 when generating the image data. Additionally or alternatively, the exposure component 29 may be implemented as a circuit, an integrated circuit, a CPLD, a PAL, a PLD, a hardware-description-language-based implementation, and/or a software system.

The control component 14 calculates adjustments to make to the valve 6 in accordance with the estimated flow rate from the flow rate estimator component 13. For example and as previously mentioned, the control component 14 may implement a PID control algorithm to adjust the valve 6 to achieve the target flow rate.

The monitoring client 8, in some embodiments, monitors operation of the system 1. For example, when a free flow condition is detected by the free flow detector component 12, the monitoring client 8 may wirelessly communicate a signal to the valve 6 to interrupt fluid flow to the patient 3.

The flow meter 7 may additionally include various input/output devices to facilitate patient safety, such as various scanners, and may utilize the transceiver 9 to communicate with electronic medical records, drug error reduction systems, and/or facility services, such as inventory control systems.

In a specific exemplary embodiment, the flow meter 7 has a scanner, such as an RFID interrogator that interrogates an RFID tag attached to the fluid reservoir 2 or a barcode scanner that scans a barcode of the fluid reservoir 2. The scanner may be used to determine whether the correct fluid is within the fluid reservoir 2, it is the correct fluid reservoir 2, the treatment programmed into the flow meter 7 corresponds to the fluid within the fluid reservoir 2 and/or the fluid reservoir 2 and flow meter 7 are correct for the particular patient (e.g., as determined from a patient's barcode, a patient's RFID tag, or other patient identification).

For example, the flow meter 7 may scan the RFID tag of the fluid reservoir 2 to determine if a serial number or fluid type encoded within the RFID tag is the same as indicated by the programmed treatment stored within the flow meter 7. Additionally or alternatively, the flow meter 7 may interrogate the RFID tag of the fluid reservoir 2 for a serial number and the RFID tag of the patient 3 for a patient serial number, and also interrogate the electronic medical records using the transceiver 9 to determine if the serial number of the fluid reservoir 2 within the RFID tag attached to the fluid reservoir 2 matches the patient's serial number within the RFID tag attached to the patient 3 as indicated by the electronic medical records.

Additionally or alternatively, the monitoring client 8 may scan the RFID tag of the fluid reservoir 2 and the RFID tag of the patient 3 to determine that it is the correct fluid within the fluid reservoir 2, it is the correct fluid reservoir 2, the treatment programmed into the flow meter 7 corresponds to the fluid within the fluid reservoir 2, and/or the fluid reservoir 2 is correct for the particular patient (e.g., as determined from a patient's barcode, RFID tag, electronic medical records, or other patient identification or information). Additionally or alternatively, the monitoring client 8 or the flow meter 7 may interrogate the electronic medical records database and/or the pharmacy to verify the prescription or to download the prescription, e.g., using the serial number of the barcode on the fluid reservoir 2 or the RFID tag attached to the fluid reservoir 2.

Figure 2:
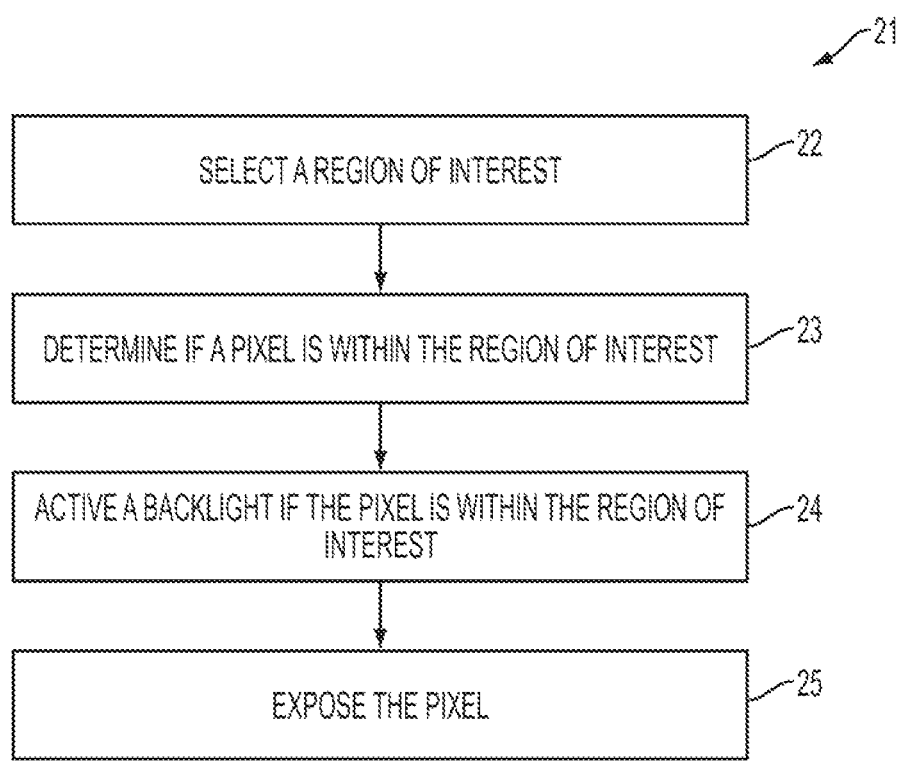
FIG. 2 shows a flowchart diagram of a method for exposing an image sensor in accordance with an embodiment of the present disclosure.

FIG. 2 shows a flow chart diagram of a method 21 for exposing an image sensor, e.g., the image sensor 11 of FIG. 1, in accordance with an embodiment of the present disclosure. The method 21 includes acts 22, 23, 24, and 25. Method 21 may be implemented by the processor 15 of FIG. 1 (e.g., as the exposure component 29) and may be implemented as a processor-implemented method, as a set of instructions configured for execution by one or more processors, in hardware, in software, the like, or some combination thereof.

Act 22 selects a region of interest. For example, referring again to FIG. 1, the image sensor 11 includes a field of view that includes the drip chamber 4. However, the drip chamber 4 may not occupy the entire field of view of the image sensor 11. Act 22 selects only the pixels of the image sensor 11 that show, for example, the drip chamber 4.

Act 23 determines if a pixel is within the region of interest 23. If the pixel of act 23 is a pixel that images, for example, the drip chamber 4, then act 23 determines that it is within the region of interest. Likewise, in this example, if the pixel of act 23 is a pixel that does not image the drip chamber 4, act 23 determines that the pixel is not within the region of interest.

Act 24 activates a backlight, e.g., the backlight 18 of FIG. 1, if the pixel is within the region of interest. Pixels of an image sensor may be exposed during different times. Thus, the backlight 18 may be activated only when pixels within the region of interest are being exposed. For example, some image sensors include vertical and horizontal sync signals. The backlight may be synchronized with these signals to turn on when a pixel of interest is being exposed.

In some embodiments of the present disclosure, a subset of LEDs of the backlight (e.g., a subset of the LED array 20, which may be a 2-dimensional array) may be turned on. The subset may be a sufficient subset to sufficiently illuminate the pixel being exposed if the pixel is within the region of interest.

Act 25 exposes the pixel. If in act 23 it was determined that the pixel is within the region of interest, the pixel will be exposed with at least a portion of the backlight turned on in act 25. Additionally, if in act 23 it was determined that the pixel is not within the region of interest, the pixel will be exposed without at least a portion of the backlight turned on in act 25.

Figure 3:
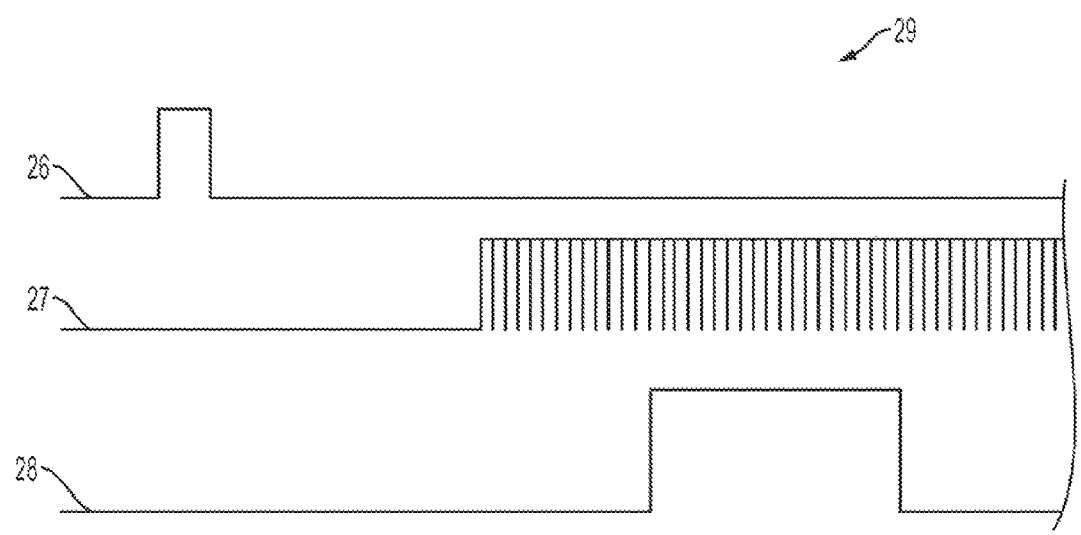
FIG. 3 shows a timing diagram illustrating an embodiment of the method of FIG. 2 in accordance with an embodiment of the present disclosure.

FIG. 3 shows a timing diagram 29 illustrating an embodiment of the method of FIG. 2 in accordance with an embodiment of the present disclosure. The timing diagram 29 includes traces 26, 27, and 28. Trace 26 is a vertical sync signal from an image sensor and trace 27 is a horizontal sync signal from the image sensor (e.g., image sensor 11 of FIG. 1). A circuit or software routine (e.g., the exposure component 29 found in the flow meter 7 of FIG. 1) may use the sync traces 26, 27 to generate a backlight-enable signal 28 that is used to activate a backlight or a subset thereof.

Figure 4A:
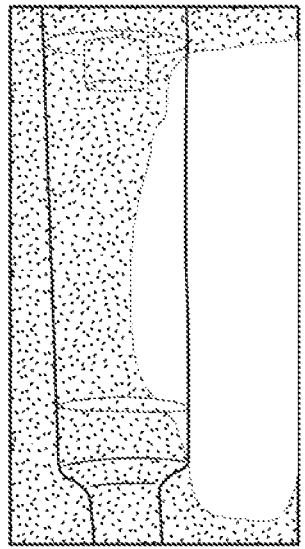
FIGS. 4A-4B show illustrations of image data (i.e., images) captured by a flow meter of a drip chamber to illustrate an embodiment of the method for exposing an image sensor of FIG. 2 in accordance with the timing diagram of FIG. 3 in accordance with an embodiment of the present disclosure.
Figure 4B:
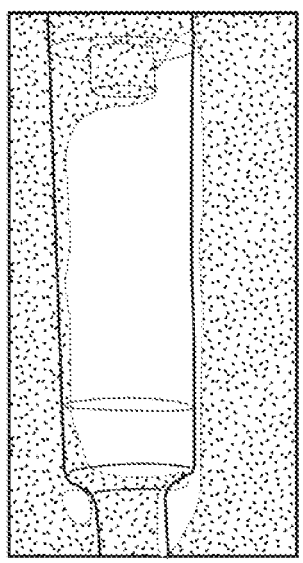

FIGS. 4A-4B show illustrations of image data of a flow meter 7 illustrating an embodiment of the method of FIG. 2 in accordance with the timing diagram of FIG. 3 in accordance with an embodiment of the present disclosure. FIG. 4A illustrates the image data taken by a flow meter, such as the flow meter 7 of FIG. 1, without the use of the exposure algorithm illustrated in FIGS. 2 and 3; FIG. 4B illustrates the image data taken by the flow meter with the use of the exposure algorithm illustrated in FIGS. 2 and 3. Less power is needed to provide illumination during the capture of the image of FIG. 4B than to provide illumination for the capture of the image of FIG. 4A because of less use of the backlight.

Figure 5:
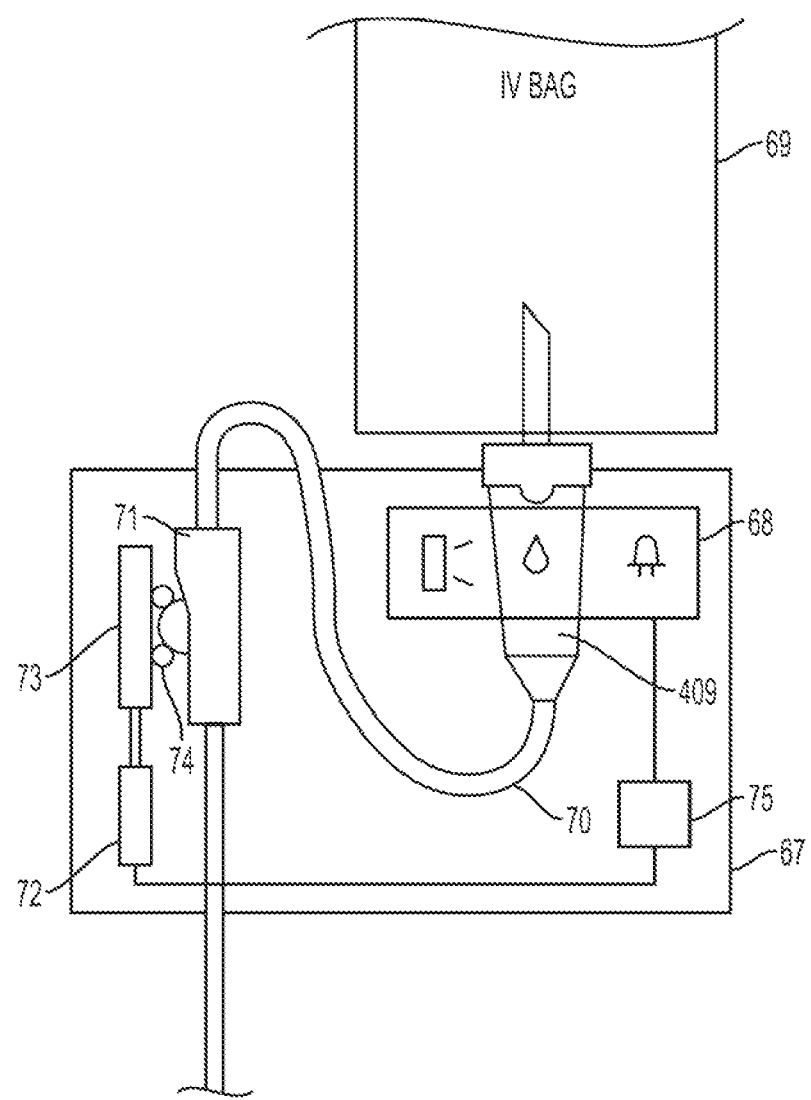
FIG. 5 shows a diagram of a flow meter and valve that are integrated together for coupling to a drip chamber and an IV bag in accordance with an embodiment of the present disclosure.

FIG. 5 shows a diagram of a flow meter 67 and a valve 71 that are integrated together for coupling to a drip chamber 409 and an IV bag 69 in accordance with an embodiment of the present disclosure. The flow meter 67 includes an optical drip counter 68 that receives fluid from the IV bag 69. The optical drip counter 68 may be an image sensor, a pair of image sensors, a capacitive drip counter, and/or the like. The flow meter 67 is coupled to a tube 70 coupled to a roller clamp 71 that is controlled by a motor 72. The motor 72 is coupled to a lead screw mechanism 73 to control a roller clamp 71 via interaction with interacting members 74.

The motor 72 may be a servo motor and may be used to adjust the flow rate through the tube 70. That is, the flow meter 67 may also function as a flow meter and regulator. For example, a processor 75 within the flow meter 67 may adjust the motor 72 such that a desired flow rate is achieved as measured by the optical drip counter 68. The processor 75 may implement a control algorithm using the optical drip counter 68 as feedback, e.g., a PID control loop with the output supplied to the motor 72 and the feedback received from the optical drip counter 68.

In alternative embodiments, the motor 72, the lead screw mechanism 73, and the roller clamp 71 may be replaced and/or supplemented by an actuator that squeezes the tube 70 (e.g., using a cam mechanism or linkage driven by a motor) or they may be replaced by any sufficient roller, screw, or slider driven by a motor. For example, in some embodiments of the present disclosure, the roller clamp 71 may be replaced by any valve as described herein, including a valve having two C-shaped members, a valve having two curve-shaped support members, a valve having two flexible sheets, a valve that pinches on the tube over a significant length of the tube, or the like.

The flow meter 67 may also optionally include a display. The display may be used to set the target flow rate, display the current flow rate, and/or provide a button, e.g., a touch screen button to stop the flow rate.

Figure 6:
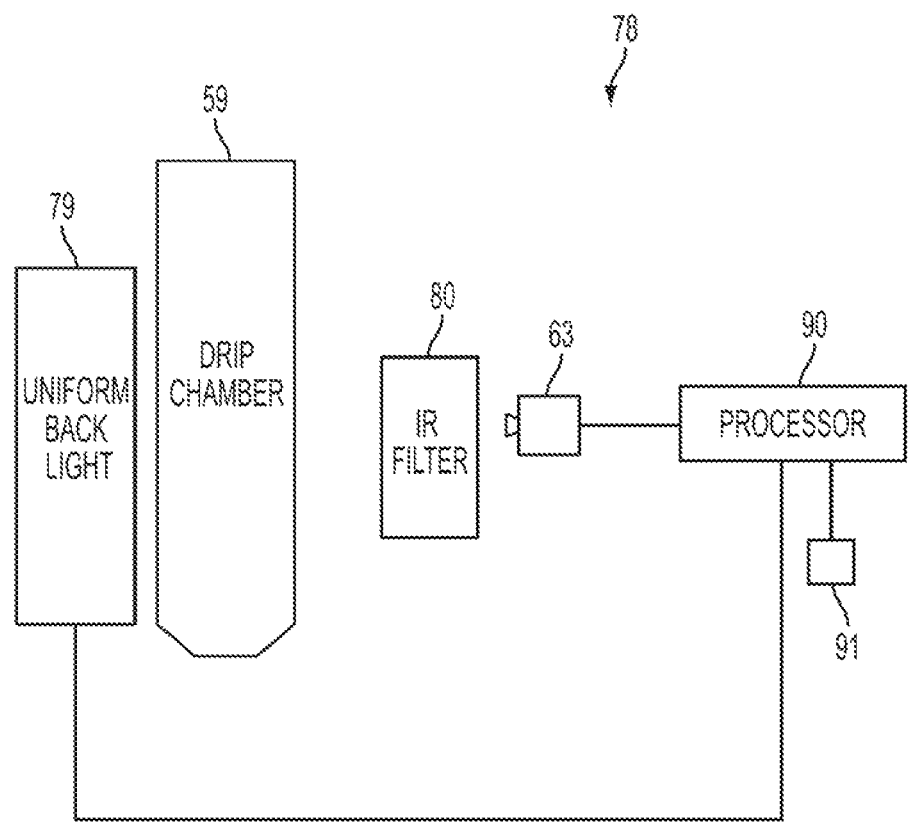
FIG. 6 is a block diagram of an imaging system of a flow meter for imaging a drip chamber in accordance with an embodiment of the present disclosure.

FIG. 6 is a block diagram of an imaging system 78 of a flow meter for imaging a drip chamber in accordance with an embodiment of the present disclosure. The imaging system 78 as shown in FIG. 6 may be used within any flow meter described herein, including the flow meter 7 of FIG. 1 and/or the flow meter 67 of FIG. 5.

The imaging system 78 of FIG. 6 includes an image sensor 63, a uniform backlight 79 to shine light at least partially through the drip chamber 59, and an infrared ("IR") filter 80 that receives the light from the uniform backlight 79.

System 78 also includes a processor 90 that may be operatively coupled to the image sensor 63 and/or the uniform backlight 79. The processor 90 implements an algorithm to determine when a free flow condition exists and/or to estimate a flow rate (e.g., using the free flow detector component 12 or the flow rate estimator component 13 of FIG. 1). The processor 90 may be in operative communication with a processor-readable memory 91 (e.g., a non-transitory, processor-readable memory) to receive one or more instructions to implement the algorithm to determine if a free flow condition exists and/or to estimate the flow rate. The one or more instructions from the processor-readable memory 91 are configured for execution by the processor 90.

The uniform backlight 79 may be an array of light-emitting diodes ("LEDs") having the same or different colors, a light bulb, a window to receive ambient light, an incandescent light, and the like. In some embodiments, the uniform backlight 79 may include one or more point-source lights.

The processor 90 may modulate the uniform backlight 79 in accordance with the image sensor 63. For example, the processor 90 may activate the uniform backlight 79 for a predetermined amount of time and signal the image sensor 63 to capture at least one image, and thereafter signal the uniform backlight 79 to turn off. The one or more images from the image sensor 63 may be processed by the processor 90 to estimate the flow rate and/or detect free flow conditions. For example, in one embodiment of the present disclosure, the system 78 monitors the size of the drops being formed within the drip chamber 59, and counts the number of drops that flow through the drip chamber 59 within a predetermined amount of time; the processor 90 may average the periodic flow from the individual drops over a period of time to estimate the flow rate. For example, if X drops each having a volume Y flow through the drip chamber in a time Z, the flow rate may be calculated as $(X*Y)/Z$.

Additionally or alternatively, the system 78 may determine when the IV fluid is streaming through the drip chamber 59 (i.e., during a free flow condition). The uniform backlight 79 shines light through the drip chamber 59 to provide sufficient illumination for the image sensor 63 to image the drip chamber 59. The image sensor 63 can capture one or more images of the drip chamber 59.

Other orientations and configurations of the system 78 may be used to account for the orientation and output characteristics of the uniform backlight 79, the sensitivity and orientation of the image sensor 63, and the ambient light conditions. In some embodiments of the present disclosure, the processor 90 implements an algorithm that utilizes a uniformity of the images collected by the image sensor 63. The uniformity may be facilitated by the uniform backlight 79. For example, consistent uniform images may be captured by the image sensor 63 when a uniform backlight 79 is utilized.

Ambient lighting may cause inconsistencies in the images received from the image sensor 63; for example, direct solar illumination provides inconsistent lighting because the sun may be intermittently obscured by clouds and the sun's brightness and angle of illumination depend upon the time of the day. Therefore, in some embodiments of the present disclosure, an IR filter 80 is optionally used to filter out some of the ambient light to mitigate variations in the images captured by the image sensor 63. The IR filter 80 may be a narrow-band infrared light filter placed in front of the image sensor 63; and the uniform backlight 79 may emit light that is about the same wavelength as the center frequency of the passband of the filter 80. The IR filter 80 and the uniform backlight 79 may have a center frequency of about 850 nanometers. In some embodiments, the imaging system 78 may be surrounded by a visually translucent, but IR-blocking, shell. In alternative embodiments, other optical frequencies, bandwidths, center frequencies, or filter types may be utilized in the system 78.

Figure 7:
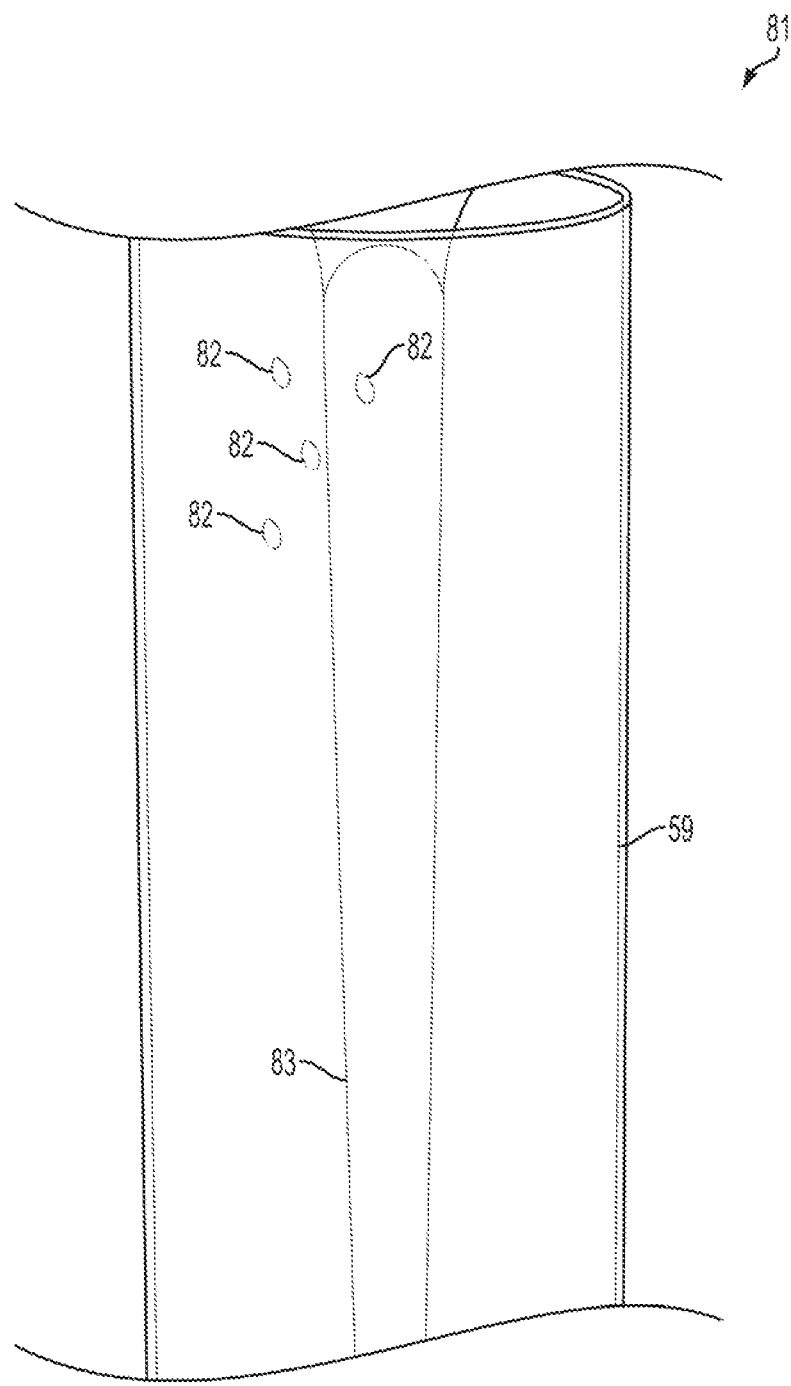
FIG. 7 is a graphic illustration of an image captured by the image sensor of the system of FIG. 6 in accordance with an embodiment of the present disclosure.

FIG. 7 is a graphic illustration of an image 81 captured by the image sensor 63 of the system 78 of FIG. 6 in accordance with an embodiment of the present disclosure. The image 81 is an image of a drip chamber 59 having condensation 82 and a stream 83 caused by a free flow condition therein. Edge detection may be used to determine the position of the stream 83 and/or the condensation 82, in some embodiments. Additionally or alternatively, a background image or pattern may be used.

Figure 8:
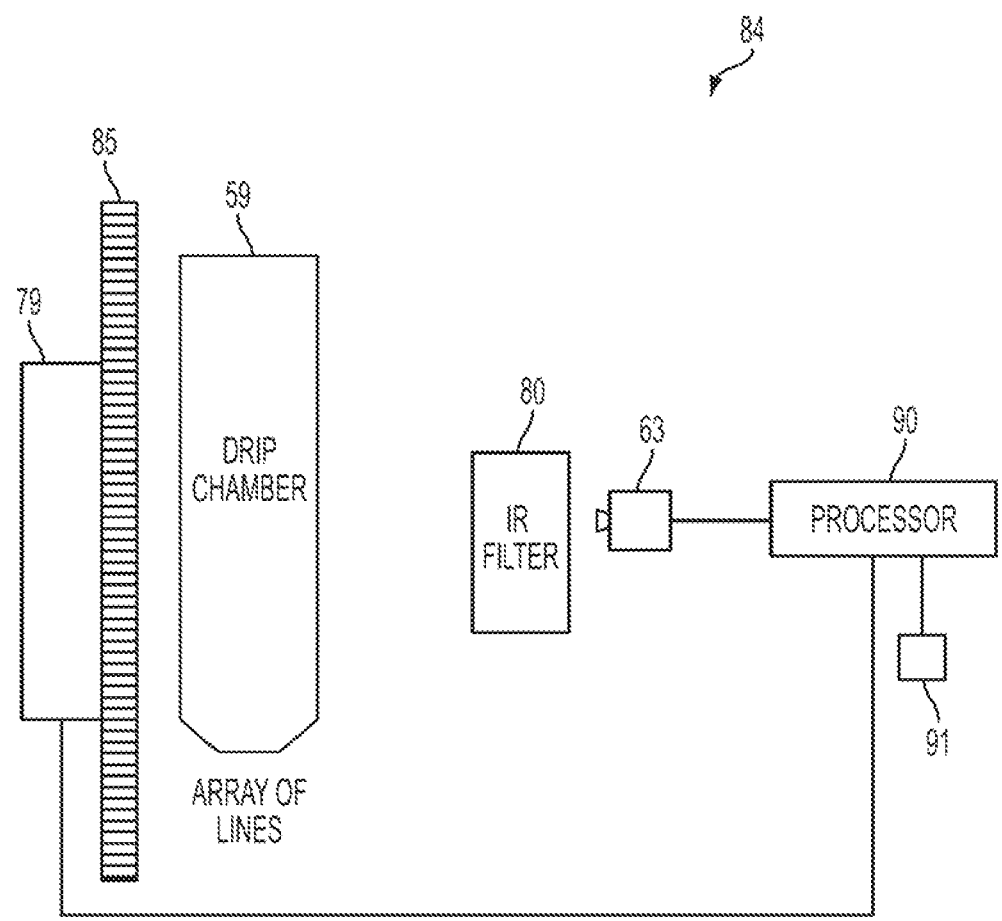
FIG. 8 is a block diagram of an imaging system of a flow meter for imaging a drip chamber utilizing a background pattern in accordance with an embodiment of the present disclosure.

FIG. 8 is a block diagram of an imaging system 84 of a flow meter for imaging a drip chamber in accordance with an embodiment of the present disclosure. The imaging system 84 may be used with any flow meter disclosed herein, including the flow meter 7 of FIG. 1 and the flow meter 67 of FIG. 5.

System 84 includes an array of lines 85 that are opaque behind the drip chamber 59. System 84 uses the array of lines 85 to detect a free flow condition. The free flow detection algorithm (e.g., the free flow detector component 12 of FIG. 1) may use the presence or absence of drops for determining whether or not a streaming condition (e.g., a free flow condition) exists.

In some specific embodiments, the lines 85 are only present on a fraction of the image (e.g., the background pattern only occupies a fraction of the backlight 18 or the binary optics only causes the pattern to appear in a fraction of the image, such as the lower or upper half). For example, a lower fraction of the image may include a background pattern of stripes.

Figure 9:
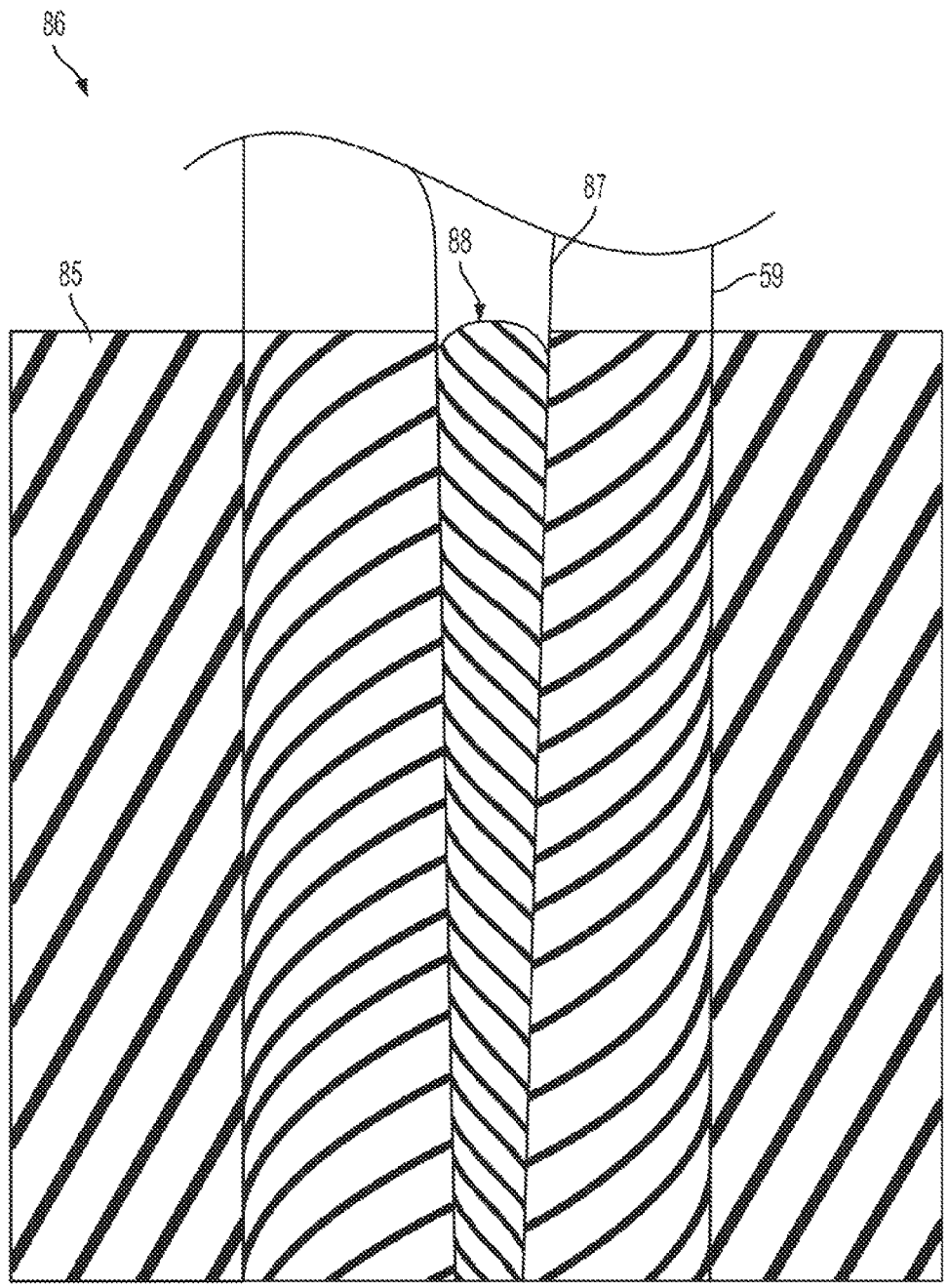
FIG. 9 is a graphic illustration of an image captured by an image sensor of a flow meter disclosed herein when a free flow condition exists in accordance with an embodiment of the present disclosure.

Referring now to FIG. 9, a graphic illustration of an image 86 is shown as captured by the image sensor 63 of FIG. 8 when a free flow condition exists in the drip chamber 59 in accordance with an embodiment of the present disclosure. The image 86 illustrates the condition in which the drip chamber 59 experiences a free flow condition and illustrates the effect that the stream of fluid 87 acts as a positive cylindrical lens. That is, as shown in FIG. 9, the array of lines 85 as captured in an image by the image sensor 63 are shown as a reversed line pattern 88 from the array of lines 85 as compared to a non-free flow condition. The appearance of the reversed line pattern 88 is caused by changes to the light when the light passes through the stream of fluid 87 as the light approaches the image sensor 63.

In some embodiments of the present disclosure, illumination by light having an optical wavelength of about 850 nanometers may be used to create the image 86. Some materials may be opaque in the visible spectrum and transparent in the near IR spectrum at about 850 nanometers and therefore may be used to create the array of lines 85. The array of lines 85 may be created using various rapid-prototyping plastics. For example, the array of lines 85 may be created using a rapid-prototype structure printed with an infrared-opaque ink or coated with a metal for making the array of lines 85. Additionally or alternatively, in some embodiments of the present disclosure, another method of creating the array of lines 85 is to create a circuit board with the lines laid down in copper. In another embodiment, the array of lines 85 is created by laying a piece of ribbon cable on the uniform backlight 79; the wires in the ribbon cable are opaque to the infrared spectrum, but the insulation is transparent such that the spacing of the wires may form the line for use during imaging by the image sensor 63 (see FIG. 8). In yet additional embodiments, a piece of thin EDMed metal may be utilized. Metal is opaque to light and the spaces between the metal material deposits may be very finely controlled during manufacture to allow the IR light to pass through the spaces.

The processor 90 implements an algorithm to determine when a free flow condition exists (e.g., using the free flow detector component 12 of FIG. 1). The processor 90 may be in operative communication with a processor-readable memory 91 (e.g., a non-transitory, processor-readable memory) to receive one or more instructions to implement the algorithm to determine if a free flow condition exists. The one or more instructions from the processor-readable memory 91 are configured for execution by the processor 90.

Referring again to FIG. 8, blood may be used by the system 84. For example, system 84 may determine when a free flow condition of blood exists when utilizing the image sensor 63, the IR filter 80, and the uniform backlight 79 configured, for example, for use using optical light having a wavelength of 850 nanometers or 780 nanometers, e.g., when using bovine blood. The blood may appear opaque compared to the images taken using water.

The following algorithm implemented by the processor 90 and received from the processor-readable memory 91 may be used to determine when a free flow condition exists: (1) establish a background image 89 (see FIG. 10); and (2) subtract the background image 89 from the current image. Additionally processing may be performed on the resulting image.

Figure 10:
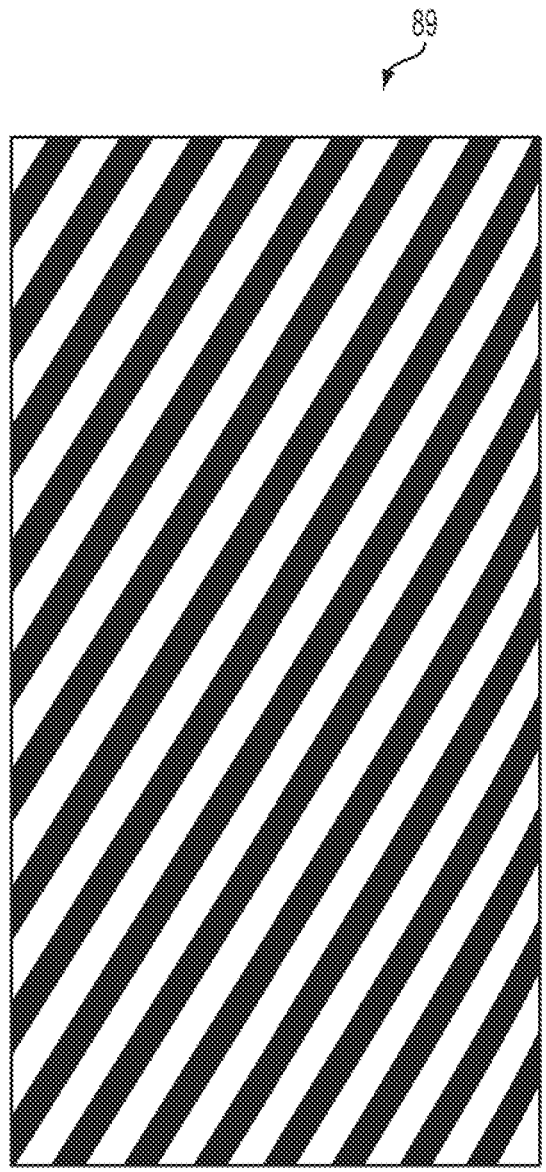
FIG. 10 is a graphic illustration of an image captured by an image sensor of a flow meter for use as a background image in accordance with an embodiment of the present disclosure.

In some embodiments of the present disclosure, the background image 89 of FIG. 10 may be dynamically generated by the processor 90. The dynamic background image may be used to account for changing conditions, e.g. condensation or splashes 82 on the surface of the drip chamber 59 (see FIG. 7). For example, in one specific embodiment, for each new image captured by the image sensor (e.g., 63 of FIG. 8), the background image has each pixel multiplied by 0.96 and the current image (e.g., the most recently captured image) has a respective pixel multiplied by 0.04, after which the two values are added together to create a new value for a new background image for that respective pixel; this process may be repeated for all of the pixels. In yet another example, in one specific embodiment, if a pixel of the new image is at a row, x, and at a column, y, the new background image at row, x, and column, y, is the value of the previous background image at row, x, and column, y, multiplied by 0.96, which is added to the value of the pixel at row, x, and column, y of the new image multiplied by 0.04.

When the system 84 has no water flowing through the drip chamber 59 (see FIG. 8) the resulting subtraction should be almost completely back, i.e., low pixel magnitudes, thereby facilitating the algorithm to determine that the drip chamber 59 has no water flowing therethrough.

Figure 13:
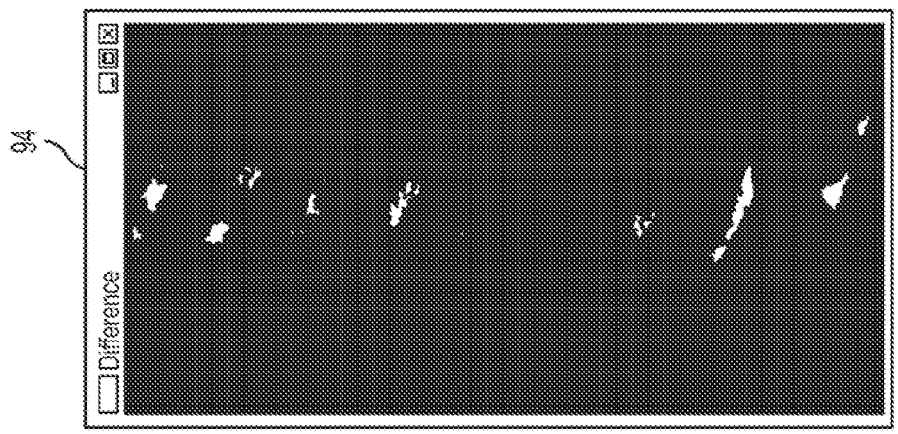
FIG. 13 is a graphic illustration of a difference between the images of FIGS. 11 and 12 with additional processing in accordance with an embodiment of the present disclosure.
Figure 12:
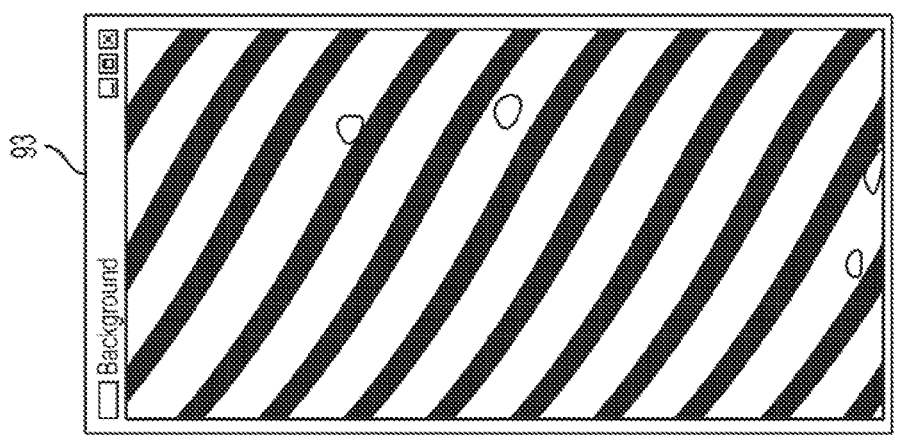
FIG. 12 is a graphic illustration of an image captured by an image sensor for use as a background image in accordance with an embodiment of the present disclosure.
Figure 11:
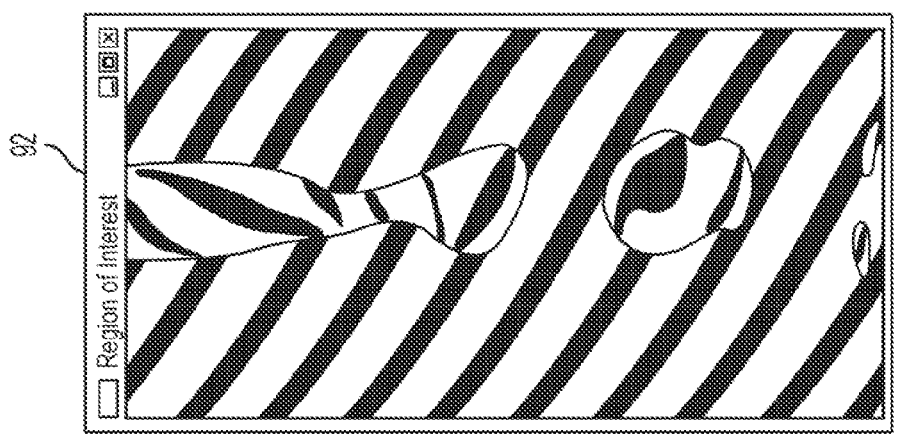
FIG. 11 is a graphic illustration of an image captured by an image sensor when drops are being formed within a drip chamber in accordance with an embodiment of the present disclosure.

FIG. 11 shows an image 92 from the image sensor 63 when there is a drop within the drip chamber 59 (see FIG. 8). FIG. 12 shows a background image 93 used by the system 84. When the system 84 has a drop as shown in image 92 of FIG. 11, the system 84 of FIG. 8 has a few high contrast-spots where the image of the array of lines is warped by the lensing of the droplet as illustrated by an image 94 of FIG. 13. Image 94 of FIG. 13 is generated by taking, for each respective pixel, the absolute value of the subtraction of the image 92 of FIG. 11 from image 93 of FIG. 12, and converting each respective pixel to a white pixel if the value is above a predetermined threshold or otherwise converting the pixel to a black pixel when the value is below the predetermined threshold. Each white pixel within the image 94 of FIG. 13 is a result of there being a difference for that pixel location between the images 92 and 93 that is greater than a predetermined threshold.

For example, consider three respective pixels of FIGS. 11, 12, and 13 having a location of row x and column y. To determine the pixel of row x and column y for the image 94 of FIG. 13, the pixel at row x and column y of image 92 of FIG. 11 is subtracted from the pixel at row x and column y of image 93 of FIG. 12, then the absolute value of the result of the subtraction is taken; and if the absolute value of the result is above a predetermined threshold (e.g., above a grayscale value of 128, for example), the pixel at the location of row x and column y of image 94 of FIG. 13 is white, otherwise the pixel at the location of row x and column y of image 94 of FIG. 13 is black.

When it is determined that a few high-contrast spots exist within the image 94 of FIG. 13, the processor 90 of system 84 (see FIG. 8) determines that drops are being formed within the drip chamber 59 and no free flow condition exists. The images of the drops may be utilized to determine the size of the drops to estimate a flow rate as described herein.

Figure 14:
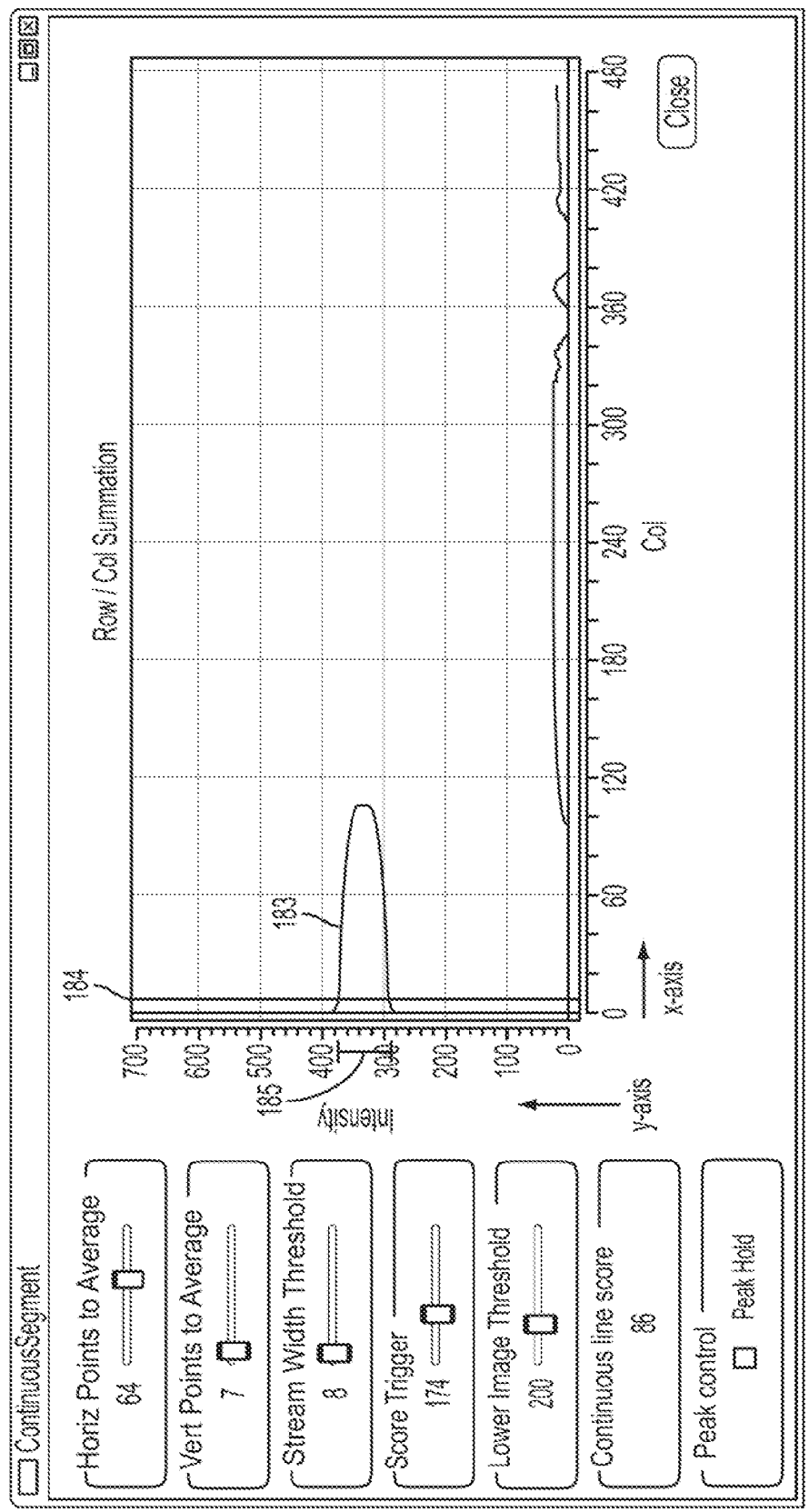
FIG. 14 is a graphic representation of some of the image processing performed using FIGS. 11-13 to determine if a free flow condition exists in accordance with an embodiment of the present disclosure.

FIG. 14 is a graphic representation of some of the image processing that may be performed using FIGS. 11-13 to determine if a free flow condition exists in accordance with an embodiment of the present disclosure. Referring to FIGS. 14 and 13, all of the white pixels for each row are summed together, and are illustrated in FIG. 14 as results 183. The y-axis represents the row number, and the x-axis represents the summed number of white pixels for each respective row.

Referring now to only FIG. 14, as previously mentioned, the number of white pixels for each row is summed together and is illustrated as results 183, which are used to determine if or when a free flow condition exists. In some specific embodiments, the processor 90 of system 84 (see FIG. 8) determines that a free flow condition exists when a predetermined number of contiguous values of the summed rows of the results 183 exists above a threshold 184. For example, within the results 183, a range of a plurality of contiguous rows represented generally by 185 has a total value above the threshold 184. When greater than a predetermined number of contiguous summed rows is determined to exist within the results 183 above a predetermined threshold (e.g., threshold 184), a free flow condition is determined to exist by the processor 90 of FIG. 8. For example, as shown in FIG. 14, the range of the plurality of contiguous summed rows 185 is below the predetermined number of contiguous summed rows (i.e., the range 185 is not wide enough) and therefore a free flow condition is determined to not exist.

Figure 17:
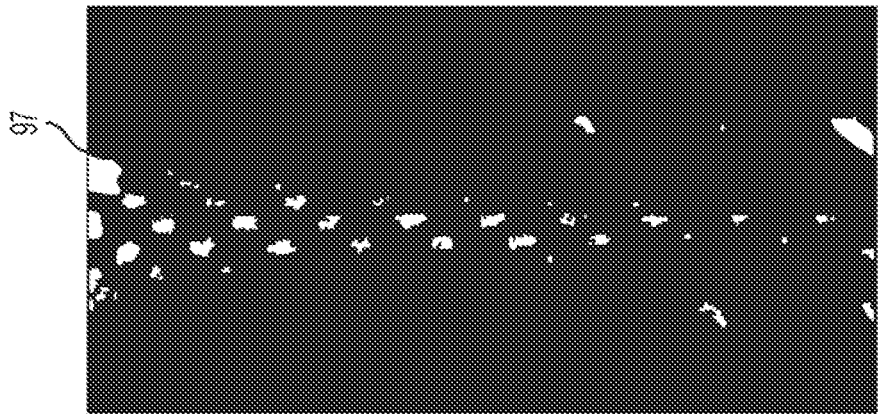
FIG. 17 is a graphic illustration of a difference between the images of FIGS. 15 and 16 with some additional processing for use in detecting a free flow condition in accordance with an embodiment of the present disclosure.
Figure 16:
FIG. 16 is a graphic illustration of an image captured by the image sensor for use as a background image in accordance with an embodiment of the present disclosure.
Figure 15:
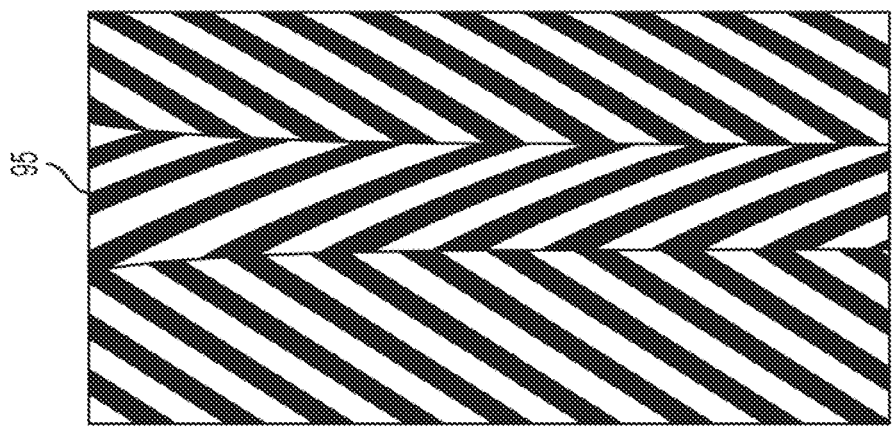
FIG. 15 is a graphic illustration of an image captured by the image sensor when a free flow condition exists in accordance with an embodiment of the present disclosure.

FIG. 15 shows an image 95 showing a stream as captured by the image sensor 63 of FIG. 8 when a free flow condition exists. FIG. 16 shows a background image 96. FIG. 17 shows an image 97 formed by the absolute value of the difference between the image 96 of FIG. 16 and the image 95 from FIG. 15 when the absolute value is converted either to a white pixel (when the absolute value of the difference is above a threshold) or to a black pixel (when the absolute value of the difference is below the threshold). As shown in FIG. 17, high-contrast spots caused by the reverse orientation of the lines in the stream that run from top to bottom are detectable by the processor 90. The processor 90 of FIG. 8 can use the image 97 to determine if a free flow condition exists using the algorithm described above.

Figure 18:
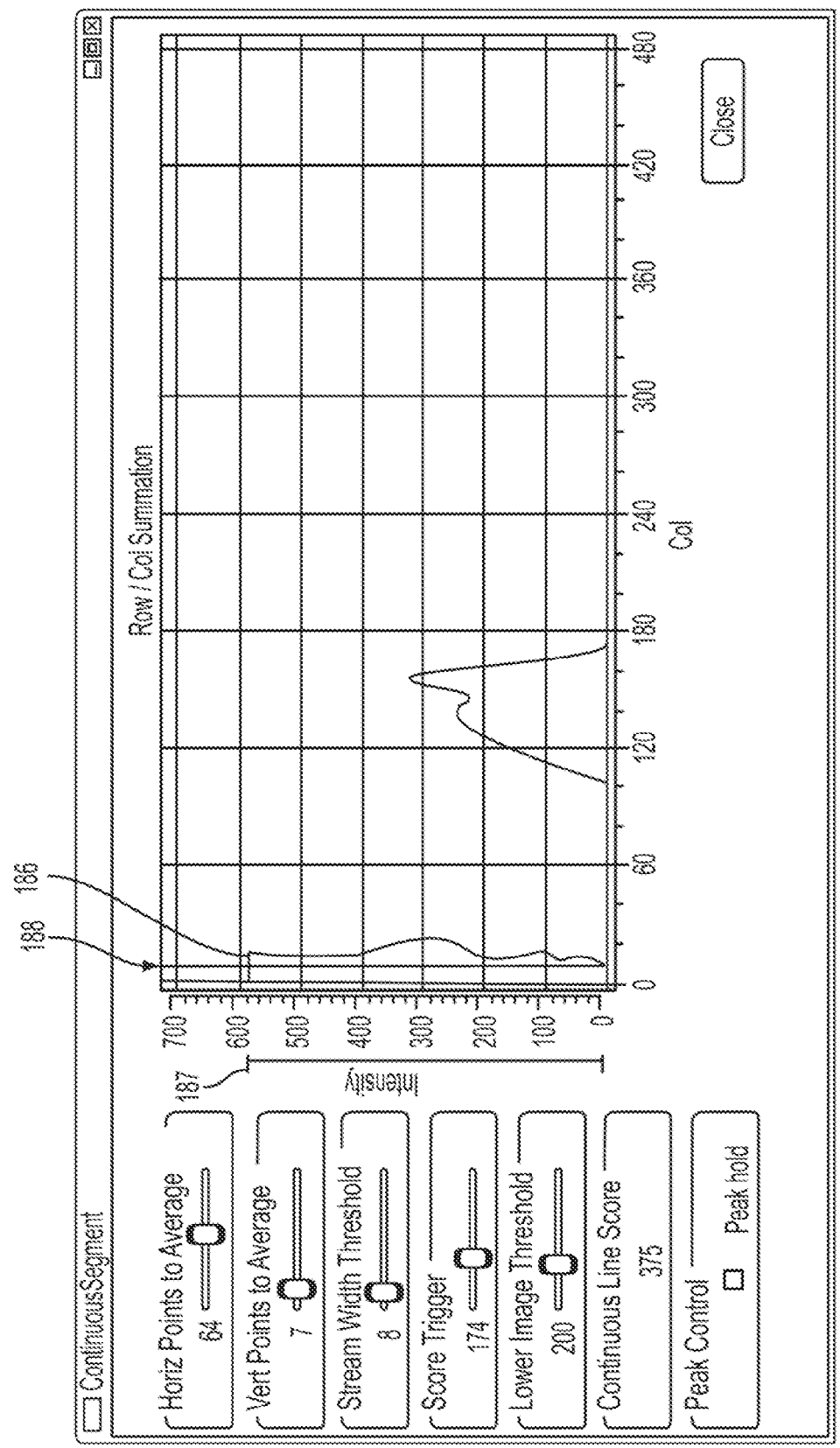
FIG. 18 is a graphic representation of some of the image processing performed using FIGS. 15-17 to determine if a free flow condition exists in accordance with an embodiment of the present disclosure.

That is, as shown in FIG. 18, results 186 are shown as having a contiguous range 187 of the results 186 that are above a threshold 188. Because the contiguous range 187 of summed rows is greater than a predetermined threshold number of contiguous values above the threshold 188, a free flow condition is determined to exist by the processor 90 (see FIG. 8). That is, the contiguous range of the results 186 above the threshold 188 is greater than a predetermined threshold range of contiguous values; therefore, the processor 90 determines that a free flow condition exists when using the results 186 of FIG. 18.

In yet an additional embodiment of the present disclosure, the intensity, the intensity squared, or other function may be used to produce the results 183 of FIG. 14 and/or the results 186 of FIG. 18. In yet an additional embodiment, one or more data smoothing functions may be used to smooth the results 183 and/or 186, such as a spline function, a cubic spline function, a B-spline function, a Bezier spline function, a polynomial interpolation, a moving average, or other data smoothing function.

For example, an image of the image sensor 63 of FIG. 8, e.g., image 95 of FIG. 15, may be subtracted from a background image, e.g., the image 96 of FIG. 16, to obtain intensity values. That is, a pixel of row x and column y of FIG. 15 may be subtracted from a pixel of row x and column y of the image 96 of FIG. 16 to create an intensity value at row x and column y; this may be repeated for all pixel locations to obtain all of the intensity values. The intensity values of each row may be summed together to obtain the results 183 and/or 186 (see FIGS. 14 and 18, respectively), such that the processor 90 may determine that a free flow condition exists when the summed rows of the intensity values has a contiguous range of summed rows above a threshold. In some embodiments, the intensity values are converted to absolute values of the intensity values, and the summed rows of the absolute values of the intensity values are used to determine if a contiguous range of summed rows of the absolute values is above a threshold range of contiguous values. Additionally or alternatively, the intensity may be squared and then the processor 90 may sum the squared intensity rows and determine if a contiguous range of summed rows of the intensity squared values exists beyond a threshold range of contiguous values to determine if a free flow condition exists.

In some embodiments, a predetermined range of contiguous values above a threshold (e.g., min and max ranges) of the summed rows of intensity values or intensity squared values may be used by the processor 90 to determine if a drop of liquid is within the image. For example, each row of the rows of the intensity values (or the intensity squared values) may be summed together and a range of the summed values may be above a threshold number; if the range of contiguous values is between a minimum range and a maximum range, the processor 90 may determine that the range of contiguous values above a predetermined threshold is from a drop within the field of view of the image sensor 63 (see FIG. 8). In some embodiments of the present disclosure, the summed rows of intensity values or intensity squared values may be normalized, e.g., normalized to have a value between 0 and 1.

The following describes a smoothing function similar to the cubic spline (i.e., the cubic-spline-type function) that may be used on the summed rows, the summed rows of intensity values, or the summed rows of the intensity values squared prior to the determination by the processor 90 to determine if a free flow condition exits. In some specific embodiments, the cubic-spline-type function may be used to identify blocks, as described infra, which may facilitate the processor's 90 identification of free flow conditions.

The cubic-spline-type function is an analog to the cubic spline, but it smoothes a data set rather than faithfully mimics a given function. Having data sampled on the interval from [0, 1] (e.g., the summation along a row of intensity squared or intensity that is normalized) the processor 90 (see FIG. 6 or 8) may find the best fit set of cubic functions on the intervals $[x_0, x_1], [x_1, x_2], \ldots, [x_{N-1}, x_N]$ with $x_0=0$ and $x_N=1$ where the total function is continuous with continuous derivatives and continuous curvature.

The standard cubic spline definition is illustrated in Equation (1) as follows:

$$\chi(x) = A_i(x)y_i + B_i(x)y_{i+1} + C_i(x)y''_i + D_i(x)y''_{i+1}, x_i \leq x \leq x_{i+1} \quad (1),$$

with the functions $A_i$, $B_i$, $C_i$, $D_i$ defined as in the set of Equations (2):

$$A_i(x) = \frac{x_{i+1}-x}{x_{i+1}-x_i} = \frac{x_{i+1}-x}{\Delta_i}, B_i = \frac{x-x_i}{x_{i+1}-x_i} = \frac{x-x_i}{\Delta_i} \quad (2)$$

$$C_i(x) = \frac{\Delta_i^2}{6}(A_i^3(x) - A_i(x)), D_i = \frac{\Delta_i^2}{6}(B_i^3(x) - B_i(x)).$$

The Equations (1) and (2) guaranty continuity and curvature continuity. The only values which can be freely chosen are $y_i$, $y''_0$ and $y''_N$. Please note that Equation (3) is chosen as follows:

$$y''_0 = y''_1 = 0 \quad (3),$$

i.e., the function is flat at 0 and 1. The remaining $y''_i$ must satisfy the following set of Equations (4):

$$\frac{y_1 - y_0}{\Delta_0} + \frac{y''_1 \Delta_0}{3} = \frac{y_2 - y_1}{\Delta_1} - \frac{y''_1 \Delta_1}{3} - \frac{y''_2 \Delta_1}{6} \quad (4)$$

$$\frac{y_2 - y_1}{\Delta_1} + \frac{y''_1 \Delta_1}{6} + \frac{y''_2 \Delta_1}{3} = \frac{y_3 - y_2}{\Delta_2} - \frac{y''_2 \Delta_2}{3} - \frac{y''_3 \Delta_2}{6}$$

$$\frac{y_3 - y_2}{\Delta_2} + \frac{y''_2 \Delta_2}{6} + \frac{y''_3 \Delta_2}{3} = \frac{y_4 - y_3}{\Delta_3} - \frac{y''_3 \Delta_3}{3} - \frac{y''_4 \Delta_3}{6}$$

$$\vdots$$

$$\frac{y_{N-2} - y_{N-3}}{\Delta_{N-3}} + \frac{y''_{N-3} \Delta_{N-3}}{6} + \frac{y''_{N-2} \Delta_{N-3}}{3} =$$

$$\frac{y_{N-1} - y_{N-2}}{\Delta_{N-2}} - \frac{y''_{N-2} \Delta_{N-2}}{3} - \frac{y''_{N-1} \Delta_{N-2}}{6}$$

$$\frac{y_{N-1} - y_{N-2}}{\Delta_{N-2}} + \frac{y''_{N-2} \Delta_{N-2}}{6} + \frac{y''_{N-1} \Delta_{N-2}}{3} = \frac{y_N - y_{N-1}}{\Delta_{N-1}} - \frac{y''_{N-1} \Delta_{N-1}}{3}.$$

The set of Equations (4) can be rewritten as the set of Equations (5) as follows:

$$\frac{\Delta_0 + \Delta_1}{3} y''_1 + \frac{\Delta_1}{6} y''_2 = \frac{y_0}{\Delta_0} - \left[\frac{1}{\Delta_0} + \frac{1}{\Delta_1}\right] y_1 + \frac{y_2}{\Delta_1} \quad (5)$$

$$\frac{\Delta_1}{6} y''_1 + \frac{\Delta_1 + \Delta_2}{3} y''_2 + \frac{\Delta_2}{6} y''_3 = \frac{y_1}{\Delta_1} - \left[\frac{1}{\Delta_1} + \frac{1}{\Delta_2}\right] y_2 + \frac{y_3}{\Delta_2}$$

$$\frac{\Delta_2}{6} y''_2 + \frac{\Delta_2 + \Delta_3}{3} y''_3 + \frac{\Delta_3}{6} y''_4 = \frac{y_2}{\Delta_2} - \left[\frac{1}{\Delta_2} + \frac{1}{\Delta_3}\right] y_3 + \frac{y_4}{\Delta_3}$$

$$\vdots$$

$$\frac{\Delta_{N-4}}{6} y''_{N-3} + \frac{\Delta_{N-3} + \Delta_{N-2}}{3} y''_{N-2} + \frac{\Delta_{N-2}}{6} y''_{N-1} =$$

$$\frac{y_{N-3}}{\Delta_{N-3}} - \left[\frac{1}{\Delta_{N-3}} + \frac{1}{\Delta_{N-2}}\right] y_{N-2} + \frac{y_{N-1}}{\Delta_{N-2}}$$

$$\frac{\Delta_{N-1}}{6} y''_{N-2} + \frac{\Delta_{N-2} + \Delta_{N-1}}{3} y''_{N-1} =$$

$$\frac{y_{N-2}}{\Delta_{N-2}} - \left[\frac{1}{\Delta_{N-2}} + \frac{1}{\Delta_{N-1}}\right] y_{N-1} + \frac{y_N}{\Delta_{N-1}}$$

In turn, this becomes the matrix Equation (6):

$$\begin{bmatrix} \frac{\Delta_0 + \Delta_1}{3} & \frac{\Delta_1}{6} & 0 & 0 & 0 & 0 \\ \frac{\Delta_1}{6} & \frac{\Delta_1 + \Delta_2}{3} & \frac{\Delta_2}{6} & \cdots & 0 & 0 & 0 \\ 0 & \frac{\Delta_2}{6} & \frac{\Delta_2 + \Delta_3}{3} & & 0 & 0 & 0 \\ & \vdots & & \ddots & & \vdots & \\ 0 & 0 & 0 & & \frac{\Delta_{N-4} + \Delta_{N-3}}{3} & \frac{\Delta_{N-3}}{6} & 0 \\ 0 & 0 & 0 & \cdots & \frac{\Delta_{N-3}}{6} & \frac{\Delta_{N-3} + \Delta_{N-2}}{3} & \frac{\Delta_{N-2}}{6} \\ 0 & 0 & 0 & 0 & \frac{\Delta_{N-2}}{6} & \frac{\Delta_{N-2} + \Delta_{N-1}}{3} \end{bmatrix} \quad (6)$$

$$\begin{Bmatrix} y''_1 \\ y''_2 \\ y''_3 \\ \vdots \\ y''_{N-3} \\ y''_{N-2} \\ y''_{N-1} \end{Bmatrix} = \begin{bmatrix} \frac{1}{\Delta_0} & -\frac{1}{\Delta_0} - \frac{1}{\Delta_1} & \frac{1}{\Delta_1} & & 0 & 0 & 0 \\ 0 & \frac{1}{\Delta_1} & -\frac{1}{\Delta_1} - \frac{1}{\Delta_2} & \cdots & 0 & 0 & 0 \\ 0 & 0 & \frac{1}{\Delta_2} & & 0 & 0 & 0 \\ & \vdots & & \ddots & & \vdots & \\ 0 & 0 & 0 & & \frac{1}{\Delta_{N-3}} & 0 & 0 \\ 0 & 0 & 0 & \cdots & -\frac{1}{\Delta_{N-3}} - \frac{1}{\Delta_{N-2}} & \frac{1}{\Delta_{N-2}} & 0 \\ 0 & 0 & 0 & & \frac{1}{\Delta_{N-2}} & -\frac{1}{\Delta_{N-2}} - \frac{1}{\Delta_{N-1}} & \frac{1}{\Delta_{N-1}} \end{bmatrix} \begin{Bmatrix} y_0 \\ y_1 \\ y_2 \\ y_3 \\ \vdots \\ y_{N-3} \\ y_{N-2} \\ y_{N-1} \\ y_N \end{Bmatrix}$$

The matrix Equation (6) may be rewritten as the set of Equations (7) as follows:

$$Fy_{dd} = Gy$$

$$y_{dd} = F^{-1}Gy = Hy \quad (7)$$

Choosing the values in the vector y using a least squares criterion on the collected data is shown in Equation (8) as follows:

$$E = \Sigma [\psi_k - A_{i_k}(\xi_k) y_{i_k} - B_{i_k}(\xi_k) y_{i_k+1} - C_{i_k}(\xi_k) y''_{i_k} - D_{i_k}(\xi_k) y''_{i_k}]^2 \quad (8).$$

Equation (8) is the minimum deviation between the data and the spline, i.e., Equation (8) is an error function. The y values are chosen to minimize the error as defined in Equation (8). The vector of predicted values can be written as illustrated in Equation (9) as follows:

$$\hat{y} = (A_{\{k\}} + B_{\{k\}})y + (C_{\{k\}} + D_{\{k\}})y_{dd} \quad (9)$$
$$= (A_{\{k\}} + B_{\{k\}})y + (C_{\{k\}} + D_{\{k\}})Hy$$
$$= [A_{\{k\}} + B_{\{k\}} + C_{\{k\}}H + D_{\{k\}}H]y$$
$$= Ay.$$

The elements of the matrix in brackets of Equation (9) depend upon the x-value corresponding to each data point (but this is a fixed matrix). Thus, the final equation can be determined using the pseudo-inverse. In turn, the pseudo-inverse only depends upon the x-locations of the data set and the locations where the breaks in the cubic spline are set. The implication of this is that once the geometry of the spline and the size of the image are selected, the best choice for y given a set of measured values $y_m$, is illustrated in Equation (10) as follows:

$$y = (A^T A)^{-1} A \cdot y_m \quad (10).$$

The cubic spline through the sum intensity-squared function of the image will then be given by Equation (11) as follows:

$$y_{cs} = A \cdot y \quad (11).$$

Because the maximum values of the cubic spline are of interest, the derivative of the cubic spline is determined and utilized to determine the maximum values of the cubic spline. The cubic spline derivative is given by Equation (12) as follows:

$$\chi'(x_k) = A'_{i_k}(x_k)y_{i_k} + B'_{i_k}(x_k)y_{i_k+1} + \quad (12)$$
$$C'_{i_k}(x_k)y''_{i_k} + D'_{i_k}(x_k)y''_{i_k+1}$$
$$= -\frac{y_{i_k}}{\Delta_{i_k}} + \frac{y_{i_k+1}}{\Delta_{i_k}} - \frac{\Delta_{i_k} y''_{i_k}}{6}(3A_{i_k}^2(x_k) - 1) +$$
$$\frac{\Delta_{i_k} y''_{i_k+1}}{6}(3B_{i_k}^2(x_k) - 1)$$

Equation (12) can be written as Equation (13) as follows:

$$y'_{cs} = (A'_{\{k\}} + B'_{\{k\}})y + (C'_{\{k\}} + D'_{\{k\}})y_{dd} \quad (13)$$
$$= [A'_{\{k\}} + B'_{\{k\}} + C'_{\{k\}}H + D'_{\{k\}}H]y$$
$$= A'y.$$

Once the current values of y are found, the cubic spline, $y_{cs}$, and its derivative, $y'_{cs}$, can be calculated. The cubic spline data may include "blocks" of data that includes values above a predetermined threshold. A pipe block is formed by the liquid flowing out of the tube into the drip chamber 59 and a pool block is formed as the liquid collects at the gravity end of the drip chamber 59 (see FIG. 8).

The following algorithm may be applied to the cubic spline data: (1) determine the local maxima of the cubic spline data using the derivative information; (2) determine the block surrounding each local maxima by including all points where the cubic spline value is above a threshold value; (3) merge all blocks which intersect; (4) calculate information about the block of data including the center of mass (intensity), the second moment of the mass (intensity), the lower x-value of the block, the upper x-value of the block, the mean value of the original sum of intensity squared data in the block, the standard deviation of the original sum of intensity squared data in the block, and the mean intensity of a high-pass filtered image set in the block; and (5) interpret the collected data to obtain information about when drops occur and when the system is streaming.

The mean intensity of a high-pass filtered image set in the block is used to determine if the block created by each contiguous range of spline data is a result of a high frequency artifact (e.g., a drop) or a low frequency artifact. This will act as a second background filter which tends to remove artifacts such as condensation from the image. That is, all previous images in an image memory buffer (e.g., 30 previous frames, for example) are used to determine if the data is a result of high frequency movement between frames. If the block is a result of low frequency changes, the block is removed, or if it is a result of high frequency changes, the block is kept for further analysis. A finite impulse response filter or an infinite impulse response filter may be used.

Each block is plotted over its physical extent with the height equal to the mean value of the data within the block. If a block has a mean value of the high-pass filtered image less than the threshold, it is an indication that it has been around for several images and thus may be removed.

Free flow conditions may be determined by the processor 90 (see FIG. 6 or 8) to exist using the blocks when the pipe block extends nearly to the pool block, the pipe block and the pool block merge together, and/or the summed range of widths of the pool and pipe blocks (or all blocks) is greater than a predetermined threshold, e.g., the total extent of the blocks exceeds 380 pixels in width. The processor 90 may detect a drop when the transition of the pipe block from a larger width to a shorter width occurs as a result of a drop formation in the tube and as the drop leaves the pipe (i.e., tube) opening of the drip chamber 59. The processor 90 may detect this by looking at the ratio of the current pipe block width to the previous image's pipe block width, e.g., an image where the ratio is less than 0.9 as is also a local minima may be considered by the processor 90 to be an image formed immediately after a drop has formed.

Various filtering algorithms may be used to detect condensation or other low frequency artifacts, such as: if a block has a low mean value in the high-pass filtered image, then it may be condensation. This artifact can be removed from consideration. Additionally or alternatively, long blocks (e.g., greater than a predetermined threshold) with a low high-pass mean value are possibly streams because stream images tend to remain unchanging; the processor 90 may determine that long blocks greater than a predetermined threshold corresponds to a streaming condition. Additionally or alternatively, an algorithm may be used on the current image to detect free flow conditions.

The processor 90 may, in some specific embodiments, use the block data to count the drops to use the system 84 as a drop counter. The processor 90 may also use width changes in the pool block as a drop disturbs the water to determine if a bubble formed when the drop hits the pool. For example, the processor 90 may determine that blocks that form below the pool block are from bubbles that formed when the drop hit the water. The bubble may be filtered out by the processor 90 when determining if a predetermined value of total block ranges indicates that a free flow condition exists.

In some embodiments of the present disclosure, the depth of field of the system 84 may have a narrow depth of field to make the system 84 less sensitive to condensation and droplets on the chamber walls. In some embodiments, a near focus system may be used.

Figure 19:
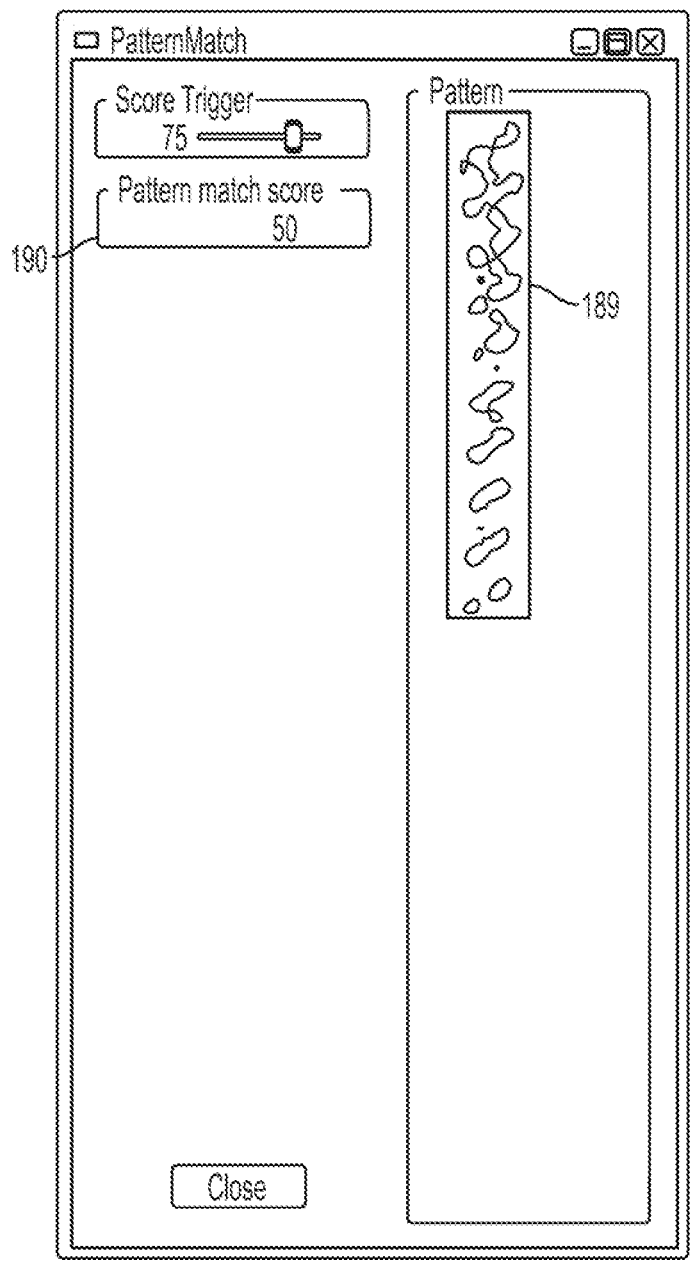
FIG. 19 illustrates a template for pattern matching to determine if a free flow condition exits in accordance with an embodiment of the present disclosure.

Referring now to FIG. 19, in another embodiment of the present disclosure, a template 189 is used to determine if a free flow condition exists. The template 189 is used by the processor 90 of FIG. 8 to determine a pattern match score 190 when performing a template match algorithm on an image, e.g., the image 94 of FIG. 13. For example, the template 189 may be compared to the image 94 to determine if a portion or all of the image 94 closely matches the template 189. As previously mentioned, the image 94 of FIG. 13 is a difference between a background image and an image captured by the image sensor 63 of FIG. 8 that has each pixel converted to either a black pixel if the difference value for that pixel is below a threshold value or a white pixel if the difference value for that pixel is above a threshold value. All pixels of the image 94 will be either a white pixel or a black pixel. If the pattern match score 190 is above a predetermined threshold, a free flow condition is determined to exist. The template matching method may utilize a template matching algorithm as found in the Open Source Computer Vision ("OpenCV") library. For example, the template 189 may be used with the matchTemplate( ) function call of the OpenCV library using the CV_TM_CCOEFF method or the method of CV_TM_CCOEFF_NORMED. The CV_TM_CCOEFF method uses the pattern matching algorithm illustrated in Equation (14) as follows:

$$R(x, y) = \sum_{x',y'} (T'(x', y') \cdot I'(x + x', y + y')),\, , \quad (14)$$

where:

$$T'(x', y') = T(x', y') - 1/(w \cdot h) \cdot \Sigma_{x'',y''} T(x'', y'')$$

$$I'(x+x', y+y') = I(x+x', y+y') - 1/(w \cdot h) \cdot \Sigma_{x'',y''} I(x+x'', y+y'');$$

The I denotes the image, the T denotes the template, and the R denotes the results. The summation is done over the template and/or the image patch, such that: x'=0 . . . w−1 and y'=0 . . . h−1.

The results R can be used to determine how much the template T is matched at a particular location within the image I as determined by the algorithm. The OpenCV template match method of CV_TM_CCOEFF_NORMED uses the pattern matching algorithm illustrated in Equation (15) as follows:

$$R(x, y) = \frac{\sum_{x',y'} (T'(x', y') \cdot I'(x + x', y + y'))}{\sqrt{\sum_{x',y'} T'(x', y')^2 \cdot \sum_{x',y'} I'(x + x', y + y')^2}}. \quad (16)$$

In another embodiment of the present disclosure, the template matching algorithm uses a Fast Fourier Transform ("FFT"). In some embodiments, any of the methods of the matchTemplate( ) function of OpenCV may be used, e.g., CV_TM_SQDIFF, CV_TM_SQDIFF_NORMED, CV_TM_CCORR, and/or CV_TM_CCORR_NORMED.

The CV_TM_SQDIFF uses the pattern matching algorithm illustrated in Equation (17) as follows:

$$R(x, y) = \sum_{x',y'} (T(x', y') - I(x + x', y + y'))^2. \quad (17)$$

CV_TM_SQDIFF_NORMED uses the pattern matching algorithm illustrated in Equation (18) as follows:

$$R(x, y) = \frac{\sum_{x',y'} (T(x', y') - I(x + x', y + y'))^2}{\sqrt{\sum_{x',y'} T(x', y')^2 \cdot \sum_{x',y'} I(x + x', y + y')^2}}. \quad (18)$$

CV_TM_CCORR uses the pattern matching algorithm illustrated in Equation (19) as follows:

$$R(x, y) = \sum_{x',y'} (T(x', y') \cdot I(x + x', y + y')). \quad (19)$$

CV_TM_CCORR_NORMED uses the pattern matching algorithm illustrated in Equation (20) as follows:

$$R(x, y) = \frac{\sum_{x',y'} (T(x', y') \cdot I'(x + x', y + y'))}{\sqrt{\sum_{x',y'} T(x', y')^2 \cdot \sum_{x',y'} I(x + x', y + y')^2}}. \quad (20)$$

In yet another embodiment of the present disclosure, a template of a grayscale image of a free flow condition is compared to an image taken by the image sensor 63 of FIG. 8 to determine if a free flow condition exists. In some embodiments, the template matching function within the OpenCV library may be utilized.

Figure 20:
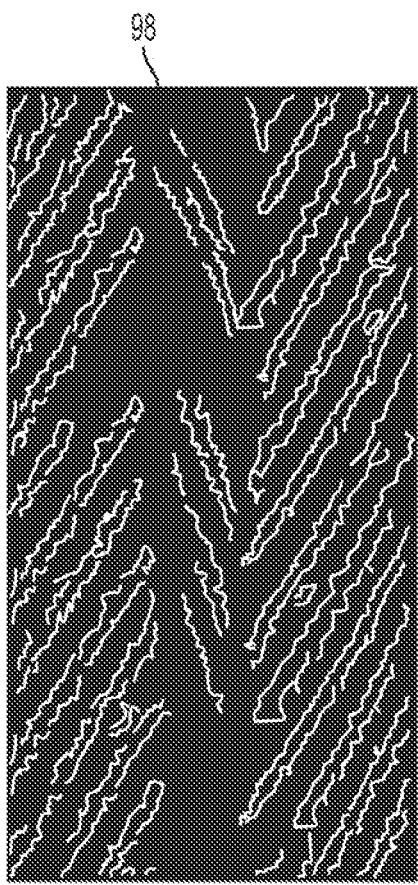
FIG. 20 is a graphic illustration of a difference between a reference image and an image containing a stream processed with edge detection and line detection for use in detecting a free flow condition in accordance with an embodiment of the present disclosure.
Figure 21:
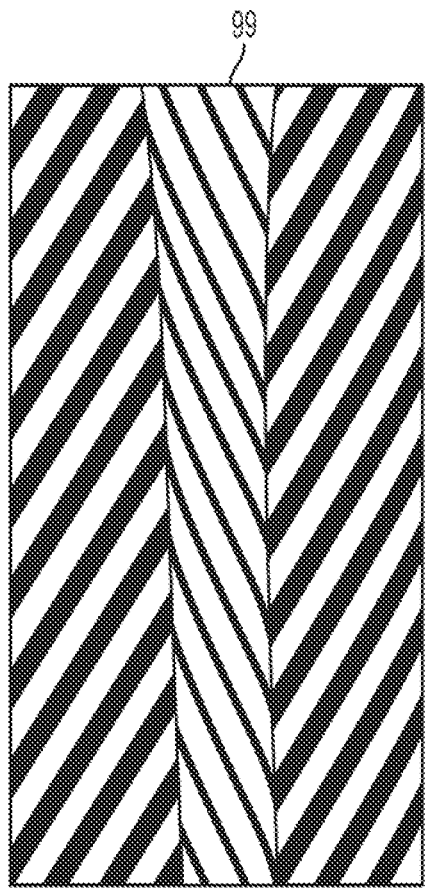
FIG. 21 is a graphic illustration of an image of a drip chamber captured by an image sensor when a free flow condition exists in accordance with an embodiment of the present disclosure.

Refer now to FIGS. 20 and 21; in yet an additional embodiment of the present disclosure, the algorithm to determine when a free flow condition exists, e.g., as executed by the processor 90 of FIG. 8, may utilize an algorithm to determine if a template pattern matches an array of pixels utilizing edge detection followed by line detection. As shown in FIG. 20, an image 98 is formed from an image 99 of FIG. 21, by using edge detected followed by line detection. The resulting lines may be utilized by the processor 90 to determine that a free flow condition exists. As shown in FIG. 20, the feature which shows up after this processing by the processor 90 are lines that have a different slope than the expected 45° slope of the background reference image. The lines having the angle of the background image may be filtered out of FIG. 20, in some embodiments. The lines may be detected as edges using a Canny algorithm as found in the OpenCV library. The Hough algorithm also found in the OpenCV library may be used to determine the slope of the lines.

One type of Hough transfer uses an algorithm described in *Progressive Probabilistic Hough Transform* by J. Matas, C. Galambos, and J. Kittler in 1998 ("Algorithm 1"). However, the following "Alternative Hough" transform may be utilized and is shown in pseudo code form in Table 1 ("Algorithm 2"). Algorithm 2 selects two pixels at random and calculates the Hough transform of the line passing through these two points. Algorithm 2 is shown in Table 1 as follows:

TABLE 1

Alternative Hough Transform Pseudocode

1. If the image is empty, then exit.
2. Randomly select two pixels and update the accumulator
   a. Required Operations
      i. Two random numbers
      ii. One inverse tangent
3. Check if the new location is higher than the threshold/. If not, goto 1
   a. Operations
      i. One logical operation
4. Look along a corridor specified by the peak in the accumulator, and find the longest segment of pixels either continuous or exhibiting a gap not exceeding a given threshold.
5. Remove the pixels in the segment from the input image.
6. Unvote from the accumulator all the pixels from the line that have previously voted.
7. If the line segment is longer than the minimum length add it to the output list
8. Goto 1.

If the line comprises a proportion, p, of the total points, then the likelihood that we will see a result in the representative (r, θ)-bin is p for Algorithm 1 and $p^2$ for Algorithm 2. Generally, in some embodiments, a proportion test has at least 5 positive results and 5 negative results. Assuming that it is more likely to see negative results than positive results, in some embodiments, the Algorithms 1 and 2 continue to search for lines until there are at least 5 positive results in a particular bin.

The probability of seeing a fifth positive result in Algorithm 1 after N≥5 tests is shown in Equation (21) as follows:

$$p_1(5 \text{ on } N) = p(4 \text{ in } N-1) \cdot p = \frac{(N-1)!}{4!(N-5)!} p^5 (1-p)^{N-5}, \quad (21)$$

and the probability in Algorithm 2 is shown in Equation (22) as follows:

$$p_2(5 \text{ on } N) = p(4 \text{ in } N-1) \cdot p^2 = \frac{(N-1)!}{4!(N-5)!} p^{10} (1-p^2)^{N-5}. \quad (22)$$

Table 2, shown below, shows the number of tries to have a 50% chance of seeing 5 successes, $p_{1,50}$ and $p_{2,50}$, as well as the number of tries to have a 90% chance of seeing 5 successes, $p_{1,90}$ and $p_{2,90}$.

TABLE 2

| p | $p_{1,50}$ | $p_{1,90}$ | $p_{2,50}$ | $p_{2,90}$ | $r_{50}$ | $r_{90}$ |
|---|---|---|---|---|---|---|
| 0.5 | 9 | 14 | 20 | 31 | 2.22 | 2.21 |
| 0.25 | 19 | 30 | 76 | 127 | 4 | 4.23 |
| 0.125 | 39 | 62 | 299 | 511 | 7.67 | 8.24 |
| 0.0625 | 76 | 127 | 1197 | 2046 | 15.75 | 16.11 |

Table 2 shows that the increase in the number of tries between Algorithm 1 and Algorithm 2 to see 5 positive results is approximately 1/p. There should be 1 positive result in 1/p trials when the proportion is p.

Algorithm 2's computationally expensive operation is, in some embodiments, the arc tangent function, which may be about 40 floating point CPU operations. There are approximately 2 N floating point operations in Algorithm 1's equivalent step. The Hough transform of a 640×480 pixel image with full resolution has N equal to 2520, while the Hough transform of a 1080×1920 pixel image has N equal to 7020. This implies that Algorithm 2 has a speed advantage over Algorithm 1 when p is greater than 0.008 for a 640×480 image and when p is greater than 0.003 for a 1080×1920 image.

In some embodiments, it is assumed that every bin in the Hough transform space is equally likely to be occupied in the presence of noise. This simplification speeds up the thresholding decision; however, in some embodiments, this assumption is not true. The primary effect of the simplification is to underestimate the probability that is seen in values greater than one in the Hough transform with a corresponding likelihood of falsely declaring that a line exists. For a particular combination of image size and Hough transform bin arrangement, the true probabilities can be pre-computed. This allows the false alarm rate to be minimized without a corresponding increase in computation. With additional restrictions on the type of imagery, even more accurate estimates of the probability of seeing a value in a bin of the Hough transform is possible.

There are additional forms of the Hough transform which parameterizes different features. For example, there is a three-element parameterization of circles, (x, y, r), where x and y specify the center and r is the radius. Algorithm 2 can work using these parameterizations as well. For the circle example, Algorithm 2 would select three pixels at random and calculate the circle passing through them.

Algorithm 2 would have a similar speed advantage for features comprising a suitably large portion of the total pixels considered. It would also have a significant advantage in storage required, since the Hough transform could be stored in a sparse matrix, while the Algorithm 1's analog would require a full-size matrix.

Referring now to FIGS. 22-26, which illustrate various background patterns that may be used to detect a free flow condition or estimate the size of a drop of liquid. The image sensor 103 may be used with the background patterns of FIGS. 22-26 and may be the image sensor 11 of FIG. 1, the image sensor 68 of FIG. 5, the image sensor 63 of FIG. 6, or the image sensor 63 of FIG. 8, each of which may be coupled to a respective processor for processing the images from the image sensor, such as the processor 15 of FIG. 1 or the processor 90 of FIG. 8.

Figure 22:
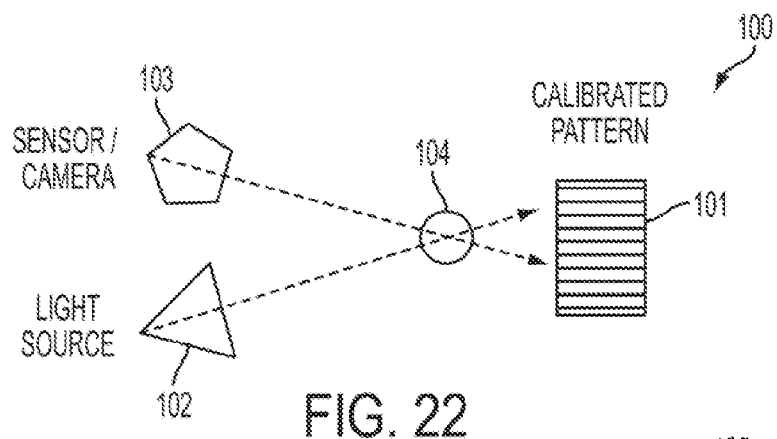
FIG. 22 is a block diagram of an imaging system for use with a flow meter having a background pattern with stripes and a light source shining on the stripes from an adjacent location to an image sensor in accordance with an embodiment of the present disclosure.

FIG. 22 is a block diagram of an imaging system 100 for use with the drip chamber 104 (e.g., a drip chamber 4 of FIG. 1) having a background pattern 101 with stripes and a light source 102 shining on the stripes from an adjacent location to an image sensor 103 in accordance with an embodiment of the present disclosure. Any drops or free flow streams within the drip chamber 104 distorts the image taken by the image sensor 103. A processor coupled to the image sensor 103 (e.g., processor 15 of FIG. 1) can use the distortions of the background pattern 101 as captured by the image sensor 103 to estimate a flow rate and/or detect free flow conditions.

Figure 23:
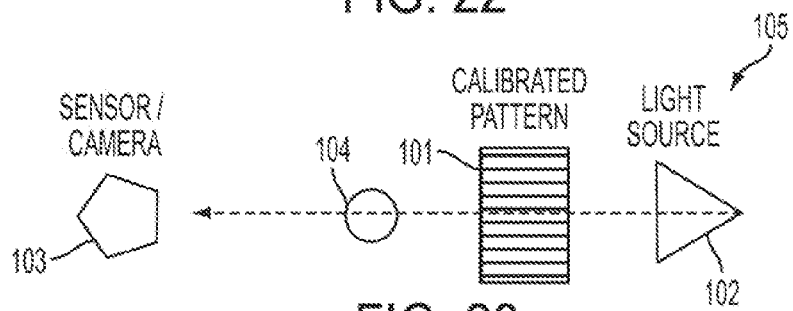
FIG. 23 is a block diagram of an imaging system for use with a flow meter having a background pattern with stripes and a light source shining on the stripes from behind the background pattern relative to an opposite end of an image sensor in accordance with an embodiment of the present disclosure.
Figure 24:
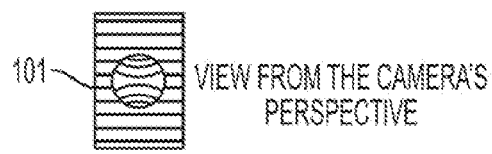
FIG. 24 illustrates an image from an image sensor when a drop distorts the background pattern of FIG. 23 in accordance with an embodiment of the present disclosure.

FIG. 23 is a block diagram of an imaging system 105 for use with the drip chamber 104 having a background pattern 101 with stripes and a light source 102 shining on the stripes from behind the background pattern 101 relative to an opposite end to an image sensor 103 in accordance with an embodiment of the present disclosure. FIG. 24 shows an image from the image sensor 103 of FIG. 23 when a drop distorts the background pattern 101 of FIG. 23 in accordance with an embodiment of the present disclosure. Note that as shown in FIG. 24, the background pattern's 101 stripes are distorted by the drop (or will be distorted by a free flow stream) in the drip chamber 104 as captured in images by the image sensor 103. This distortion may be used to estimate the drop size, to calculate the flow rate through a drip chamber, or to determine if a free flow condition exists within the drip chamber.

Figure 25:
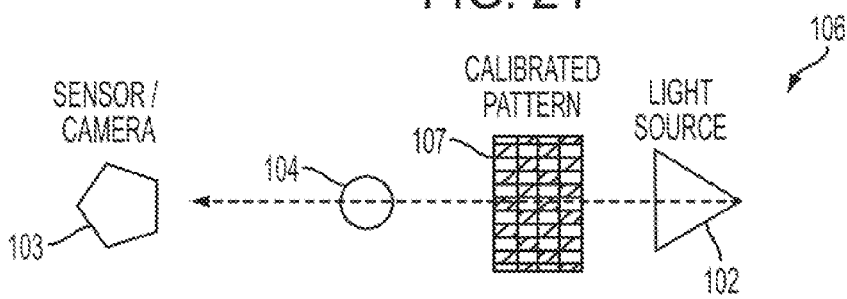
FIG. 25 is a block diagram of an imaging system for use with a flow meter having a background pattern with a checkerboard pattern and a light source shining on the stripes from behind the background pattern relative to an opposite end of an image sensor in accordance with an embodiment of the present disclosure.
Figure 26:
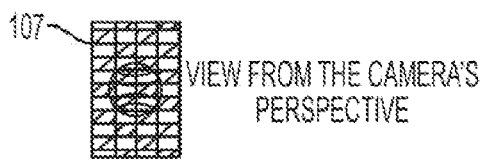
FIG. 26 shows an image from the image sensor of FIG. 25 when a drop distorts the background pattern in accordance with an embodiment of the present disclosure.

FIG. 25 shows a block diagram of an imaging system 106 for use with a flow meter having a background pattern 107 with a checkerboard pattern and a light source 102 shining on the stripes from behind the background pattern 107 relative to an opposite end to an image sensor 103 in accordance with an embodiment of the present disclosure. FIG. 26 shows an image from the image sensor 103 of FIG. 25 when a drop distorts the background pattern 107 of FIGS. 25-26 in accordance with an embodiment of the present disclosure. In yet another embodiment of the present disclosure, a background pattern having a plurality of random dots and/or circles may be utilized by an imaging system disclosed herein.

Referring to FIGS. 22-26, the "lensing" of a drop (i.e., the distortion of the background pattern from the view of an image sensor) may be used to measure the radius of the drop. The radius of the drop corresponds to how much and what effect the drop has on any light passing through it. By measuring the change to the calibration grid (i.e., the background pattern) as seen through the drop, the radius, and hence the volume of the drop, can be calculated. For example, the magnification of a test grid of known size as seen through the drop could be measured optically and the radius inferred from this measurement. In some embodiments of the present disclosure, the relationship between the radius and the drop may be calculated and/or may be determined using a lookup table that has been generated empirically.

Figure 27:
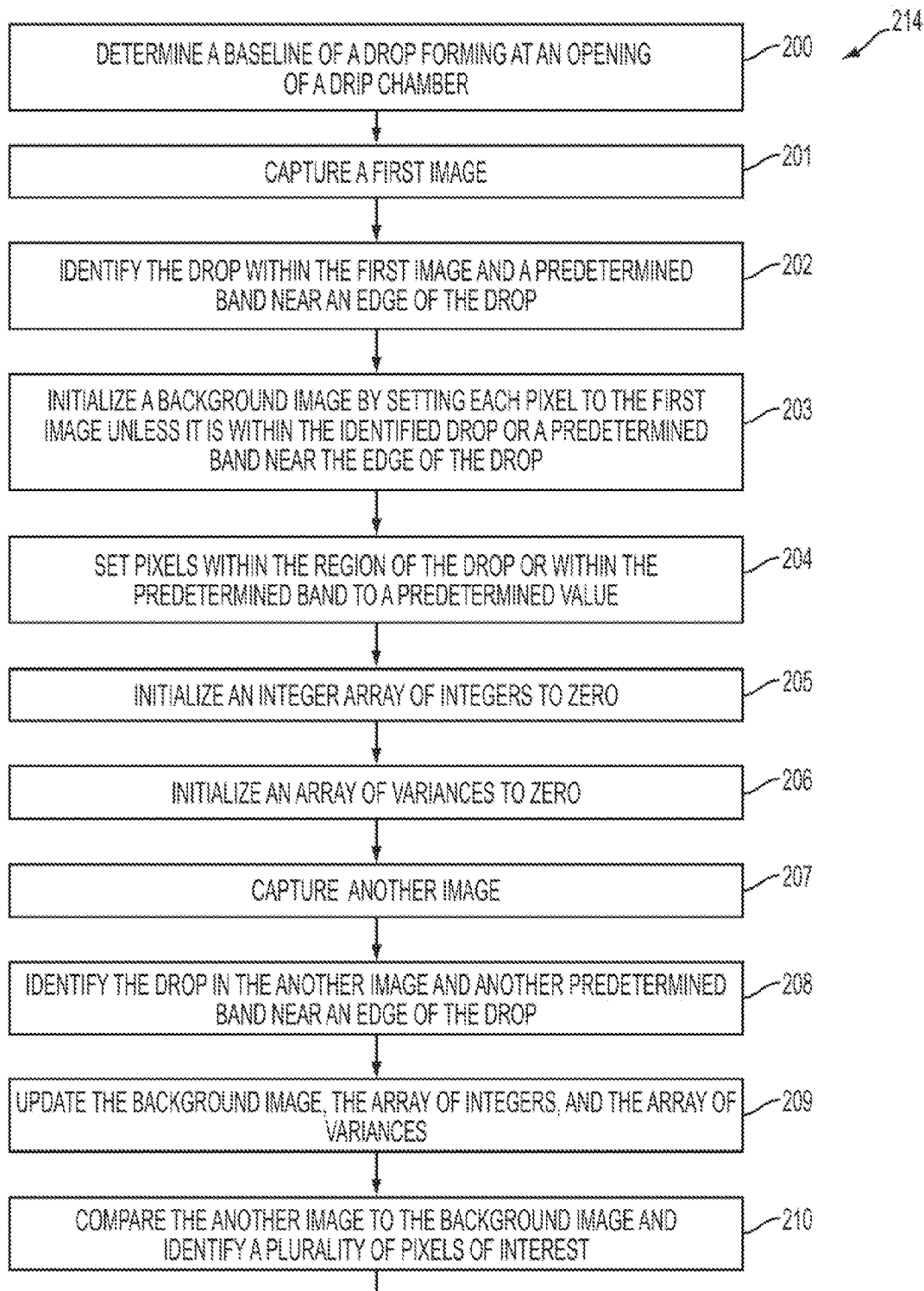
FIGS. 27-28 show a flow chart illustration of a method for estimating a volume of a drop within a drip chamber in accordance with an embodiment of the present disclosure.
Figure 28:
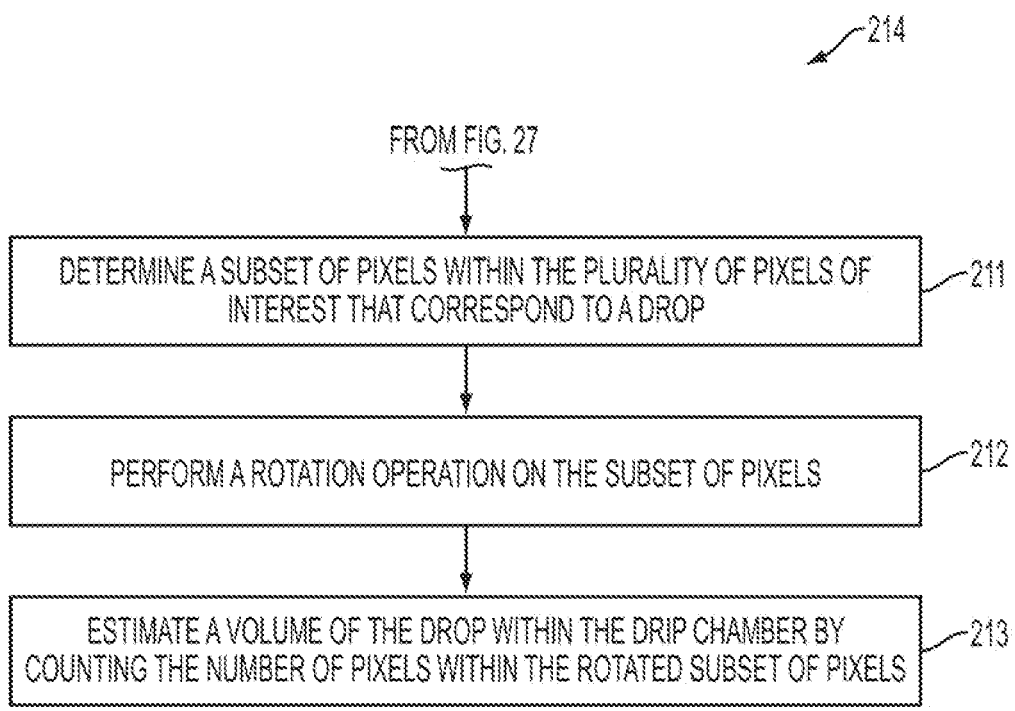

FIGS. 27-28 show a flow chart diagram illustrating a method for estimating a volume of a drop within a drip chamber in accordance with an embodiment of the present disclosure. That is, FIGS. 27-28 illustrate a method 214. Method 214 will be also described with reference to FIGS. 29-37. FIGS. 29-31 and 33-36 illustrate images used or generated by a flow meter to estimate a volume of a drop within a drip chamber in accordance with an embodiment of the present disclosure. FIGS. 32 and 37 illustrate pseudo code that may be used by the method 214 of FIGS. 27-28.

The method 214 of FIGS. 27 and 28 may be implemented by the flow meter 7 of FIG. 1, the flow meter 67 of FIG. 5, the imaging system 78 of FIG. 6, the imaging system 84 of FIG. 8, or other flow meter of an imaging system disclosed herein (each with or without a background pattern and/or with or without active illumination).

Figure 29:
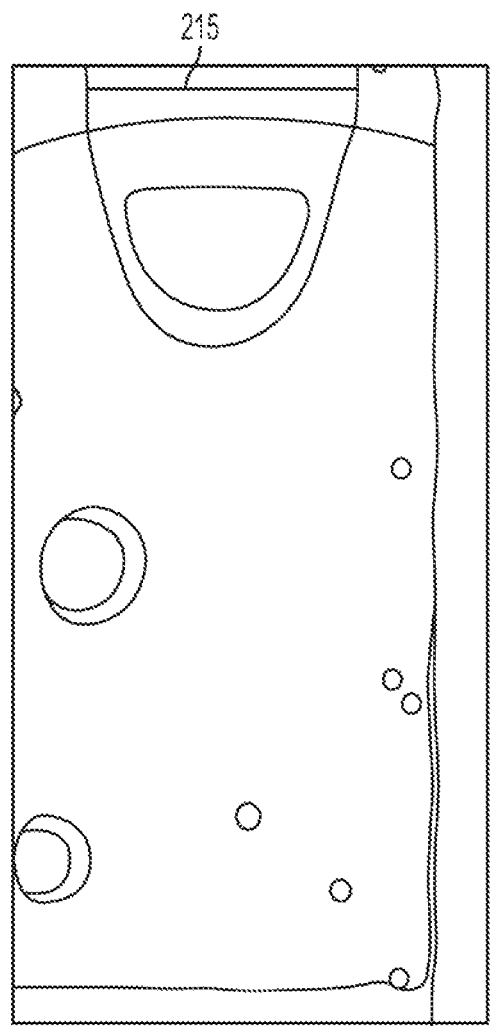
FIGS. 29-31 illustrate images used or generated by a flow meter to estimate a volume of a drop within a drip chamber using the method illustrated by FIGS. 27-28 in accordance with an embodiment of the present disclosure.

The method 214 includes acts 200-213. Act 200 determines a baseline of a drop forming at an opening of a drip chamber. Act 201 captures a first image. The first image may be captured using a uniform backlight. In some embodiments, the first image may be captured using a background pattern and/or an exposure algorithm as described herein. Acts 200 and 201 may be performed simultaneously. FIG. 29 shows an image with the baseline 215 overlaid. The baseline 215 may be a predetermined group of pixels or may be generated using fiducial markers disposed on the opening of the drip chamber and/or on a background pattern (not shown in FIG. 29). The first image is used by the method 214 to initialize a background image, $\mu_{i,j}$, a variance array, $S_{i,j}$, and an integer array, $I_{i,j}$. The background image may have i by j pixels, while the variance array and the integer array may be 2-D arrays that also have a size of i by j.

Figure 30:
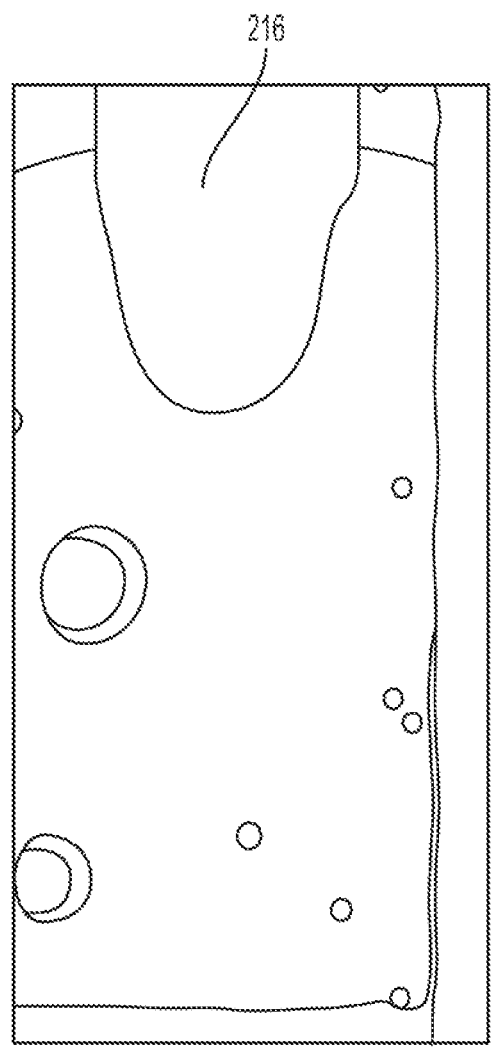
Figure 31:
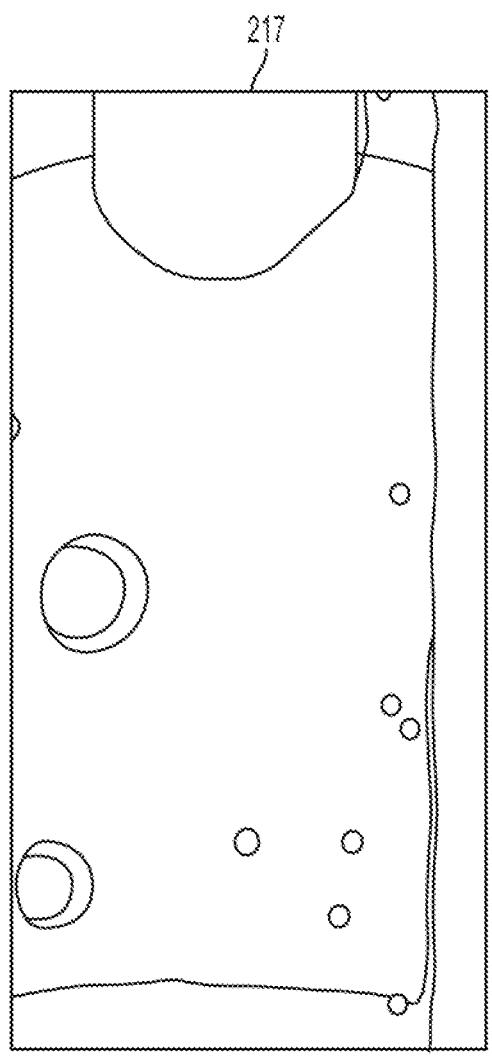

Act 202 identifies the drop within the first image and a predetermined band near an edge of the drop (e.g., the band may be a predetermined number of pixels beyond the edge of the drop). Act 203 initializes a background image by setting each pixel to the same value as the first image (for that respective location) unless it is within the identified drop or a predetermined band near the edge of the drop. Act 204 sets pixels within the region of the drop or within the predetermined band to a predetermined value. FIG. 30 shows an example background image created after initialization. In the exemplary image of FIG. 30, the area of the drop and of a band beyond the edge of the drop, designated generally as 216, is set to a predetermined value, e.g., 140.

For example, when the method creates the first background image, every pixel in the background image that is part of the drop or a band outside of an edge of the drop is set to a default threshold value, e.g. 140 out of an intensity range of 0-255.

Act 205 initializes the integers of the array of integers to zeros. Act 206 initializes the values within the array of variances to zeros. The integer array is the same size as the image. The integer array counts how often each pixel of the background image has been updated with new information and is initialized to all zeros. The array of variances (e.g., an array of the data type "double") is also the same size as the background image and contains an estimate of the variance of the intensity of each pixel within the background image.

Act 207 captures another image, and act 208 identifies the drop in the another image and another predetermined band near an edge of the drop. Act 209 updates the background image, the array of integers, and the array of variances.

As additional images are captured, the background image may be updated. For example, when an image is collected by the system, the background algorithm evaluates every pixel. If a pixel is considered part of the drop or its guard band, then its value in the background image is not altered.

If a pixel is not considered part of the drop or its guard band: (1) if the pixel's corresponding integer in the integer array is zero, the pixel's value in the background image is set equal to the pixel's value in the input image; or (2) if the pixel's count is greater than 0, then the background image value for that pixel is updated using a low pass filter. In some embodiments, any style of filter may be used, such as a high pass filter, a bandpass filter, etc. One low pass filter that may be used is illustrated in Equation (23) as follows:

$$P_{background,i,j} = P_{background,i,j}(1-\alpha_{background}) + \alpha_{background}P_{input,i,j} \quad (23)$$

In addition, the variance array may be updated using Equations (24) as follows:

$$\sigma_{temp}^2 = (P_{background,i,j} - P_{input,i,j})^2$$

$$\sigma_{background,i,j}^2 = \sigma_{background,i,j}^2(1-\beta_{background}) + \beta_{background}\sigma_{temp}^2 \quad (24).$$

Note that the filter used for both operations is an exponential filter; however, in additional embodiments, other suitable filters may be used, such as other low-pass filters. The variance estimate can be performed in any known way or using a stand in for the estimate, e.g., using standard deviation.

The new estimates of each pixel's background intensity (mean value), the number of images used to update each pixel's mean and variance, and each pixel's variance (e.g., an approximation to the true variance and/or a value that is proportional to the variance) are used to update the arrays. That is, each additional image captured may be used to update the background image, the array of integers, and the array of variances. After several images have been processed, the background image may appear as FIG. 31. Note that this image still has a region (the uniformly medium gray area, designated generally as 217) where the pixels have never changed from the initial threshold value. This region has been considered part of the drop or its guard band in every image.

Act 210 compares the another image (e.g., current or most recent image) to the background image and identifies a plurality of pixels of interest. Act 211 determines a subset of pixels within the plurality of pixels of interest that corresponds to a drop.

The comparison of act 210 compares the another image pixel-by-pixel to the background image. Out of this comparison comes an array the same size as the image where every pixel has a value of zero or not zero (255).

Act 210 may be implemented by the pseudo code shown in FIG. 32. That is, the determination of this threshold value is made in accordance with the following: If the input pixel is to the left or right of the baseline in the image, then its output value is set to zero (Line 1); if the input pixel's background count array indicates that fewer than a pre-determined number of images (e.g., 100) have been used to make this pixel's background value (Line 2), then: if the input pixel's intensity is less than the threshold intensity (e.g., 140 in a range of 0-255), then set the pixel's output value to not-zero (255) (Line 2a); or if the input pixel's intensity is greater than or equal to the threshold intensity, then set the pixel's output value to zero (Line 2b); and if the input pixel's background count array is greater than the pre-determined number of images (Line 3), then: if the square of the difference between the input pixel intensity and the background pixel intensity is greater than the pixel's estimate of background variance times a constant $\gamma^2$, then set the pixel's output value to not-zero (255) (Line 3a) (that is, if the difference between current pixel value and the background image is more than $\gamma$, then the pixel is distinct); or if the square of the difference between the input pixel intensity and the background pixel intensity is less than or equal to the pixel's estimate of background variance times a constant $\gamma^2$, then set the pixel's output value to zero (see Line 3b). Line 3 captures portions of the image that are altered by the presence of a drop, but which are made a higher intensity.

Figure 33:
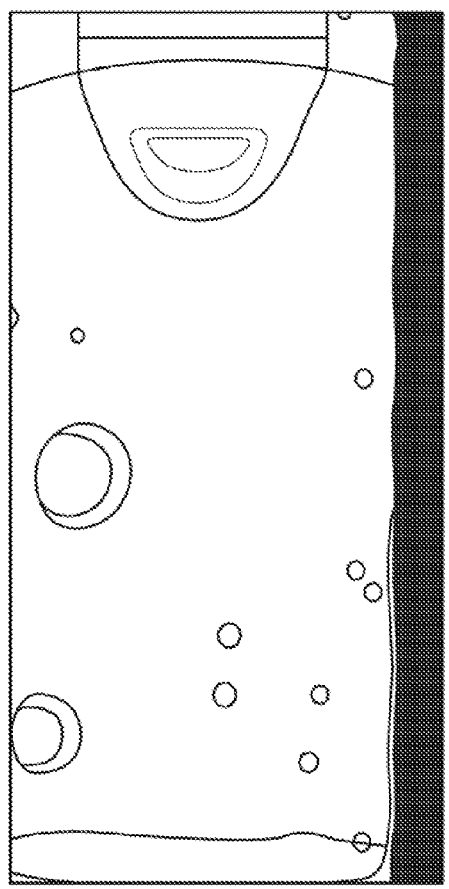
FIGS. 33-36 illustrate additional images used or generated by a flow meter to estimate a volume of a drop within a drip chamber using the method illustrated by FIGS. 27-28 in accordance with an embodiment of the present disclosure.
Figure 34:
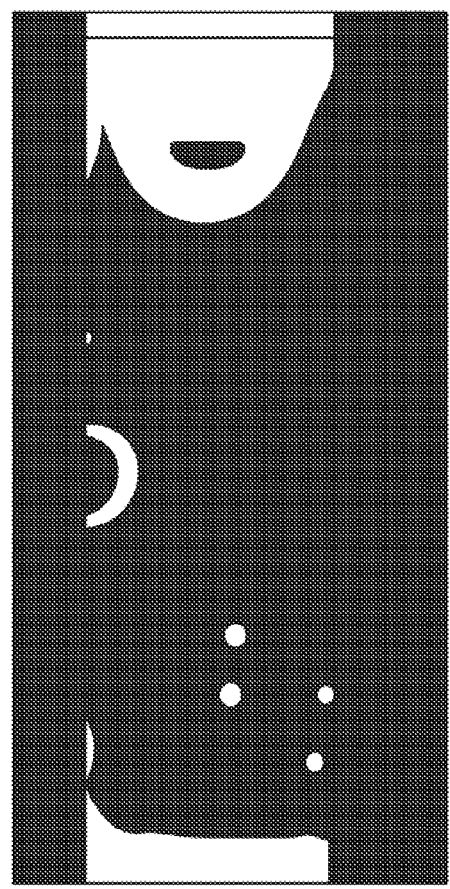

When act 210 is implemented as an algorithm, the algorithm is initialized, and the input and output of this thresholding algorithm will look like the images in FIGS. 33 and 34, respectively. Because the number of images used in estimating the background image is initially small, the only criterion applied are shown as lines (1) and (2) above because there have not been enough images used for the integer array to have a value beyond the threshold for certain respective pixels. This may result in many low-intensity regions being identified as distinct, including poorly illuminated edges and condensation on the chamber walls.

Figure 35:
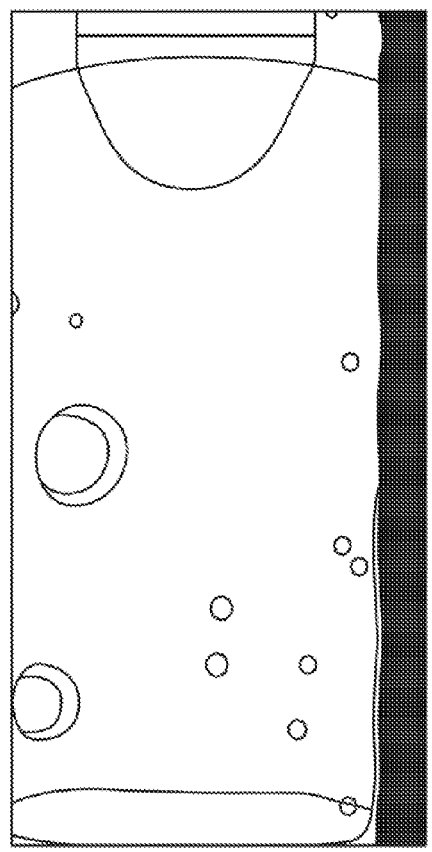
Figure 36:
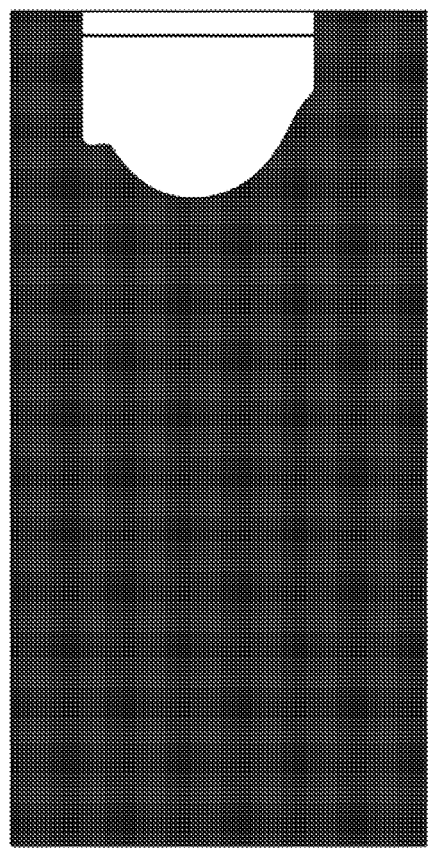

After enough images have been gathered such that most (or all) of the pixels of the background image have been generated with a sufficient number of pixels, lines (3), (3a), and (3b) of FIG. 32 are utilized. After thresholding, the background is largely black with an occasional noisy pixel exceeding the variance threshold, as shown in FIGS. 35 and 36 (which show an image captured by the camera and the results of the comparison algorithm described above, respectively).

As previously mentioned, after act 210, act 211 determines which of a subset of pixels within the plurality of pixels of interest corresponds to a drop. Act 211 may be implemented by the pseudo code shown in FIG. 37. That is, the threshold image is passed to an algorithm which finds the connected component representing the drop as illustrated by the pseudo code of FIG. 37.

The binary image after processing the pseucode of FIG. 32 is evaluated to find the binary component which occupies the space given by the drop. The algorithm is passed the location of a pixel on the baseline which is white (or it is passed the center pixel of the longest stretch of contiguous white pixels on the line).

Once the algorithm has an initial white pixel, it performs the algorithm illustrated by the pseudo code shown in FIG. 37. The pseudo code determines locations that include white pixels that have a path to the baseline (i.e., a white pixel path). Line 1 pushes the location of the first pixel onto a stack. Line 2 performs a while loop while the stack is not empty. The while loop includes lines (2a)-(2d). Line 2a pops the next location (i, j) off of the stack. Line 2b makes the output pixel value at (i, j) white. Line 2c examines the eight pixels adjacent to (i, j). Line (2ci) is an "if statement," and if the adjacent input pixel (l, φ) is white, but the output pixel (l, φ) is black, line 2c adds the location) (l, φ) to the stack. Line 2d return to line 2 to continue the while loop (if the stack remains empty).

This algorithm will set to white all output-pixel locations which can be connected to the input pixel's location by a continuous path of white input pixels. The left boundary of the drop is found by stepping through each row of pixels from the left edge until the algorithm hits a white pixel. The right boundary is found by stepping from the right edge of the image until it hits a white pixel. The first row where it is possible to step from the left edge to the right edge without hitting a white pixel is where the drop is considered to end.

The pseudo code shown in FIG. 37 is a one-pass version of a connected-component labeling algorithm. However, other connected-component labeling algorithms or other suitable algorithms may be used to determine which pixels correspond to the drop.

Act 212 of FIG. 28 performs a rotation operation on the subset of pixels. Act 213 estimates a volume of the drop within the drip chamber by counting the number of pixels within the rotated subset of pixels. The total number of pixels within the 3-D version of the drop is counted; and because each pixel corresponds to a distance, the number of pixels may be used to estimate the volume of the drop.

Imaging System Optics

FIGS. 38-42 facilitate the following description of the optics of an imaging system disclosed herein. For example, an image sensor disclosed herein may be an image sensor cube manufactured by OmniVision of 4275 Burton Drive, Santa Clara, Calif. 95054; and, for example, the image sensor cube may be one manufactured for phone image sensor applications. In some embodiments of the present disclosure, an image sensor disclosed herein may use a fixed focus and have a depth of field ("DOF") from 15 centimeters to infinity.

The image sensor may have the blur circle of a point imaged in the range of the image sensor entirely contained within the area of a single pixel. The focal length of the image-sensor lens may be 1.15 millimeters, the F# may be 3.0, and the aperture of the lens of the image sensor may be 0.3833 millimeter. A first order approximation of the optical system of one or more of the image sensors may be made using matrix equations, where every ray, r, is represented as the vector described in Equation (25) as follows:

$$r = \left\{ \begin{array}{c} h \\ \theta \end{array} \right\}. \tag{25}$$

Figure 38:
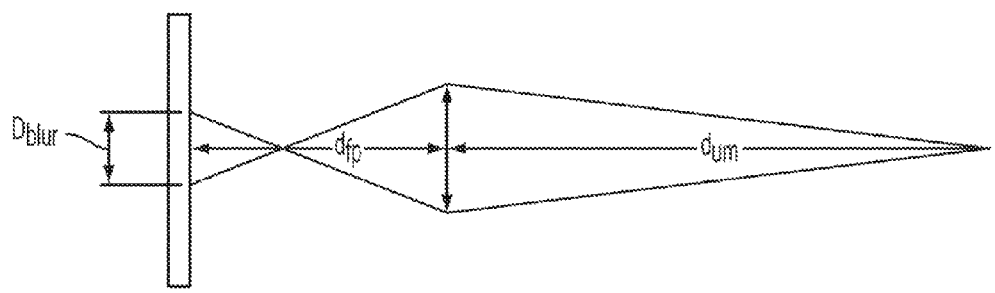
FIG. 38 shows a ray diagram illustrating the diameter of a blur circle to illustrate aspects of an image sensor of an imaging system disclosed herein in accordance with an embodiment of the present disclosure.

In Equation (25) above, h is the height of the ray at the entrance to the image sensor, and θ is the angle of the ray. Referring to FIG. 38, when imaging a hypothetical point at a distance $d_{im}$ from the lens of one of the image sensors (which has focal length f) and the lens is a distance $d_{fp}$ from the focal plane, the corresponding matrix, $M_{cam}$, describing the image sensor is described by Equation (26) as follows:

$$M_{cam} = \begin{bmatrix} 1 & d_{fp} \\ 0 & 1 \end{bmatrix} \cdot \begin{bmatrix} 1 & 0 \\ -\frac{1}{f} & 1 \end{bmatrix} \cdot \begin{bmatrix} 1 & d_{im} \\ 0 & 1 \end{bmatrix}. \quad (26)$$

To find the place on the focal plane, fp, where the ray strikes, a matrix multiplication as described in Equation (27) as follows may be used:

$$\begin{Bmatrix} h_{fp} \\ \theta_{fp} \end{Bmatrix} = M_{cam} \cdot \begin{Bmatrix} h_{im} \\ \theta_{im} \end{Bmatrix}. \quad (27)$$

As illustrated in FIG. 38, the diameter of the blur circle, $D_{blur}$, is shown as approximately the distance between the two points illustrated in FIG. 38. This distance is found by tracing rays from the point, $d_{im}$, away from the lens on the optical axis to the edges of the lens and then to the focal plane. These rays are given by the vectors shown in (28) as follows:

$$\begin{Bmatrix} 0 \\ \left(\pm \tan^{-1} \frac{D_{lens}}{2 * d_{im}}\right) \end{Bmatrix}. \quad (28)$$

Figure 39:
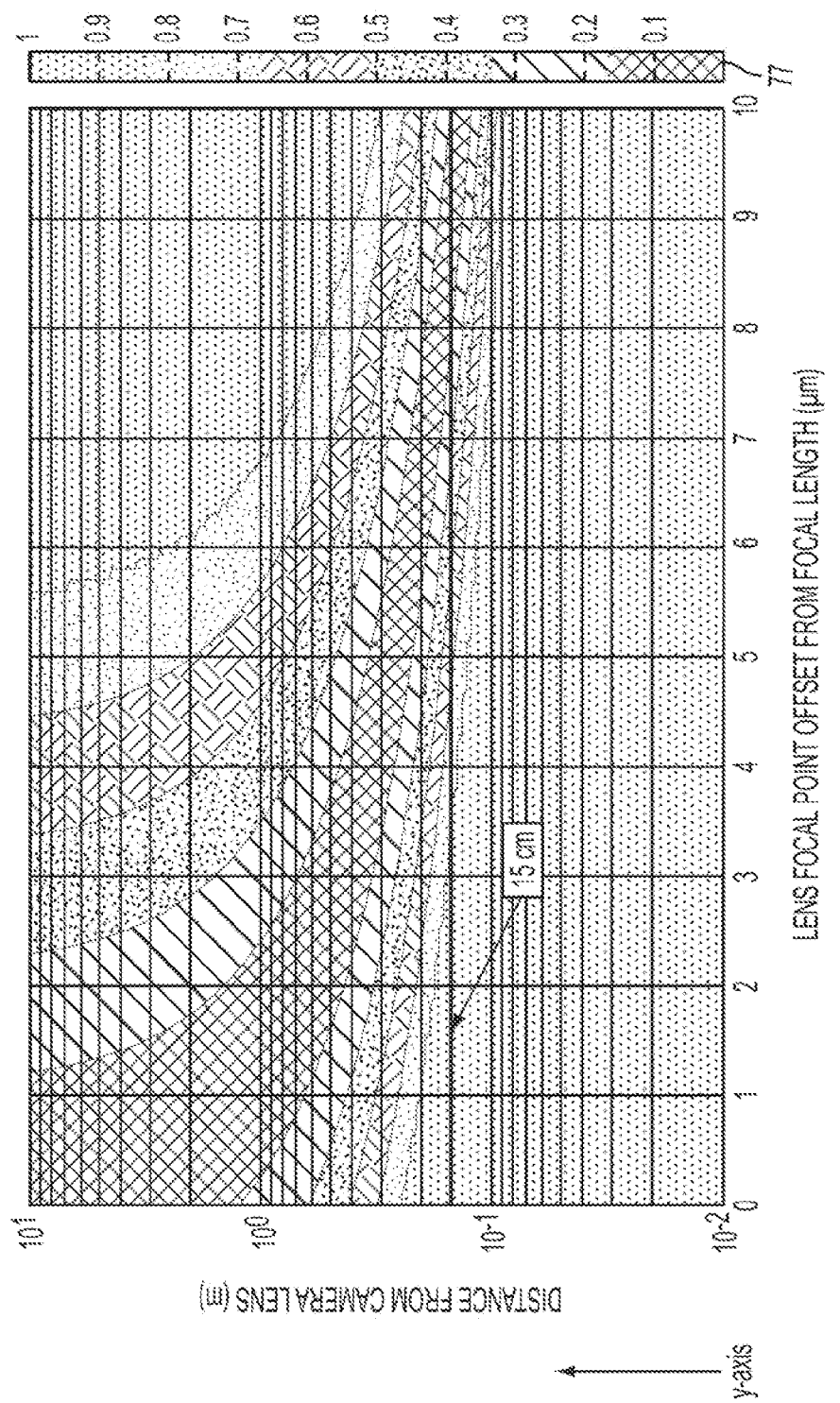
FIG. 39 is a graphic illustrating a calculated blur circle for a variety of lens-to-focal plane separations and lens-to-image separations for an image sensor of an imaging system disclosed herein in accordance with an embodiment of the present disclosure.

As shown in FIG. 39, the blur circle, $D_{blur}$, is calculated and shown for a variety of lens-to-focal plane separations and lens-to-image separations. A contour map 77 is also shown in FIG. 39. The x-axis shows the distance in microns between the focal plane and a point located a focal length away from the lens of an image sensor. The y-axis shows the distance in meters between the lens and the point being imaged. The values creating the contour map 77 is the blur size divided by the pixel size; therefore, anything about 1 or less is sufficient for imaging. As shown in FIG. 39, the focal plane is located a focal length and an additional 5 micrometers away from the lens.

The image sensor may utilize a second lens. For example, an image sensor may utilize a second lens to create a relatively larger depth of field and a relatively larger field of view. The depth of field utilizing two lenses can be calculated using the same analysis as above, but with the optical matrix modified to accommodate for the second lens and the additional distances, which is shown in Equation (29) as follows:

$$M_{sys} = \begin{bmatrix} 1 & d_{fp} \\ 0 & 1 \end{bmatrix} \cdot \begin{bmatrix} 1 & 0 \\ -\frac{1}{f_{cam}} & 1 \end{bmatrix} \cdot \begin{bmatrix} 1 & d_{lens} \\ 0 & 1 \end{bmatrix} \cdot \begin{bmatrix} 1 & 0 \\ -\frac{1}{f_{lens}} & 1 \end{bmatrix} \cdot \begin{bmatrix} 1 & d_{im} \\ 0 & 1 \end{bmatrix}. \quad (29)$$

Figure 40:
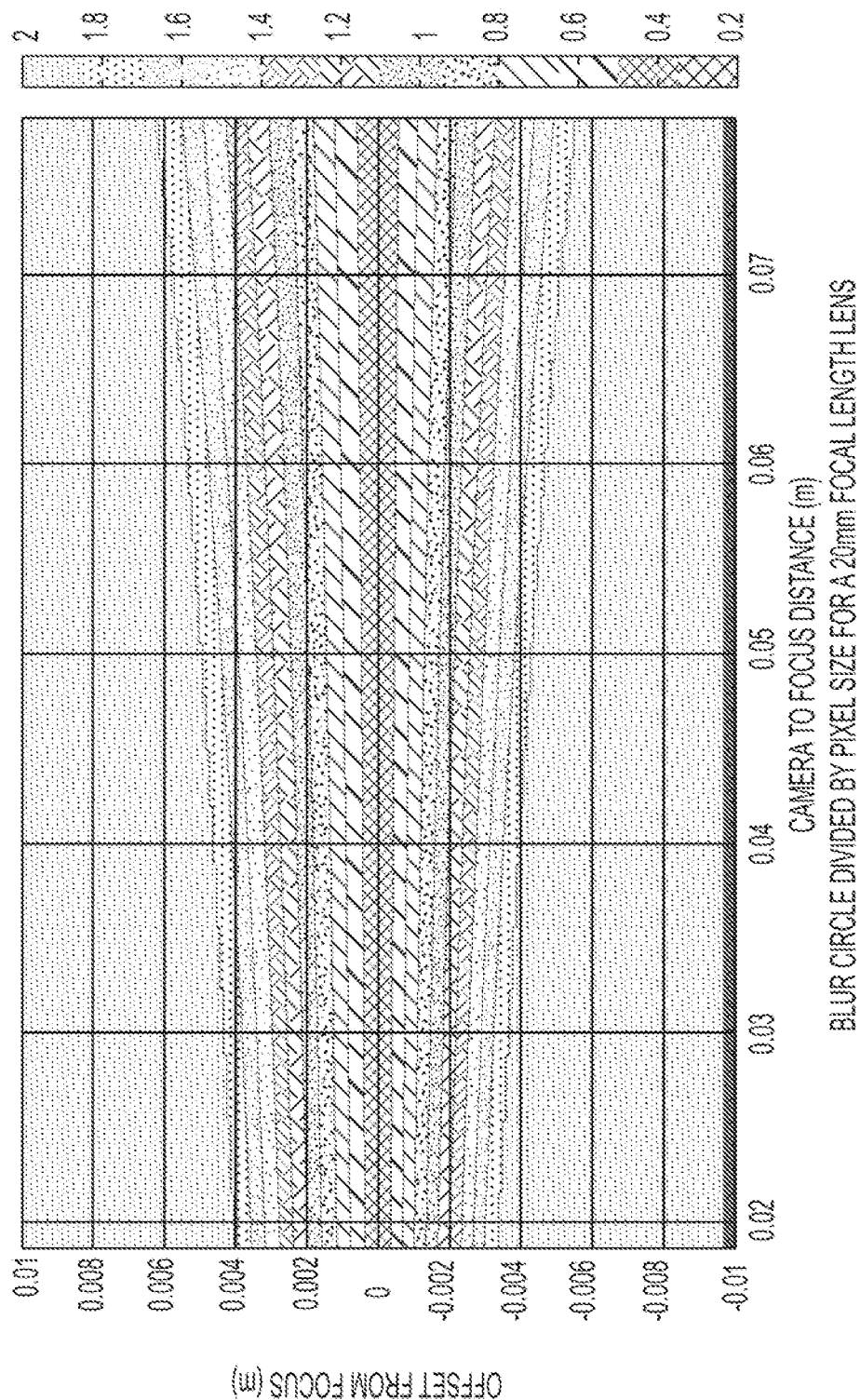
FIG. 40 is a graphic illustrating a blur circle divided by a pixel size when a 20 millimeter focal length lens of an image sensor of an imaging system disclosed herein is used in accordance with an embodiment of the present disclosure.
Figure 41:
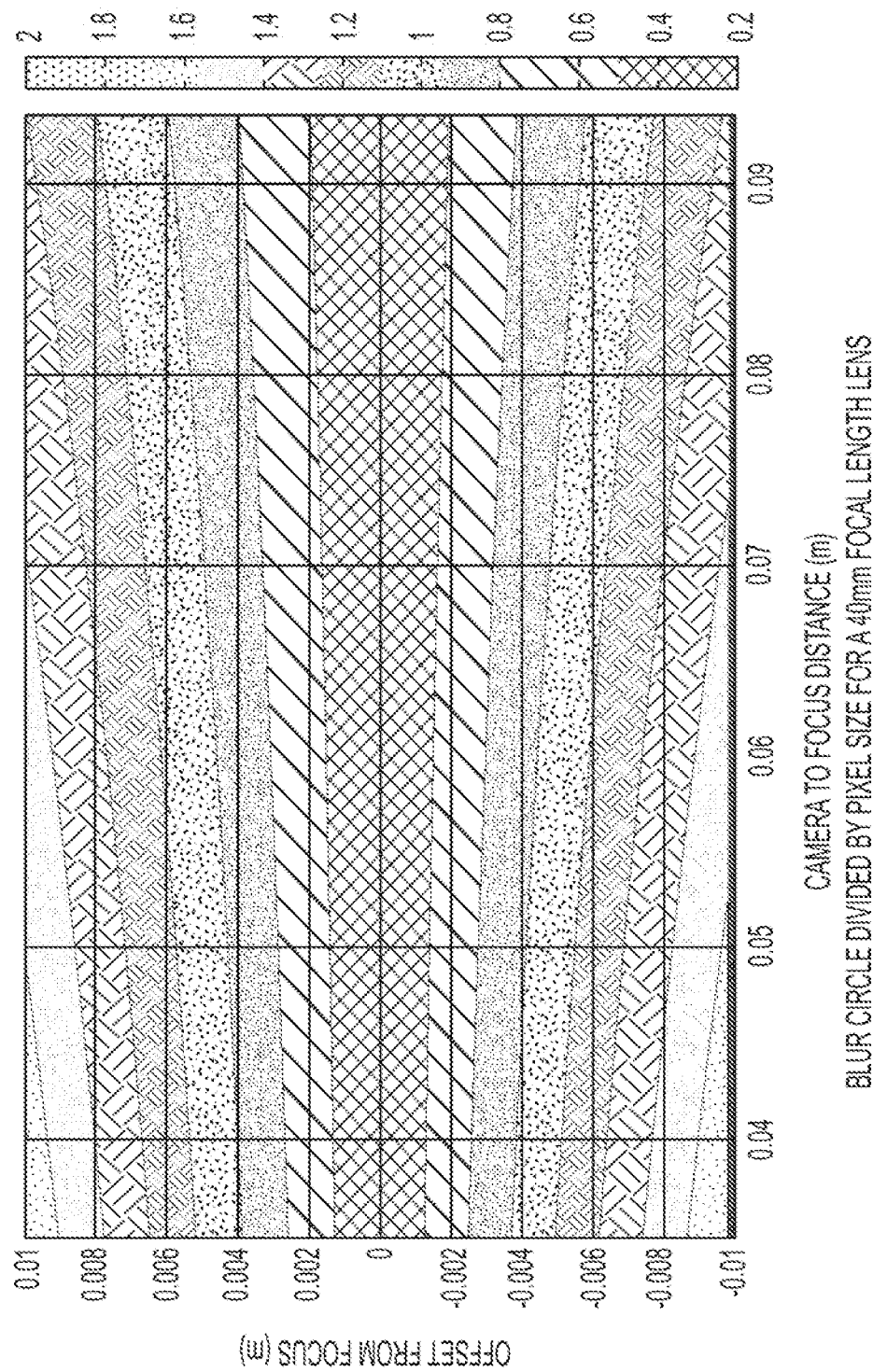
FIG. 41 is a graphic illustrating a blur circle divided by a pixel size when a 40 millimeter focal length lens of an image sensor of an imaging system disclosed herein is used in accordance with an embodiment of the present disclosure.

FIGS. 40 and 41 illustrate the field changes with the separation between the lens and the image sensor and the corresponding change in the focus of the image sensor. FIGS. 40 and 41 show the blur circle divided by the pixel size. FIG. 40 shows the blur circle divided by pixel size when a 20 millimeter focal-length lens is used. FIG. 41 shows the blur circle divided by pixel size when a 40 millimeter focal length lens is used. The corresponding fields of view about the optical axis for the corners of the two configurations of FIGS. 40 and 41 are shown in the table in FIG. 42.

As shown in FIG. 42, in some embodiments, the image sensor may utilize a 40 mm to 60 mm focal-length lens; this configuration may include placing an image sensor about 2 inches from the focus. In other embodiments of the present disclosure, other configurations may be used including those not shown in FIG. 42.

For example, the following analysis shows how the depth of field can be set for an image sensor using a lens of focal length, f, a distance, z, from the focal plane, and a distance, d, from a point in space; a matrix of the system is shown in Equation (30) as follows:

$$M = \begin{bmatrix} 1 & z \\ 0 & 1 \end{bmatrix} \cdot \begin{bmatrix} 1 & 0 \\ -\frac{1}{f} & 1 \end{bmatrix} \cdot \begin{bmatrix} 1 & d \\ 0 & 1 \end{bmatrix}. \quad (30)$$

Equation (30) reduces to Equation (31) as follows:

$$M = \begin{bmatrix} 1 & z \\ 0 & 1 \end{bmatrix} \cdot \begin{bmatrix} 1 & d \\ -\frac{1}{f} & 1 - \frac{d}{f} \end{bmatrix}. \quad (31)$$

Equation (31) reduces to Equation (32) as follows:

$$M = \begin{bmatrix} 1 - \frac{z}{f} & d + z - \frac{dz}{f} \\ -\frac{1}{f} & 1 - \frac{d}{f} \end{bmatrix}. \quad (32)$$

Considering the on-axis points, all of the heights will be zero. The point on the focal plane where different rays will strike is given by Equation (33) as follows:

$$\left(d + z - \frac{dz}{f}\right)\theta. \quad (33)$$

As shown above in (33), θ is the angle of the ray. The point in perfect focus is given by the lens maker's equation given in Equation (34) as follows:

$$\frac{1}{f} = \frac{1}{z} + \frac{1}{d}. \quad (34)$$

Equation (34) may be rearranged to derive Equation (35) as follows:

$$d = \frac{1}{\frac{1}{f} - \frac{1}{z}} = \frac{fz}{z - f}. \quad (35)$$

Inserting d from Equation (35) into Equation (33) to show the striking point results in Equation (36) as follows:

$$\left[\frac{fz}{z-f} + z - \frac{\frac{fz}{z-f}z}{f}\right]\theta = \frac{f^2z + fz^2 - f^2z - fz^2}{f(z-f)}\theta = 0. \quad (36)$$

All rays leaving this point strike the focal plane at the optical axis. As shown in Equation (37), the situation when the image sensor is shifted by a distance δ from the focus is described as follows:

$$\left[\frac{fz}{z-f} + \delta + z - \frac{\left[\frac{fz}{z-f} + \delta\right]z}{f}\right]\theta = \quad (37)$$

$$\frac{f^2z + fz\delta - f^2\delta + fz^2 - f^2z - fz^2 - \delta z^2 + f\delta z}{f(z-f)}\theta =$$

$$\frac{fz - f^2 - z^2 + fz}{f(z-f)}\delta\theta = -\frac{(z-f)^2}{f(z-f)}\delta\theta = \frac{f-z}{f}\delta\theta.$$

Equation (37) shows that by properly positioning the lens of the image sensor with respect to the focal plane, we can change the depth of field. Additionally, the spot size depends upon the magnitude of the angle θ. This angle depends linearly on the aperture of the vision system created by the image sensor.

Additionally or alternatively, in accordance with some embodiments of the present disclosure, an image sensor may be implemented by adjusting for various parameters, including: the distance to the focus as it affects compactness, alignment, and sensitivity of the vision system to the environment; the field of view of the system; and the lens-focal plane separation as it affects the tolerances on alignment of the system and the sensitivity of the system to the environment.

Embodiments of the Flow Meter with or without Valves Connected Thereto

Figure 44:
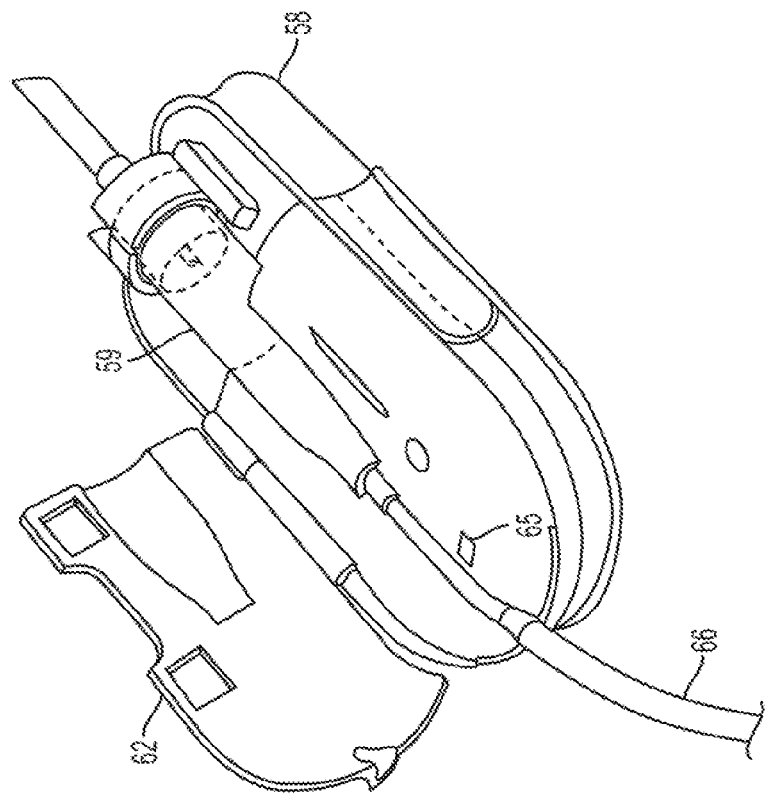
FIG. 44 shows the flow meter and drip chamber of FIG. 43 with the door open in accordance with an embodiment of the present disclosure.
Figure 43:
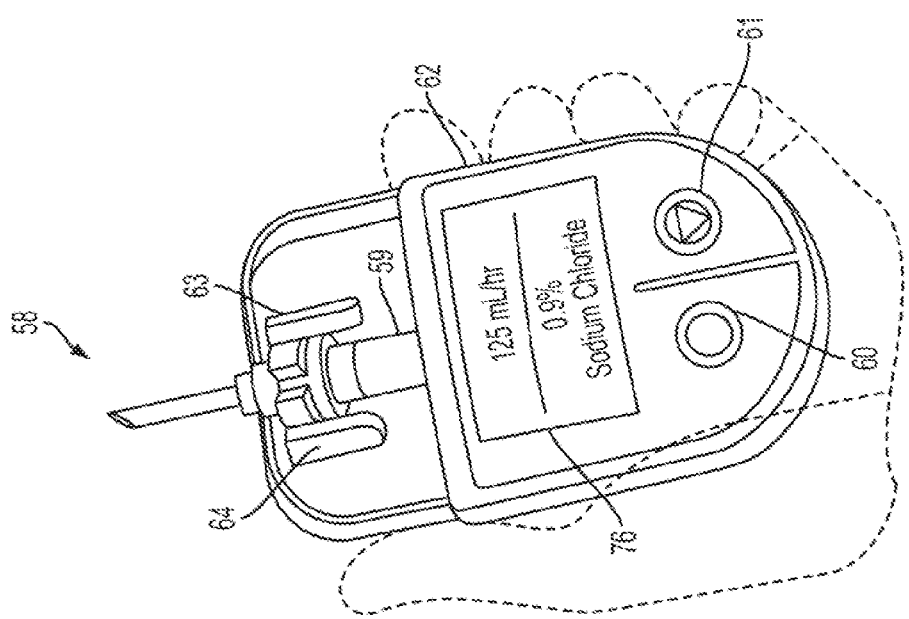
FIG. 43 shows a flow meter coupled to a drip chamber in accordance with an embodiment of the present disclosure.

Referring to the drawings, FIGS. 43 and 44 show a flow meter 58 coupled to a drip chamber 59. As described infra, the flow meter 58 may optionally include a free flow detector component 12 (see FIG. 1) in accordance with an embodiment of the present disclosure. Additionally, alternatively, or optionally, the flow meter 58 may include a flow rate estimator component 13 (see FIG. 1) in accordance with some embodiments of the present disclosure. FIG. 43 shows the flow meter 58 with a shut door 62, and FIG. 44 shows the flow meter 58 with an open door 62. The flow meter 58 may be the flow meter 7 of FIG. 1 with a valve 6 or with no valve. The flow meter 58 includes a start button 60 and a stop button 61. Additionally or optionally, the flow meter 58 may include a backup valve to stop fluid from flowing therethrough or may signal another valve to stop the fluid from flowing in response to error conditions.

The flow meter 58 optionally includes image sensors 63 and 64 that can estimate fluid flow and/or detect free flow conditions. Although the flow meter 58 includes two image sensors (e.g., 63 and 64), only one of the image sensors 63 and 64 may be used in some embodiments. The image sensors 63 and 64 can image a drop while being formed within the drip chamber 59 and estimate its size. The size of the drop may be used to estimate fluid flow through the drip chamber 59. For example, in some embodiments of the present disclosure, the image sensors 63 and 64 use an edge detection algorithm to estimate the outline of the size of a drop formed within the drip chamber 59; a processor therein (see processor 15 of FIG. 1, processor 75 of FIG. 5, or processor 90 of FIG. 6 or 8) may assume the outline is uniform from every angle of the drop and can estimate the drop's size from the outline. In the exemplary embodiment shown in FIGS. 43 and 44, the two image sensors 63 and 64 may average together the two outlines to estimate the drop's size. For example, the algorithm may average the measured outlines of the two image sensor 63 and 64 to determine the size of the drop. The image sensors 63 and 64 may use a reference background pattern to facilitate the recognition of the size of the drop as described herein.

In another embodiment of the present disclosure, the image sensors 63 and 64 image the fluid to determine if a free flow condition exists. The image sensors 63 and 64 may use a background pattern to determine if the fluid is freely flowing (i.e., drops are not forming and the fluid streams through the drip chamber 59). As previously mentioned, although the flow meter 58 includes two image sensors (e.g., 63 and 64), only one of the image sensors 64 and 64 may be used in some embodiments to determine if a free flow condition exists and/or to estimate the flow of fluid through the drip chamber.

Additionally or alternatively, in some embodiments of the present disclosure, another image sensor 65 monitors the fluid tube 66 to detect the presence of one or more bubbles within the fluid tube. In alternative embodiments, other bubble detectors may be used in place of the image sensor 65. In yet additional embodiments, no bubble detection is used in the flow meter 58.

Figure 45:
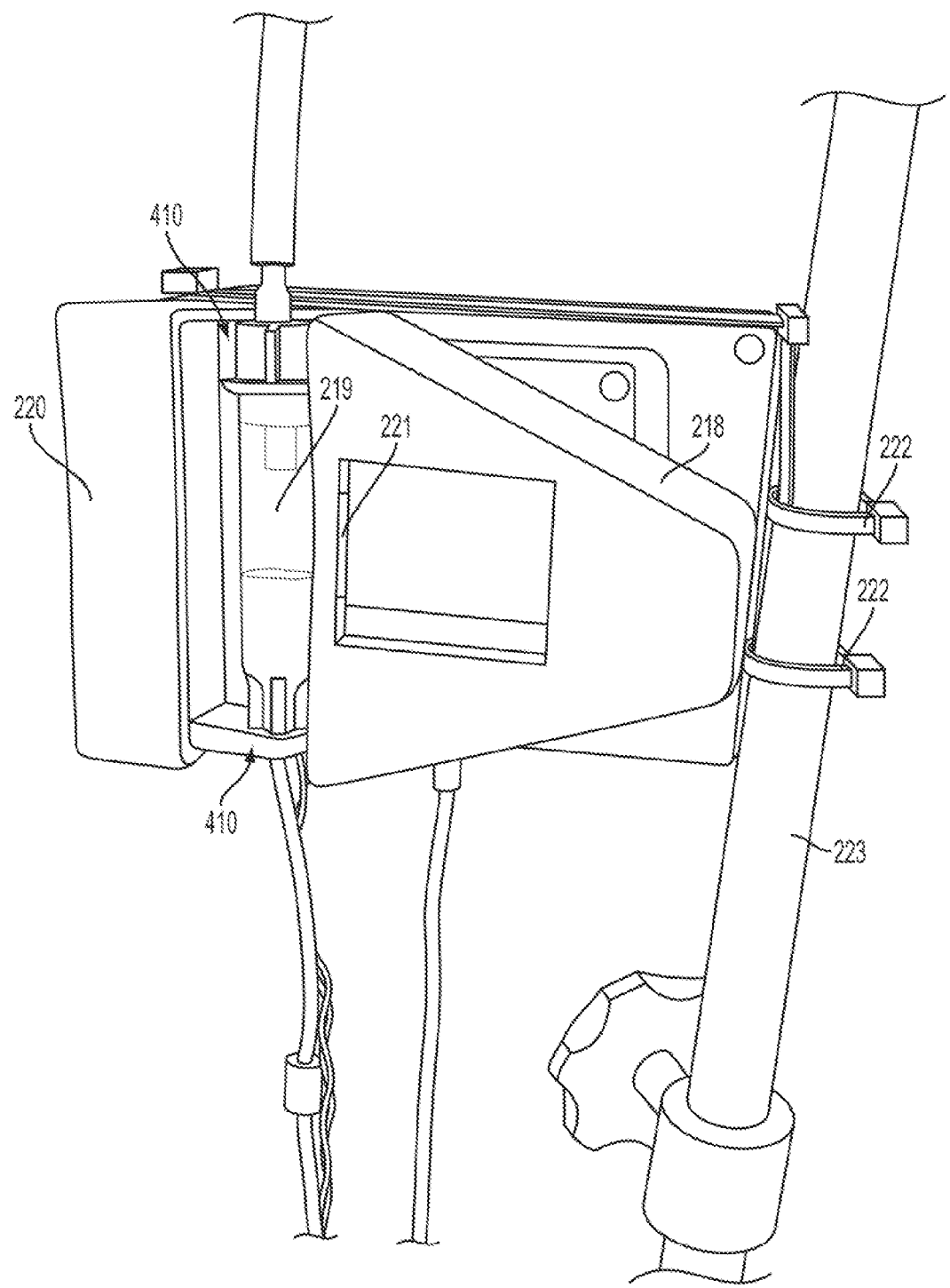
FIG. 45 shows a flow meter coupled to a drip chamber in accordance with an embodiment of the present disclosure.

Referring now to the drawings, FIG. 45 shows a flow meter 218 coupled to a drip chamber 219 in accordance with an embodiment of the present disclosure. The drip chamber 219 is secured to the flow meter 218 via couplers 410. A backlight 220 shines light through the drip chamber toward the image sensor 221 (shown in outlined form).

The flow meter 218 may electronically transmit a flow rate to a monitoring client 8 (see FIG. 1). Additionally or alternatively, in some optional embodiments, the flow meter 218 may include a display that displays a flow rate (e.g., a touch screen, an LED display, and the like). The flow meter 218 may be coupled to a pole 223 via clamps 222.

In some embodiments, the flow meter 218 may be coupled to an actuator which is coupled to a valve (not shown in FIG. 45) to form a closed-loop system (e.g., the control component 14 of FIG. 1, such as a PID, bang-bang, neural network, or fuzzy logic control system) to regulate the flow of fluid through the drip chamber 219.

The flow meter 218 may use any flow algorithm described herein and may include any imaging system described herein. Additionally or alternatively, the flow meter 218 may include a free flow detector component (e.g., the free flow detector component 12 of FIG. 1).

Figure 46:
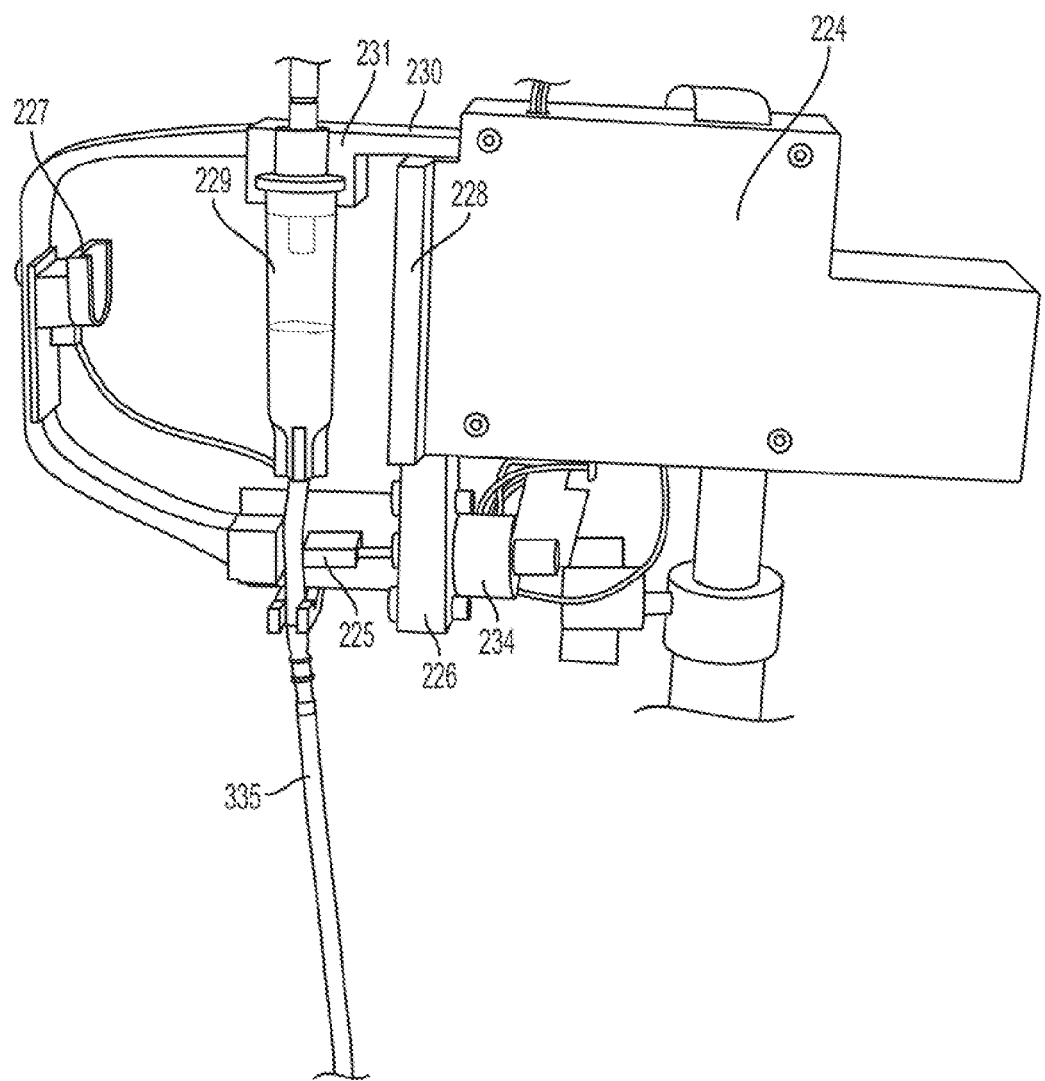
FIG. 46 shows a flow meter and a pinch valve coupled to the body of the flow meter to control the flow of fluid into a patient in accordance with an embodiment of the present disclosure.

FIG. 46 shows a flow meter 224 and a pinch valve 225 coupled to the body 226 of the flow meter 224 to control the flow of fluid to a patient in accordance with an embodiment of the present disclosure. The flow meter 224 includes an image sensor 227 and a backlight 228.

The image sensor 227 images a drip chamber 229 and can receive illumination from the backlight 228. The flow meter 224 includes a support member 230 coupled to a coupler 231 that couples the drip chamber 229 to the flow meter 224.

The flow meter 224 may implement any flow rate estimator described herein (e.g., the flow rate estimator component 13 of FIG. 1) and/or a free flow detector disclosed herein (e.g., the free flow detector component 12 of FIG. 1). The flow meter 224 may use the pinch valve 225 in a close-loop fashion to control the flow of fluid to a patient (e.g., using a control component 14 as shown in FIG. 1).

Figure 47:
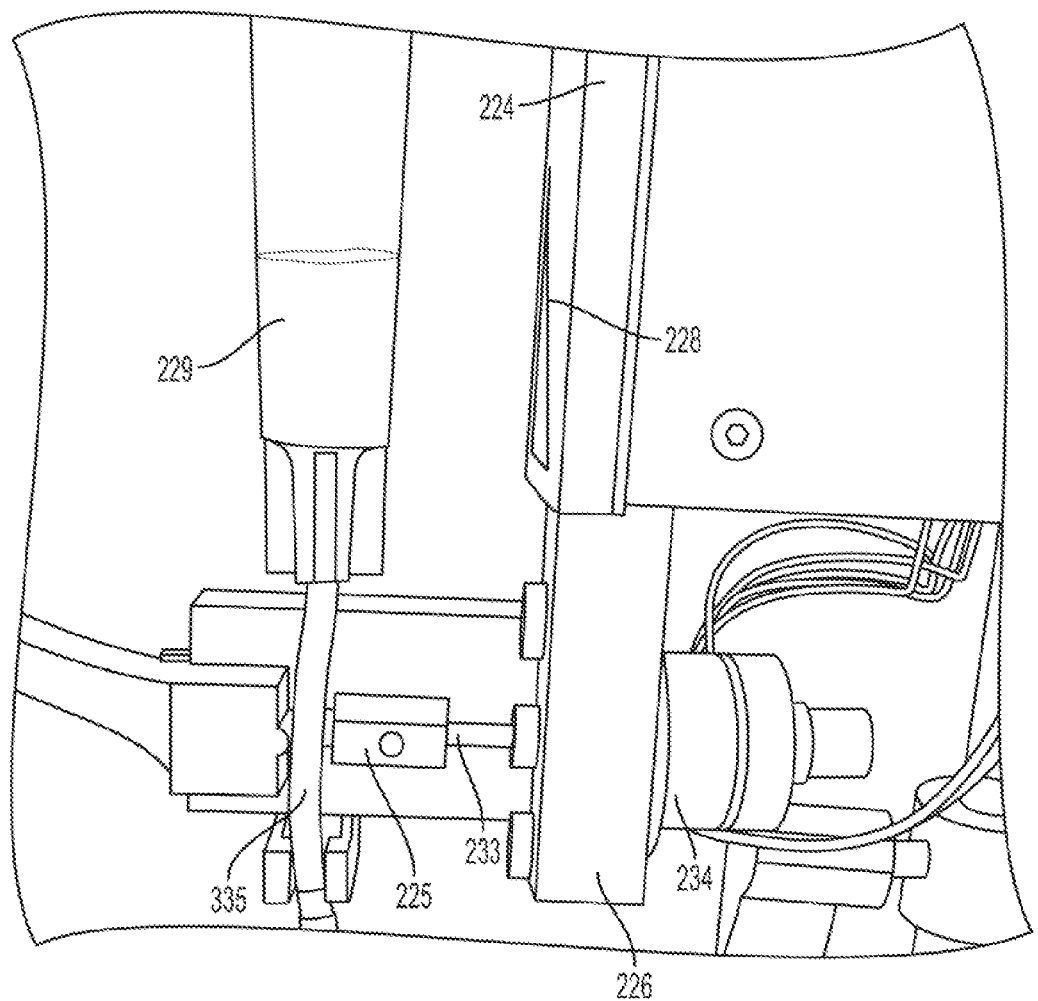
FIG. 47 shows a close-up view of the pinch valve that is coupled to the body of the flow meter of FIG. 46 in accordance with an embodiment of the present disclosure.

The pinch valve 225, as is more easily seen in FIG. 47, is coupled to a shaft 233 which is coupled to an actuator 234.

The actuator 234 may be a solenoid or any actuator that can move the pinch valve 225 toward a tube 335.

Figure 48:
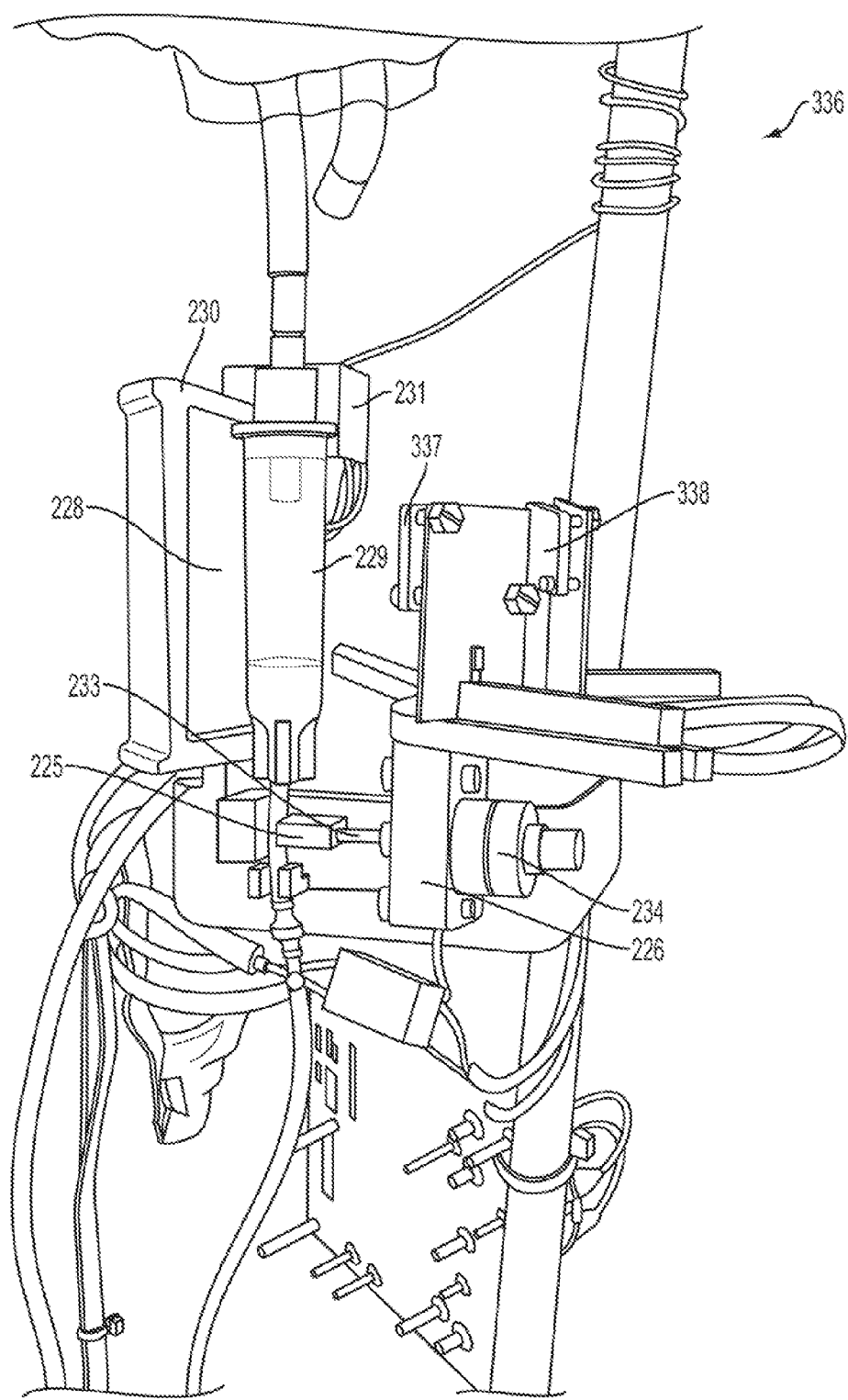
FIG. 48 shows a flow meter and a pinch valve wherein the flow meter includes two image sensors in accordance with another embodiment of the present disclosure.

FIG. 48 shows a flow meter 336 and a pinch valve 225 in accordance with an embodiment of the present disclosure. The flow meter includes two image sensors 337 and 338. The flow meter 336 may use the pinch valve 225 in a closed-loop feedback configuration. The flow meter 336 may implement a volume estimation algorithm described herein using both image sensors 337 and 338 to estimate the flow of fluid through the drip chamber 229. For example, the flow meter 336 may average the two volumes together for use in the feedback loop.

Figure 49:
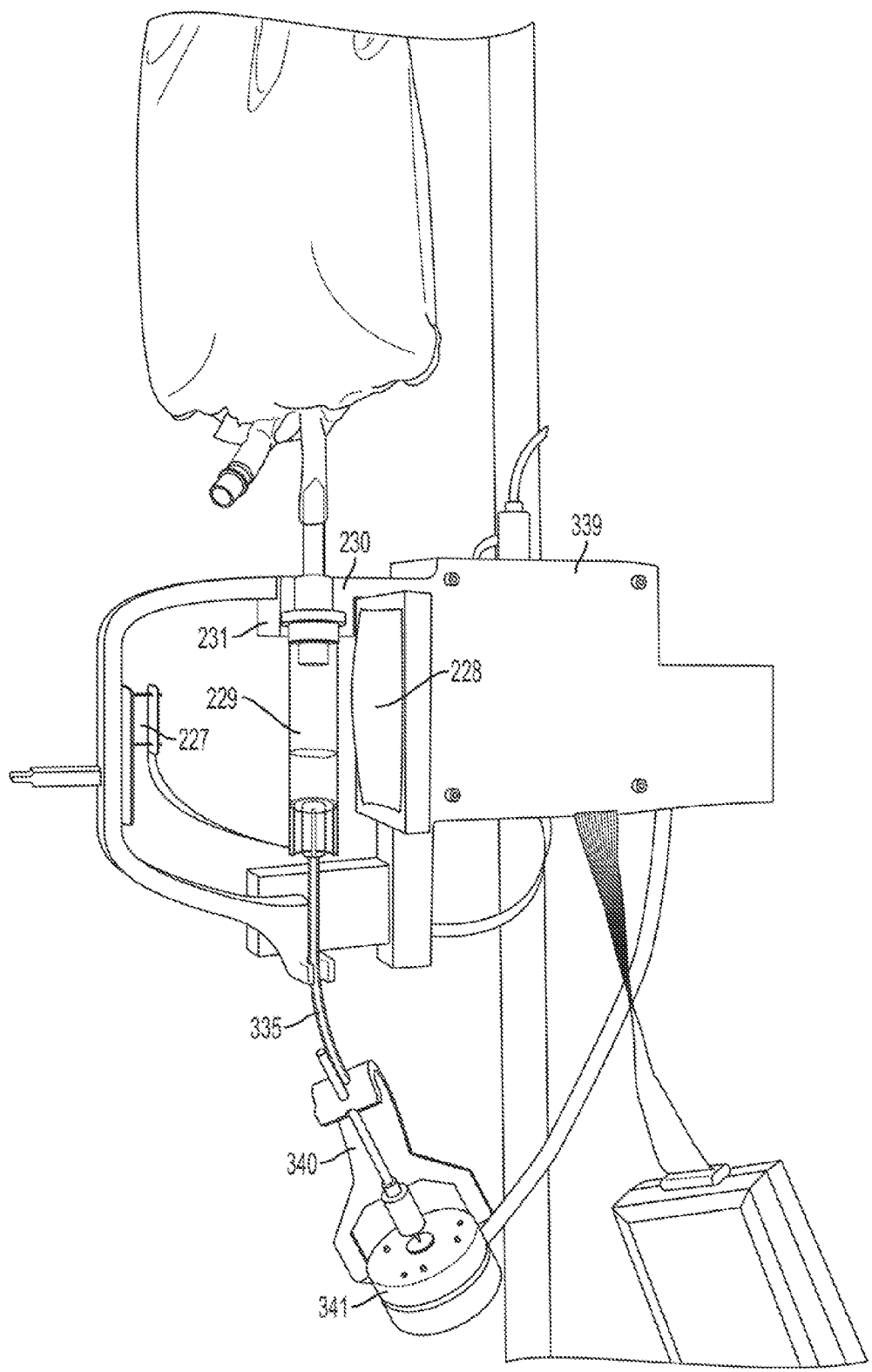
FIG. 49 shows a flow meter and a valve including two curved, elongated support members to control the flow of fluid into a patient in accordance with an embodiment of the present disclosure.

FIG. 49 shows a flow meter 339 and a valve 340 coupled to an actuator 341 to control the flow of fluid into a patient in accordance with an embodiment of the present disclosure. The flow meter 339 of FIG. 49 is similar to the flow meter 224 of FIG. 46; however, the flow meter 339 of FIG. 49 includes a valve 340 that has curved, elongated support members 342 and 343 (see FIGS. 50A-50B).

The flow meter 339 includes an image sensor 227 and a backlight 228. The image sensor 227 images a drip chamber 229 and can receive illumination from the backlight 228. The flow meter 339 includes a support member 230 coupled to a coupler 231 that couples the drip chamber 229 to the flow meter 339.

The flow meter 339 can implement any flow rate estimator described herein (e.g., the flow rate estimator component 13 of FIG. 1) and/or a free flow detector disclosed herein (e.g., the free flow detector component 12 of FIG. 1). The flow meter 339 may use the valve 340 in a close-loop fashion to control the flow of fluid into a patient (e.g., using the control component 14 of FIG. 1).

The flow meter 339 may actuate the actuator 341 to actuate the valve 340, which thereby regulates the fluid flowing through the IV tube 335 in a feedback (i.e., closed-loop) configuration using any control algorithm.

Figure 50A:
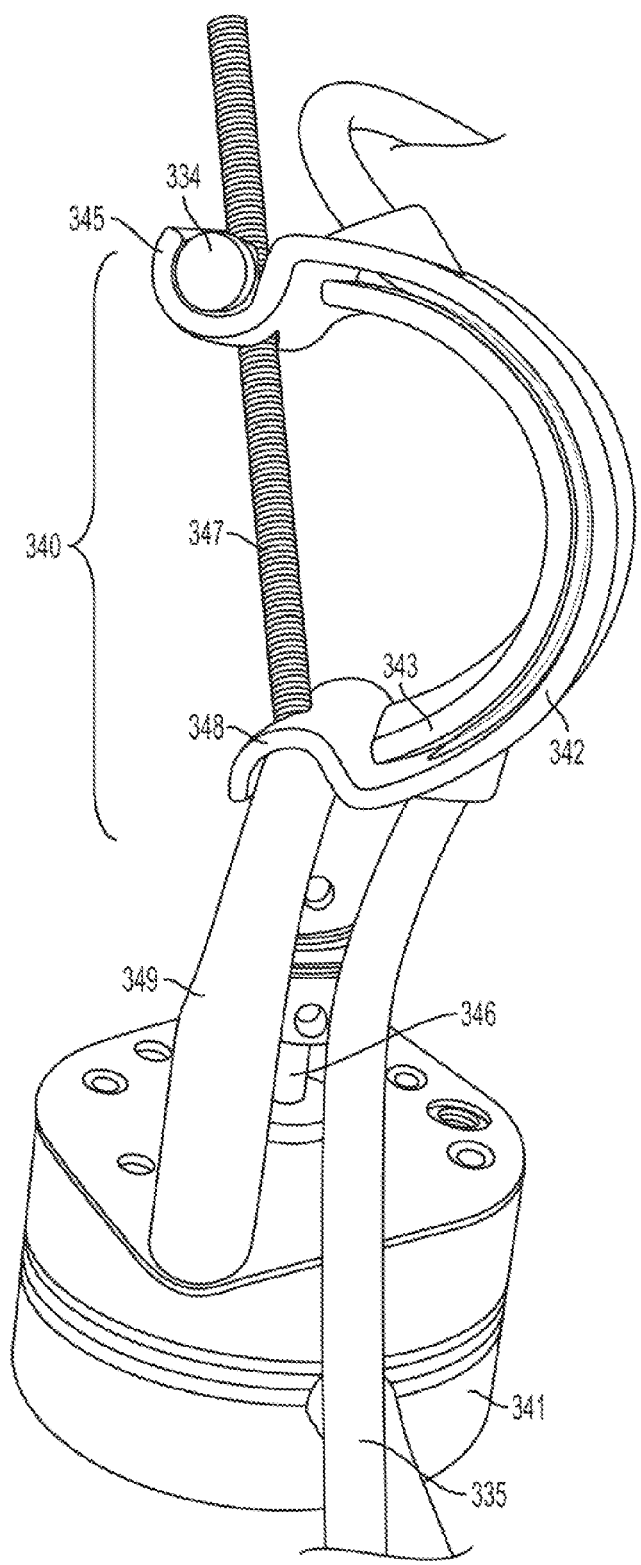
FIGS. 50A-50B show close-up views of the valve of FIG. 49 in accordance with an embodiment of the present disclosure.
Figure 50B:
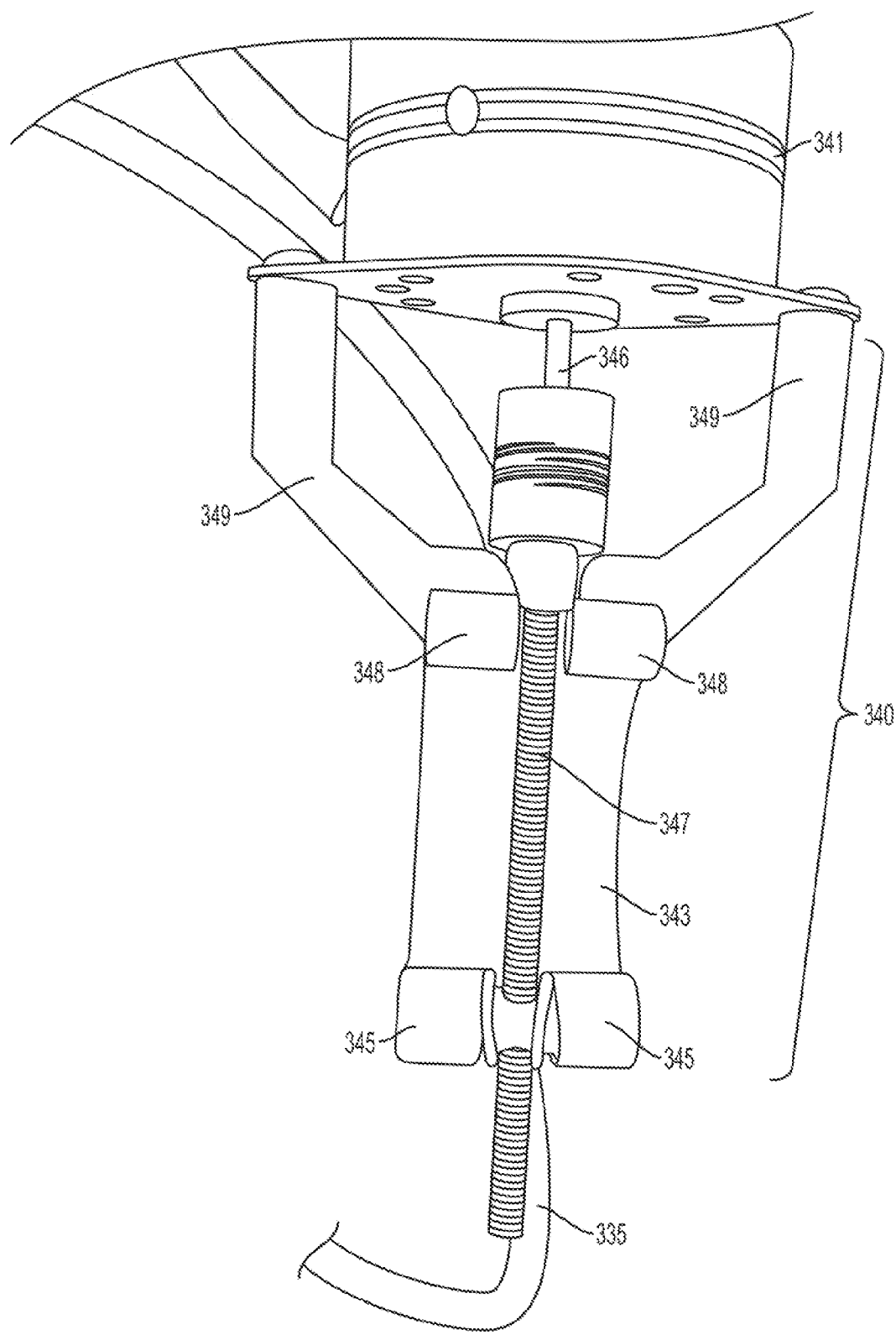

Referring now to FIGS. 50A-50B, which shows close-up views of the valve 340 of FIG. 49 in accordance with an embodiment of the present disclosure. The valve 340 includes an inner curved, elongated support member 343 and an outer curved, elongated support member 342. The tube 335 is positioned between the support members 342 and 343.

The inner support member 343 includes a barrel nut 344. The outer support member 342 is coupled to the barrel nut 344 via hooks 345. In some embodiments, the barrel nut 344 is not coupled to the valve 340 and the inner support member 342 includes a hole for the threaded rod or screw 347 to slide through. The outer support member 342 also has hooks 348 to secure it to a frame 349 of the actuator 341. The actuator 341 includes a shaft 346 coupled to a screw 347. As the actuator 341 rotates the shaft 346, the screw 347 can rotate to push the barrel nut 334 toward the actuator 341. That is, the hooks 345 and the barrel nut 334 move toward the hooks 348 and the frame 349 because the inner and outer support members 342 and 343 are flexible.

As the support members 342 and 343 are compressed, the tube 335 becomes compressed because it is positioned between the support members 342 and 343. Compression of the tube 335 restricts the flow of fluid through the tube 335. The valve 340 compresses a length of the tube 335 that is substantially greater than the diameter of the tube 335.

FIGS. 51A-51D show several views of a flow meter 350 with a monitoring client 358, a valve 352, a drip chamber 357, an IV bag 411, and a fluid tube 412 in accordance with an embodiment of the present disclosure. The flow meter 350 includes a receiving portion 351 to receive the valve 352. The valve 352 includes two curved, elongated support members 353 and 354.

The flow meter 350 includes an image sensor 355 and a backlight 356 that can monitor drops formed within the drip chamber 357. The flow meter 350 may use the image sensor 355 to implement a flow rate estimator algorithm described herein (e.g., the flow rate estimator component 13 of FIG. 1) and/or to implement a free flow detector disclosed herein (e.g., the free flow detector component 12 of FIG. 1).

The flow meter 350 includes a base 359 that can form a dock to receive the monitoring client 358. The monitoring client 358 may be a smart phone, or other electronic computing device (e.g., an Android-based device, an Iphone, a tablet, a PDA, and the like).

The monitoring client 358 may contain software therein to implement a free flow detector, a flow rate estimator, a control component, an exposure component, etc. (e.g., the free flow detector component 12, the flow rate estimator component 13, the control component 14, the exposure component 29 of FIG. 1) and may contain one or more transceivers (e.g., the transceiver 9). Additionally or alternatively, the base 359 of the flow meter 350 may implement these items.

For example, the flow meter 350 may implement a free flow detector, a flow rate estimator, a control component, an exposure component, etc. using internal software, hardware, electronics, and the like. The flow meter 350 may implement a closed-loop feedback system to regulate the fluid flowing to a patient by varying the fluid flowing through the valve 352.

Figure 51A:
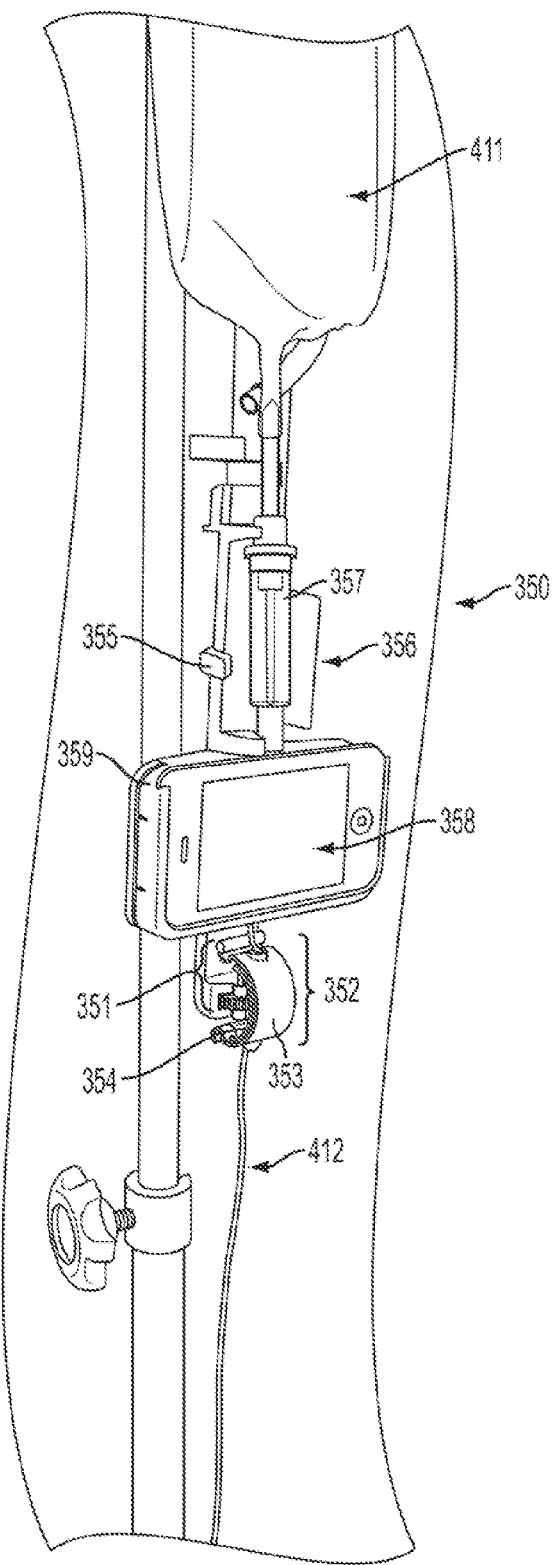
FIGS. 51A-51D show several views of a flow meter with a monitoring client, a valve, a drip chamber, an IV bag and a fluid tube wherein the flow meter includes a receiving portion to receive the valve in accordance with an embodiment of the present disclosure.
Figure 51B:
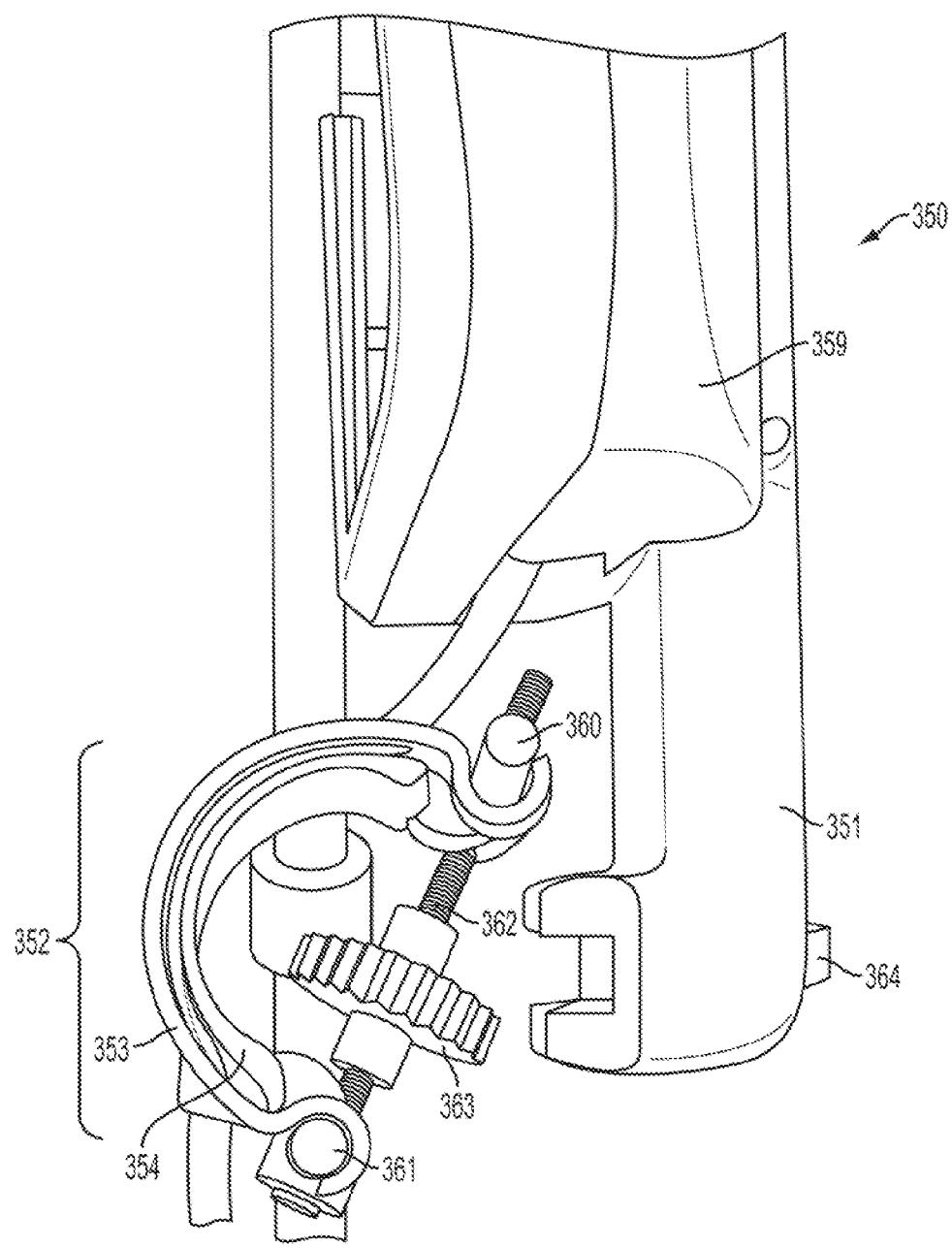

As is easily seen in FIG. 51B, the valve 352 includes an inner support member 354 and an outer support member 353. The inner support member 354 is coupled to a barrel nut 360 and to a barrel 361. In some embodiments, the barrel nut 360 is not coupled to the inner support member 354, and the inner support member 354 includes a hole for the threaded shaft 362 to slide through.

A threaded shaft 362 (e.g., a screw) spins freely within a bearing located within the barrel 361 and engages a threaded nut within the barrel nut 360 to push or pull the barrel nut 360 relative to the barrel 361 by rotation of the knob 363 (e.g., the actuator is a lead screw having a knob to actuate the lead screw.). The knob 363 may be manually rotated.

Figure 51C:
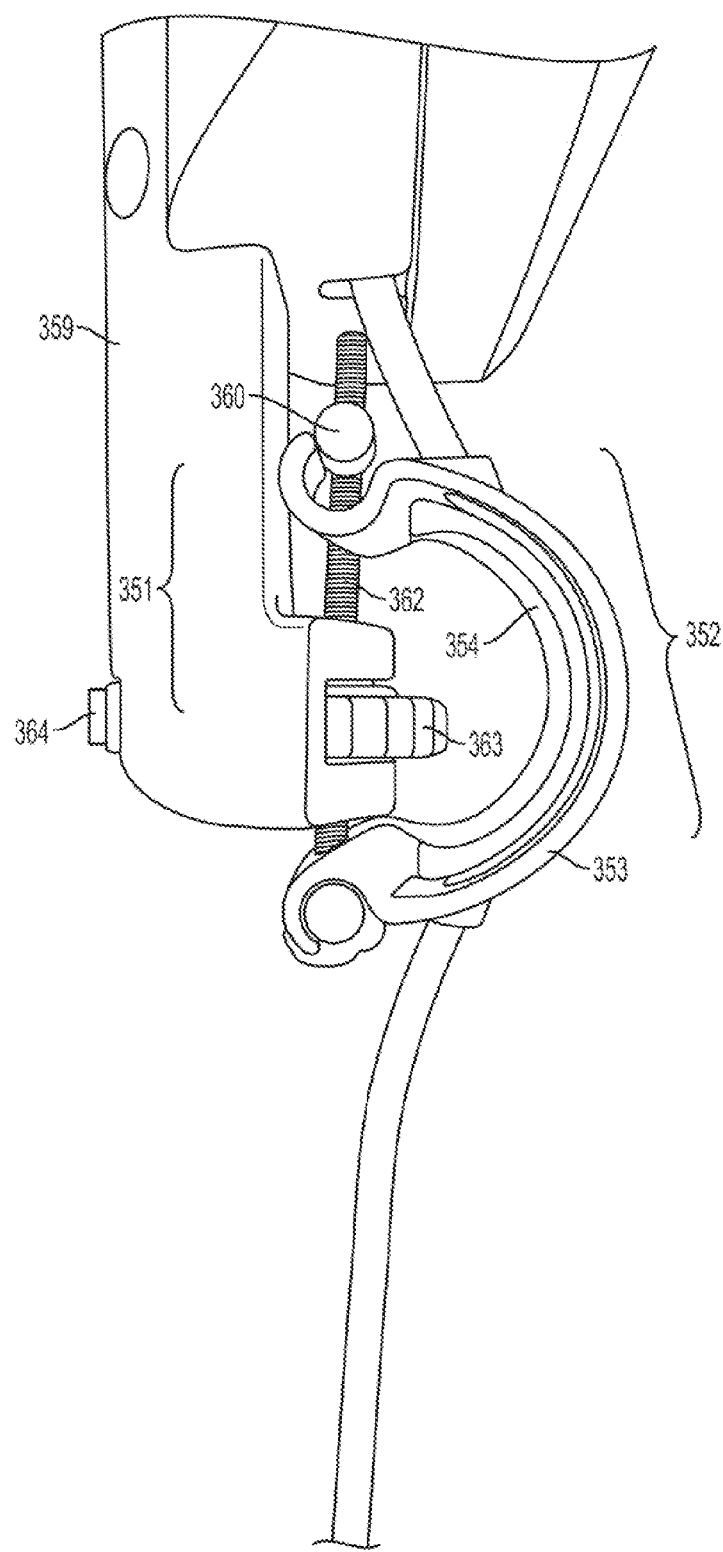
Figure 51D:
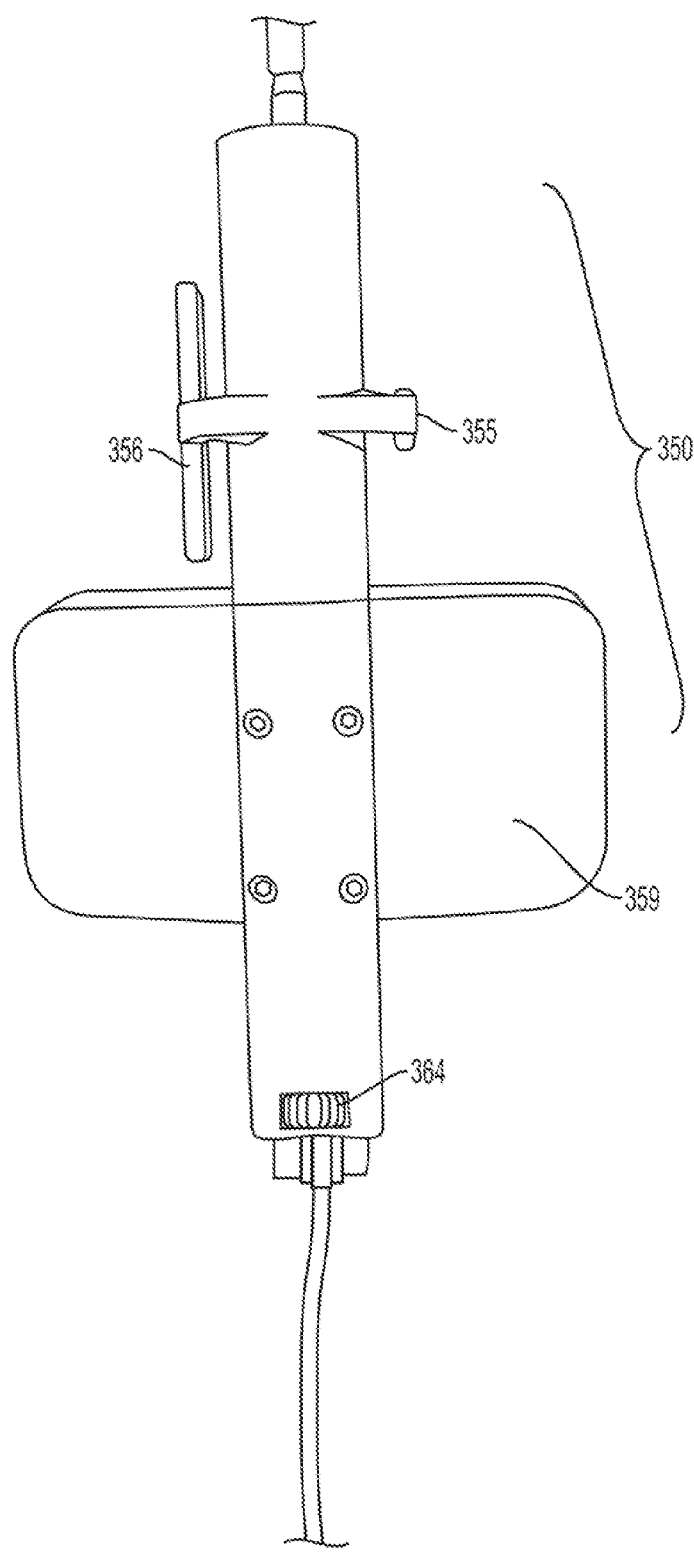

Additionally or alternatively, the valve 352 may be snapped into the receiving portion 351 which includes a rotating member 364 that engages the knob 363 within the receiving portion 351 (see FIG. 51C). The rotating member 364 engages the rotating knob 363 to actuate the valve 352. The rotating member 364 may be coupled to an electric motor which rotates the rotating member 364. The electric motor (not explicitly shown) may be controlled by the flow meter 350 in a closed-loop configuration to achieve a target flow rate of fluid flowing into a patient.

FIGS. 52A-52D show several views of another flow meter 365 with a valve 352, a drip chamber 357, and a fluid tube trench 413 having a receiving portion 351 to receive a valve 352 in accordance with an embodiment of the present disclosure. The flow meter 365 of FIGS. 52A-52D is similar to the flow meter 350 of FIGS. 51A-51D; however, the base 359 holds the monitoring client 358 in an "upright" position. Additionally, the receiving portion 351 is on an opposite side of the base 359 from the monitoring client 358 (see FIGS. 52B and 52C).

Figure 52A:
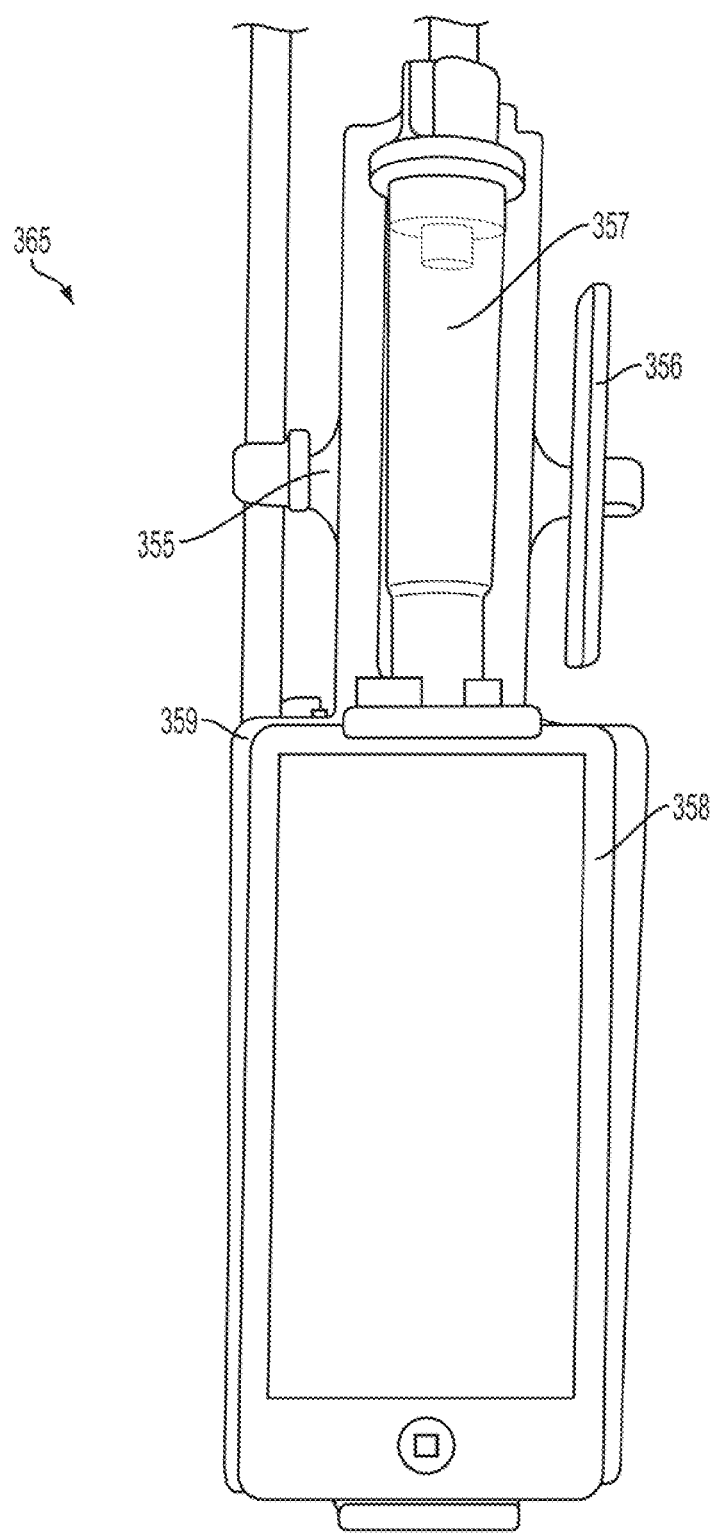
FIGS. 52A-52D show several views of another flow meter with a valve, a drip chamber, and a tube wherein the flow meter has a receiving portion to receive the valve in accordance with an embodiment of the present disclosure.
Figure 52B:
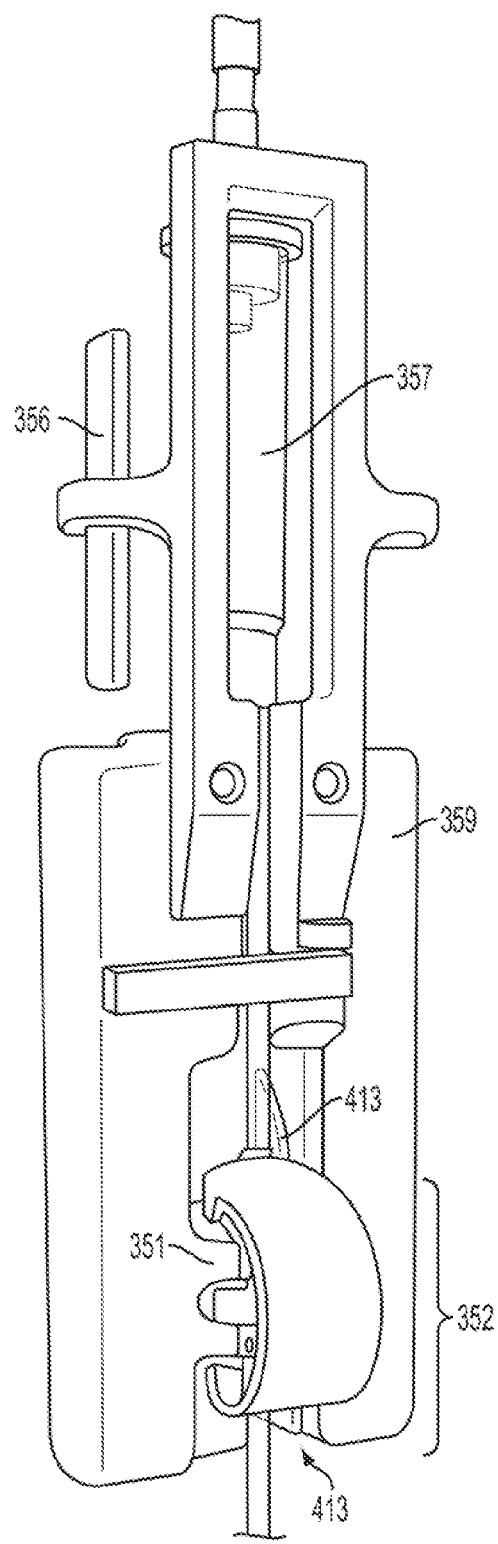
Figure 52C:
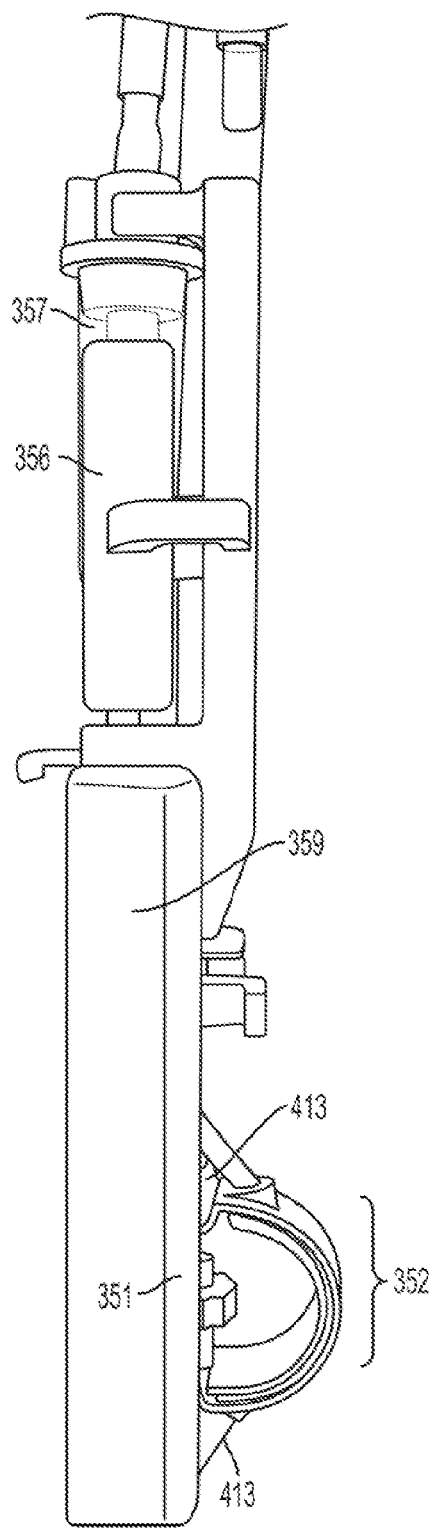
Figure 52D:
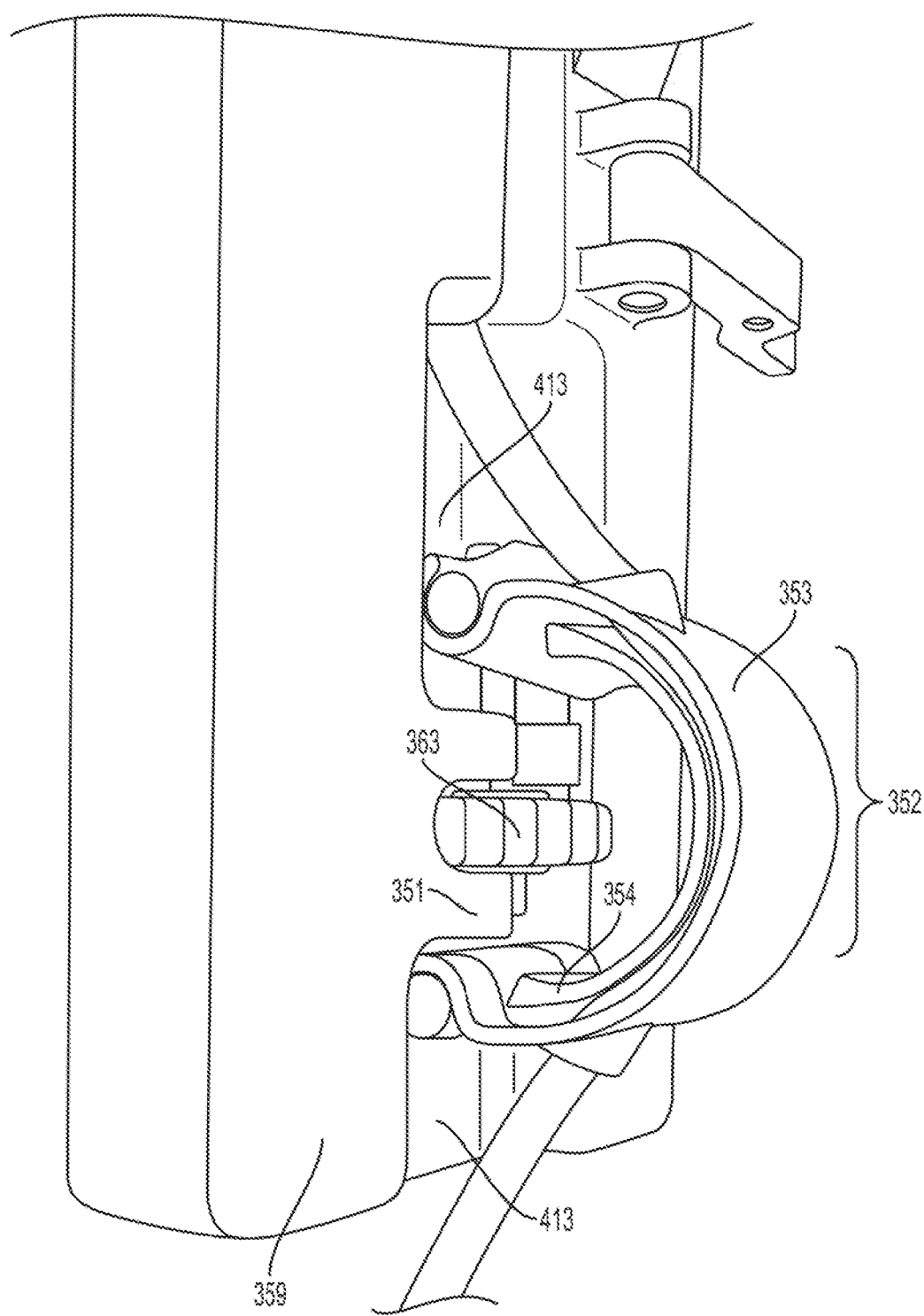

FIG. 52D shows a close-up view of the valve 352 engaging the receiving portion 351. The knob 363 engages a rotating member that is internal to the base 359 (not shown in FIG. 52D) that is coupled to a motor (also not shown in FIG. 52D).

Figure 53A:
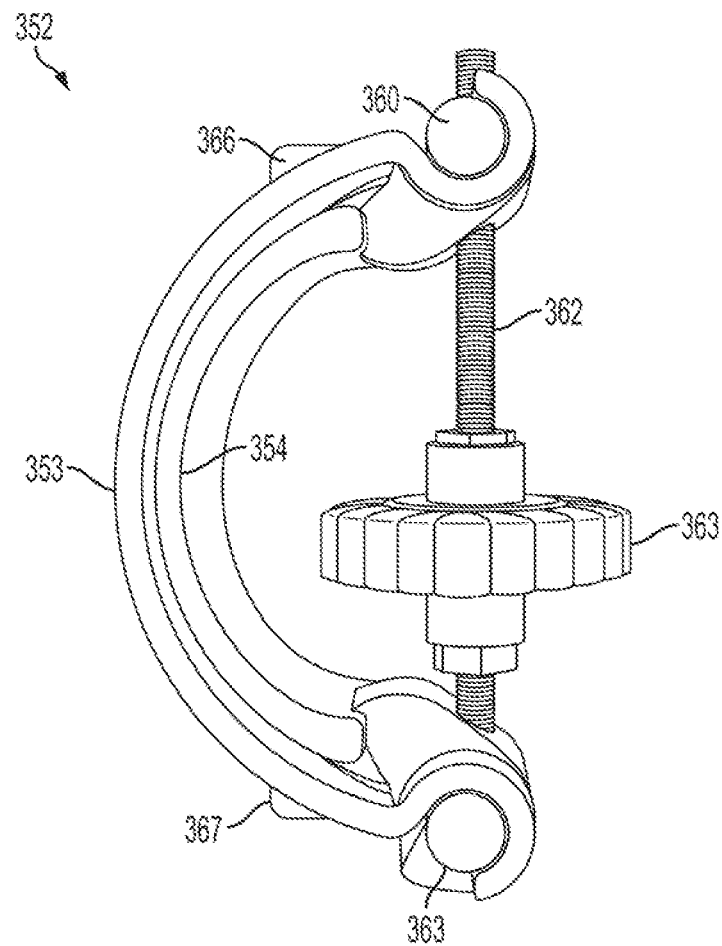
FIG. 53A shows another view of the valve of FIGS. 51A-51D and 52A-52D in accordance with an embodiment of the present disclosure.

FIG. 53A shows another view of the valve 352 of FIGS. 51A-51D and 52A-52D, and FIGS. 53B-53C show two exploded views of the valve of FIG. 53A in accordance with an embodiment of the present disclosure.

Figure 53B:
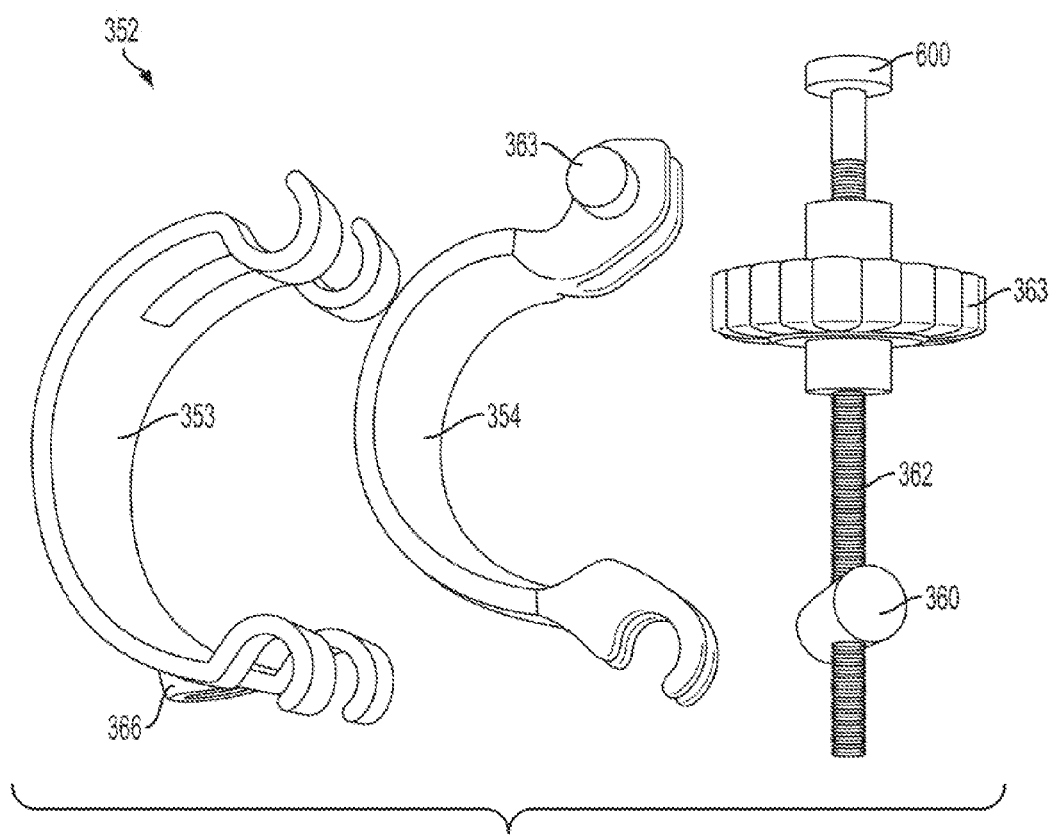
FIGS. 53B-53C show two exploded views of the valve of FIG. 53A in accordance with an embodiment of the present disclosure.
Figure 53C:
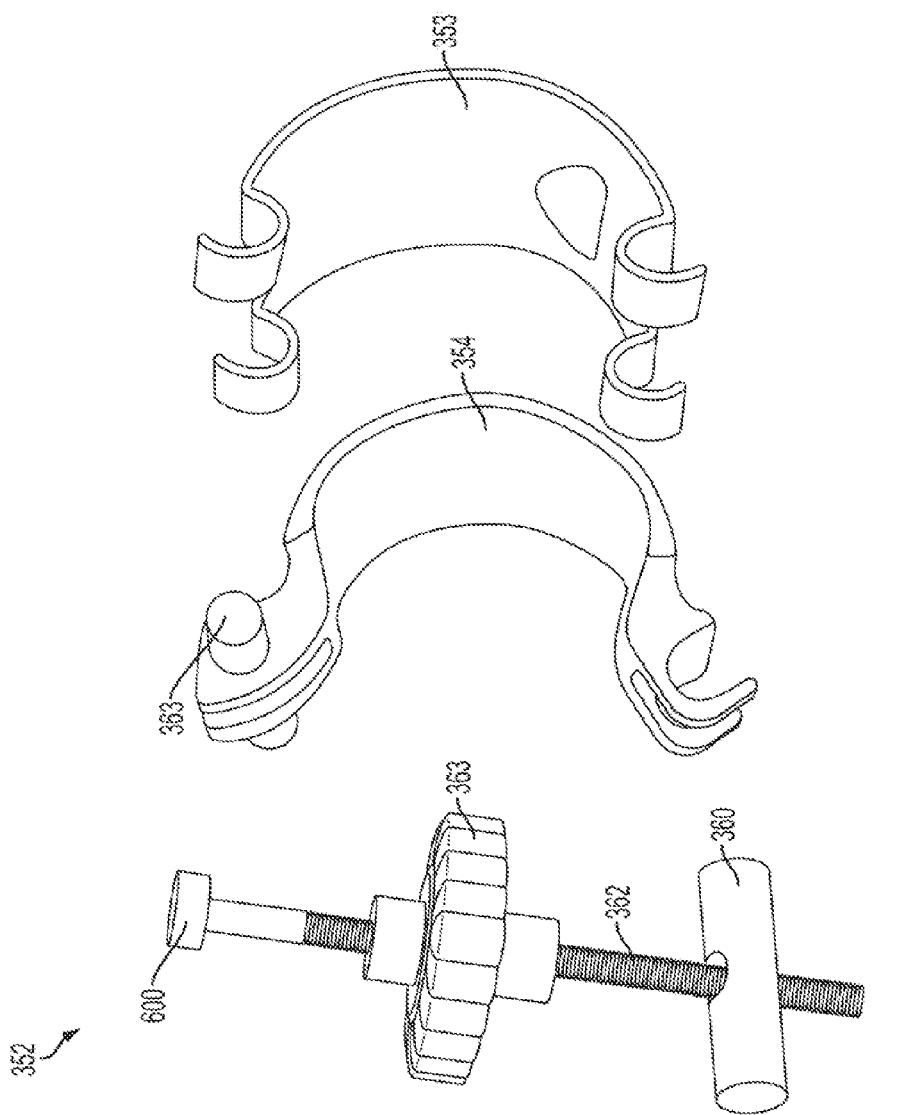

As shown in FIGS. 53A-53C, the valve 352 includes an inner support member 354 and outer support member 353. A tube may be inserted through holes 366 and 367 to position the tube between the support members 354 and 353.

Figure 54:
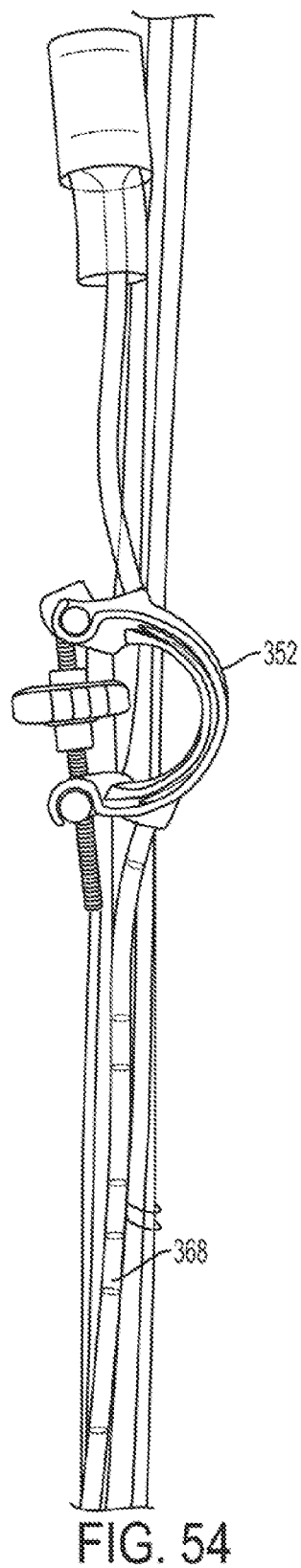
FIG. 54 shows the valve of FIG. 53 in manual use in accordance with an embodiment of the present disclosure.

The knob 363 may be turned to turn the screw 362. Rotation of the screw 362 causes the barrel nut 360 to move toward the partial barrel 363 to compress a tube positioned between the support members 353 and 354. The partial barrel 363 includes two sides, however, there is a space to hold the end 600 (e.g., the cap) of the screw 362 securely within the space (e.g., a complementary space). FIG. 54 shows the valve 352 in manual use and coupled to a tube 368.

Figure 55:
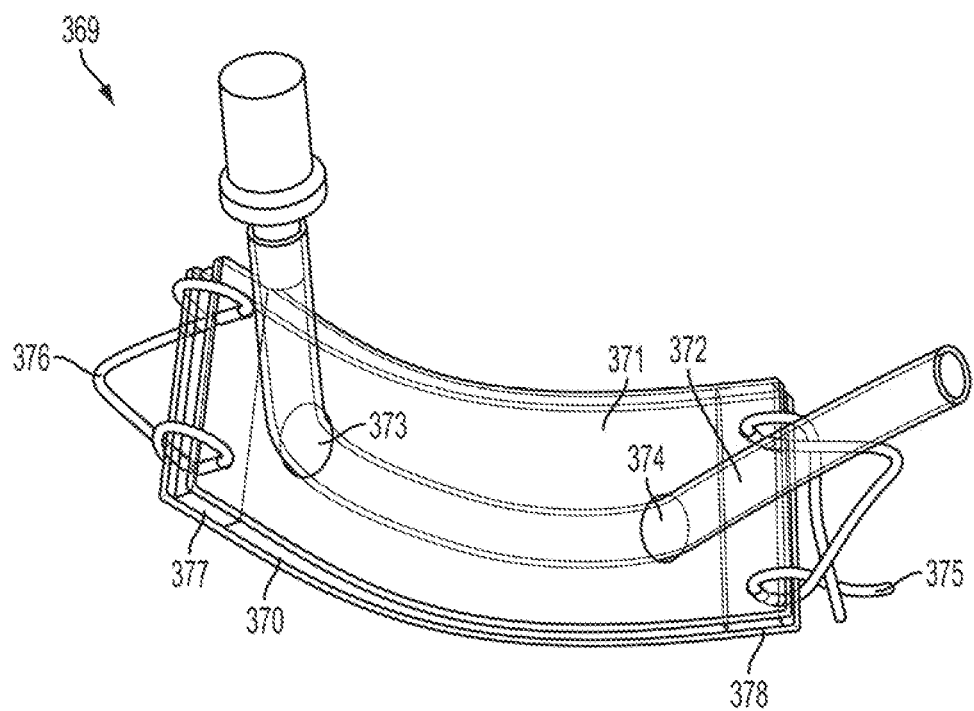
FIG. 55 shows a valve that includes two flexible members in accordance with an embodiment of the present disclosure.

FIG. 55 shows a valve 369 that includes two flexible members 370 and 371 in accordance with an embodiment of the present disclosure. The flexible members 370 and 371 may be two flexible sheets. The flexible member 371 may include holes 373 and 374 for a tube 372 to be positioned between the flexible members 370 and 371.

The flexible members 370 and 371 are coupled together via two connector members 377 and 378. The connector members 377 and 378 are coupled to coupling members 376 and 375, respectively.

Actuation of the valve 369 may be by a linear actuator that pulls the coupling members 375, 376 toward each other or away from each other. The linear actuator (not explicitly shown) may be a screw-type actuator, a piston actuator, or other actuator. In some embodiments, one of the coupling members 375 and 376 may be coupled to a stationary support while the actuator is coupled to the other one of the coupling members 375 and 376 and another stationary support for pulling the coupling members 375 and 376 together or apart.

Figure 56A:
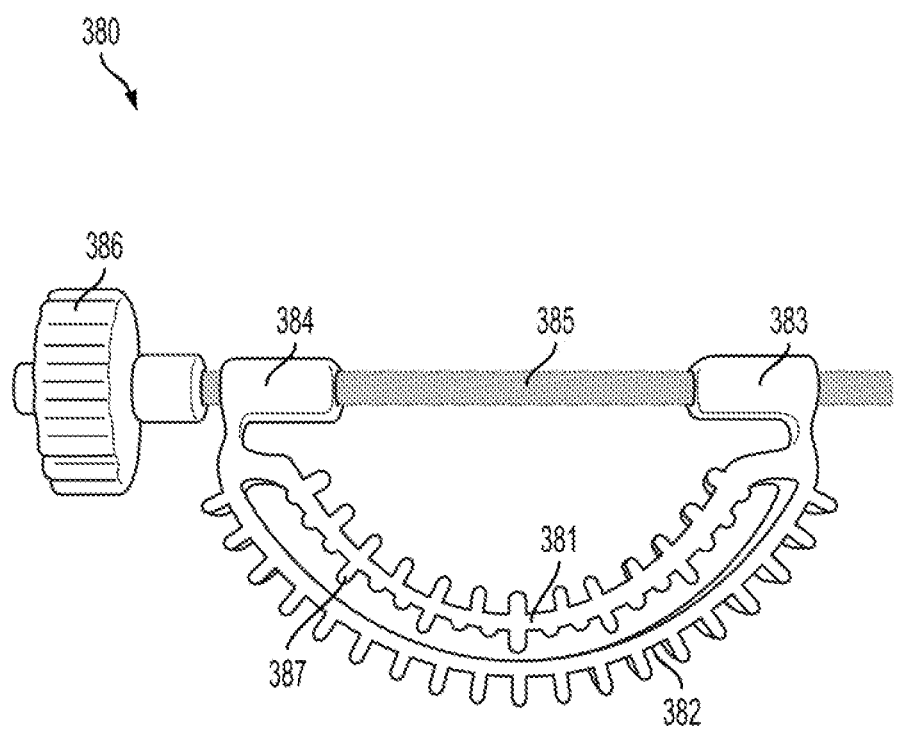
FIGS. 56A-56C show several views of a valve having two curved, elongated support members with one of the elongated support members having a plurality of ridges adapted to engage a tube in accordance with an embodiment of the present disclosure.
Figure 56B:
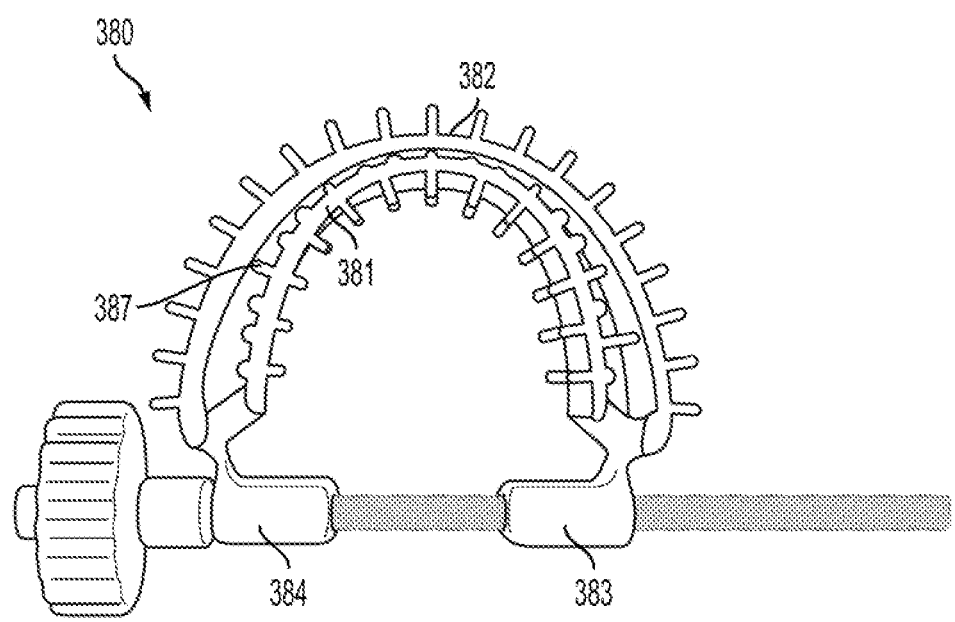
Figure 56C:
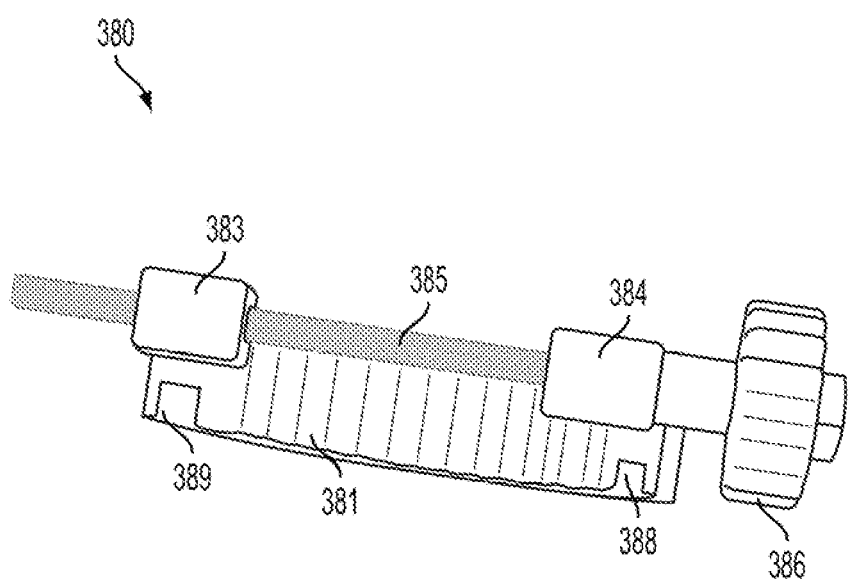

FIGS. 56A-56C show several views of a valve 380 having two curved, elongated support members 381 and 382 with one of the elongated support members 381 having a plurality of ridges 387 adapted to engage a tube positioned between the support members 381 and 382, in accordance with an embodiment of the present disclosure.

The valve 380 has both support members 381 and 382 coupled to a coupling member 383 at a first end and a second coupling member 384 at another end. That is, the coupling member 384 surrounds a screw 385, and the coupling member 383 includes internal threads for pulling the coupling member 383 toward or away from a knob 386 when the screw 385 is rotated with rotation of the knob 386. FIG. 56B shows the valve 380 when actuated to close fluid flowing through a tube coupled between the support members 381 and 382. FIG. 56C shows the support member 381 having two holes 388 and 389 to receive a tube. Also note that the support members 381 and 382 hold a tube off center from an axis of the screw 385, which is easily seen in FIG. 56C. Holding the tube off-center from the screw's 385 axis facilitates free movement of the tube.

Figure 57A:
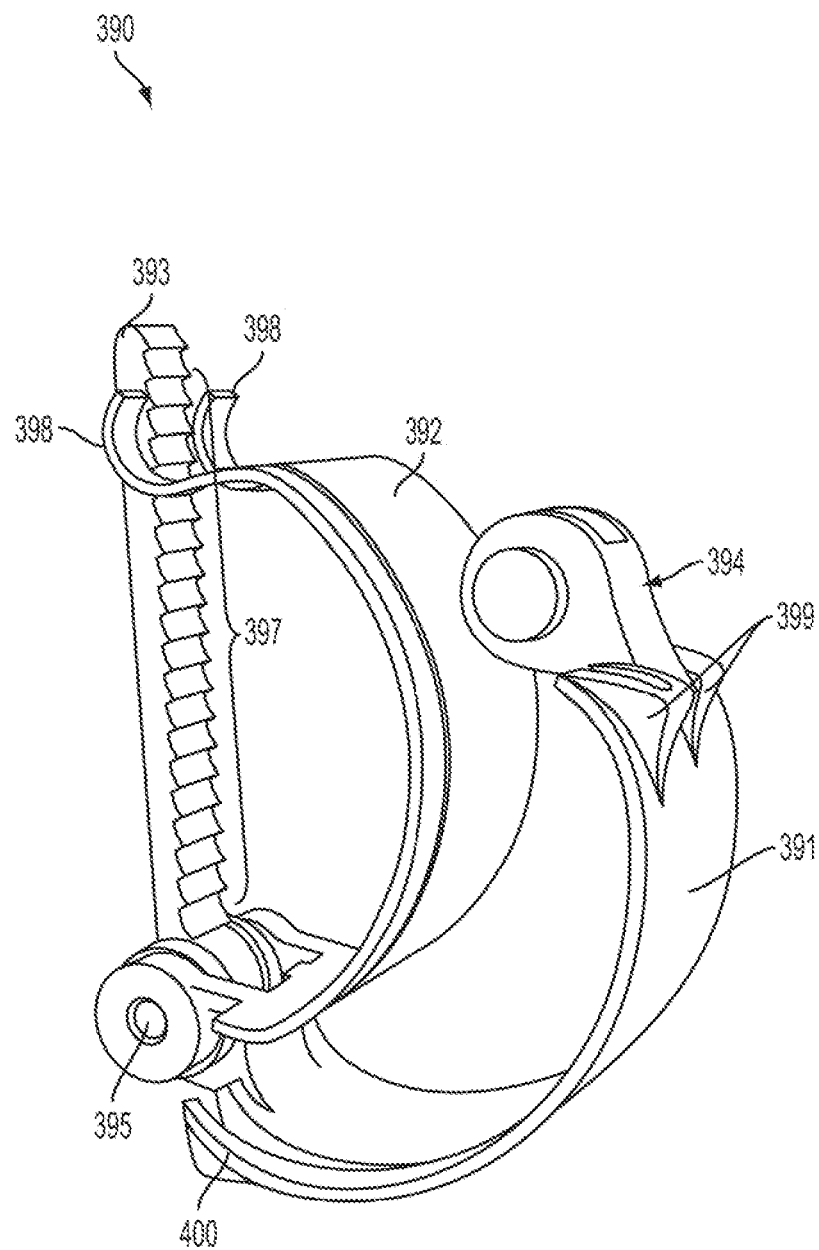
FIGS. 57A-57C show several views of a valve having a ratchet that engages a connecting member in accordance with an embodiment of the present disclosure.
Figure 57B:
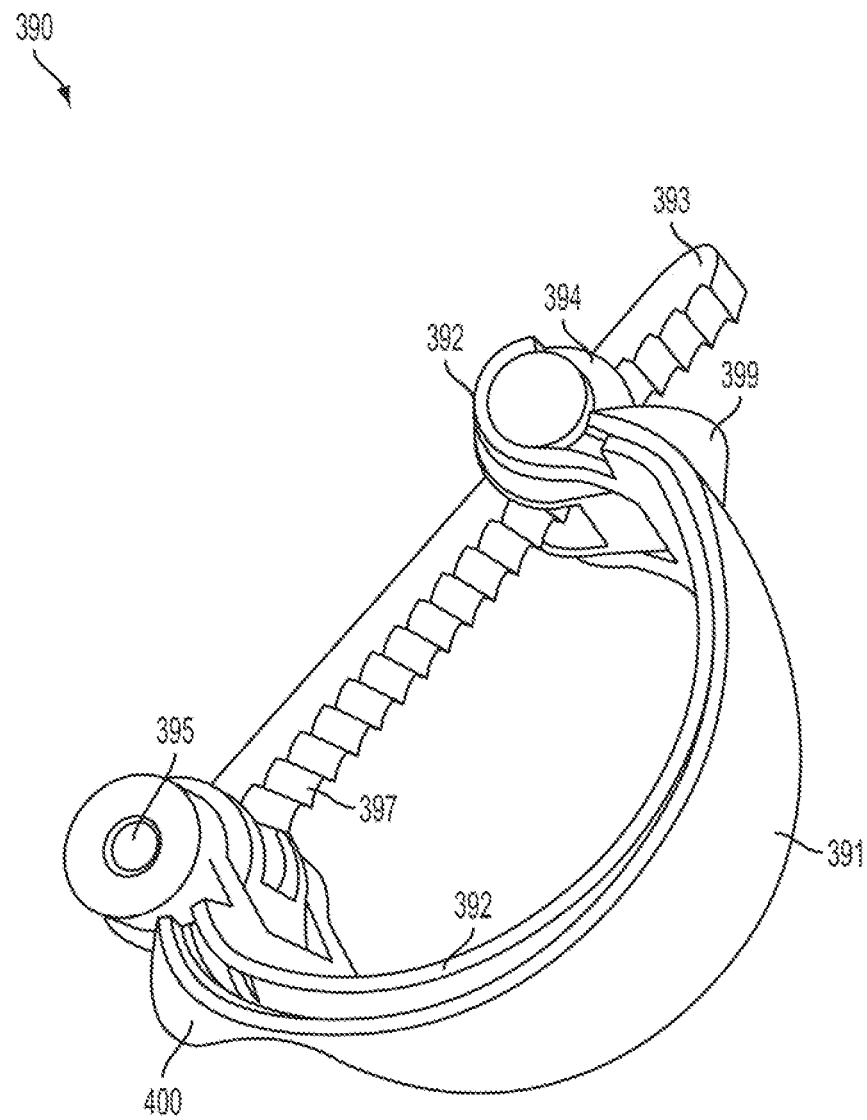
Figure 57C:
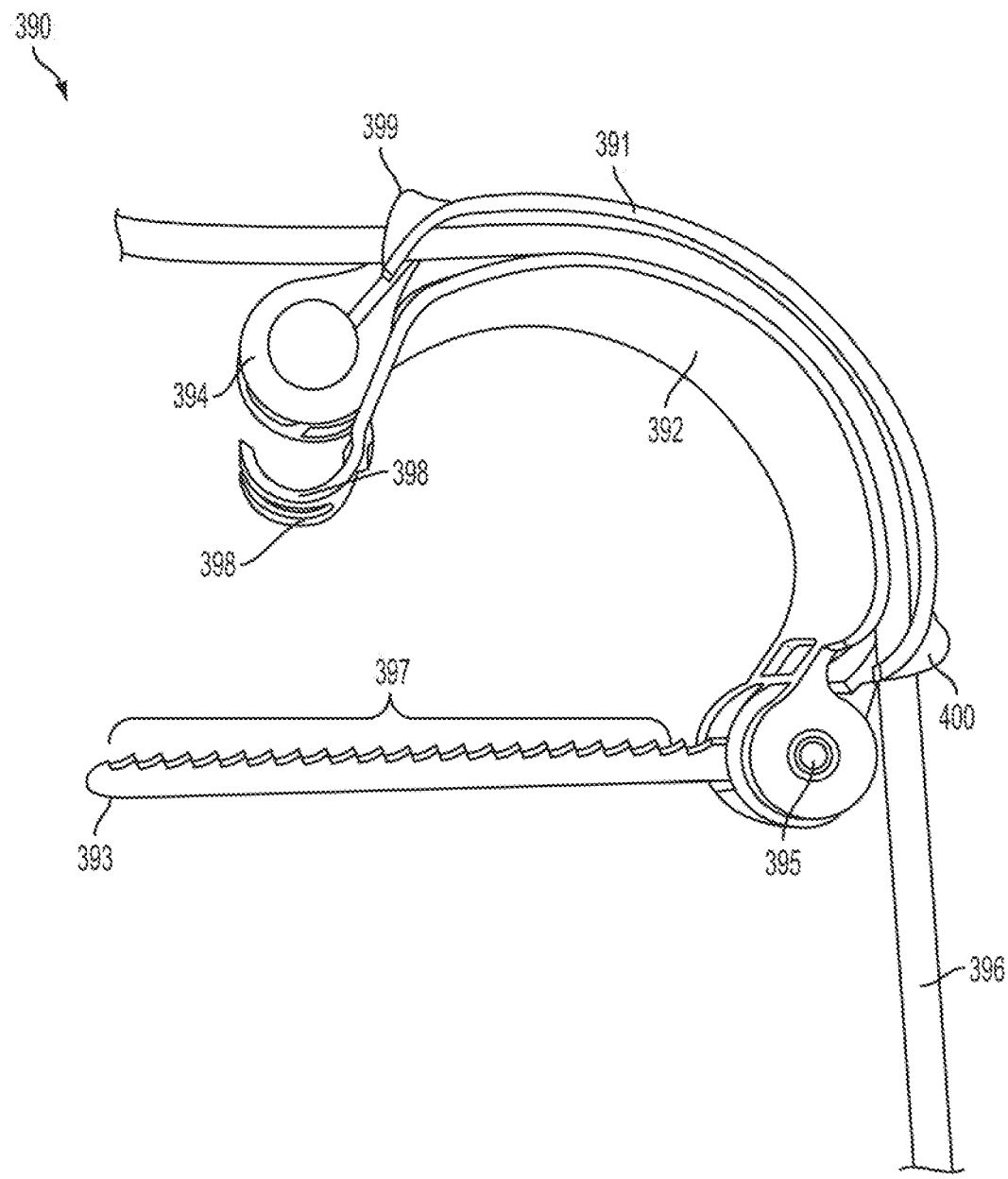
Figure 57D:
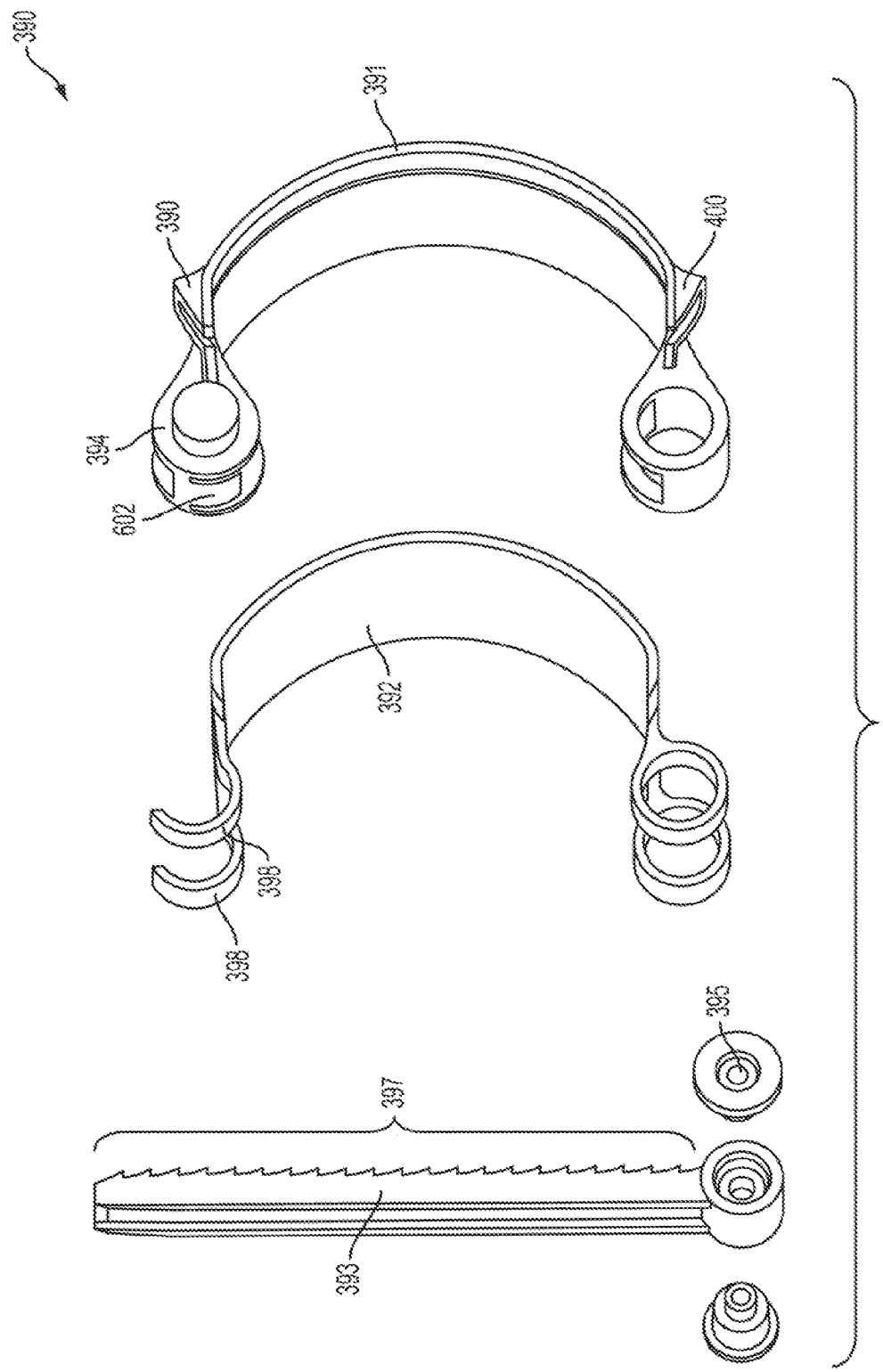

FIGS. 57A-57C show several views of a valve 390 having a ratchet 394 that engages a connecting member 393 of the valve 390 in accordance with an embodiment of the present disclosure, and FIGS. 57D-57E show two exploded views of the valve 390 of FIGS. 57A-57C. The ratchet 394 engages the connecting member 393 by interacting with a gear rack 397 disposed thereon. A finger 602 (see FIGS. 57D and 57E) interacts with a gear rack 397 to provide the ratcheting action. That is, the finger 602 may hold the gear rack 397 against an engaging finger on a side opposite of the retaining finger 602. The valve 390 includes a support member 391 having an end coupled to the ratchet 394 and another end pivotally coupled to a hinge 395. The valve 390 also includes a support member 392 having hooks 398 that can couple to the body of the ratchet 394.

As shown in FIG. 57C, a tube 396 can be positioned between the support members 391 and 392, the hooks 398 can then be fastened to the body of the ratchet 394, and the connecting member 393 can be inserted into the ratchet 394 (as shown in FIG. 57B). As shown in FIG. 57C, the tube 396 is positioned against the support member 391 via openings 399 and 400.

The ratchet 394 engages the gear rack 397 such that the ratchet 394 can be manually moved toward the hinge 395 for course fluid flow adjustments. Thereafter, a knob (not shown) may be coupled to the ratchet 394 to make fine adjustments to the distance between the ratchet 394 and the hinge 395. Additionally or alternatively, the ratchet 394 may include a release button (not shown) to release the ratchet from the connecting member 393.

FIGS. 58A-58D show several views of a valve 401 having two elongated support members 403 and 404, a connecting member 405, and a screw-type actuator 407 in accordance with another embodiment of the present disclosure.

The support members 403 and 404 may be permanently molded together at their ends with the ends of the connecting member 405. A tube 402 may be positioned between the support members 403 and 404.

Figure 58A:
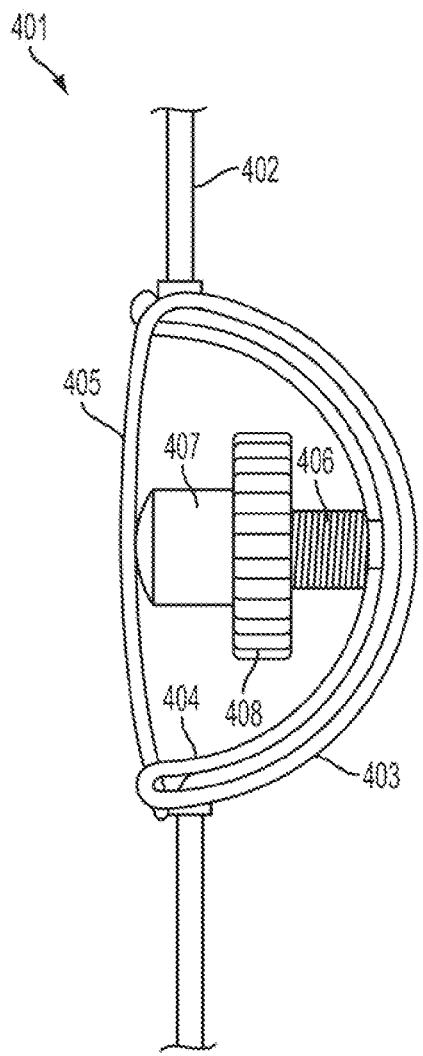
FIGS. 58A-58D show several views of a valve having two elongated support members, a connecting member, and a screw-type actuator in accordance with another embodiment of the present disclosure.
Figure 58B:
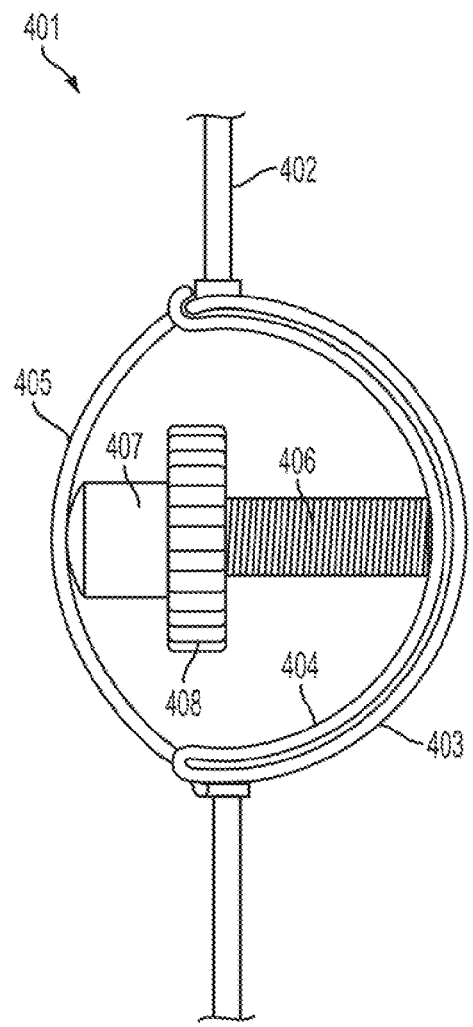
Figure 58C:
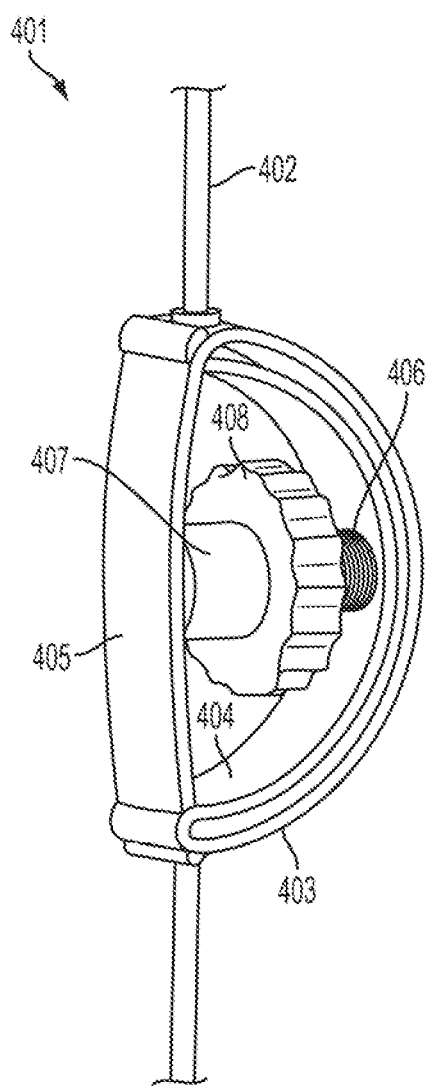
Figure 58D:
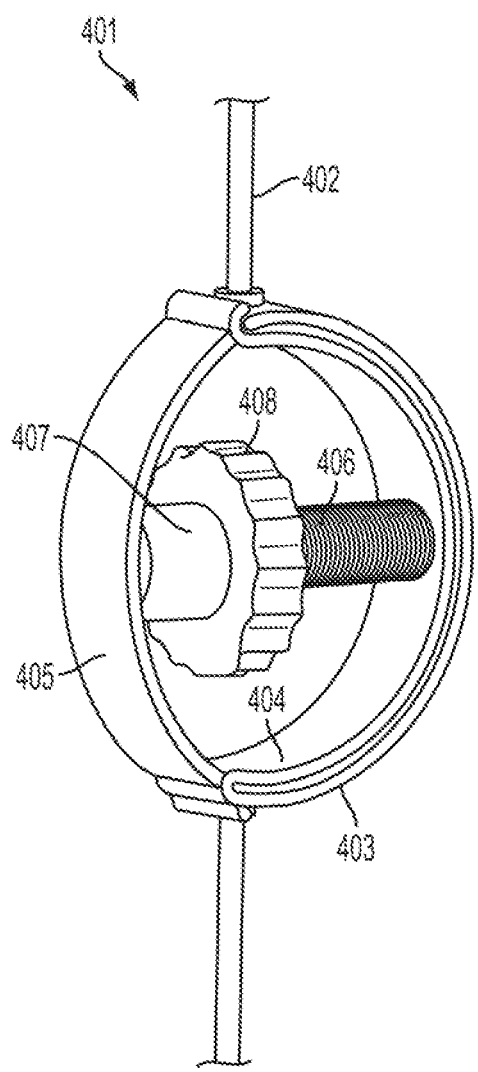

As the knob 408 is turned, the screw-type actuator 407 expands or contracts because of engagement with a threaded rod 406. FIG. 58A shows the valve in an open position while FIG. 58B shows the valve in a closed position. Note that the tube 402 is squeezed along a substantial length of the tube 402. FIGS. 58C-58D show the valve 401 in the open position and the closed position, respectively, from a perspective view.

Figure 59A:
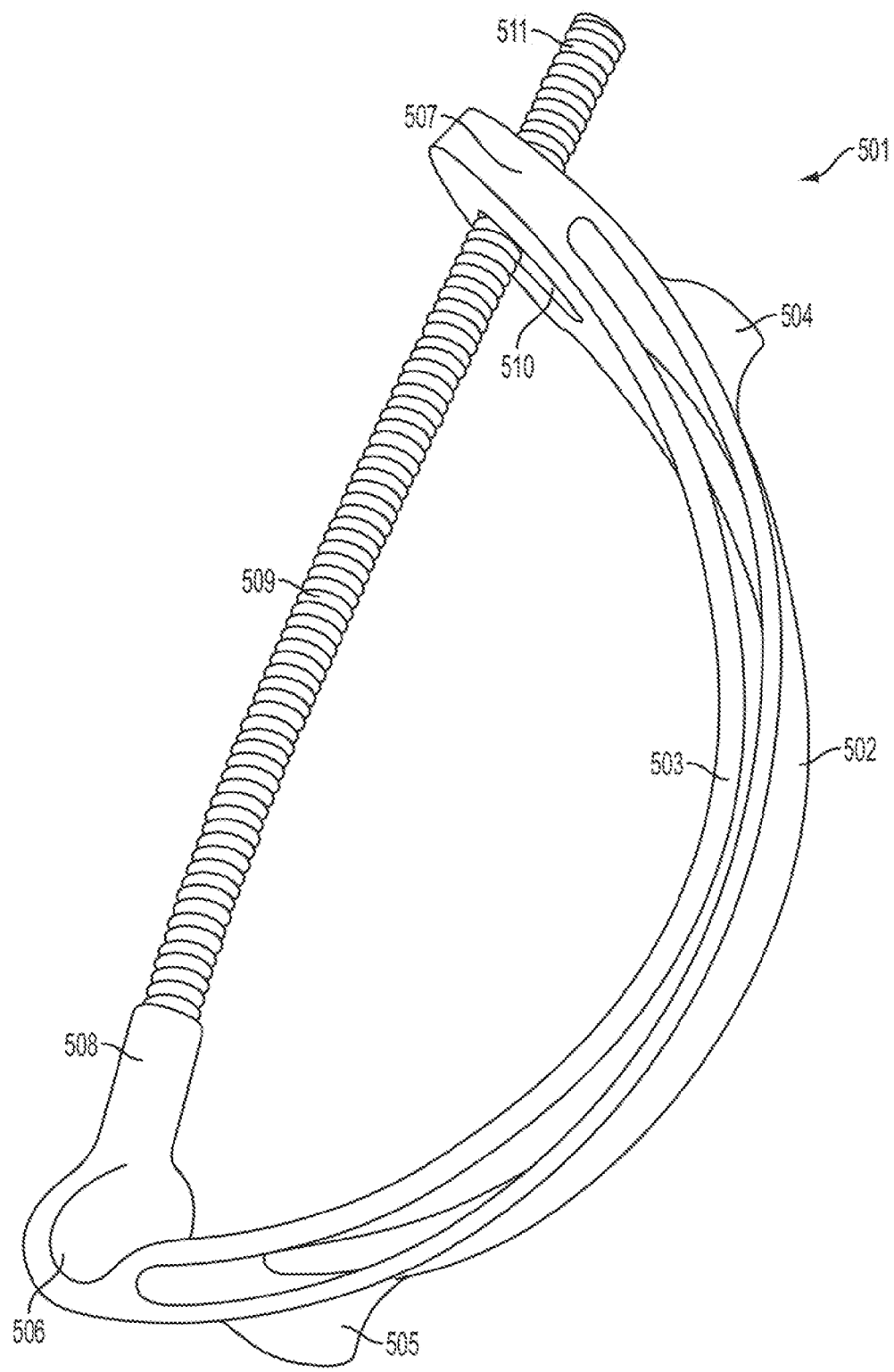
FIGS. 59A-59C show several views of a body of a valve in accordance with an embodiment of the present disclosure.
Figure 59B:
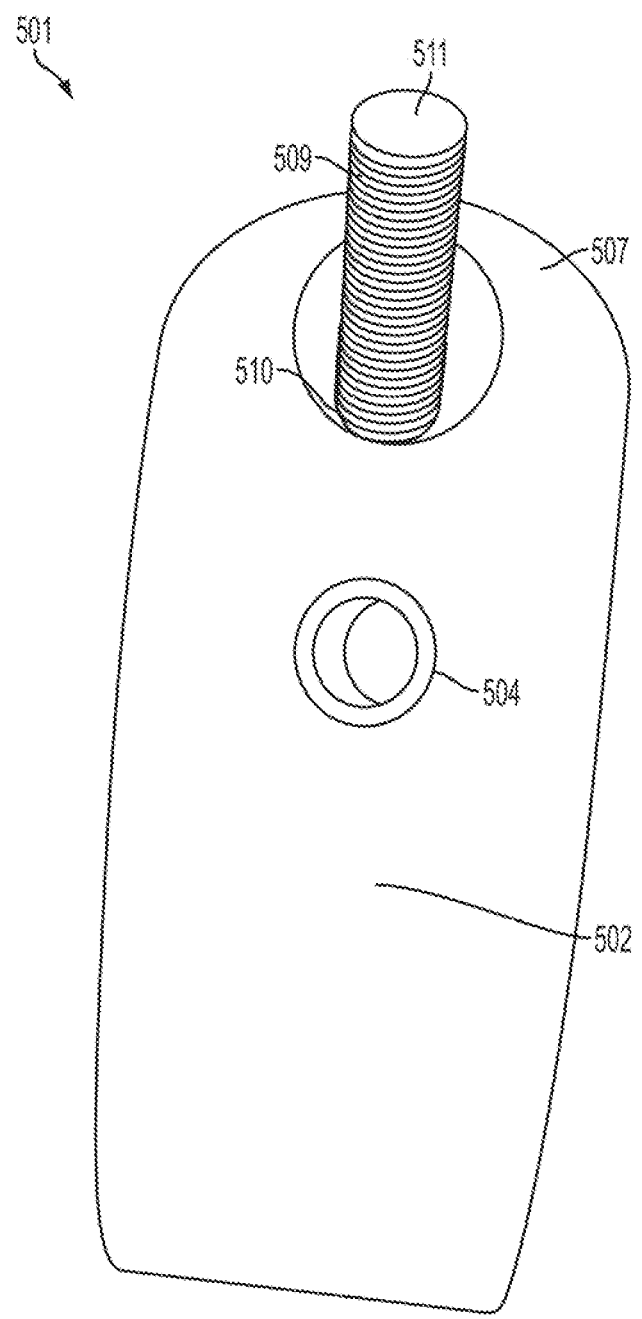
Figure 59C:
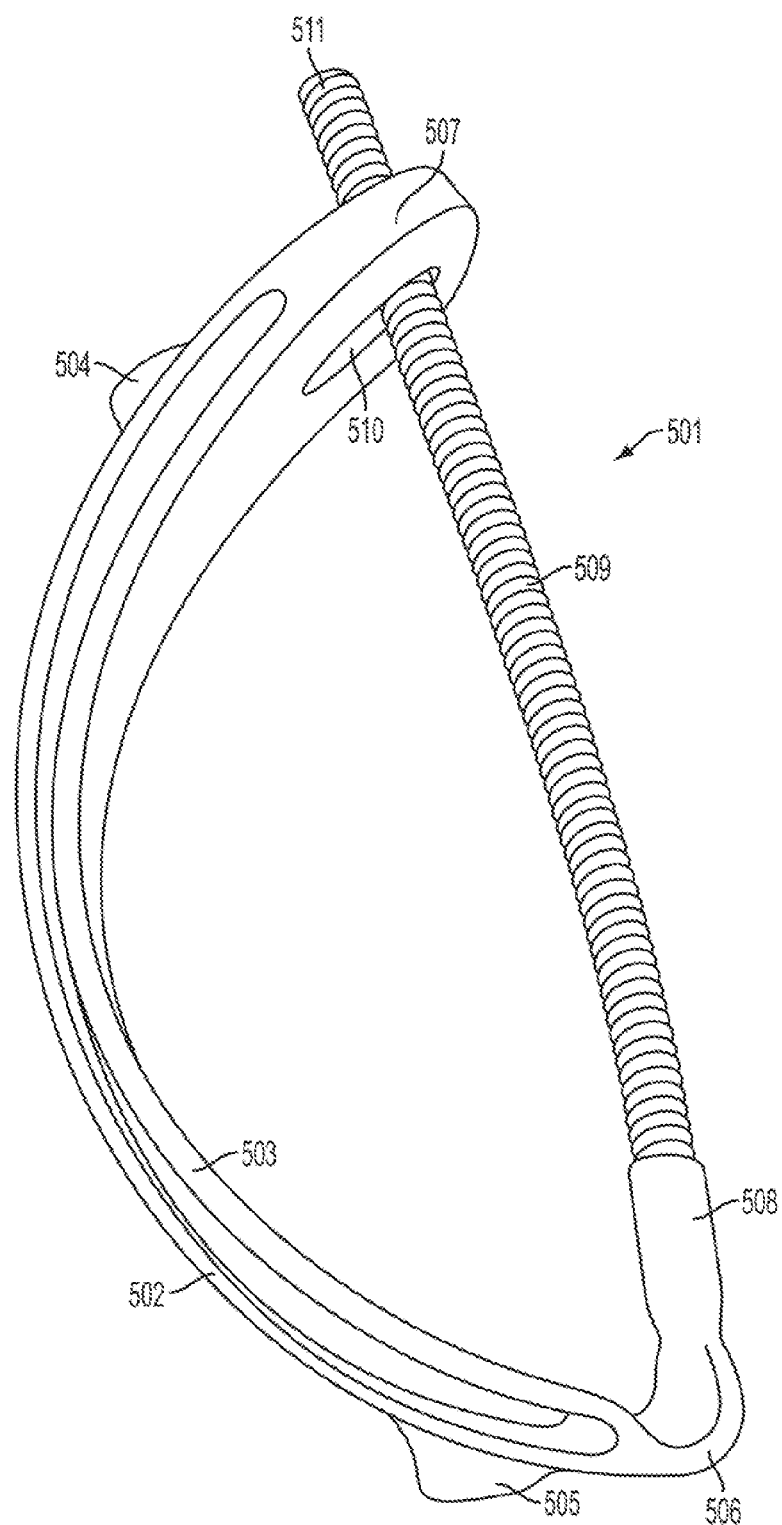
Figure 59D:
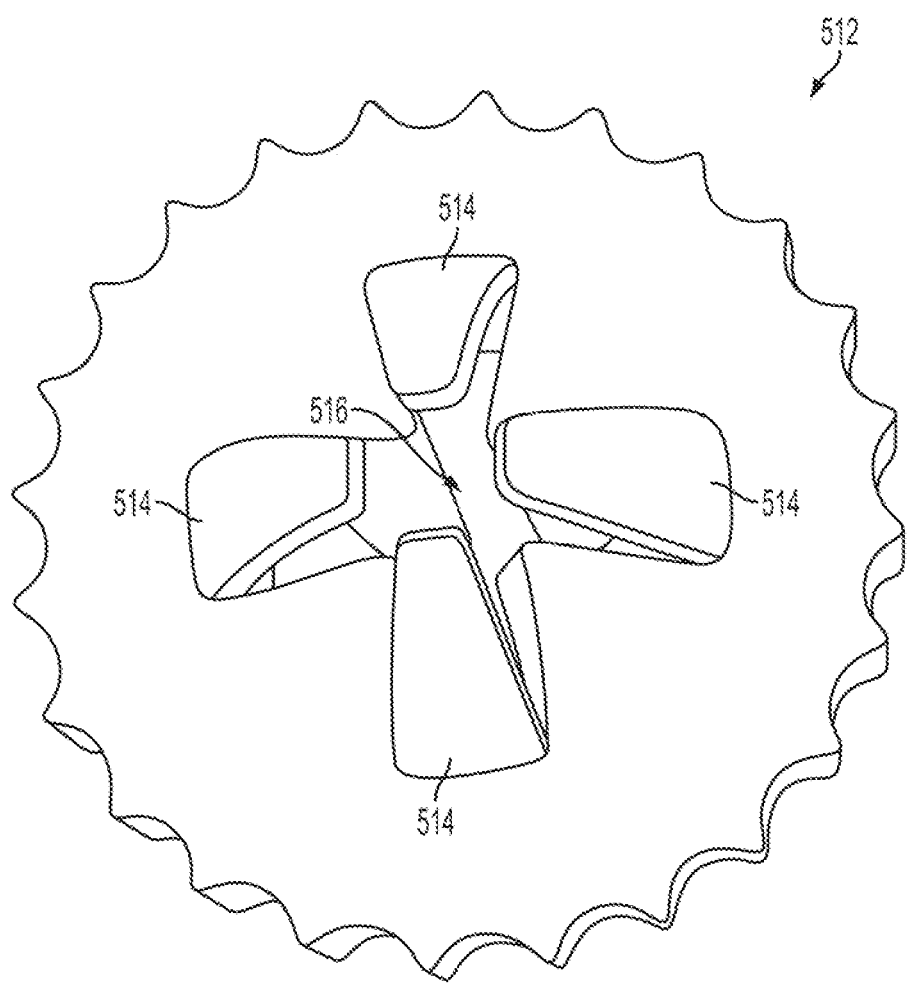
FIGS. 59D-59G show several views of a knob for use with the body shown in FIGS. 59A-59C in accordance with an embodiment of the present disclosure.
Figure 59E:
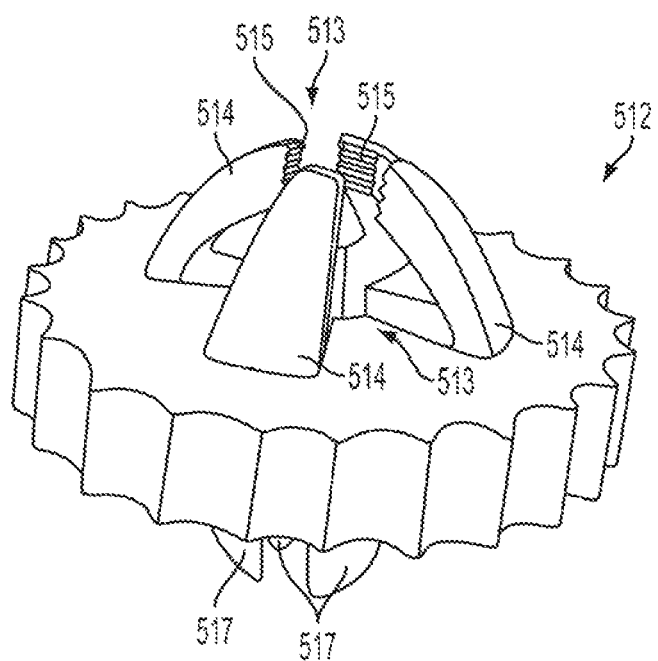
Figure 59F:
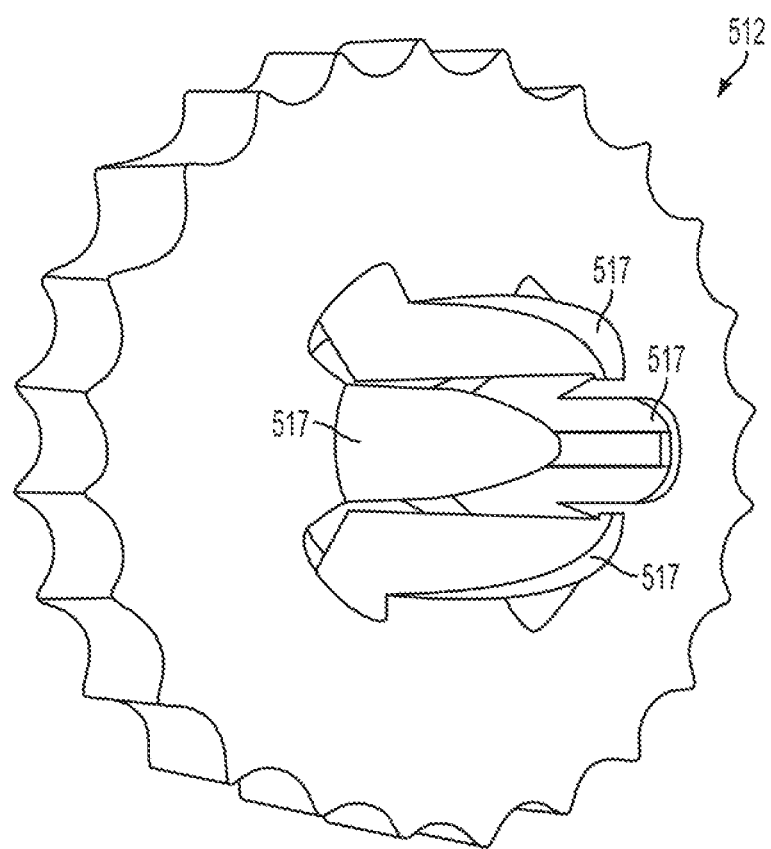
Figure 59G:
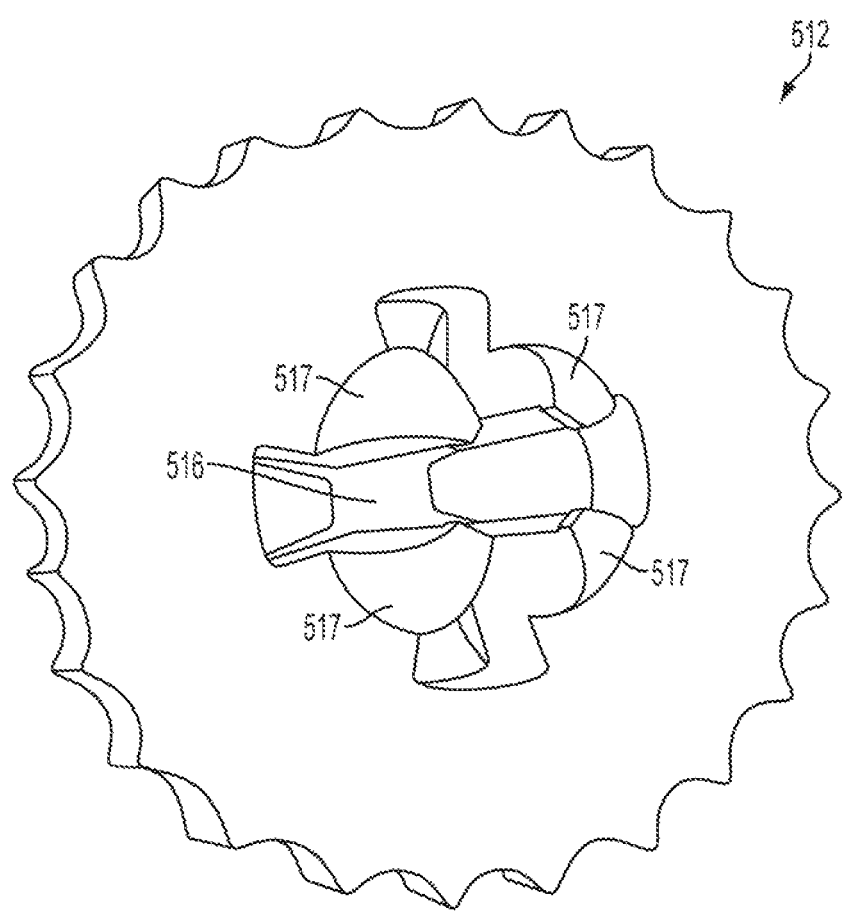

FIGS. 59A-59C show several views of a body 501 of a valve 500 (see FIG. 59H for the assembled valve 500) in accordance with an embodiment of the present disclosure. The body 501 includes a first curved, elongated support member 502 and a second curved, elongated support member 503. The first support member 502 includes raised holes 504, 505 to hold a tube between the support members 502 and 503.

The body 501 also includes a first connector 506 that is coupled to the support members 503, 504 at an end, and a second connector 507 that is coupled to the other ends of the support members 503, 504.

The first connector 506 is coupled to an end of the support members 503, 504 and to a first end 508 of a connecting member 509. The second connector 507 includes a hole 510 for positioning the second end 511 of the connector member 509 therethrough (as is easily seen in FIG. 59B).

When a tube is positioned between the support members 502, 503, movement of the second connector 507 toward the first connector 506 compresses the tube disposed between the support members 502, 503. As the second connector 507 moves towards the first connector, the hole 510 of the second connector 507 allows the second end 511 of the connector member 509 to freely slide therein.

FIGS. 59D-59G show several views of a knob 512 for use with the body 501 shown in FIGS. 59A-59C in accordance with an embodiment of the present disclosure. The knob 512 includes a ratchet 513 defined by four fingers 514. Each of the fingers 514 includes a threaded surface 515 to engage a threaded connecting member 509. The fingers 514 are arched toward a hole 516 at the center of the knob 512. The knob 512 also includes fingers 517 that engage the second connector 507 (see FIG. 59H). In some embodiments, the body 501 includes a recess 510 to receive the fingers 517 on the second connector 508.

Figure 59H:
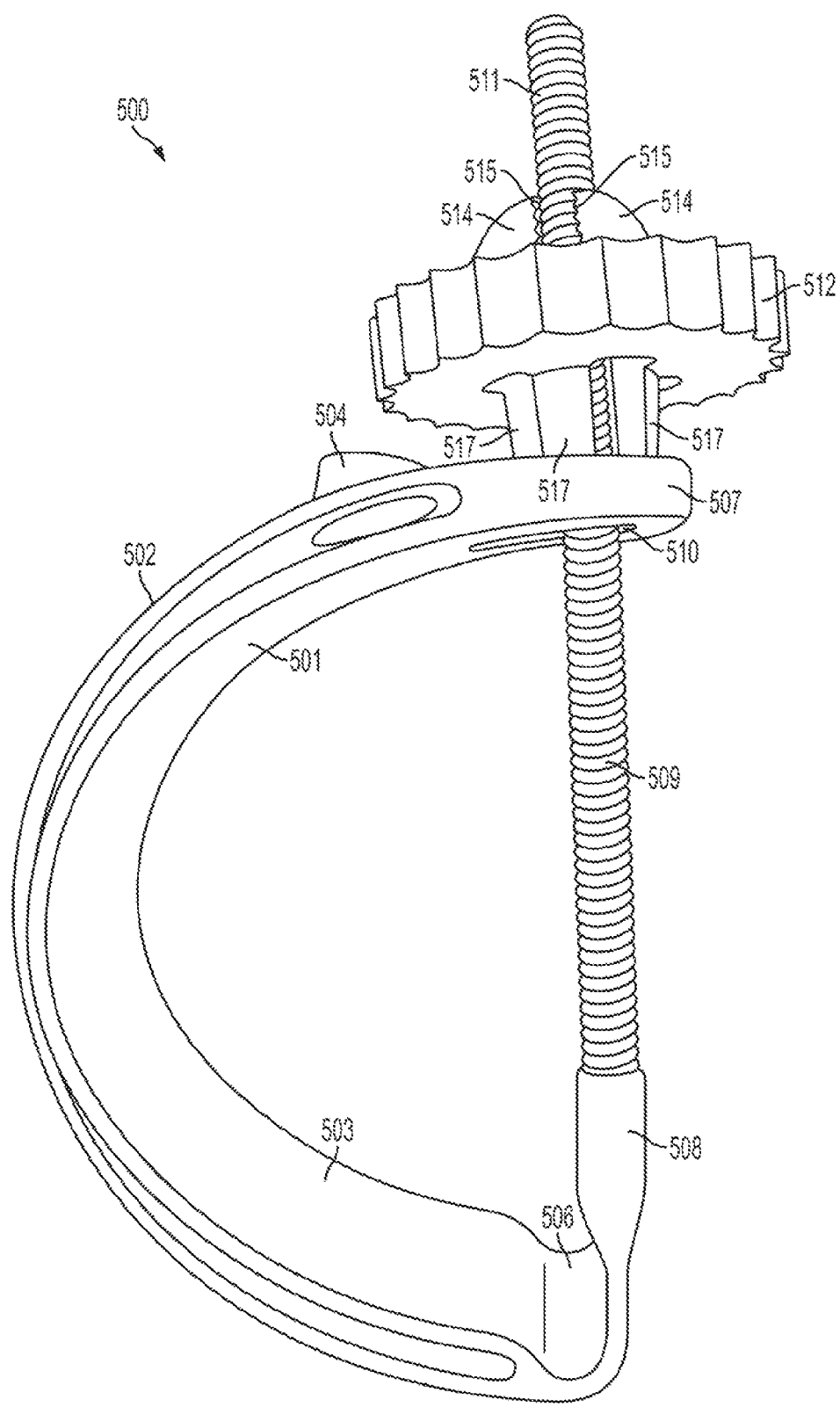
FIG. 59H shows the assembled valve that includes the body shown in FIGS. 59A-59C coupled to the knob of FIGS. 59D-59G in accordance with an embodiment of the present disclosure.

FIG. 59H shows an assembly valve 500 that includes the body 501 shown in FIGS. 59A-59C coupled to the knob 512 of FIGS. 59D-59G in accordance with an embodiment of the present disclosure. The knob 512 is slid onto the threads of the connecting member 509. The fingers 514 engage the threads of the connecting member 509 and ratchet onto the connecting member 509. That is, the knob 512 is freely moveable towards the first end 508 of the connecting member 509 along the threads of the connecting member 509, but cannot be moved away from the first end 508 of the connecting member 509 without rotating the knob 512. That is, the knob 512 may be placed onto the connecting member 509 to provide a coarse adjustment of the valve 500 by coarsely moving the connectors 507, 508 toward each other to close the valve 500. Because the threaded surfaces 515 of the four fingers 514 engage the threads of the connecting member 509, rotation of the knob 512 either reduces or increases fluid flow within a tube. Each of the fingers 514 includes a threaded surface 515 to engage the threads of the connecting member 509 such that rotation of the knob 512 moves the second connector 507 toward or away from the first connector 506 to thereby control the flow of fluid of a tube positioned between the support members 502, 503.

Figure 60:
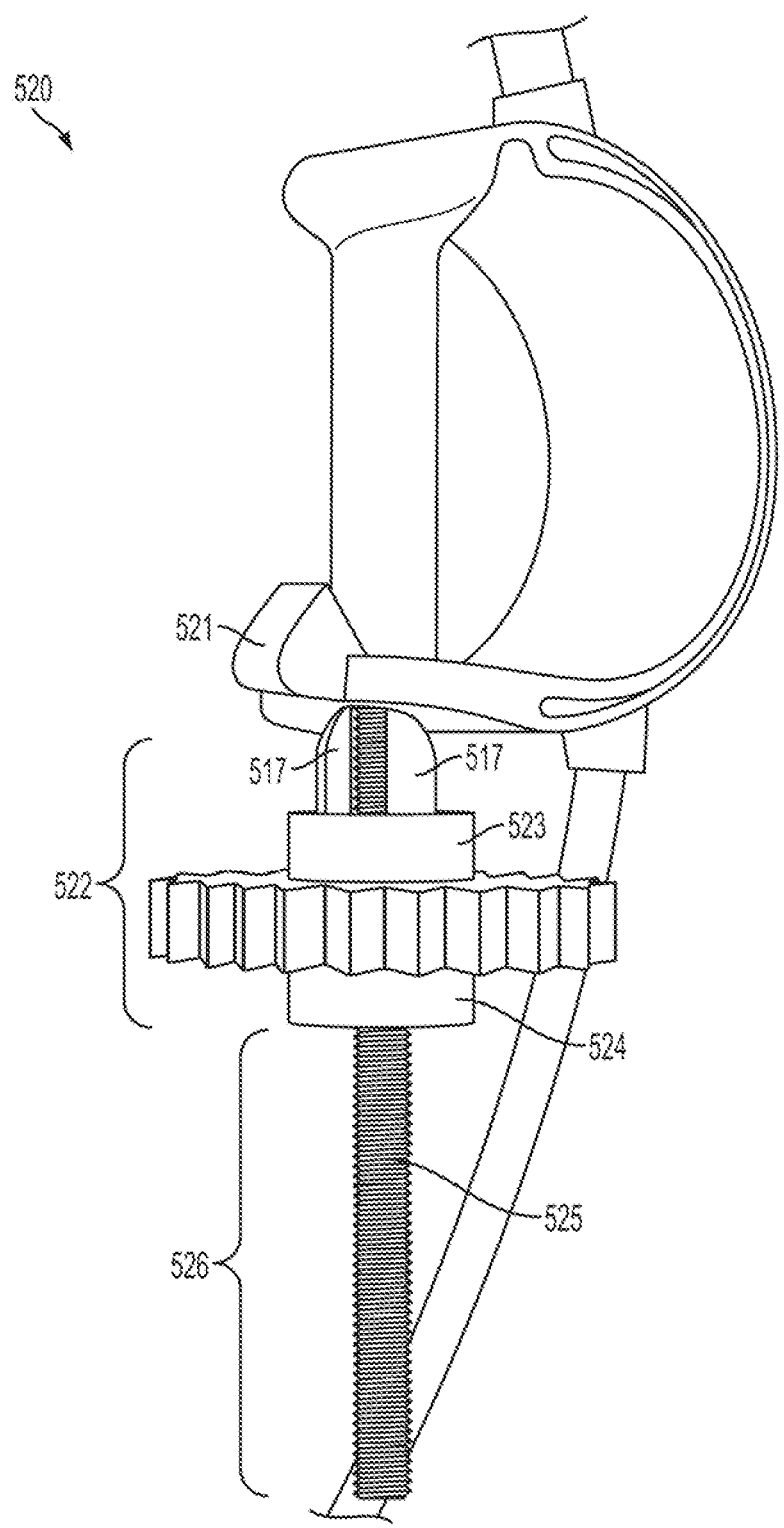
FIG. 60 shows a valve having a guiding protrusion in accordance with an embodiment of the present disclosure.

FIG. 60 shows a valve 520 having a guiding protrusion 521 in accordance with an embodiment of the present disclosure. The valve 520 is similar to the valve 500 of FIG. 59H, but includes the guiding protrusion 521 and a knob 522 having first and second collars 523, 524. The knob 522 also includes internal threads (not shown) to engage threads 525 of a connecting rod 526. In some embodiments, the internal threads may be ratcheting, and in other embodiments, the internal threads may be fixed without providing a ratcheting action.

Figure 61:
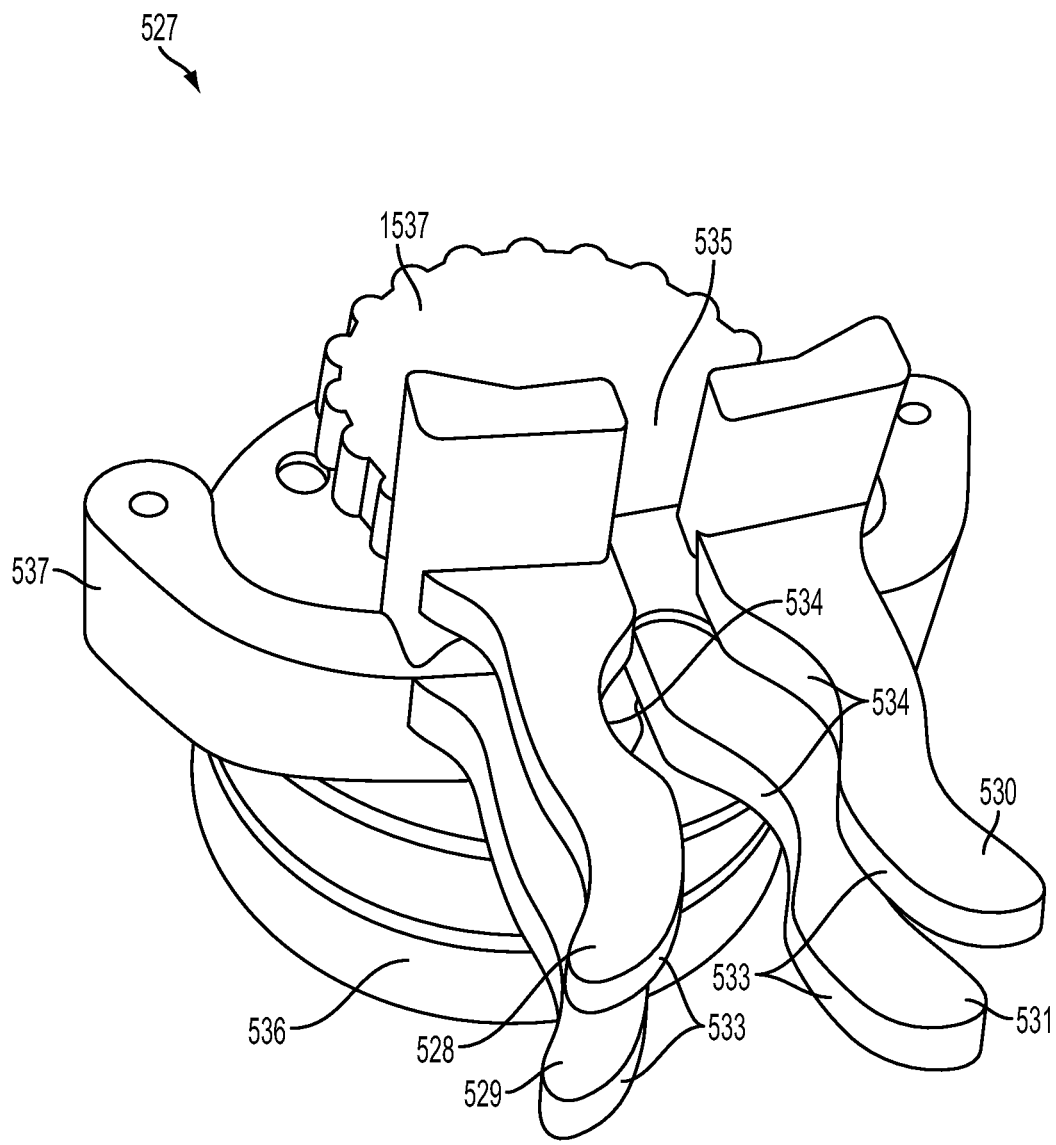
FIG. 61 shows a motor and a valve-securing structure for coupling to the valve of FIG. 60 in accordance with an embodiment of the present disclosure.

FIG. 61 shows a motor 536 and a valve-securing structure 537 for coupling to the valve 520 of FIG. 60 in accordance with an embodiment of the present disclosure. The valve-securing structure 537 includes securing fingers 528, 529, 530, 531 each having a curved portion 533 for snapping onto collars 523, 524 of a knob 522 (see FIG. 62) into respective collar-guiding portions 534.

Figure 62:
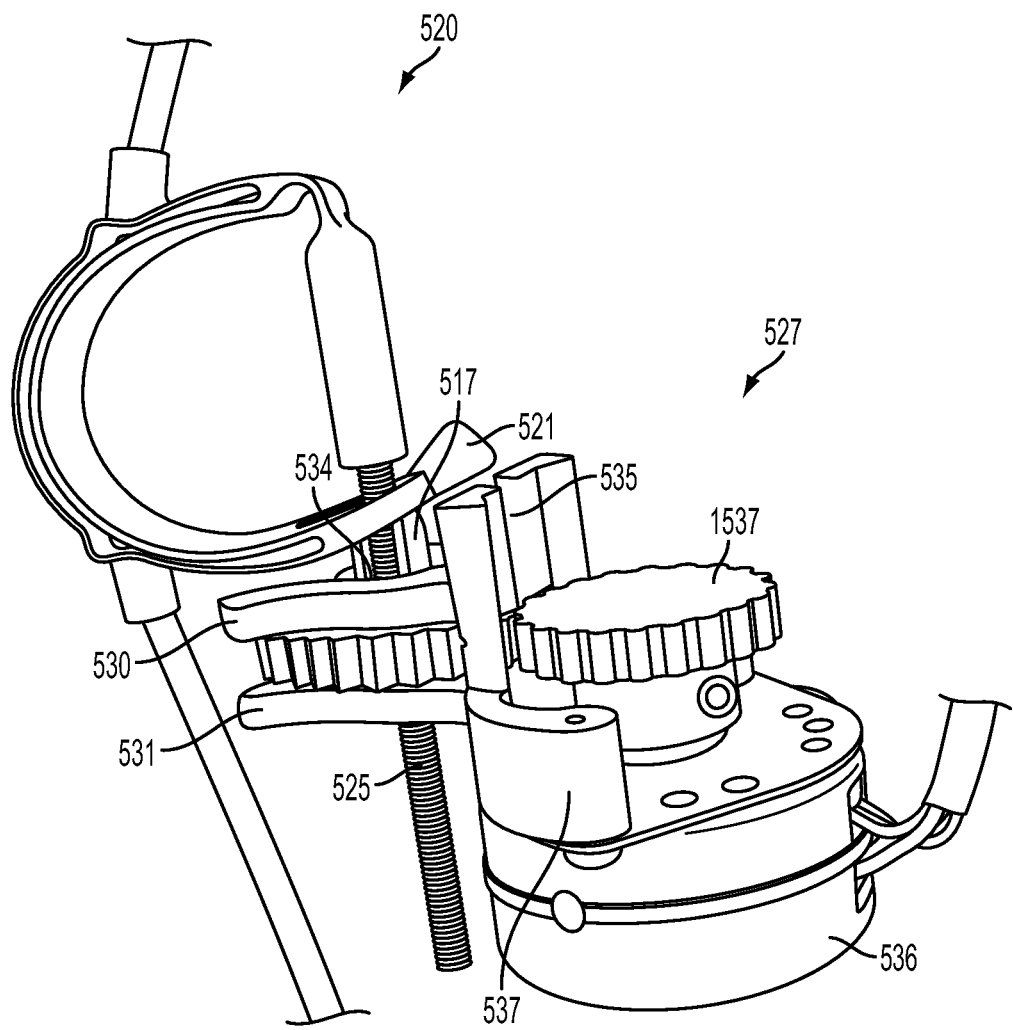
FIG. 62 shows the valve of FIG. 60 secured to the motor and the valve-securing structure of FIG. 61 in accordance with an embodiment of the present disclosure.

Referring now to FIGS. 60, 61, and 62, once the collars 523, 524 are sufficiently secured, the knob 522 is free to rotate. That is, the collar 523 may be secured between the securing fingers 528 and 530 within their respective collar-guiding portion 534 allowing the knob 522 to rotate. Likewise, the collar 524 may be secured between the securing fingers 529 and 531 within their respective collar-guiding portion 534 allowing the knob 522 to rotate.

When the valve 520 is secured to the valve-securing structure 537, rotation of the wheel 1537 (caused by the motor 536) rotates the knob 522 of the valve 520. As the valve 520 flexes, the protrusion 521 freely moves within the protrusion guide 535 or adjacent to the protrusion guide 535. FIG. 62 shows the valve of FIG. 60 secured to the motor 536 via the valve-securing structure 537.

Figure 63:
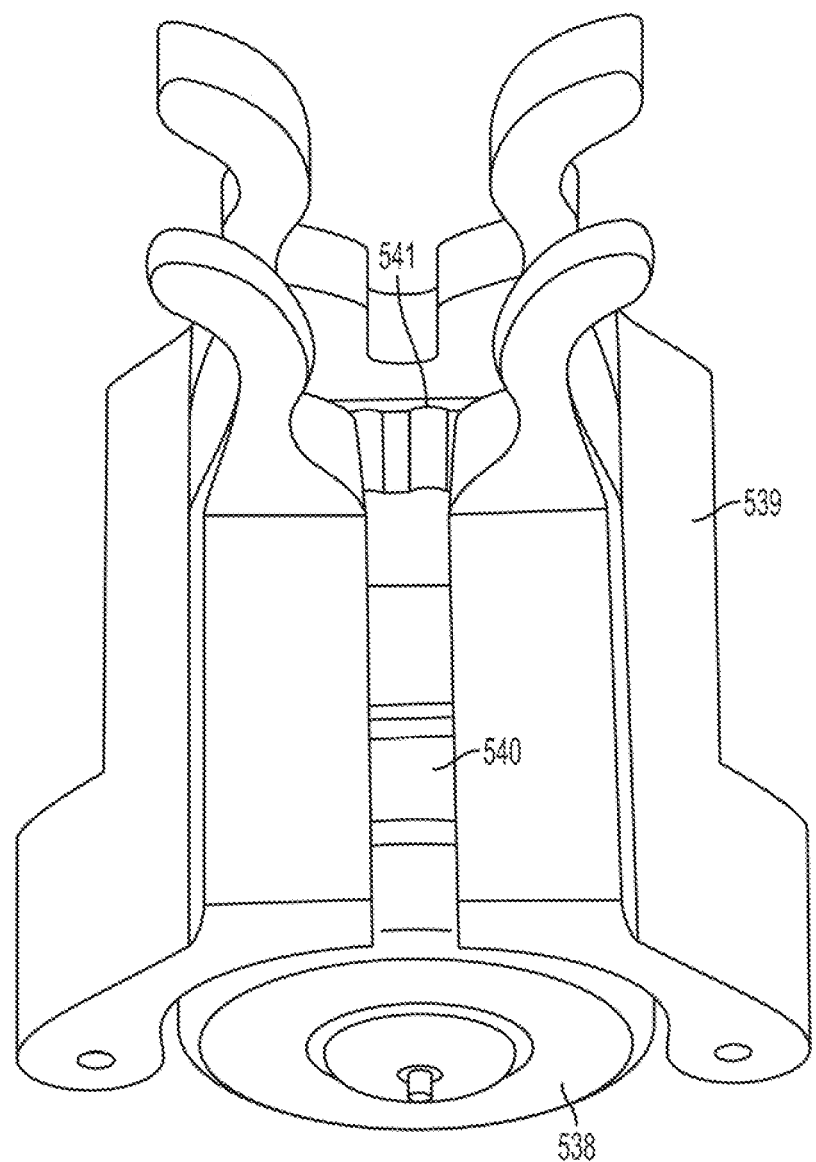
FIG. 63 shows another motor and valve-securing structure for coupling to the valve of FIG. 60 in accordance with an embodiment of the present disclosure.

FIG. 63 shows another motor 538 and valve-securing structure 539 for coupling to the valve of FIG. 60 in accordance with an embodiment of the present disclosure. The valve-securing structure 539 includes a protrusion guide 540 adjacent to the motor 538. The motor 538 is coupled to the wheel 541 to engage the knob 522 (see FIG. 60).

Figure 64A:
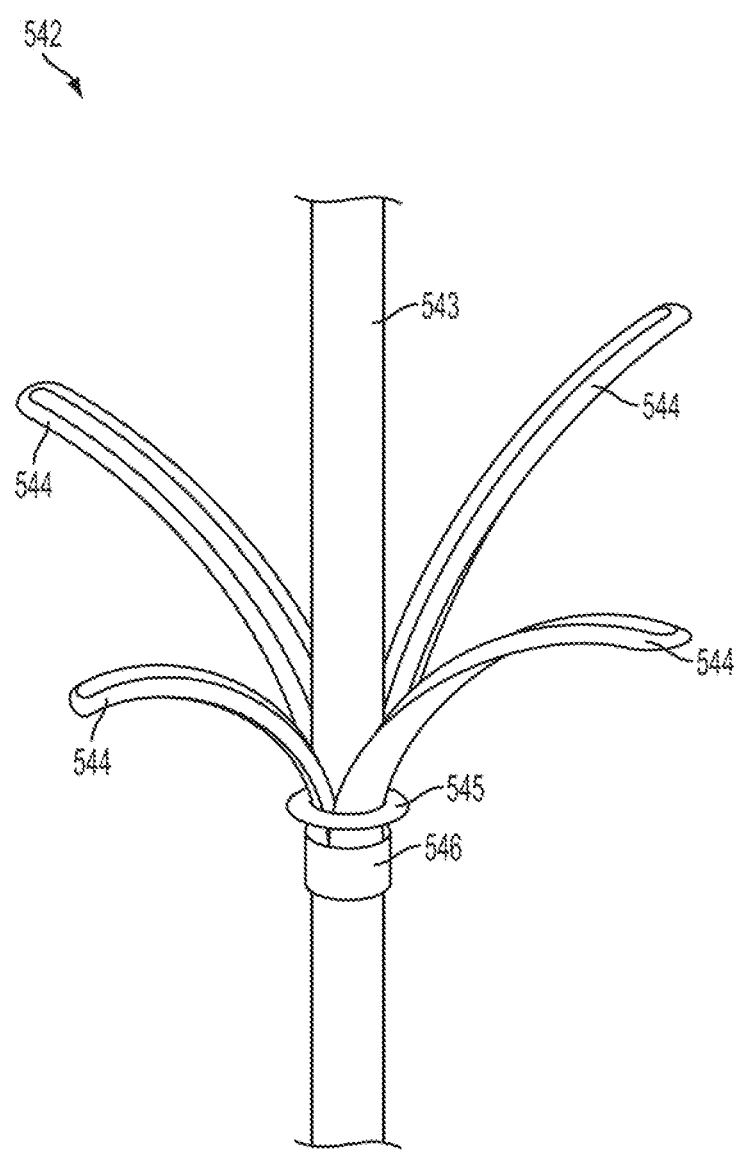
FIG. 64A shows a valve having a collar and several fingers for regulating fluid flow through a fluid line in accordance with an embodiment of the present disclosure.

FIG. 64A shows a valve 542 having a slidable collar 545 and several compressing fingers 544 for regulating fluid flow through a fluid line 543 in accordance with an embodiment of the present disclosure. The base 546 is connected to all of the fingers 544. As the slidable collar 545 is moved over the compressing fingers 544, the compressing fingers 544 compress the tube 543 to impede fluid flow therewithin.

Figure 64B:
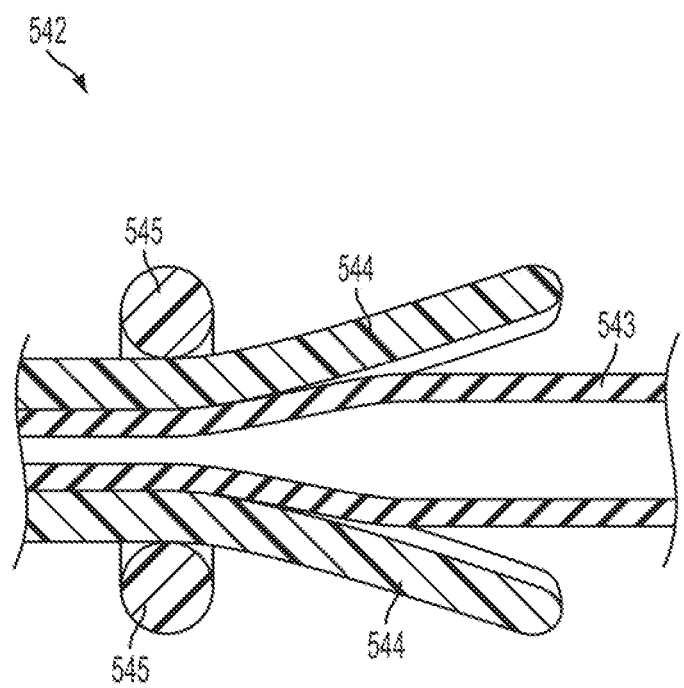
FIG. 64B shows a cross-sectional view of the valve of FIG. 64A in accordance with an embodiment of the present disclosure.
Figure 65:
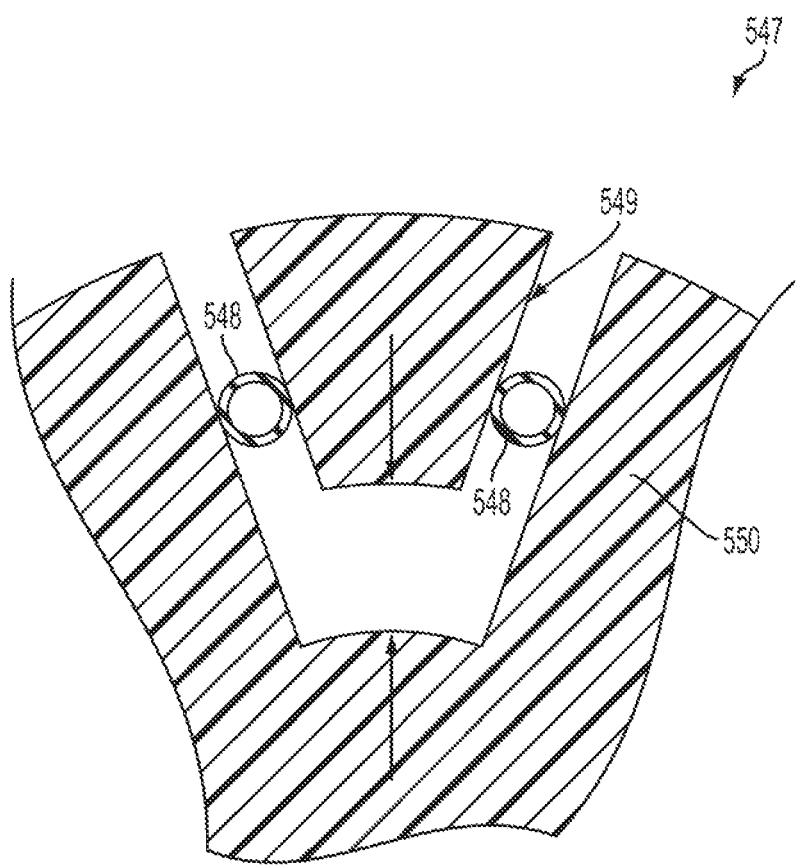
FIG. 65 shows a cross-sectional view of a valve having two curved surfaces for positioning a fluid tube therebetween to regulate fluid flow through the fluid tube in accordance with an embodiment of the present disclosure.

The fingers 544 are coupled to a base 546 such that the base 546 and fingers 544 surround the tube 543. The collar 545 is slidable away from the base 546 such that the fingers 544 compress the tube 543 which thereby reduces an internal volume of the tube 543. The reduction of the internal volume of the tube 543 reduces the fluid flow through the tube. An actuator (not shown) may be coupled to the collar 545 to control the position of the collar 545 (e.g., a linear actuator may be coupled to the collar 545 and to the base 546). FIG. 64B shows a cross-sectional view of the valve 542 of FIG. 64A. Note that the fingers 544 may be shaped away from the tube near an opposite end of the base FIG. 65 shows a valve 547 having two curved surfaces 549 and 550 for positioning a fluid tube 548 therebetween to regulate fluid flow through the fluid tube 548 in accordance with an embodiment of the present disclosure. As the surfaces 549, 550 are compressed together, the tube 548 is compressed therebetween. The two curved surfaces 549 and 550 may be compressed together using an actuator. The tube 548 may be wrapped several times around the surface 549.

FIGS. 66A-66G show several views of a valve 551 having a knob 552 to move a connecting member 553, which is locked into position after movement of the knob 552, in accordance with an embodiment of the present disclosure.

The valve 551 includes an inner curved, elongated support member 554 and an outer curved, elongated support member 556. A knob 552 is pivotally coupled to the outer support member 556 via a pin 578. A connecting member 553 engages teeth 576 of the knob 552.

The connecting member 553 may be inserted into a hole of an end 555 of the support member 556 such that rotation of the knob 552 frictionally locks an engaging finger 700 (see FIG. 66G) into the gear rack 558 of the connecting member 553. The engaging finger 700 may engage the teeth 576 to lock the knob 552 to thereby prevent rotation of the knob 552 unless sufficient torque overcomes the locking action of the engaging finger 700. A retaining finger 577 is positioned on the other side of the hole 571 to press the connecting member 552 against the teeth 576 of the knob 552.

Figure 66B:
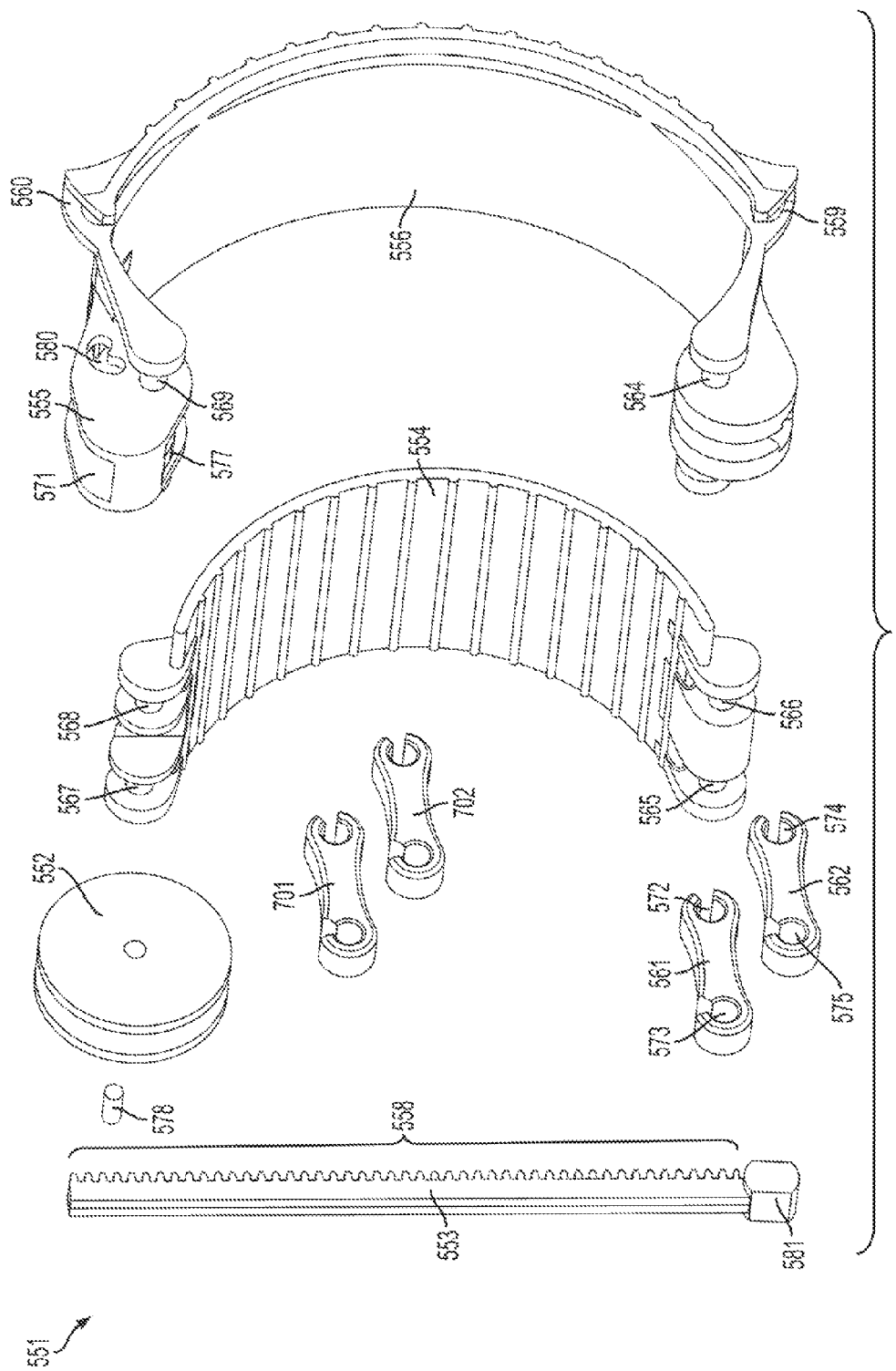
Figure 66C:
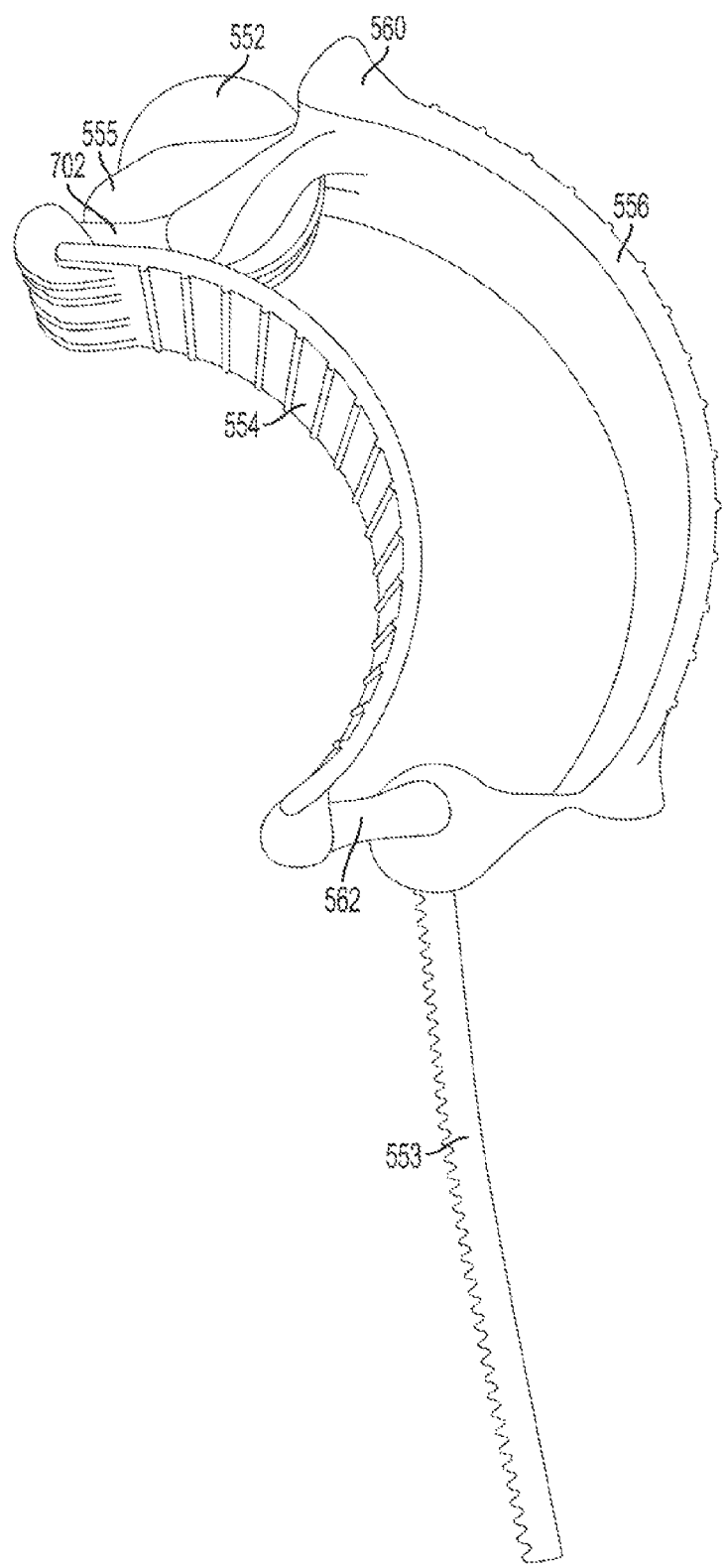
Figure 66D:
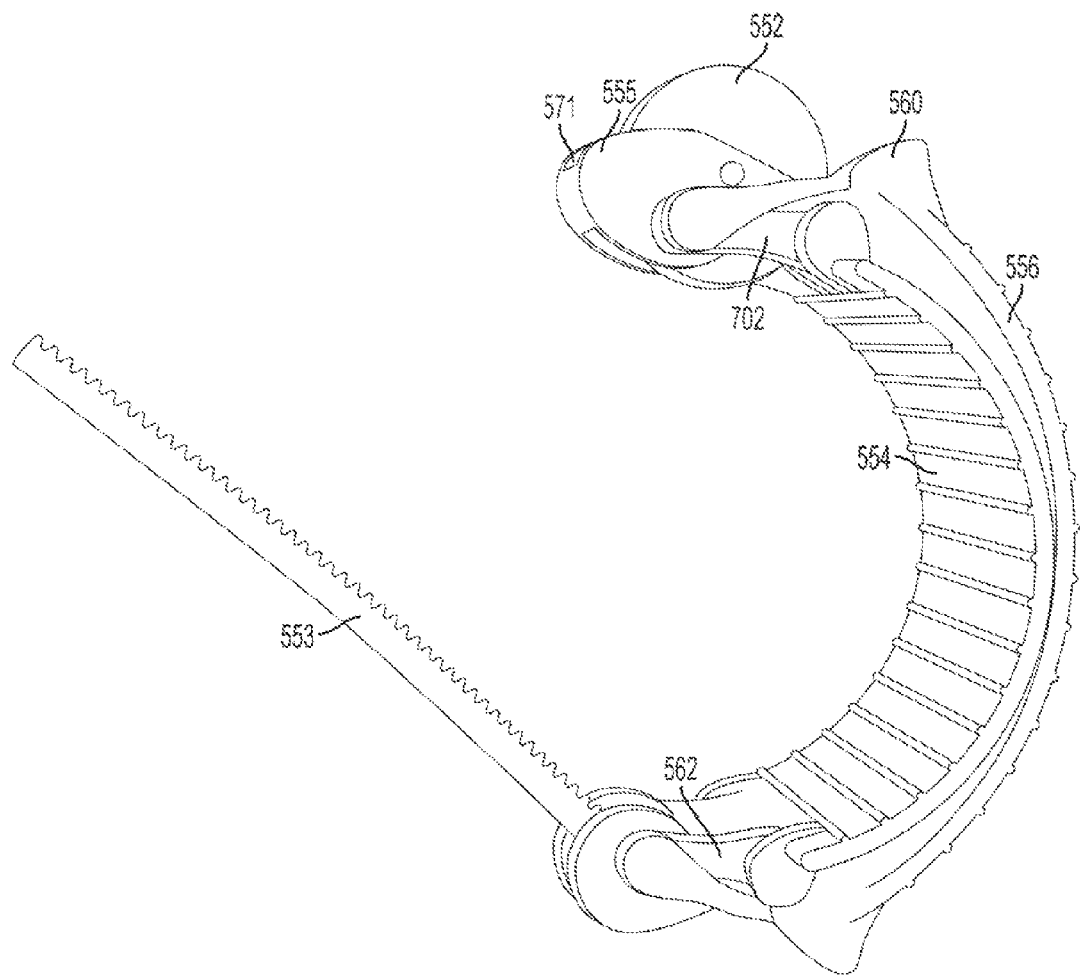
Figure 66E:
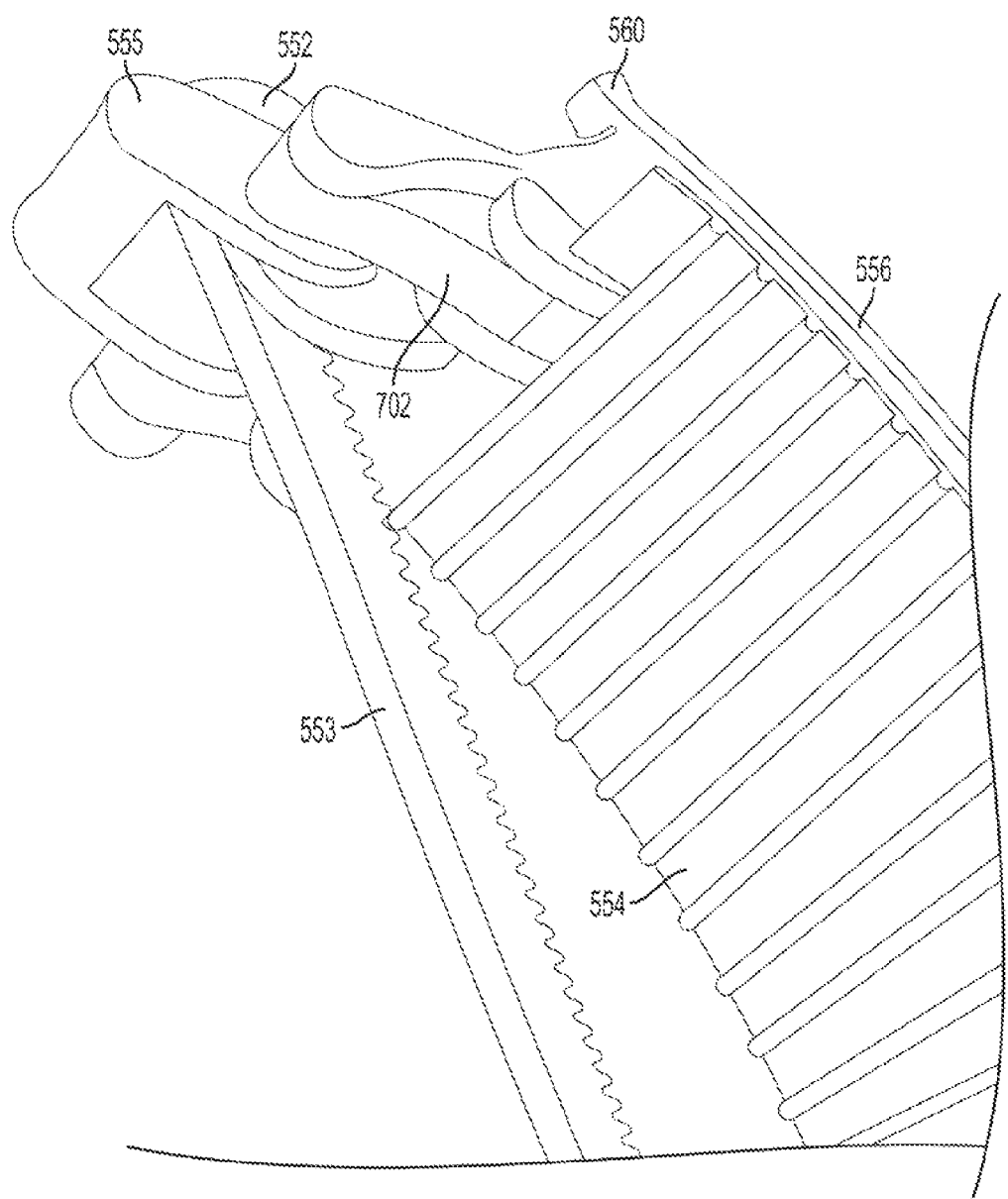
Figure 66F:
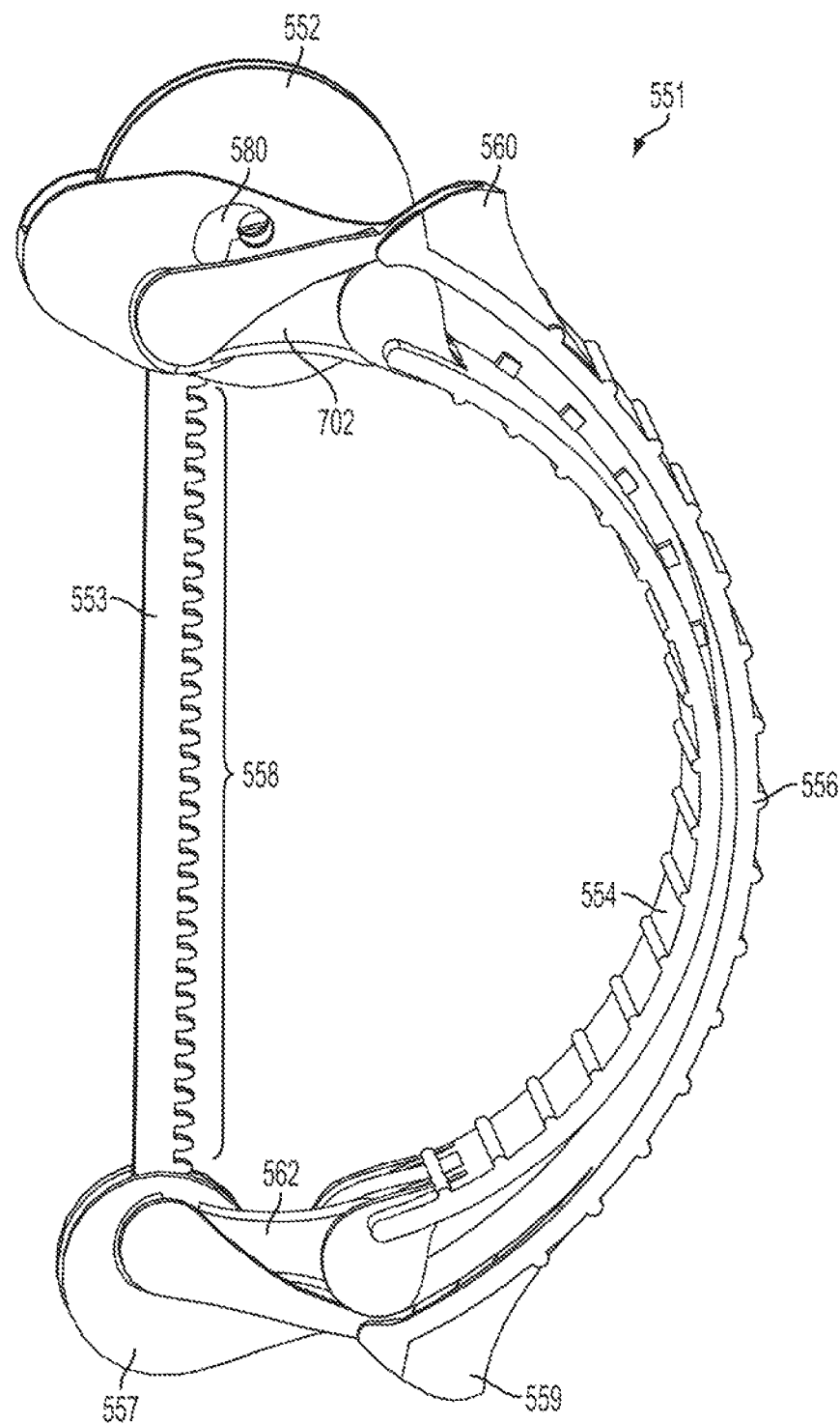
Figure 66G:
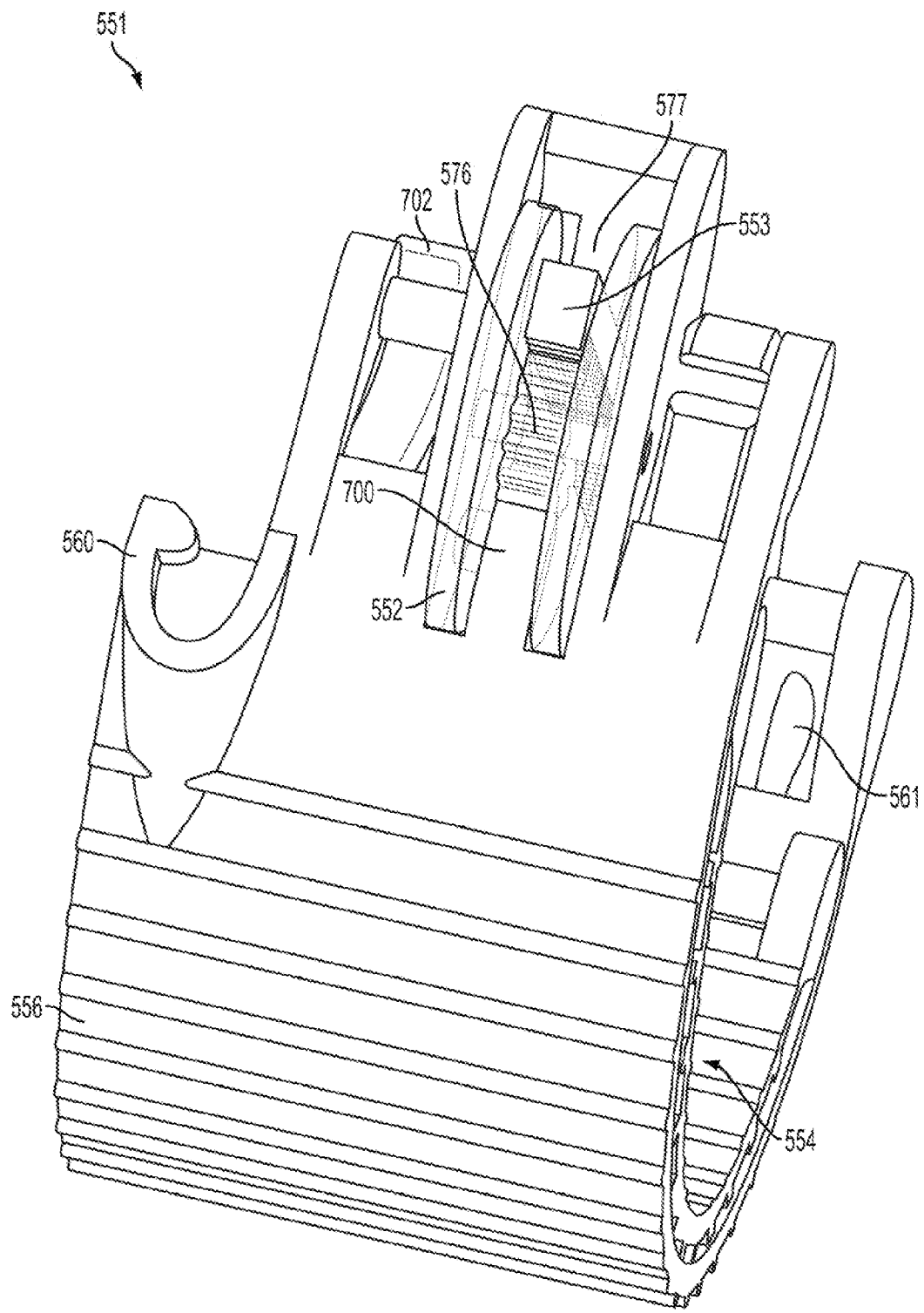

The inner support member 554 can pivot out away from the outer support member 556 such that a tube can be loaded via raised portions 559 and 560 (see FIG. 66C). The inner support member 554 pivots away from the outer support member 556 via dog bone linkers 561, 562, 701, and 702 as shown in FIG. 66C. Thereafter, the inner support member 554 pivots back towards the support member 556 as shown in FIG. 66D. The connecting member 553 is then inserted into an end 555 of the outer support member 556 (a close up of the insertion is shown in FIG. 66E) that includes the engaging finger 700 that locks onto the teeth 576 of the knob 552 which temporarily immobilizes the connecting member 553 (see FIG. 66G). The other end 581 of the connecting member 553 is locked into a hole 582 of an end 557 of the support member 556. The connecting member 553 may be pivotally connected to the end 557. The knob 552 includes teeth 576 to move the connecting member 553 in or out of the end 555. However, when the knob 552 is not moved, the engaging finger 700 locks the movement of the knob 552 unless a predetermined amount of torque clicks the finger 700 to the next tooth of the teeth 576 of the inner portion of the knob 552.

As previously mentioned, the support member 554 can swing away from the outer support member 556 as is shown in FIG. 66C, which is facilitated by the dog bone linkers 561, 562, 701, and 702. The dog bone linker 561 includes a pivot hole 572 that couples to a pivot 563 and a pivot hole 573 that couples to a pivot 565. The dog bone linker 562 includes a pivot hole 575 that couples to a pivot 566 and a pivot hole 574 that coupled to a pivot 566. The dog bone linker 701 couples to pivots 567 and 570, and the dog bone linker 702 couples to pivots 568 and 569 so that the end of the support member 556 also swings away from the inner support member 554.

Figure 67:
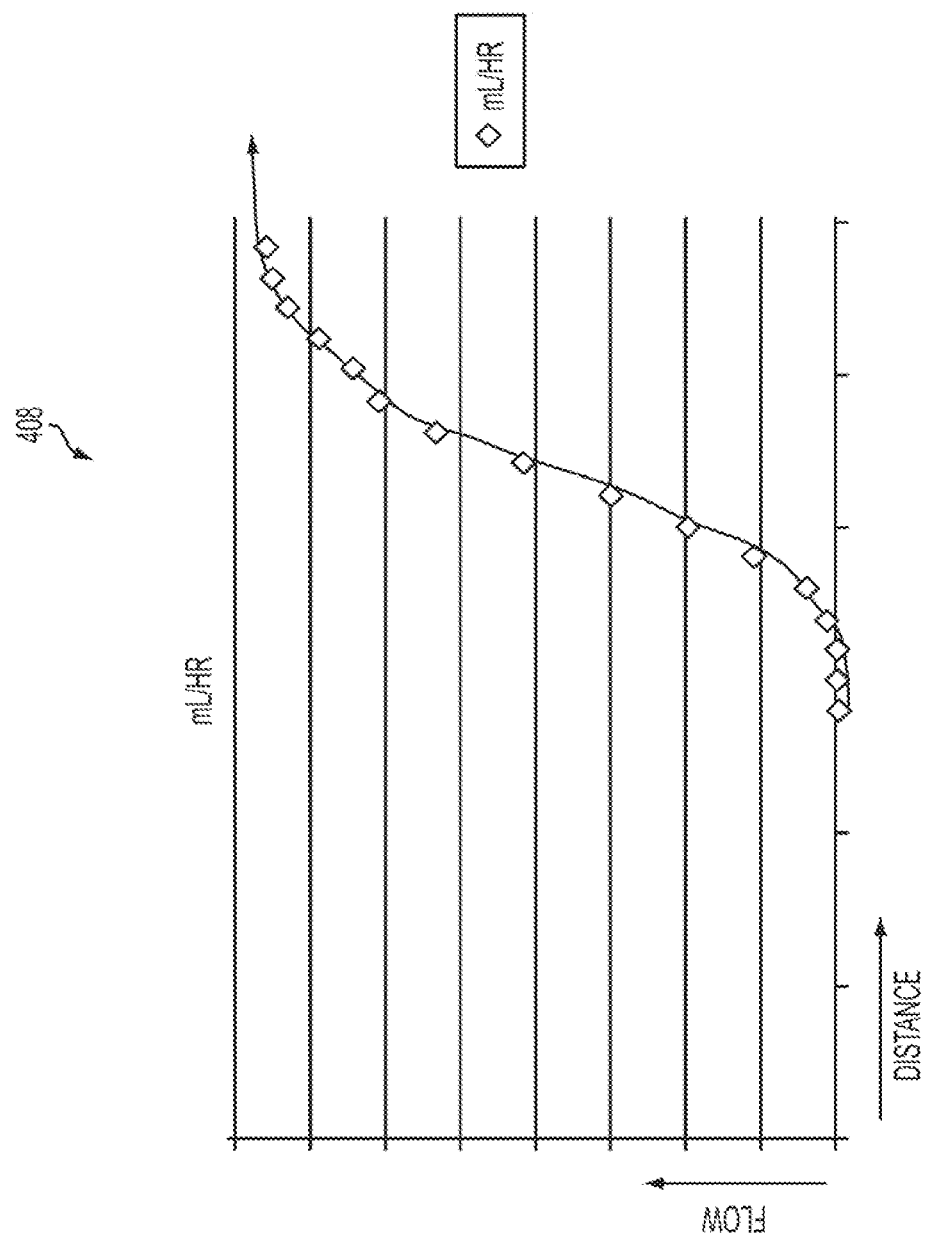
FIG. 67 shows a graphic that illustrates actuation vs. flow rates for a valve in accordance with an embodiment of the present disclosure.

FIG. 67 shows a graphic 408 that illustrates actuation vs. flow rates for a valve in accordance with an embodiment of the present disclosure. The graphic 408 shows the operation of a valve having elongated support members, such as, for example, the valve 340 of FIGS. 49 and 50A-50B, the valve 352 of FIGS. 51A-54, the valve 369 of FIG. 55, the valve 380 of FIGS. 56A-56C, the valve 380 of FIGS. 57A-57E, the valve 401 of FIGS. 58A-58D, the valve 500 of FIG. 59H, the valve 520 of FIGS. 60-60, the valve 542 of FIGS. 64A-64B, the valve 547 of FIG. 65, and/or the valve 551 of FIGS. 66A-66G. The x-axis of the graphic 408 shows the displacement between the ends of the support members of the valve, and the y-axis shows the flow rate (e.g., caused by gravity and/or a pressure source). The response of the valve is a nonlinear function, such as an S-curve, a sigmoid curve, a Gompertz curve, or a generalized logistic function. These functions may be adjusted to match the valve and/or the valve may be adjusted to match one of the curves or functions.

Figure 68A:
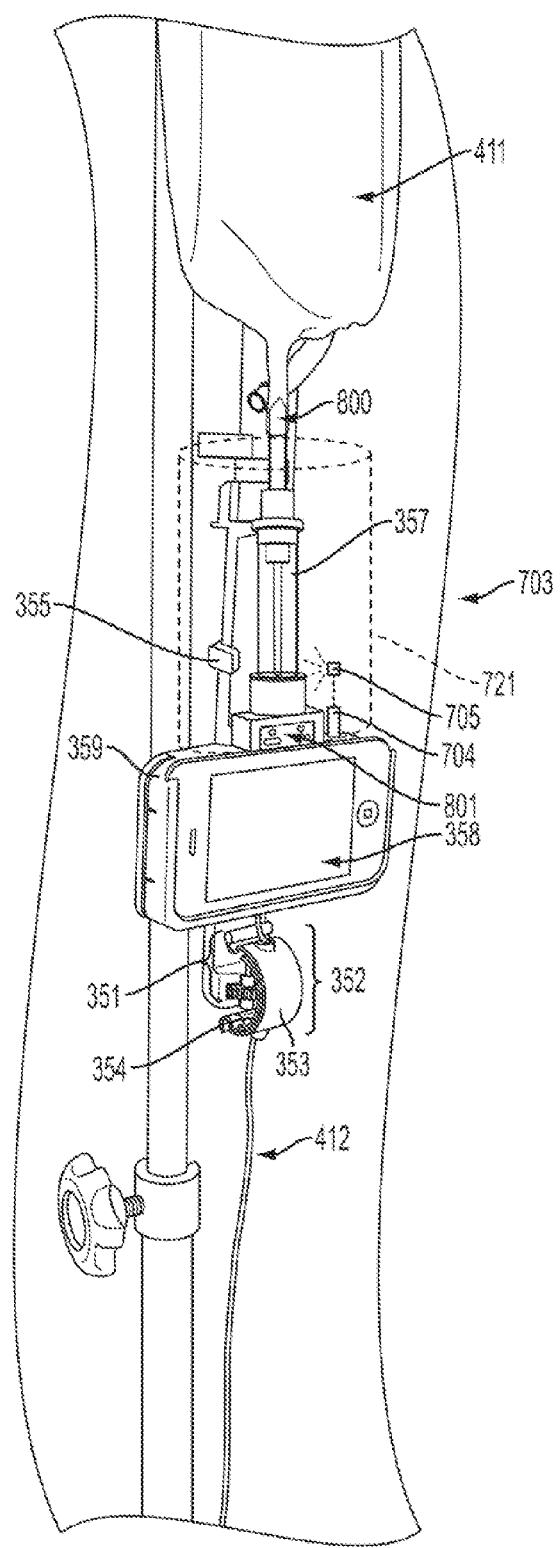
FIG. 68A shows a flow meter that uses binary optics in accordance with an embodiment of the present disclosure.

FIG. 68A shows a flow meter 703 that uses binary optics 705 in accordance with an embodiment of the present disclosure. The flow meter 703 includes a camera 355 that captures one or more images to estimate a flow rate of fluid through a drip chamber 357 using any sufficient method, e.g., the methods disclosed herein. The flow meter 703 includes a laser 704 that directs a laser beam onto a binary-optics assembly 705. The binary-optics assembly 705 thereafter redirects and reforms the laser beam through the drip chamber 357 and onto the image sensor 355 such that the image sensor 355 sees a pattern, e.g., the array of lines 85 shown in FIG. 8 which may form stripes as shown in the background pattern 89 of FIG. 10. The binary-optics assembly 705 may form the stripes by using a plurality of ovals.

The image sensor 355 may include a filter to filter out all frequencies except for the frequency of the laser 704. For example, the image sensor 355 may include an optical, bandpass filter that has a center frequency equal to (or about equal to) the optical frequency (or center frequency of the optical frequency) of the laser 704.

The monitoring client 358 may be electrically coupled to the laser 704 to modulate the laser 704. For example, the monitoring client 358 may turn on the laser 704 only when predetermined pixels are being exposed and may turn off the laser 704 when other pixels besides the predetermined pixels are being exposed.

The flow meter 703 optionally includes a first electrode 800 and a second electrode 801. The monitoring client 358 may be electrically coupled to the first and second electrodes 800, 801 to measure a capacitance defined therebetween. In streaming conditions, the capacitance changes because the relative permittivity is different for air and water. The monitoring client 358 may monitor the changes that results from a streaming condition with the drip chamber 357 by monitoring the capacitance between the first and second electrodes 800, 801 and correlate increases and/or decreases of the capacitance beyond a threshold as corresponding to either a streaming condition and/or a non-streaming condition. For example, if the capacitance between the first and second electrodes 800, 801 is higher than a threshold, a processer within the monitoring client 358 may determine that the drip chamber 357 is undergoing a streaming condition.

In an alternative embodiment, the first and second electrodes 800, 801 are loop antennas. The monitoring client 358 uses a transceiver to monitor the magnetic coupling between the loop antennas 800, 801. For example, the transceiver may transmit a coded message from one loop antenna of the antennas 800, 801, to another one of the loop antennas 800, 801 and then determine if the coded message was successfully received. If so, then a received signal strength indication ("RSSI") measurement may be made from the transceiver. See FIG. 68B for an exemplary circuit. The RSSI may be used to monitor the magnetic coupling between the antennas 800, 801. If the magnetic coupling is above a threshold, then the monitoring client 358 may determine that a streaming condition exists within the drip chamber 357. In some embodiments a change of magnetic coupling or a change of capacitive coupling may be determined to be an indication that a streaming condition has occurred.

The flow meter 703 may also include a safety valve 706. FIGS. 69A-69F show several views of the safety valve 706 that may be used with a flow meter, such as the flow meter 703 of FIG. 68, in accordance with an embodiment of the present disclosure.

Figure 69B:
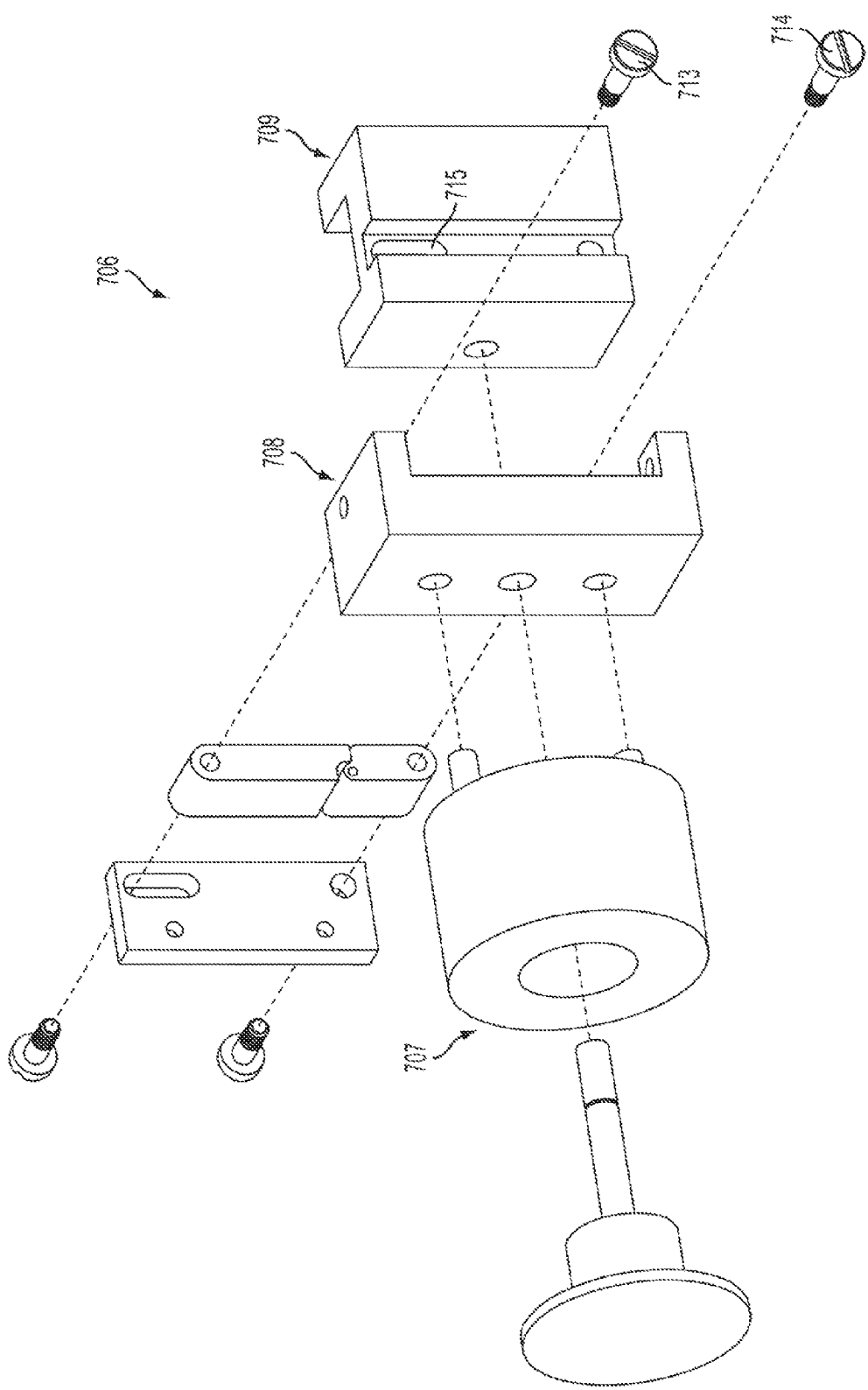

FIGS. 69A-69B show exploded views of the safety valve 706. The safety valve 706 includes a solenoid 707, an interface structure 708, a tube housing 709, a spring 720, a faceplate 712, a first axle 713, a second axle 714, a first occluding arm 710, and a second occluding arm 711. The faceplate 712 includes a hole 715, and the tube housing 709 also includes a hole 819. The holes 715, 819 allow the axle 713 to slide within the holes 715, 819.

Figure 69C:
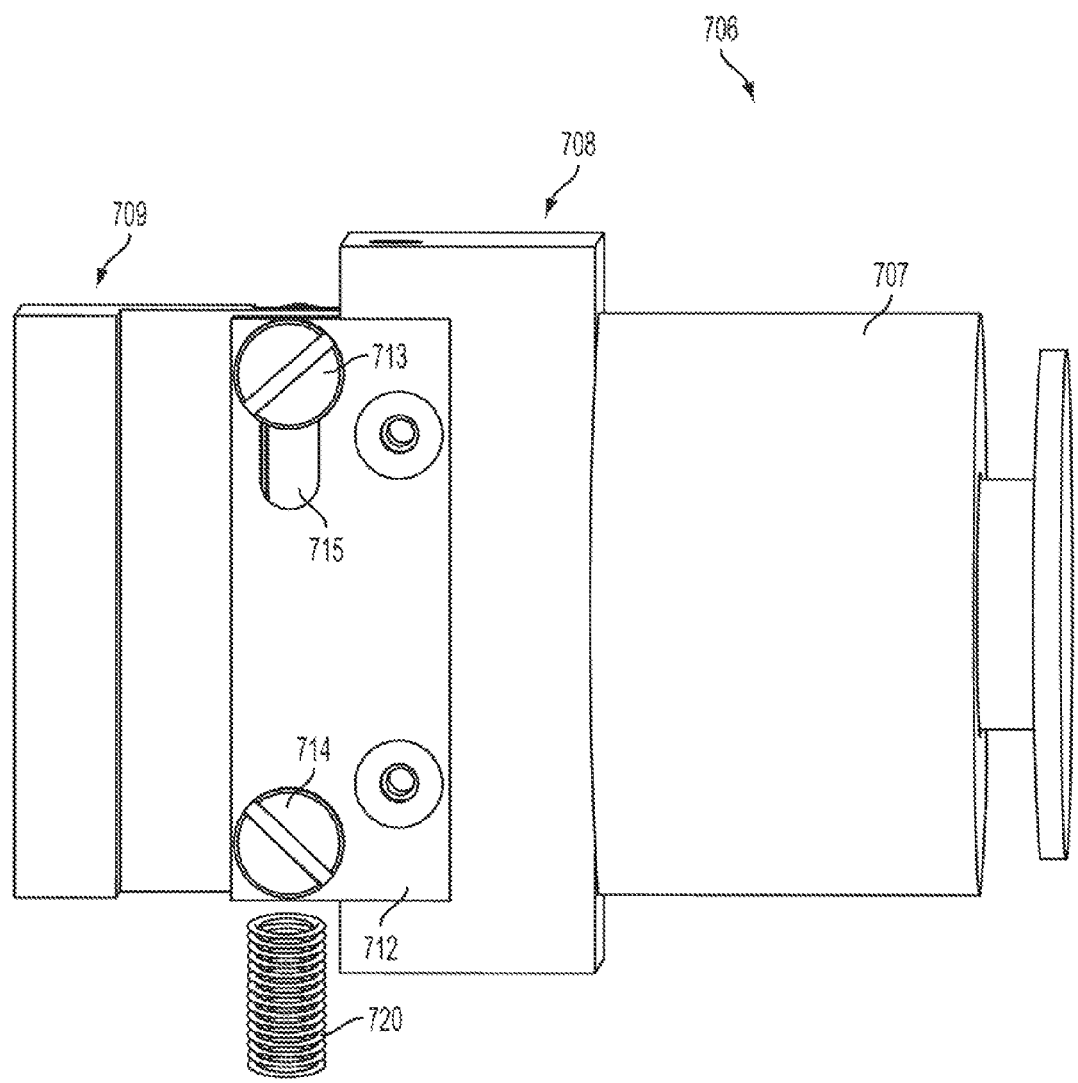
Figure 69D:
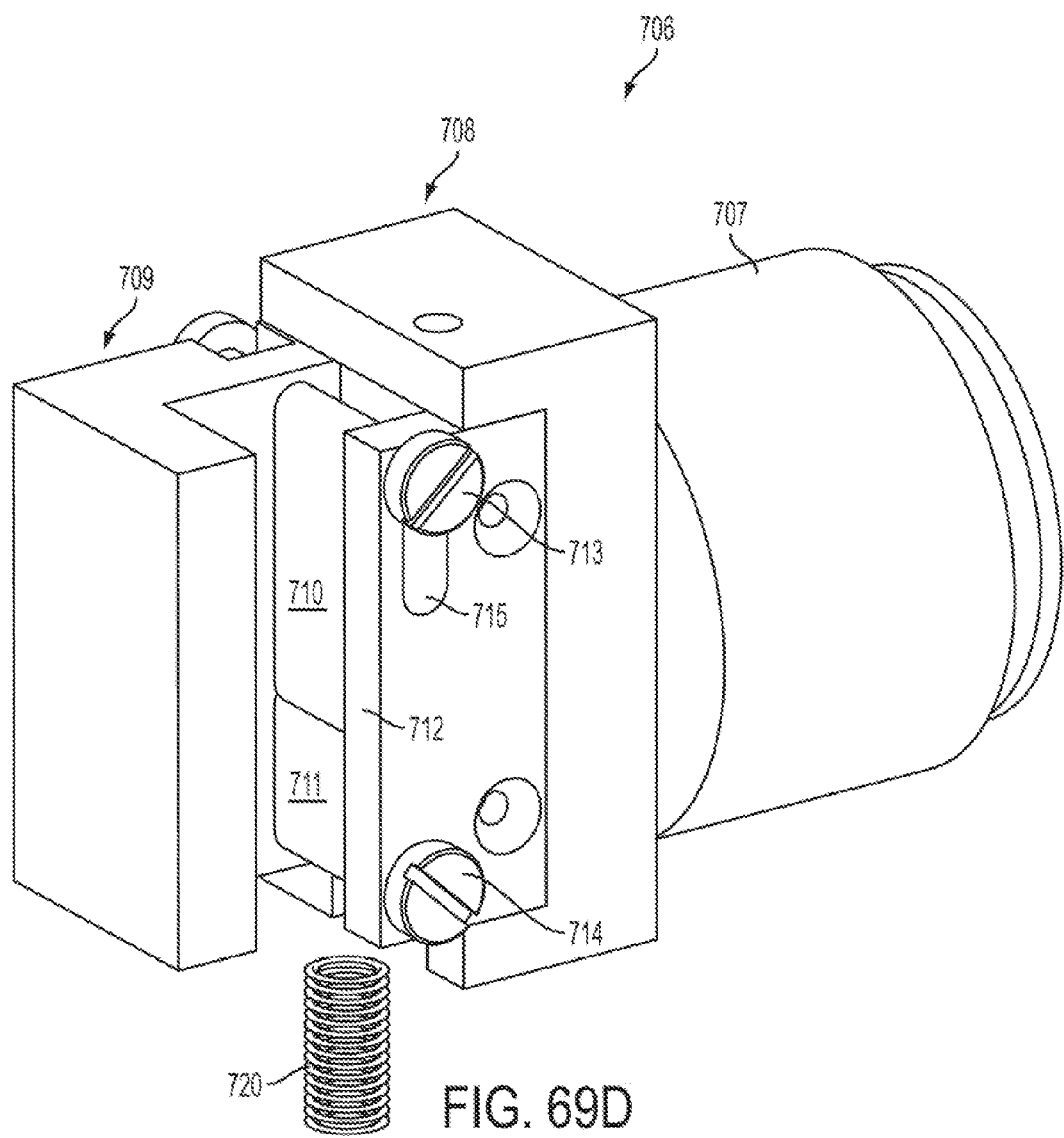
Figure 69E:
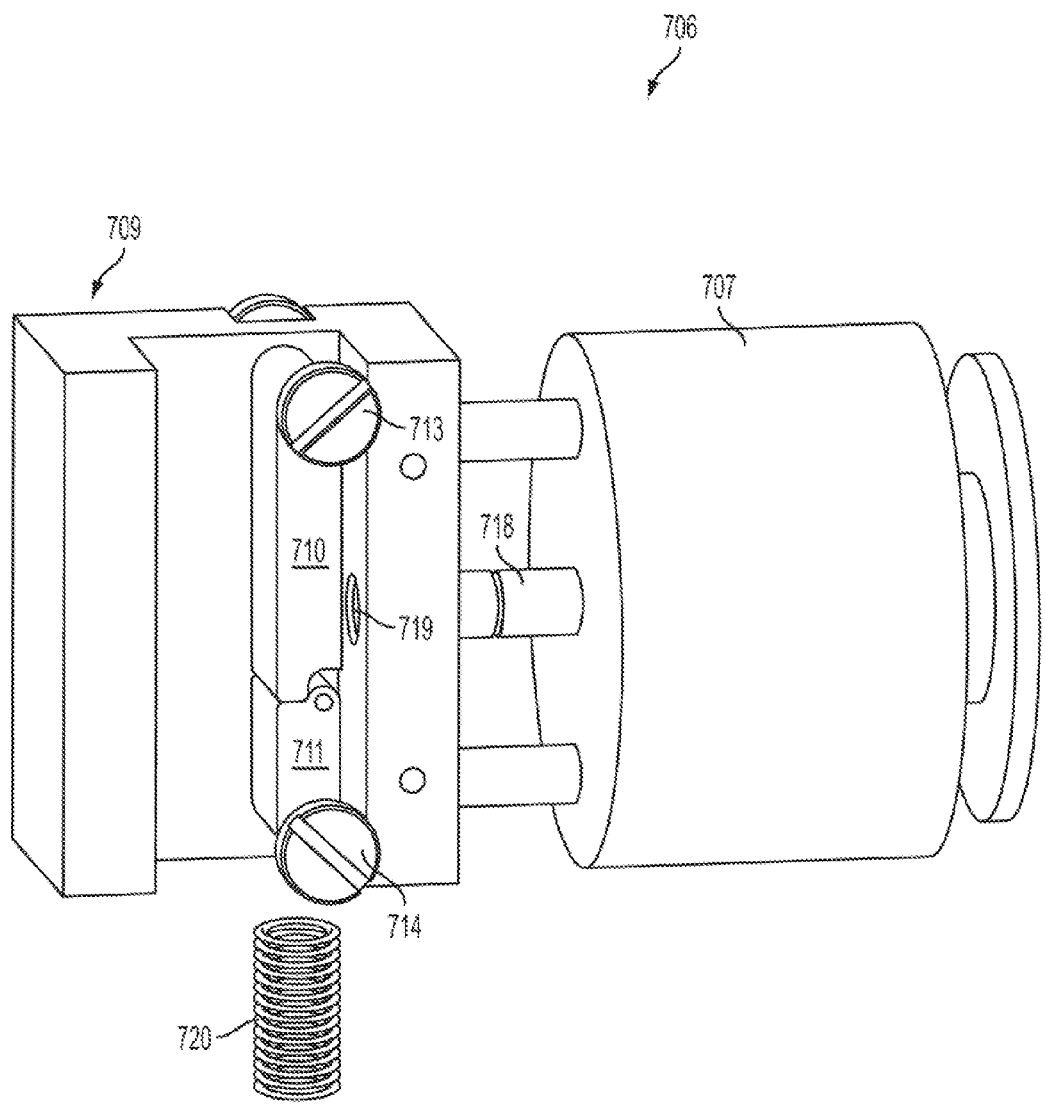
Figure 69F:
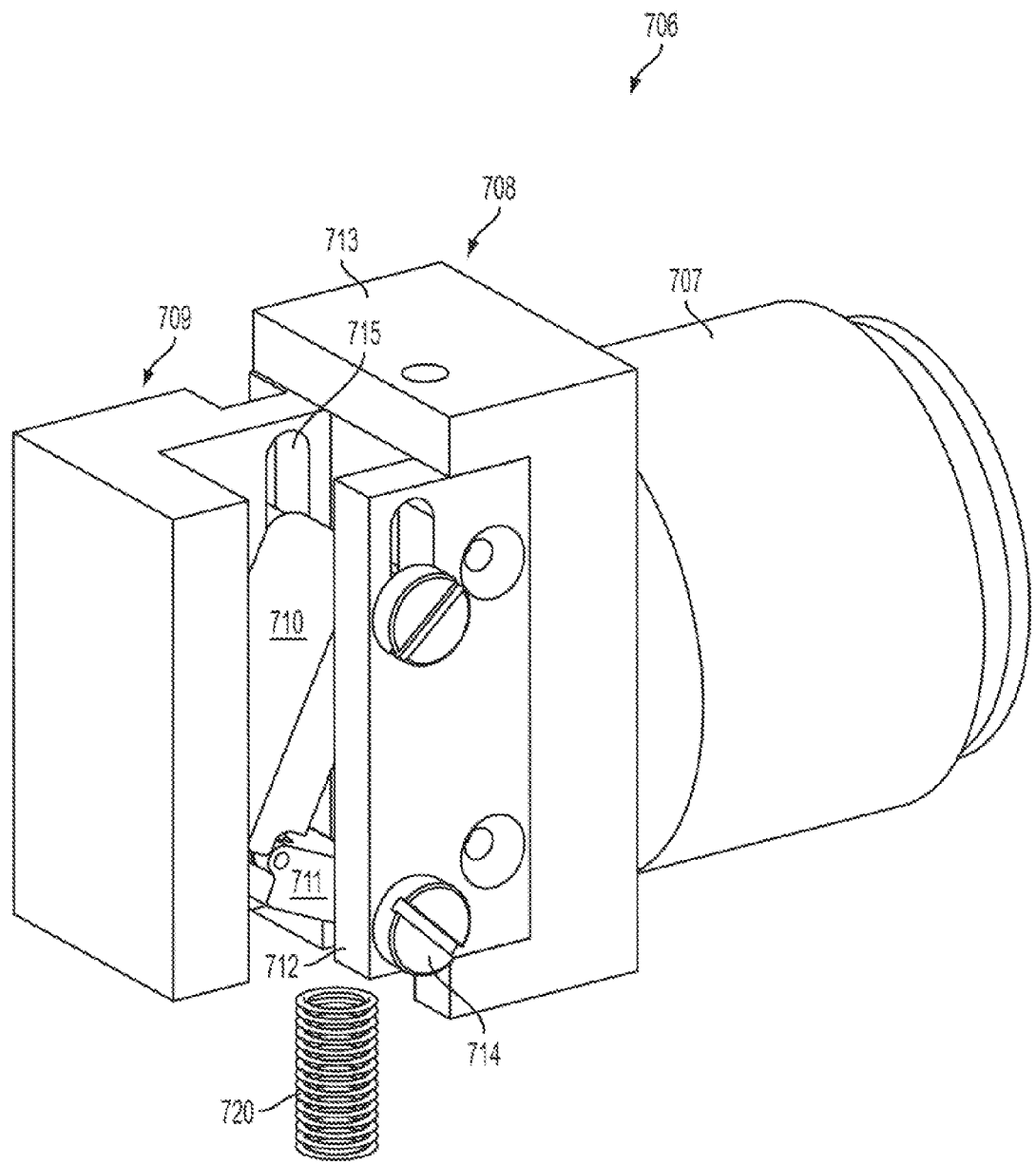

As shown in FIG. 69C, a tube 820 may be placed within the tube housing 709 which places the tube 820 next to the first and second occluding arms 710, 711, which are easily seen in FIG. 69D. A spring 720 keeps the first and second occluding arms 710, 711 retraced when in the retracted state (as shown in FIG. 69D), but stores energy such that a predetermined amount of movement of the first and second occluding arms 710, 711 towards the tube 810 cause the spring 720 to discharge its stored mechanical energy to cause the first and second occluding arms 710, 711 to extend out and occlude the tube 820. The spring 720, which may be a compression spring 720, may pull the first and second axles 713, 714 towards each other. The first and second occluding arms 710, 711 are pivotally connected together. As is easily seen in FIG. 69E, a shaft 718 of a solenoid 707 can actuate through a hole 719 to push on the spring 720 which causes the spring 720 to release its energy and occlude the tube 820 (see FIG. 69F for the case when the where the first and second occluding arms 710, 711 are in the occluding position).

Figure 70:
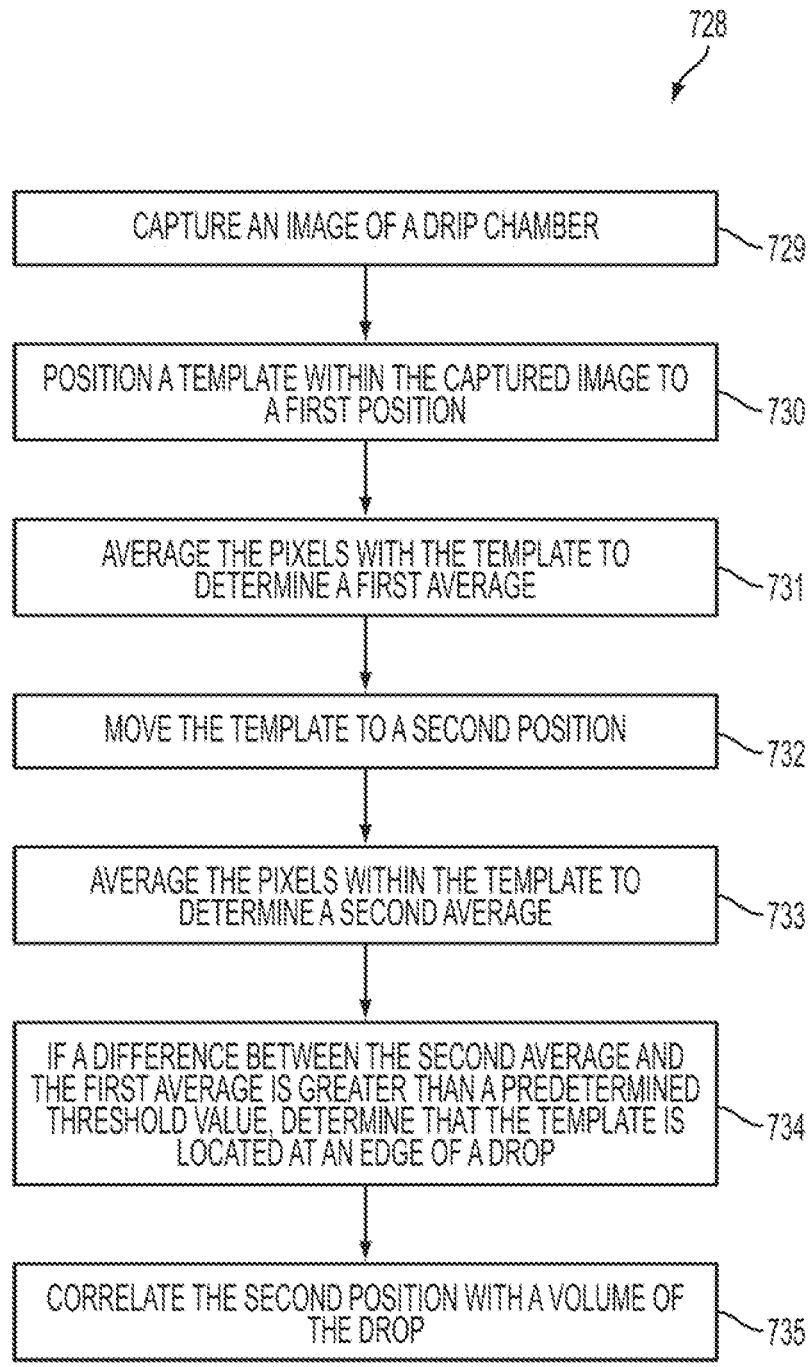
FIG. 70 shows a flow chart diagram illustrating a method of estimating drop growth and/or flow within a drip chamber in accordance with an embodiment of the present disclosure.

FIG. 70 shows a flow chart diagram illustrating a method 728 of estimating drop growth and/or flow within a drip chamber in accordance with an embodiment of the present disclosure. The method 728 includes acts 729-735. FIGS. 71A-71E show images taken by a flow meter with a template overlaid therein to illustrate the method of FIG. 70.

Figure 71A:
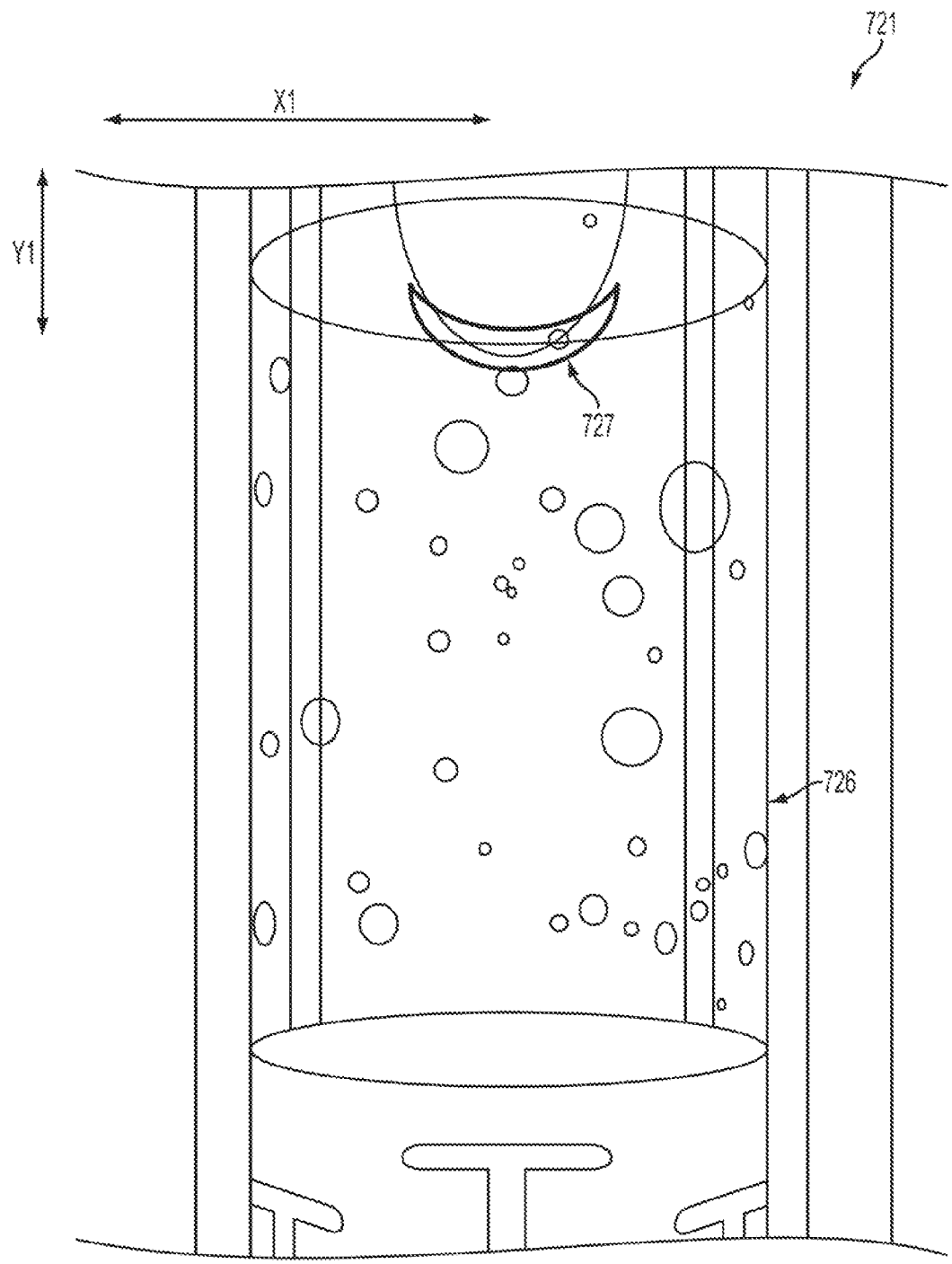
FIGS. 71A-71E show images taken by a flow meter with a template overlaid therein to illustrate the method of FIG. 70 in accordance with an embodiment of the present disclosure.

Act 729 captures an image of a drip chamber. The image captured may be the image 721 of FIG. 71A. Act 730 positions a template within the captured image to a first position. For example, as shown in FIG. 71A, a template 727 may be positioned within a predetermined position. Act 731 averages all of the pixels within the template 727. Act 732 moves the template to a second position. For example, the template 727 in FIG. 71A may move the template in the Y direction (e.g., down as seen in FIG. 71A).

Figure 71B:
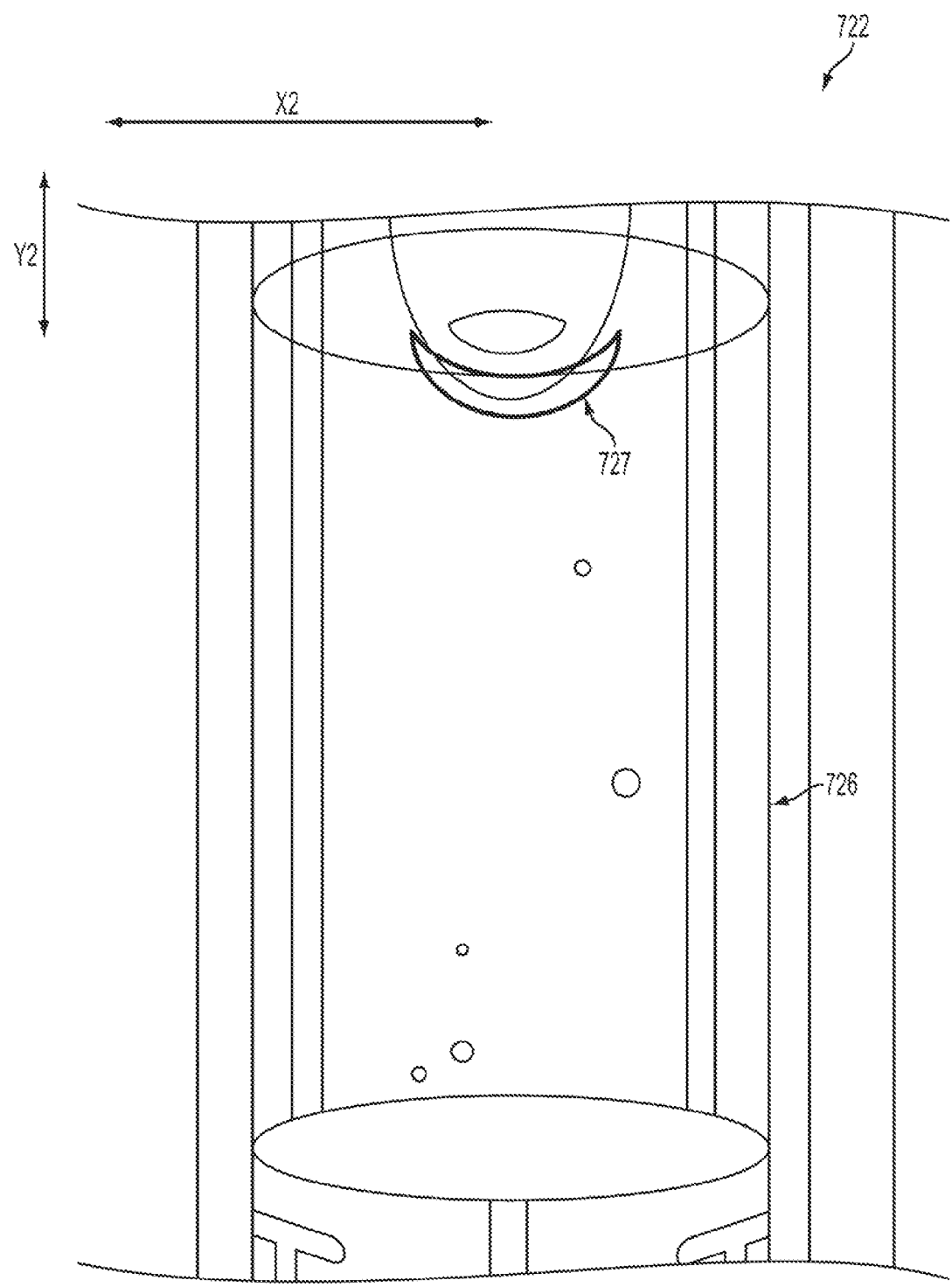
Figure 71C:
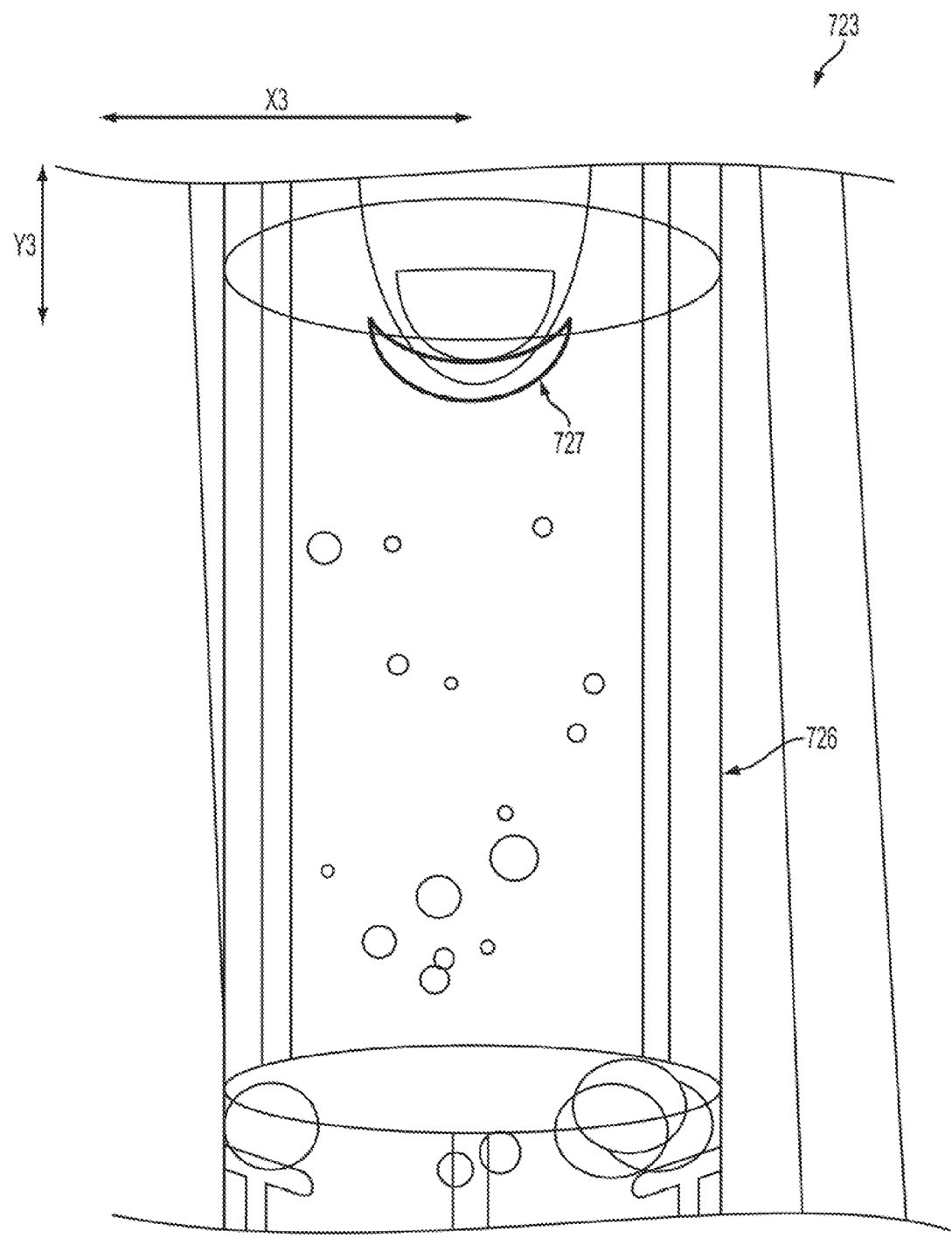
Figure 71D:
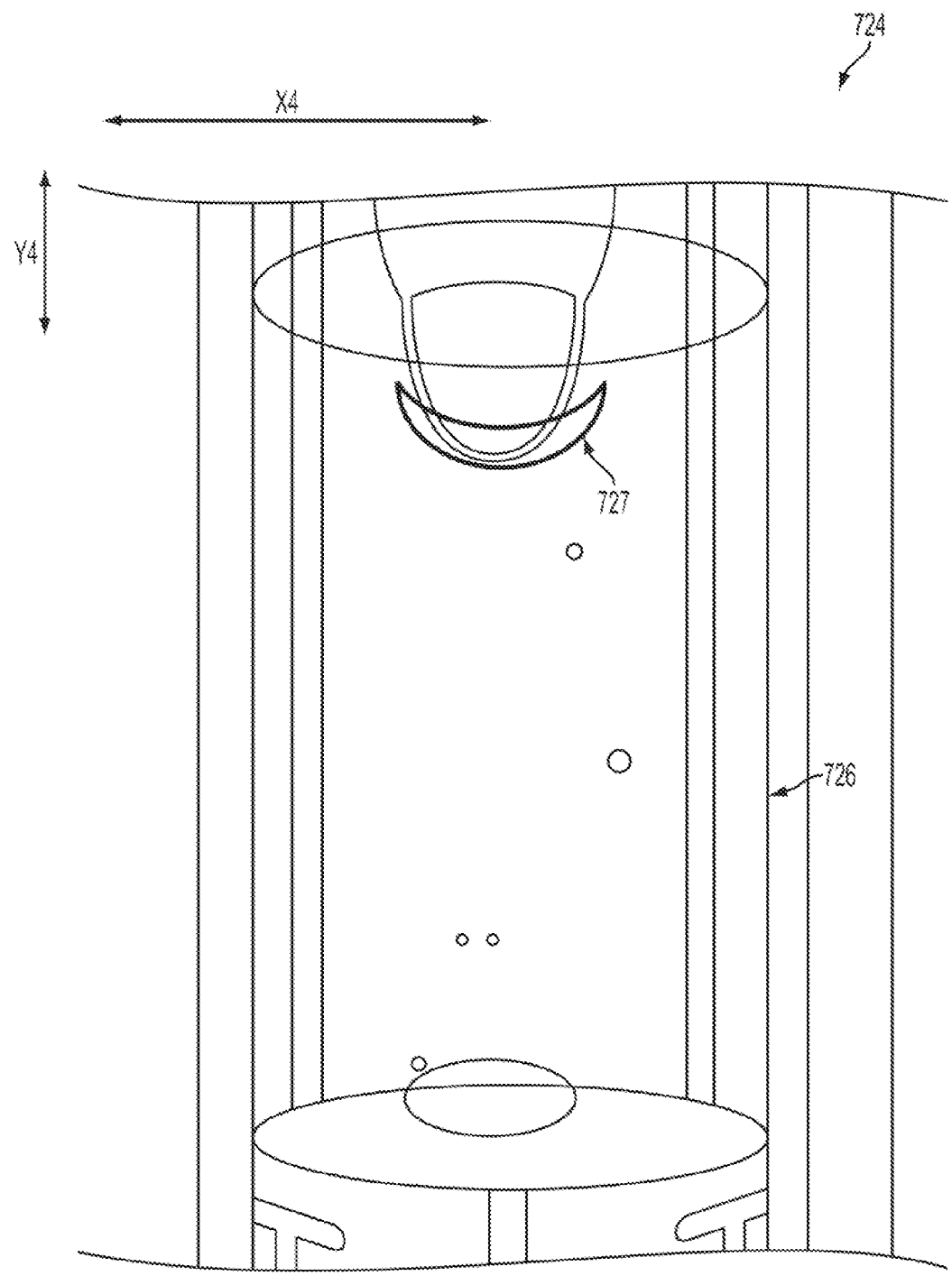
Figure 71E:
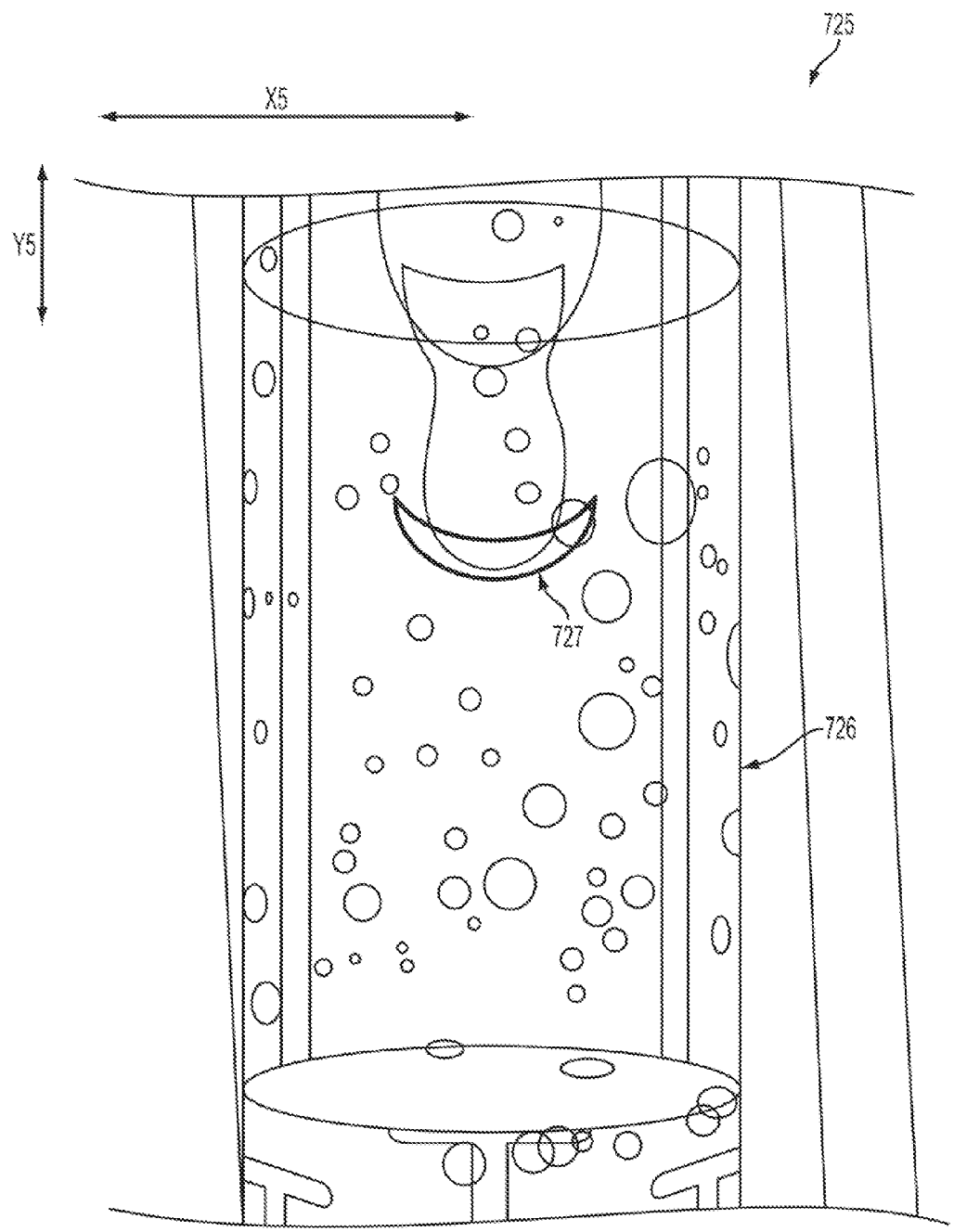

In act 733, the pixels within the template are used to determine a second average. In act 734, if a difference between the second average and the first average is greater than a predetermined threshold value, determine that the template is located at an edge of a drop. For example, referring to FIG. 71A, the template may be slowly lowered down in the Y direction, until the template 727 transitions from the edge of a drop to a portion of the image that doesn't contain the drop, in which case the average value of the pixels will transition abruptly to a dark average to a lighter average. When this transition occurs, the Y position of the template 727 is considered to be at the edge of the drop (e.g., $Y_1$ of FIG. 71A). In act 735, the second position of the drop is correlated with a volume of the drop. For example, the $Y_1$ value may be associated with a volume of a drop in a lookup table. In some embodiments of the present disclosure, multiple movements of the template 727 are needed to until the edge of the drop is detected. For example, the template 727 may be moved in the y-direction one pixel at a time (or several pixels at a time) and several template 727 movements may be needed such that the edge of the drop is detected. By monitoring the edge of the drop, the growth of the drop may be controlled by the flow meter to achieve a target flow rate (e.g., the rate of the transition between Y1 of FIG. 71A to Y2 of FIG. 71B may be controlled by a PID control loop within a flow meter). FIG. 71B shows a location, $Y_2$, that corresponds to a growth in the drop relative to the location, $Y_1$, of FIG. 71A.

Figure 72:
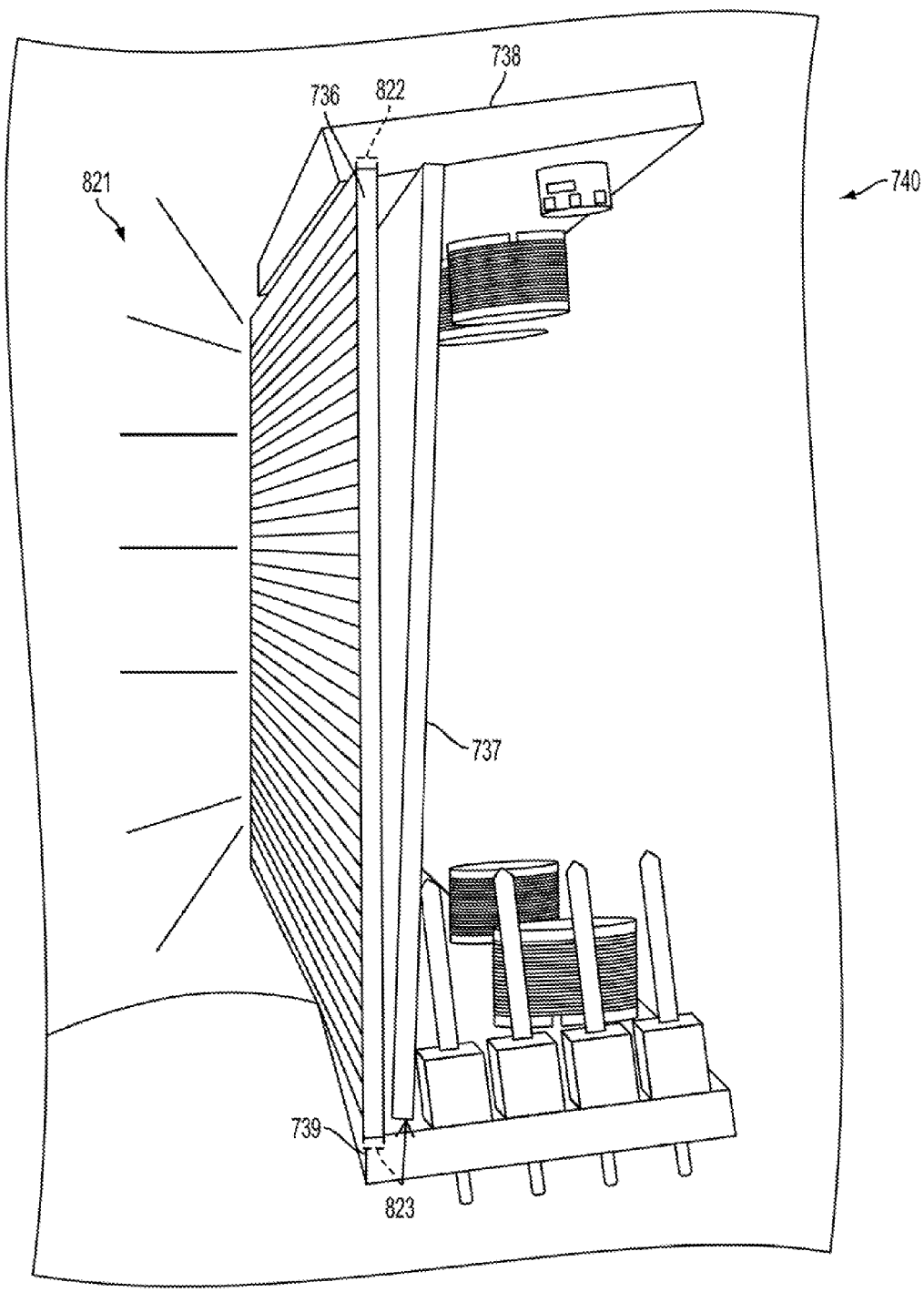
FIG. 72 shows a modulateable backlight assembly in accordance with an embodiment of the present disclosure.

FIG. 72 shows a modulateable backlight assembly 740 in accordance with an embodiment of the present disclosure. The assembly 740 may be the backlight 18 of FIG. 1 or may be used as a backlight for any sufficient flow meter disclosed herein. The assembly 740 includes a first circuit board 738, a second circuit board 739, a first backlight diffuser 736, and a second backlight diffuser 737.

The first circuit board 738 includes embedded light sources 822 that extend along the interface between the first backlight diffuser 736 and the first circuit board 738. The embedded light sources 822 shine light into the first backlight diffuser 736 which is directed outwards as indicated by 821. The light 821 may be directed towards an image sensor. The first backlight diffuser 736 only diffuses light with no "pattern" formed when viewed by an image sensor.

The second circuit board 739 includes embedded lights 823 which are shined into the second backlight diffuser 737. The second backlight diffuser 737 creates a pattern of stripes that shows up in the light 821 when viewed by an image sensor. Therefore, a monitoring client (e.g., the monitoring client 358 of FIG. 51A) and/or a flow meter (e.g., the flow meter 7 of FIG. 1) can select between a striped background pattern (by activating the embedded lights 823) and a non-striped background pattern (by activating the embedded lights 822).

For example, referring now to FIGS. 1 and 72, the flow meter 7 may use the backlight assembly 740 in some specific embodiments; The flow meter 7 may use a non-striped backlight pattern (by activating the embedded LEDs 822 without activating the embedded LEDs 823) to monitor the growth of drops and may switch to a striped background pattern (by activating the embedded LEDs 823 without activating the embedded LEDs 822) to detect streaming conditions.

Figure 73A:
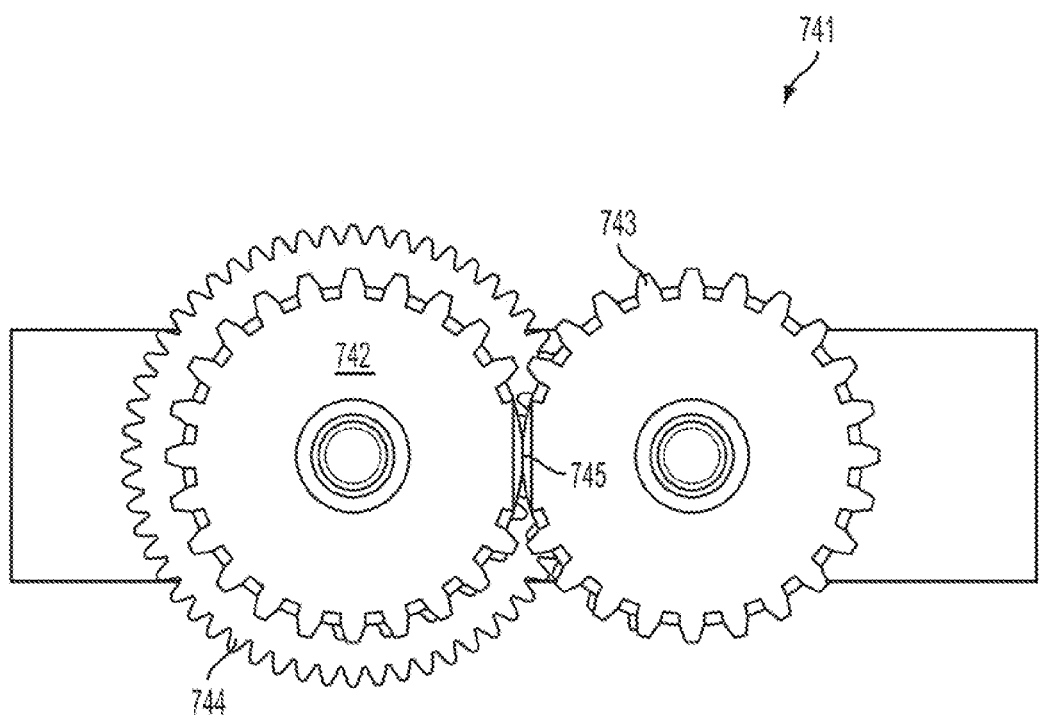
FIGS. 73A-73C show several views of a tube-restoring apparatus in accordance with an embodiment of the present disclosure.
Figure 73B:
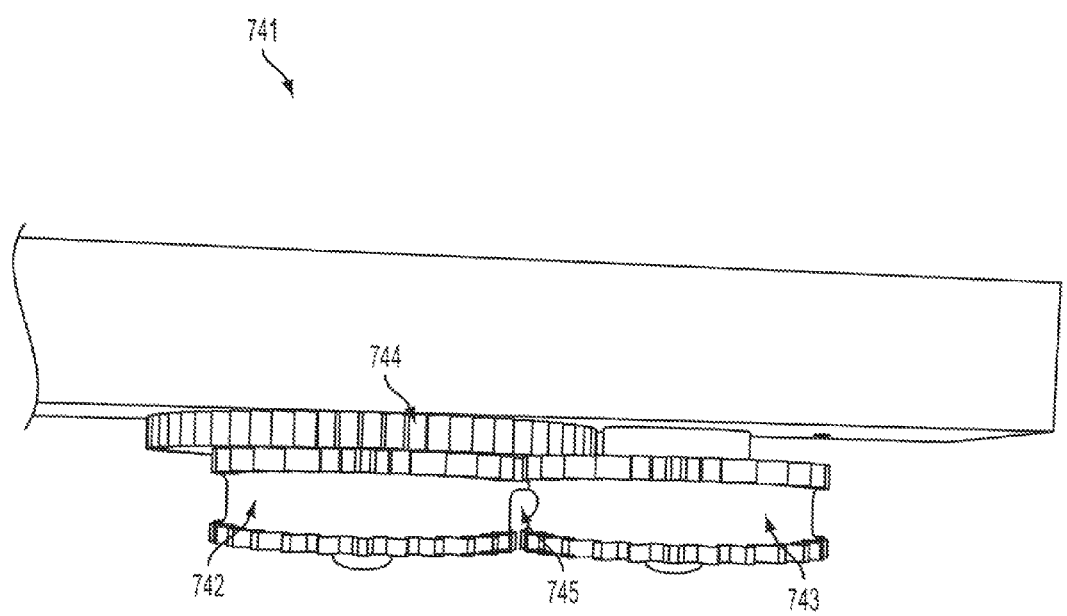
Figure 73C:
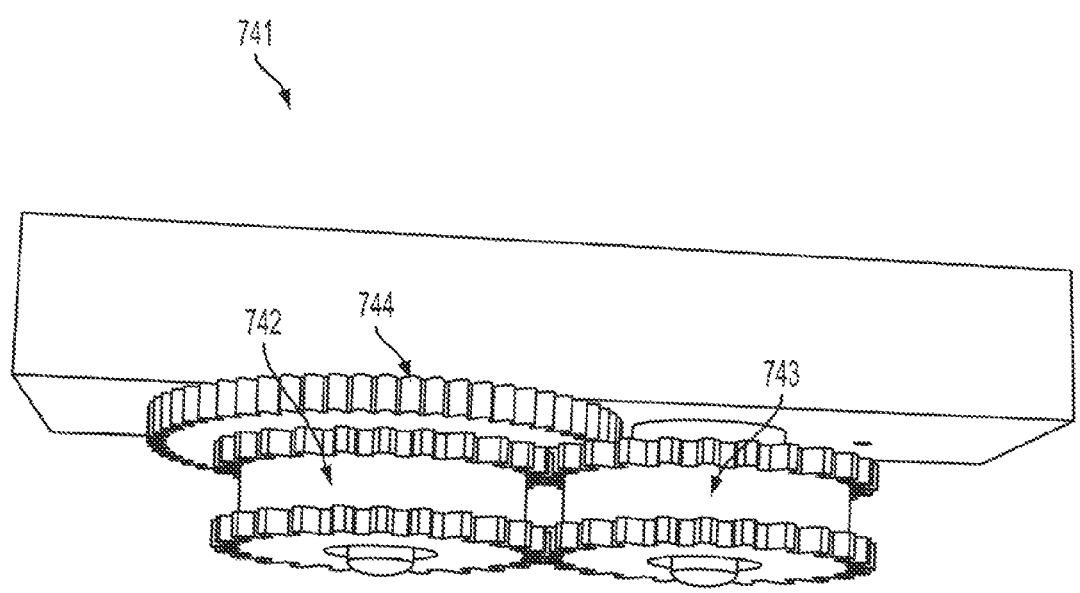

FIGS. 73A-73C show several views of a tube-restoring apparatus 741 in accordance with an embodiment of the present disclosure. The apparatus 741 includes a drive gear 744 that is coupled to a first restoring gear 742. The first restoring gear 742 is mechanically coupled to a second restoring gear 743. A tube may be placed between the first and second restoring gears 742, 743. Portions of the first and second restoring gears 742, 743 define a space 745 in which a tube may be positioned. Rotation of the first and second restoring gears 742, 743 closes the distance between the space 745 when the tube is positioned between the first and second restoring gears 742, 743. The transition from a non-restoring position to a restoring position is shown in FIG. 73B to FIG. 73C. For example, a tube may be positioned such that an occluder presses against the tube from the bottom up (as shown in FIG. 73B). If the tube becomes distorted over time, a motor connected to the driving gear 744 rotates the gears 743 and 744, to press against the walls of the tube (as shown in FIG. 73C) to restore the tube by compressing on the wall portions of the tube that are expanded beyond a center axis of the tube such that the tube is distorted into an oval shape, for example.

Figure 74:
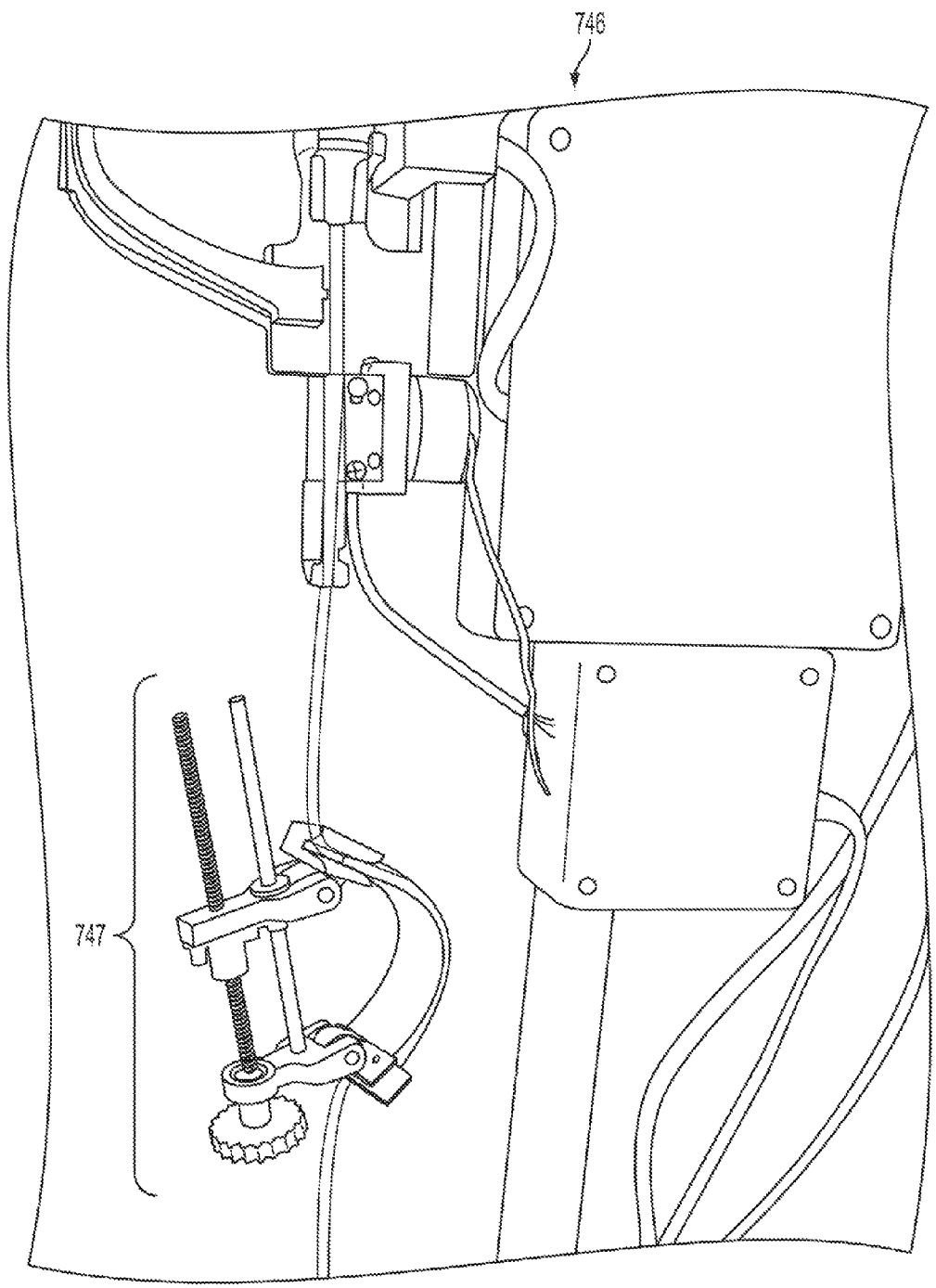
FIG. 74 shows a system for regulating fluid flow using a valve having two flexible strips in accordance with an embodiment of the present disclosure.
Figure 75:
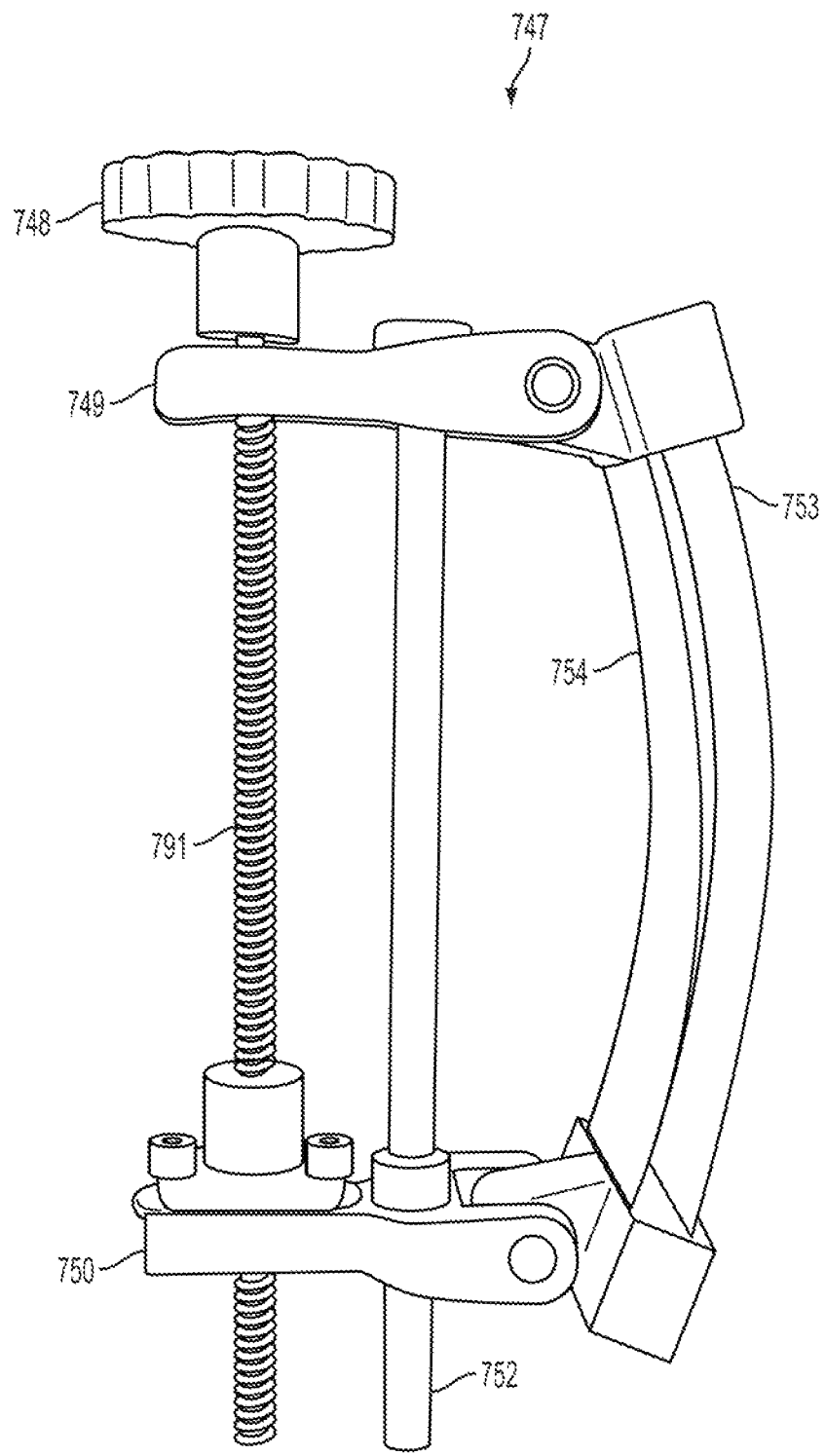
FIG. 75 shows the valve of FIG. 74 in accordance with an embodiment of the present disclosure.

FIG. 74 shows a system for regulating fluid flow 746 using a valve 747 having two flexible strips 753 and 754 (see FIG. 75); And FIG. 75 shows the valve 746 of FIG. 74 in accordance with an embodiment of the present disclosure. Optionally, a motor may be attached to the valve 746 for control by a flow meter in one embodiment.

As shown in FIG. 75, the valve 747 includes two flexible strips 753, 754 in which a tube may be disposed therebetween, a guiding shaft 752, two guidable members 749, 750, a screw 791, and a knob 748.

When the knob 748 is turned, the screw 791 rotates. Rotation of the screw 791 pulls the distal guiding member 750 toward the proximal guiding member 749 (because the distal guiding member 750 includes internal threads and the screw 791 spins freely within the proximal guiding member 749). The guide 752 guides the movement of the distal guiding member 750. The guide 752 is coupled to the proximal guiding member 749.

Figure 76A:
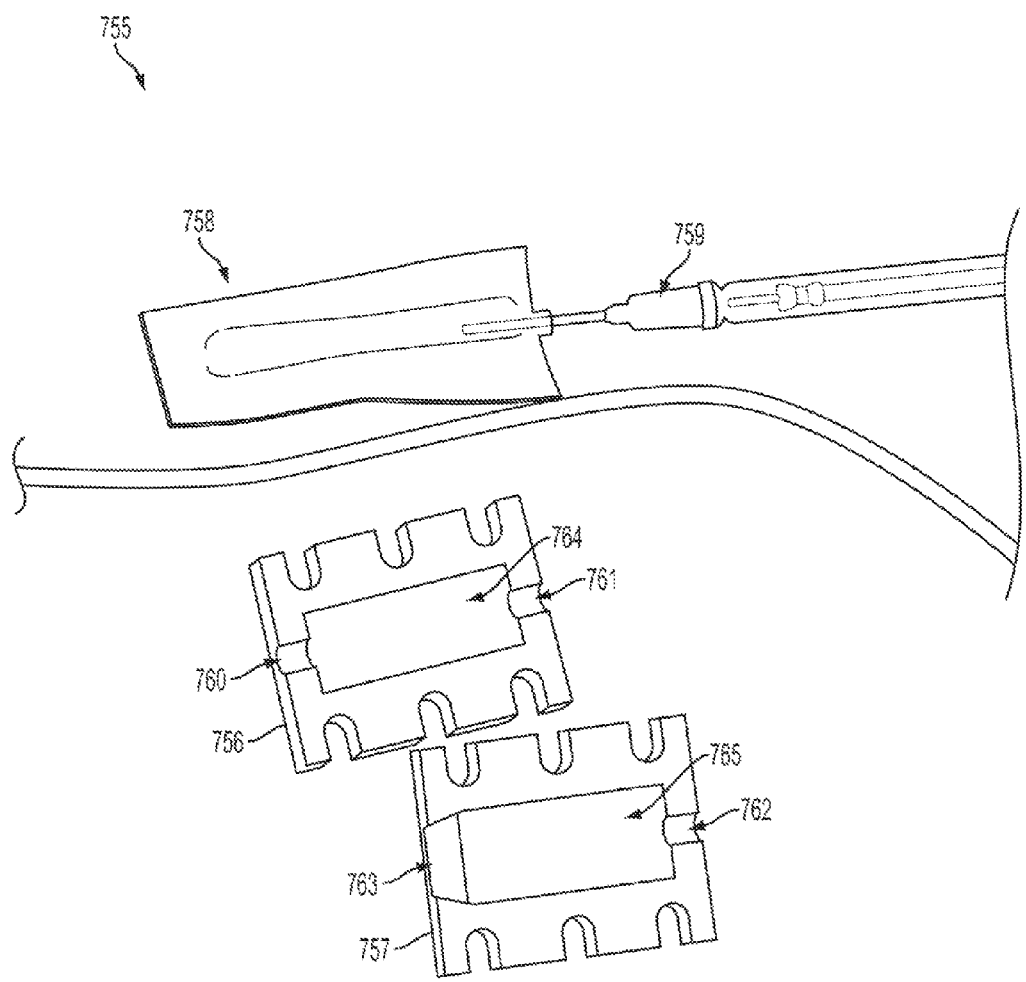
FIG. 76A shows a valve that utilizes a fluid-based bladder in accordance with an embodiment of the present disclosure.

FIG. 76A shows a valve 755 that utilizes a fluid-based bladder 758 in accordance with an embodiment of the present disclosure. The valve 755 includes two clamshells 756, 757, a bladder 758, and a piston 759. The piston 759 may be any fluid source. The bladder 758 may be placed within a cavity 764 and a tube may be placed across the bladder 758 and positioned within the throughways 760 and 761. Thereafter, the clamshell 757 may be placed over the bladder 758 such that the cavity 765 is placed over the bladder 758. The two clamshells 756, 757 may then be ultrasonically welded together, temporarily compressed together, and/or sufficiently held together. Thereafter, an actuator (e.g., an actuator controlled by a flow meter disclosed herein) may be actuated to move fluid in and out of the bladder 758 via the piston 759.

Figure 76B:
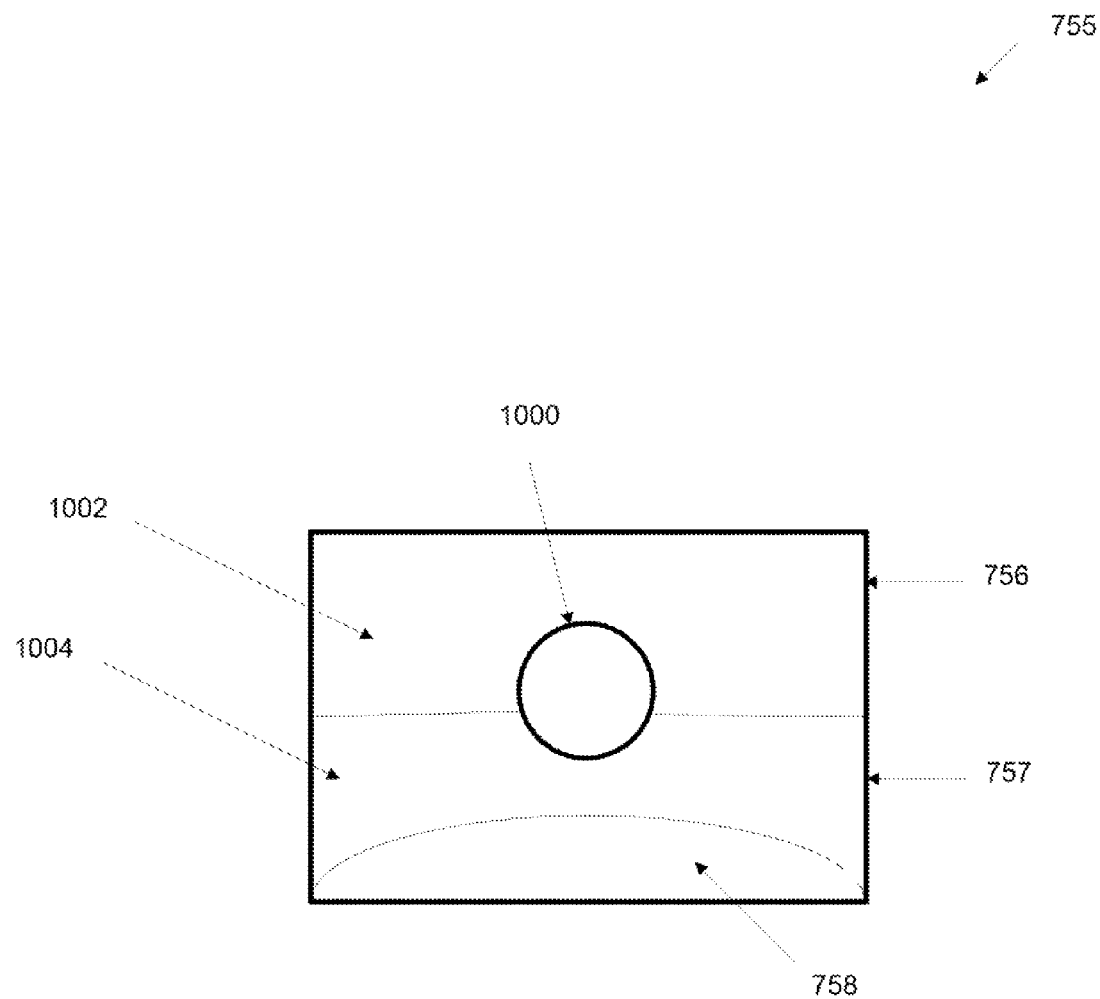
FIG. 76B shows a cross-sectional view of the assembled valve of FIG. 76A with two elastomeric fillers in accordance with an embodiment of the present disclosure.

FIG. 76B shows a cross-sectional view of the assembled valve 755 of FIG. 76A with two elastomeric fillers 1002, 1004 in accordance with an embodiment of the present disclosure. The elastomeric fillers 1002, 1004 help hold the tube 1000 into position and help restore the tube 1000 when the bladder 758 is deflated.

Figure 77:
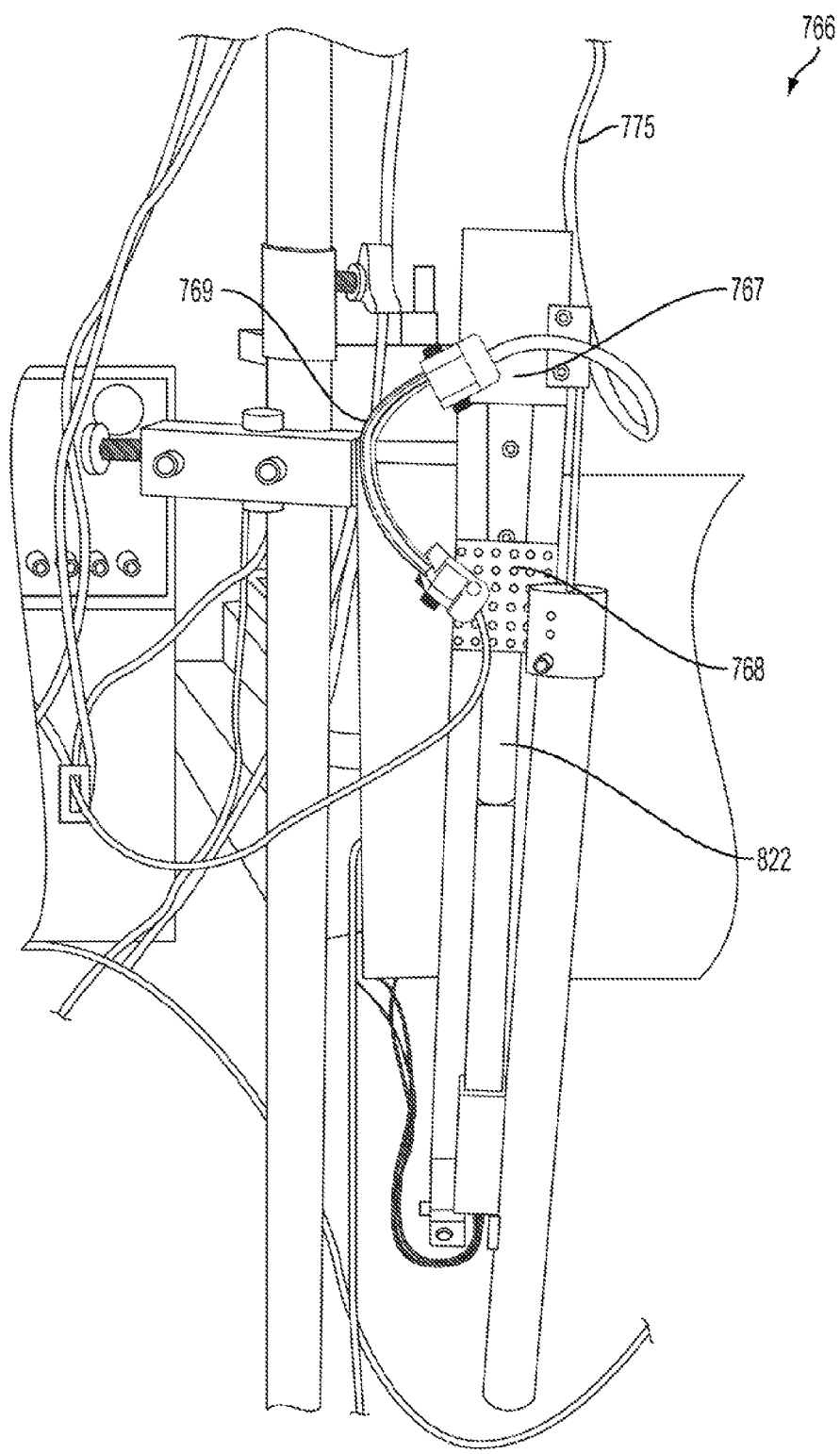
FIG. 77 shows a system for regulating fluid flow using a valve having two flexible strips actuateable by a linear actuator in accordance with an embodiment of the present disclosure.
Figure 78:
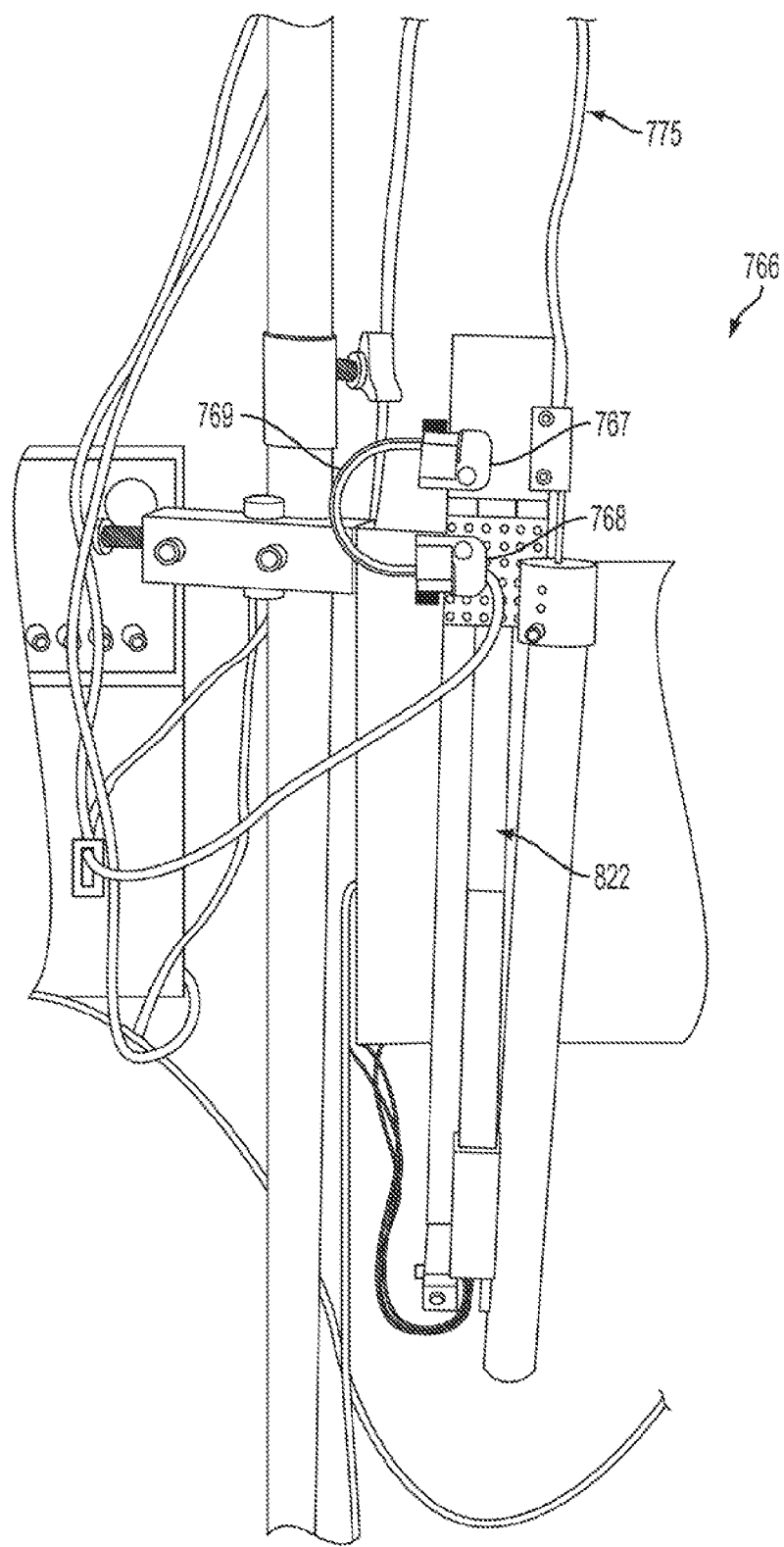
FIG. 78 shows the system of FIG. 77 with the valve actuated in accordance with an embodiment of the present disclosure.

FIG. 77 shows a system 766 for regulating fluid flow using a valve 769 having two flexible strips 771, 772 (see FIG. 79) actuateable by a linear actuator 822 in accordance with an embodiment of the present disclosure. FIG. 78 shows the linear actuator 822 actuating the valve 769 to impeded fluid flow through a tube 775. The valve 769 is coupled to two couplers 767 and 768. The proximal coupler 768 moves with the linear actuator 822 while the distal coupler 767 is fixed relative to a non-moving end of the linear actuator 822.

Figure 79:
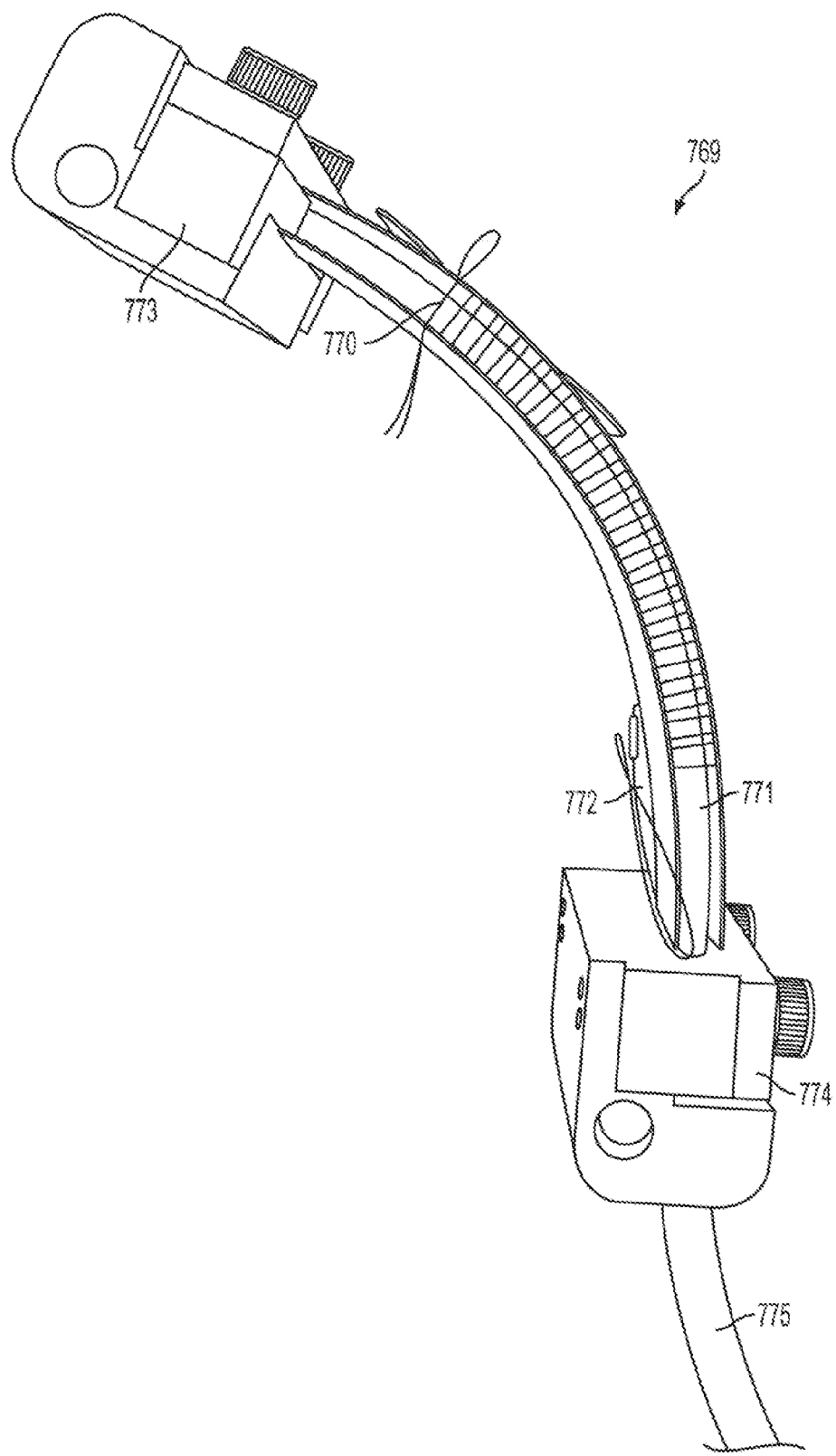
FIG. 79 shows a close-up view of the valve of FIGS. 77-78 in accordance with an embodiment of the present disclosure.
Figure 80:
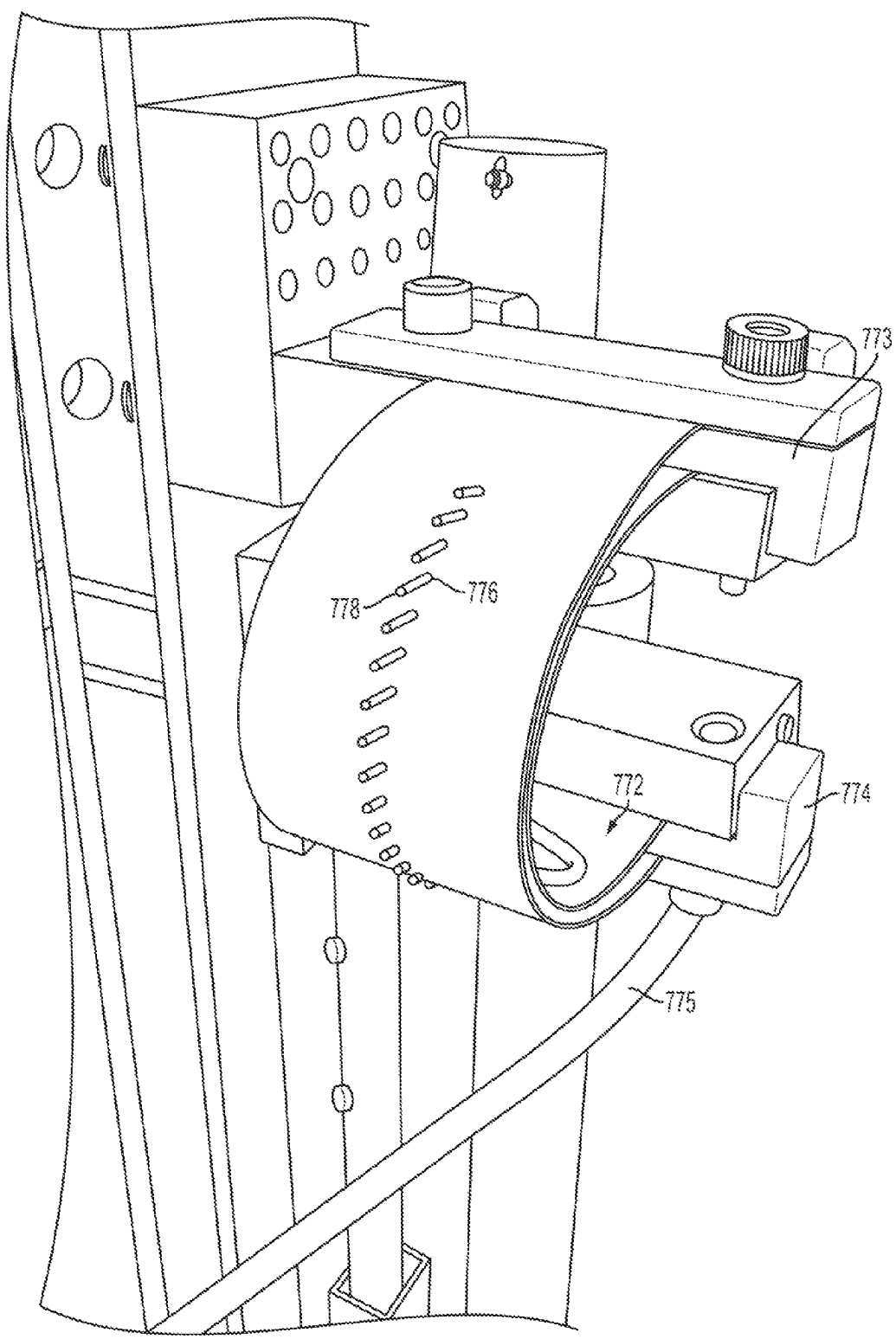
FIG. 80 shows a close-up view of the valve as actuated in FIG. 78 in accordance with an embodiment of the present disclosure.

FIG. 79 shows a close-up of the valve 769 of FIGS. 77-78. The valve 769 includes two strips 771, 772 (which may be metallic strips) in which the tube 775 may be disposed. The two strips 771, 772 of the valve 769 may be coupled to a first end structure 773 and a second end structure 774. The first end structure 773 may be coupled to the distal coupler 767 and the second end structure 774 may be coupled to the proximal coupler proximal coupler 768 (see FIGS. 77-78). A string 770 or membrane may be wrapped around the tube 775 such that, when the strips 771, 772 are straightened out, the string 770 presses against the side walls of the tube 775 to help round the tube 775. The membrane may be a flexible, but not stretchable, material (or minimally stretchable material). FIG. 80 shows a close-up of the valve as actuated in FIG. 78. Note the holes 776 and 778 that the string 770 is threaded through. The string 770 (which may metallic) is spiraled around the tube 775 such that when the valve 769 opens, the string 770 restores the tube 775.

Figure 81:
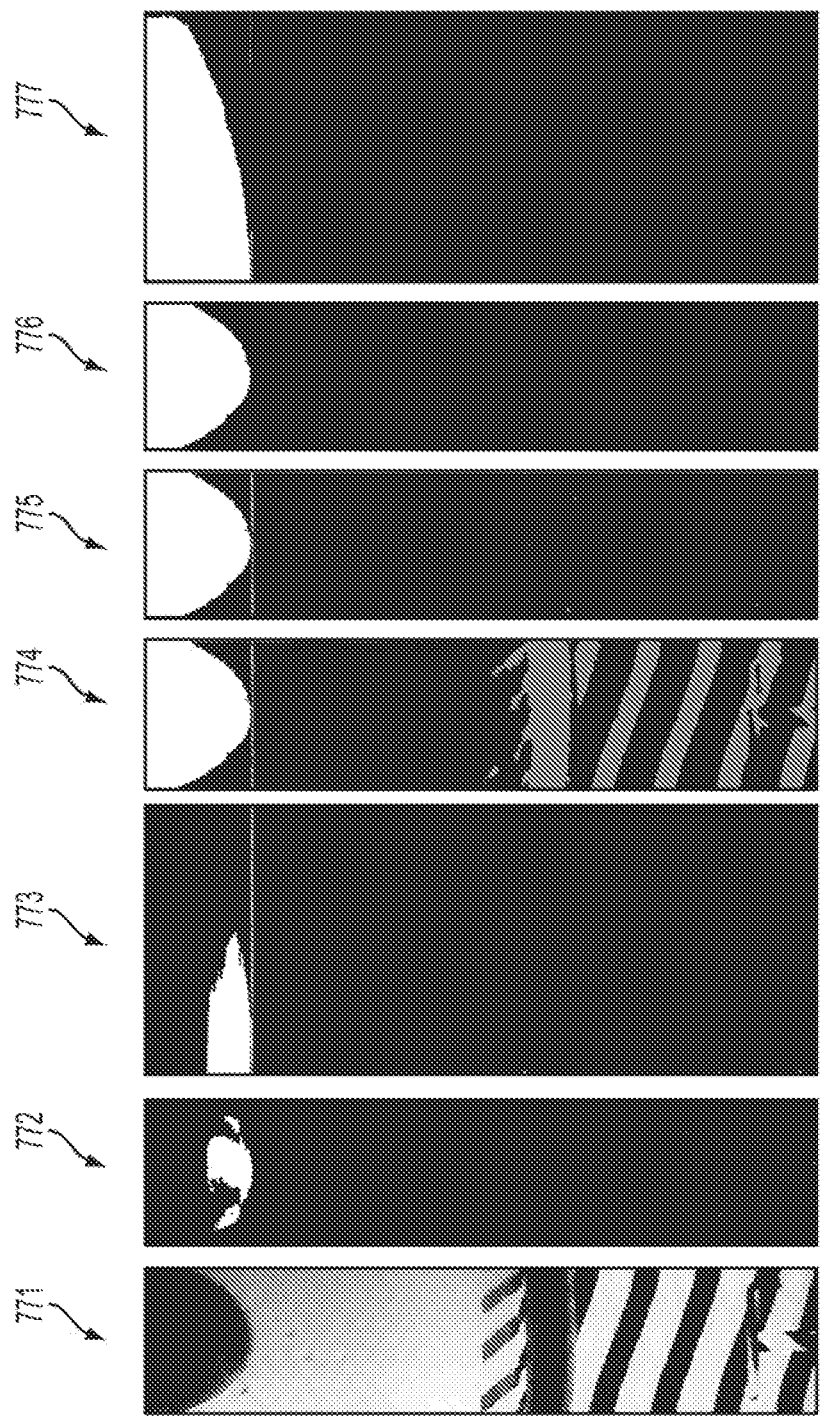
FIG. 81 shows several images for use to illustrate a method of estimating drop growth and/or fluid flow illustrated in FIGS. 82A-82B in accordance with an embodiment of the present disclosure.
Figure 82A:
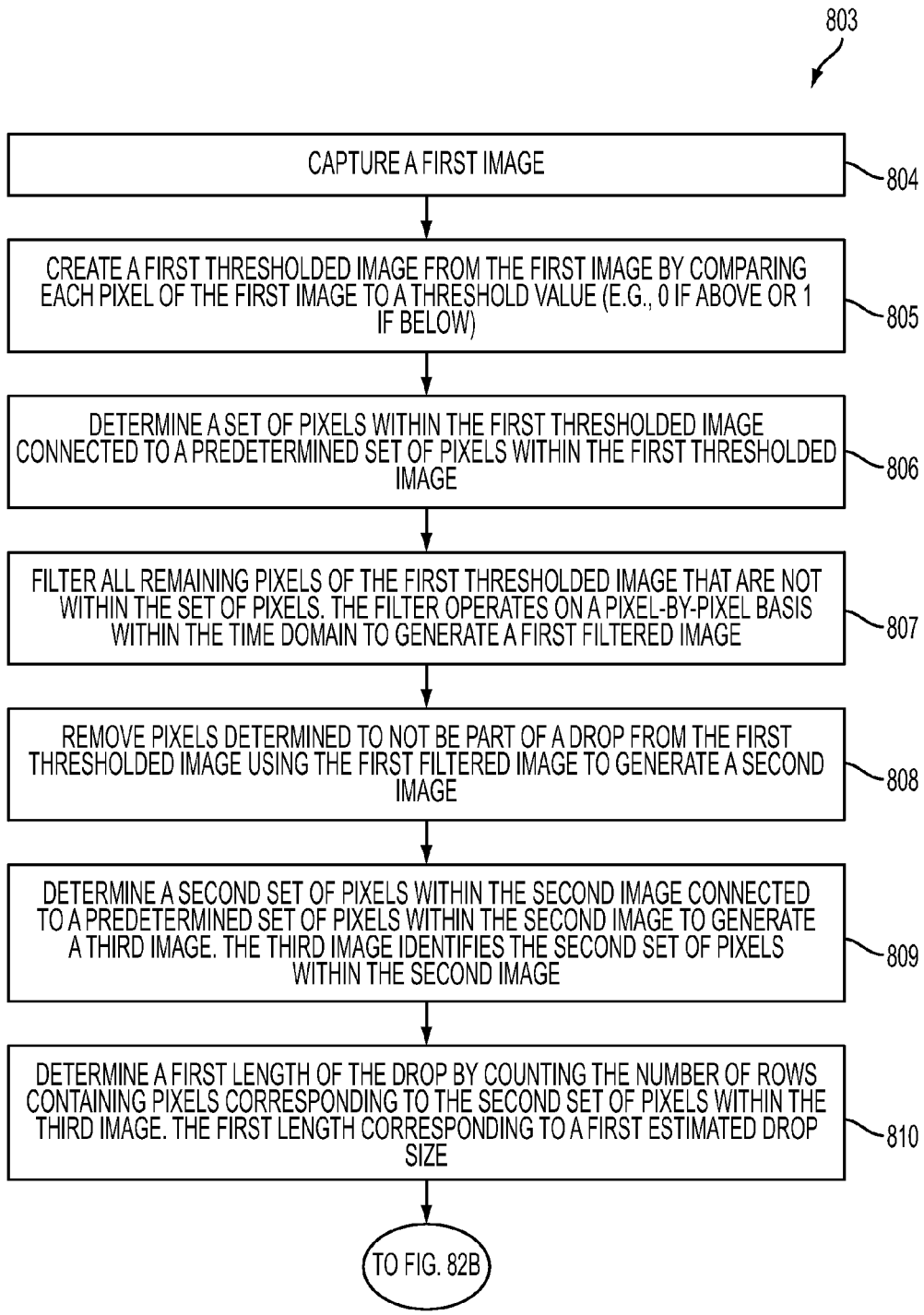
FIGS. 82A-82B show a flow chart diagram illustrating a method of estimating drop growth and/or fluid flow in accordance with an embodiment of the present disclosure.
Figure 82B:
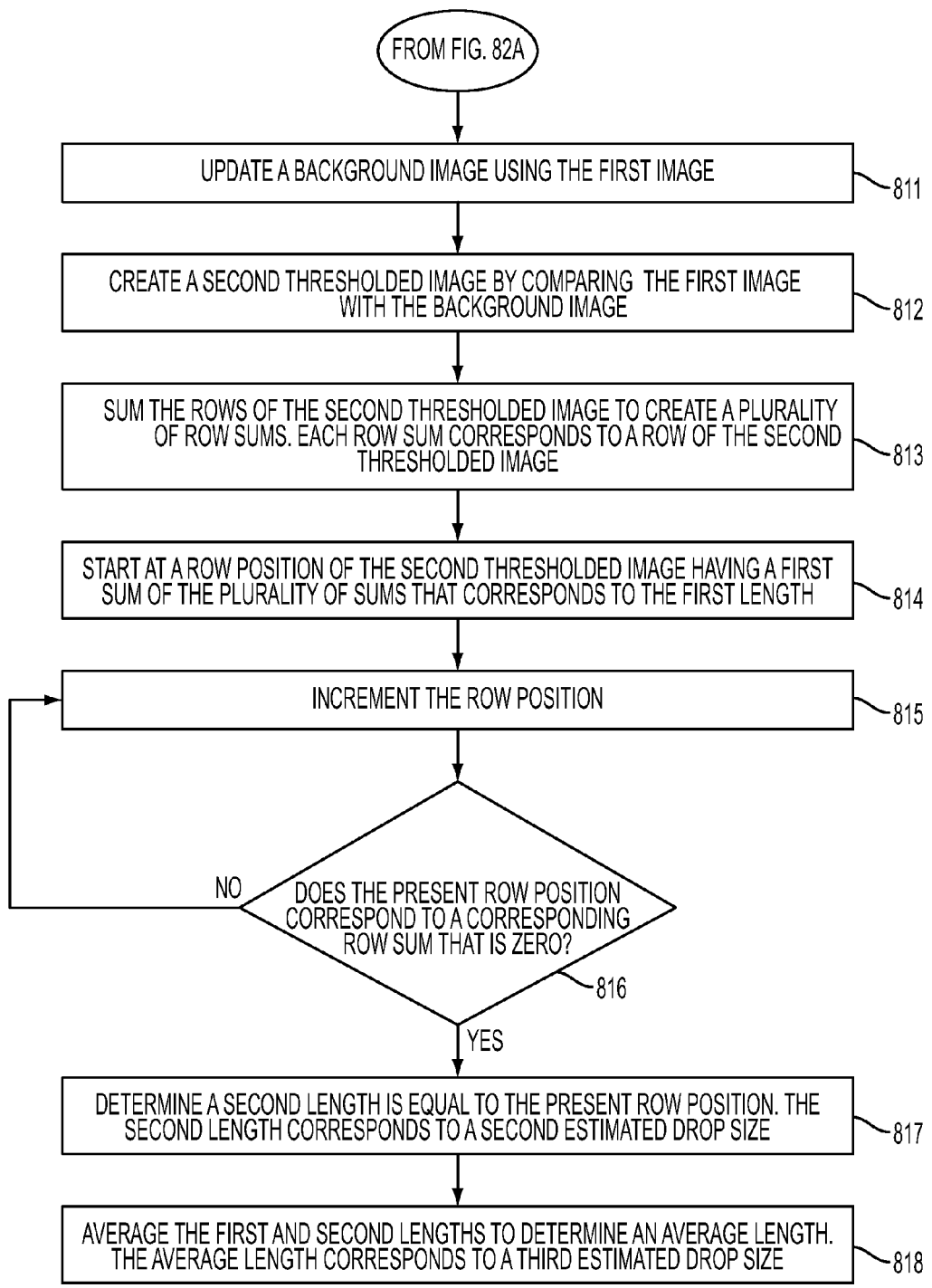

FIG. 81 shows several images for use to illustrate a method of estimating drop growth and/or fluid flow illustrated in FIGS. 82A-82B in accordance with an embodiment of the present disclosure. FIG. 81 shows images 771-777 which are referred to below regarding FIGS. 82A-82B.

FIGS. 82A-82B show a flow chart diagram illustrating a method 803 of estimating drop growth and/or fluid flow. The method 803 includes acts 804-818.

Act 804 captures a first image (e.g., image 771 of FIG. 81). The first image may be a grey scale image of the drip chamber. The drip chamber may be uniformly lit with a striped pattern on the bottom of the chamber (i.e., there is no back pattern on the top portion of the drip chamber).

Act 805 creates a first thresholded image using the first image. The first thresholded image may be the image 774 of FIG. 81. The first thresholded image may be made by comparing each pixel from the first image to a threshold value (e.g., setting a respective pixel of the thresholded image to 0 if the respective pixel of the first image is above the threshold or setting a respective pixel of the thresholded image to 1 if the respective pixel of the first image is below the threshold). This act is to highlight areas where there is water in front of the background.

In some specific embodiments, the threshold level is updated every time a new image is taken to ensure a predetermined ratio of 1 to 0 pixels is maintained to highlight the drop. The ratio may be updated for use by act 805 when used again or the update may adjust the threshold until a predetermined ratio of 1 to 0 pixels is made and then use the first thresholded image for the rest of the method 803.

Act 806 determines a set of pixels within the first thresholded image connected to a predetermined set of pixels within the first thresholded image. The predetermined set of pixels may be determined by fiducials marked on the drip chamber or an opening in which drops are formed. The predetermined set of pixels may be a predetermined set of x, y values that correspond to pixels. Act 806 may use a connected component image analysis algorithm.

Act 807 filters all remaining pixels of the first thresholded image that are not within the set of pixels. The filter operates on a pixel-by-pixel basis within the time domain to generate a first filtered image. The first filtered image is an estimate of a non-active (e.g., a result from features not of interest in the image) portion of the first thresholded image (image 774 of FIG. 81). The filter may be any filter, e.g., any filter described herein.

Act 808 removes pixels determined to not be part of a drop from the first thresholded image using the first filtered image to generate a second image (e.g., image 775 of FIG. 81). A pixel within the second image will be set to 1 if a respective pixel in the first thresholded image is 1 and a respective pixel in the first filtered image is less than 0.5; otherwise, the pixel will be set to 0.

Act 809 determines a second set of pixels within the second image connected to a predetermined set of pixels within the second image to generate a third image (e.g., the image 776 of FIG. 81). The third image identifies the second set of pixels within the second image. Act 809 finds the set of "lit" pixels in the second image connected to the predetermined set of pixels (e.g., pixels representing the opening in which drops are formed).

Act 810 determines a first length of the drop by counting the number of rows containing pixels corresponding to the second set of pixels within the third image. That is, the drop length is determined to be equal to the last "lit" row in the set of pixels found in Act 809. The first length corresponds to a first estimated drop size.

Act 811 updates a background image using the first image. A low-pass filter may be used to update each pixel's value in the background image. An infinite impulse response filter may be used to update the background image using the first image. A pixel is only updated in the background image for rows below the first length plus a predetermined safety zone. A pixel in the background image is updated by low pass filtering the value from the corresponding pixel in the first image.

Act 812 creates a second thresholded image (e.g., image 772 of FIG. 81) by comparing the first image with the background image. That is, the first image has the background image subtracted from it, and on a pixel-by-pixel basis, the absolute value of each pixel is set to 1 if it is above a second threshold value and is set to a 0 if it is below the second threshold value to generate the second thresholded image.

Act 813 sums the rows of the second thresholded image to create a plurality of row sums (see image 773 of FIG. 81). Each row sum corresponds to a row of the second thresholded image.

Act 814 starts at a row position of the second thresholded image having a first sum of the plurality of sums that corresponds to the first length. The row position is incremented in act 815. Act 816 determines whether the present row position correspond to a corresponding row sum that is below a threshold, e.g., zero. If no, then act 815 is preformed again until the present row position corresponds to a corresponding row sum that is zero and then the method 803 proceeds to act 817.

Act 817 determines a second length is equal to the present row position. The second length corresponding to a second estimated drop size. Act 818 averages the first and second lengths to determine a average length. The average length corresponding to a third estimated drop size. By using the first and second lengths to determine an average length, the effects of condensation on the inner walls of the drip chamber are mitigated. That is, the purpose of creating two estimates of drop length is to compensate for how each length is affected by the presence of condensation. The first length tends to underestimate drop length if a drop of condensation intersects the growing drop from the spigot. The second length tends to overestimates the drop length if the drop of condensation intersects the growing drop from the spigot. Their average provides a better estimate when condensation is present. In the absence of condensation, the estimates are almost equal. In other embodiments, only either the first or second length is used to estimate the drop size.

Figure 83:
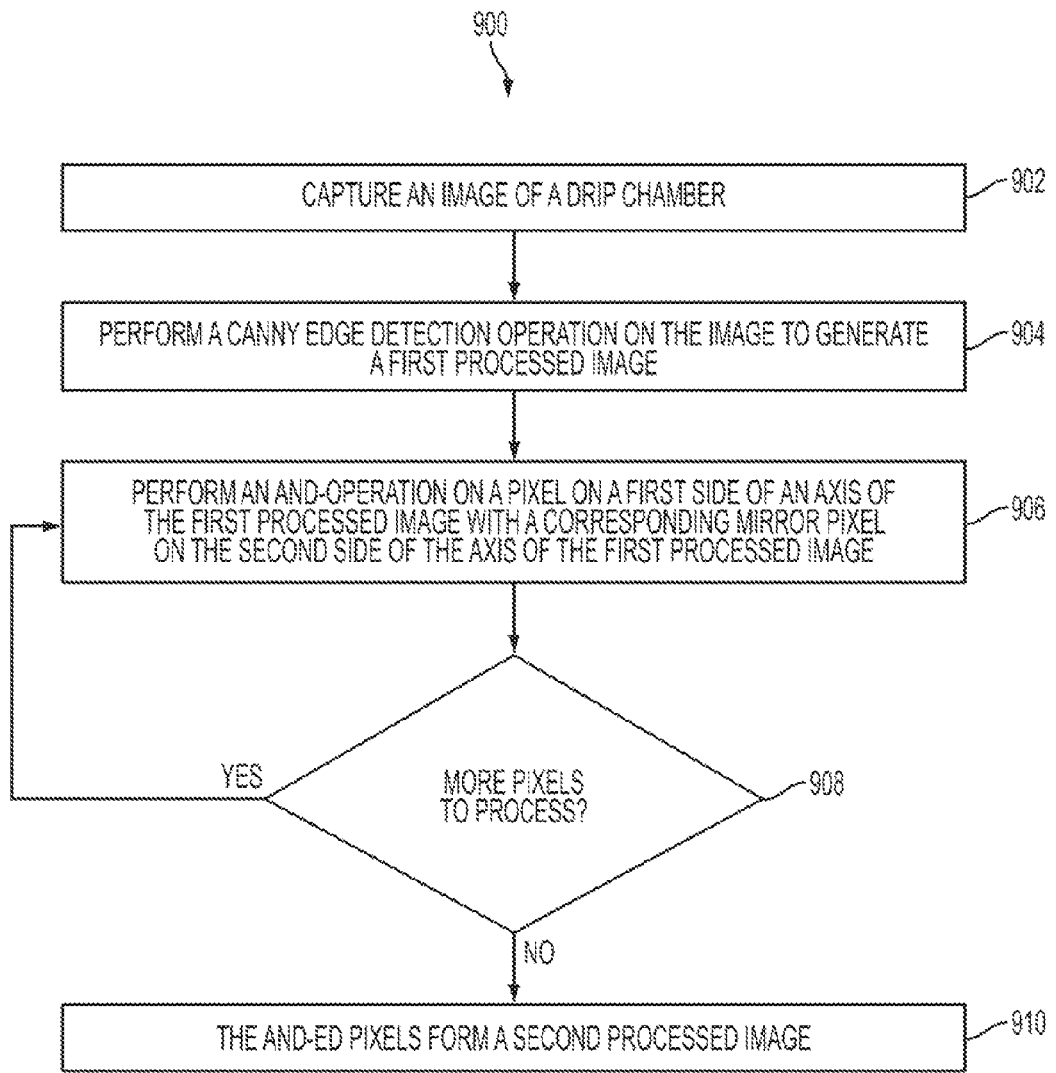
FIG. 83 shows a flow chart diagram of a method for reducing noise from condensation in accordance with an embodiment of the present disclosure.

FIG. 83 shows a flow chart diagram of a method 900 for reducing noise from condensation in accordance with an embodiment of the present disclosure. Method 900 includes acts 902-910.

Act 902 captures an image of a drip chamber. Act 904 performs a canny, edge-detection operation on the image to generate a first processed image. Act 906 performs an AND-operation on a pixel on a first side of an axis of the first processed image with a corresponding mirror pixel on the second side of the axis of the first processed image. That is, Act 902 defines an axis in the first process image, and performs an AND on each pixel on one side with a pixel on the other side, such that the pixel on the other side is symmetrical with the pixel on first side. For example, a 40 (X-axis) by 40 (Y-axis) image may have an axis defined between pixel columns 19 and 20. The top, left pixel would be pixel (1, 1) A pixel at location (1, 5) would be AND-ed with a pixel at (40, 5). The resulting pixel would be used for both locations (1, 5) and (40, 5) to generate the second processed image.

After act 906 is performed, act 908 determines whether all of the pixels have been processed. Act 908 repeats act 906 until all pixels have been processed. Act 910 provides a second processed image that is the results of all of the AND operations.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g., "a," "an," or "the," this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A flow meter, comprising:
   a coupler adapted to couple to a drip chamber;
   a support member operatively coupled to the coupler;
   a first image sensor having a first field of view and operatively coupled to the support member, wherein the first image sensor is positioned to view the drip chamber within the first field of view;
   a valve in fluid communication with the drip chamber;
   a background pattern having an array of lines positioned within the field of view of the first image sensor wherein the drip chamber is between the first image sensor and the background pattern; and
   at least one processor operatively coupled to the first image sensor, wherein the at least one processor is configured to:
   receive a first image data from the first image sensor, provide a background image; and
   determine that a free flow condition exists by:
      comparing the background image with the first image data; and
      determining that the liquid distorts the array of lines by changing angles.

2. The flow meter according to claim 1, further comprising a second image sensor having a second field of view and operatively coupled to the support member, wherein the second image sensor is positioned to view the drip chamber within the second field of view, wherein the processor receives second image data from the second image sensor, wherein the at least one processor is configured to determine an existence of the free flow condition using the first and second image data.

3. The flow meter according to claim 1, further comprising a transceiver configured to communicate with a monitoring client.

4. The flow meter according to claim 3, wherein the transceiver is configured to communicate with the monitoring client concerning at least one of free flow detection data, flow rate estimation data, control data, and exposure data.

5. The flow meter according to claim 1, wherein the valve comprises:
   a curved, elongated support member elastically deformable and having first and second ends; and
   an opposing support member configured to position a tube against the curved, elongated support member between the first and second ends, wherein deformation of the curved, elongated support member by movement of the first and second ends toward each other reduces an internal cross-section along a length of the tube.

6. The flow meter according to claim 5, wherein the valve further comprises an actuator coupled to the curved, elongated support member to deform the curved, elongated support member by movement of the first and second ends toward each other by actuation of the actuator.

7. The flow meter according to claim 6, wherein the actuator, the curved, elongated support member, and the opposing support member are configured to regulate the fluid flow by actuation of the actuator in accordance with a Gompertz curve.

8. The flow meter according to claim 7, wherein the actuator is further configured to actuate the first and second ends toward each other along a predetermined portion of the Gompertz curve to regulate the fluid flow.

9. The flow meter according to claim 6, wherein the actuator, the curved, elongated support member, and the opposing support member are configured to regulate the fluid flow by actuation of the actuator in accordance with a sigmoid curve.

10. The flow meter according to claim 9, wherein the actuator is further configured to actuate the first and second ends toward each other along a predetermined portion of the sigmoid curve.

11. The flow meter according to claim 5, wherein the curved, elongated support member is semi-rigid.

12. The flow meter according to claim 5, wherein the curved, elongated support member consists essentially of a stretchable material.

13. The flow meter according to claim 5, wherein the curved, elongated support member is an arcuate, elongated support member.

14. The flow meter according to claim 5, wherein the curved, elongated support member is C-shaped.

15. The flow meter according to claim 5, wherein the valve further comprises an elongated connecting member operatively coupled to the first and second ends of the curved, elongated support member.

16. The flow meter according to claim 15, further comprising an actuator coupled to the elongated connecting member and the curved, elongated support member to apply an outward expanding force to thereby deform the first and second ends of the curved, elongated support members toward each other.

17. The flow meter according to claim 16, wherein the actuator is a lead screw, and a knob is coupled to the lead screw to actuate the lead screw.

18. The flow meter according to claim 5, wherein the opposing support member is another curved, elongated support member.

19. The flow meter according to claim 18, wherein the curved, elongated support member is disposed about parallel to the another curved, elongated support member along a substantial portion thereof.

20. The flow meter according to claim 18, wherein:
the curved, elongated support member defines a length, and
the another curved, elongated support member defines a length and the length of the another curved, elongated support member is disposed approximately parallel with the length of the curved, elongated support member.

21. The flow meter according to claim 18, wherein the valve further comprises an actuator operatively coupled to the curved, elongated support member at the first and second ends, and to the another curved, elongated support member at first and second ends, wherein actuation of the actuator causes the first and second ends of the curved, elongated support member to approach each other and causes the first and second ends of the another curved, elongated support member to approach each other thereby causing a reduction in distance between the curved, elongated support member and the another curved, elongated support member thereby compressing the tube.

22. The flow meter according to claim 5, wherein:
the curved, elongated support member defines a length, and
the opposing support member is disposed orthogonally from the length along a portion thereof.

23. The flow meter according to claim 5, wherein the curved, elongated support member includes a plurality of ridges disposed thereon to engage the tube.

24. The flow meter according to claim 5, wherein the opposing support member includes a plurality of ridges disposed thereon and configured to engage the tube.

25. The flow meter according to claim 5, wherein the curved, elongated support member includes a flange extending from a length thereof and configured to hold the tube.

26. The flow meter according to claim 1, wherein the processor is configured to actuate the valve in accordance with the at least one parameter of liquid in a feed-back configuration.

27. A system comprising:
a drip chamber;
a fluid line coupled to the drip chamber;
a coupler adapted to couple to the drip chamber;
a support member operatively coupled to the coupler;
a first image sensor having a first field of view and operatively coupled to the support member, wherein the first image sensor is positioned to view the drip chamber within the first field of view;
a valve operatively coupled to the fluid line;
a background pattern having an array of lines positioned within the view of the first image sensor;
at least one processor operatively coupled to the first image sensor wherein:
the at least one processor is configured to receive a first image data from the first image sensor, and
the at least one processor is configured to determine whether a free flow condition exists within the drip chamber using the first image data by examining a distortion of the background pattern causing a change in the angle of the array of lines as found within the first image data.

28. The system according to claim 27, further comprising a monitoring client configured to communicate data with the at least one processor.

* * * * *